(12) United States Patent
Hill et al.

(10) Patent No.: US 7,415,359 B2
(45) Date of Patent: Aug. 19, 2008

(54) METHODS AND SYSTEMS FOR THE IDENTIFICATION OF COMPONENTS OF MAMMALIAN BIOCHEMICAL NETWORKS AS TARGETS FOR THERAPEUTIC AGENTS

(75) Inventors: Colin Hill, Ithaca, NY (US); Iya Khalil, Ithaca, NY (US)

(73) Assignees: Gene Network Sciences, Inc., Ithaca, NY (US); Cornell Research Foundation, Inc., Ithaca, NY (US)

( * ) Notice: Subject to any disclaimer, the term of this patent is extended or adjusted under 35 U.S.C. 154(b) by 179 days.

(21) Appl. No.: 10/287,173

(22) Filed: Nov. 4, 2002

(65) Prior Publication Data

US 2003/0215786 A1 Nov. 20, 2003

Related U.S. Application Data

(60) Provisional application No. 60/406,764, filed on Aug. 29, 2002, provisional application No. 60/335,999, filed on Nov. 2, 2001.

(51) Int. Cl.
G01N 33/48 (2006.01)
(52) U.S. Cl. .............................. 702/19; 702/20; 703/11; 707/102
(58) Field of Classification Search ............. 702/19–20; 703/11; 707/102
See application file for complete search history.

(56) References Cited

U.S. PATENT DOCUMENTS

| | | | |
|---|---|---|---|
| 5,047,969 A * | 9/1991 | Sloane | 703/2 |
| 5,914,891 A | 6/1999 | McAdams et al. | |
| 5,930,154 A | 7/1999 | Thalhammer-Reyero | |
| 5,947,899 A * | 9/1999 | Winslow et al. | 600/410 |
| 5,965,352 A | 10/1999 | Stoughton et al. | |
| 5,991,525 A * | 11/1999 | Shah et al. | 703/2 |
| 6,132,969 A | 10/2000 | Stoughton et al. | |
| 6,165,709 A | 12/2000 | Friend et al. | |
| 6,203,987 B1 | 3/2001 | Friend et al. | |
| 6,983,227 B1 * | 1/2006 | Thalhammer-Reyero | 703/2 |
| 7,076,472 B2 * | 7/2006 | Addison | 706/13 |
| 2002/0019705 A1 | 2/2002 | Kauffman et al. | |
| 2002/0068269 A1 | 6/2002 | Allen et al. | |
| 2002/0155422 A1 * | 10/2002 | Ingber et al. | 435/4 |
| 2003/0130798 A1 * | 7/2003 | Hood et al. | 702/19 |
| 2005/0273305 A1 * | 12/2005 | Thalhammer-Reyero | 703/11 |

FOREIGN PATENT DOCUMENTS

| | | | |
|---|---|---|---|
| WO | WO 96/22575 | * | 7/1996 |
| WO | WO01/80151 | | 10/2001 |
| WO | WO02/065119 | | 8/2002 |

OTHER PUBLICATIONS

Kohn, K. Molecular Biology of the Cell, 1999 vol. 10: 2703.*
Glass et al., Ordered and disordered dynamics in random networks. *Europhysics Letters*, vol. 41, No. 6, 1998, pp. 599-604.
Tomita et al, E-CELL; Software environment for whole-cell simulation. *Bioinformatics*. vol. 15, No. 1, 1999 pp. 72-84.
Goryanin et al. Mathematical simulation and analysis of cellular metabolism and regulation. *Bioinformatics*, 1999, vol. 15, No. 9, pp. 749-758.
Huang Sui, Gene expression profiling, genetic networks, and cellular states; An integrating concept for tumorigenesis and drug discovery. *Journal of Molecular Medicine*, Springer Verlag, DE, vol. 77, No. 6, Jun. 1999, pp. 469-480.
Schuster Stefan et al., A general definition of metabolic pathways for systemic organization and analysis of complex metabolic networks. *Nature Biotechnology* (Nature America), vol. 18, No. 3, Mar. 2000, pp. 326-333.
Scherf U. et al., A gene expression database for the molecular pharmacology of cancer. *Nature Genetics* (Nature America), New York, vol. 24 No. 3, Mar. 2000, pp. 236-244.
Voit et al. Biochemical systems analysis of genome wide expression data. *Bioinformatics*, vol. 16, No. 11, (2000) pp. 1023-1037.
Marhl et al, Complex calcium oscillations and the role of mitochondria and cytosolic proteins. *BioSystems*, vol. 57 (2000), pp. 75-86.
Haberichter et al., Birhyhmicity, trihythmicity and chaos in bursting calcium oscillations, *Biophysical Chemistry* vol. 90, (2001), pp. 17-30.
Bader et al., BIND- The biomolecular interaction network database. *Nucleic Acids Research*, vol. 29, No. 1 (2001), pp. 242-245.
Hasty Jeff et al., Computational studies of gene regulatory networks: In numero molecular biology. *Nature Reviews/Genetics*. vol. 2, No. 4, Apr. 2001, pp. 268-279.
Ideker et al., Integrated genomic and proteomic analyses of a systematically perturbed metabolic network. *Science*, American Association for the Advancement of Science; vol. 292, No. 4, May 2001, pp. 929-934.

(Continued)

*Primary Examiner*—Mary K Zeman
(74) *Attorney, Agent, or Firm*—Kramer Levin Naftalis & Frankel LLP; Barry Evans, Esq.; Aaron Haleva, Esq.

(57) ABSTRACT

Systems and methods are presented for cell simulation and cell state prediction. For example, a cellular biochemical network intrinsic to a phenotype of a cell can be simulated by specifying its components and their interrelationships. The various interrelationships can be represented with one or more mathematical equations which can be solved to simulate a first state of the cell. The simulated network can then be perturbed, and the equations representing the perturbed network can be solved to simulate a second state of the cell which can then be compared to the first state, identifying the effect of such perturbation on the network, and thereby identifying one or more components as targets. Alternatively, components of a cell can be identified as targets for interaction with therapeutic agents based upon an analytical approach, in which a stable phenotype of a cell is specified and correlated to the state of the cell and the role of that cellular state to its operation. A cellular biochemical network believed intrinsic to that phenotype can then be specified, mathematically represented, and perturbed, and the equations representing the perturbed network solved, thereby identifying one or more components as targets.

17 Claims, 62 Drawing Sheets

OTHER PUBLICATIONS

Somogyi Roland et al., The dynamics of molecular networks: applications to therapeutic discovery. *Drug Discovery Today*, vol. 6, No. 24, 2001, pp. 1267-1277.

Wagner A: How to reconstruct a large genetic network from n gene perturbations in fewer than n2 east steps. *Bioinformatics*, Oxford University Press, vol. 17, No. 12, 2001, pp. 1183-1197.

Browning et al., Towards the Development of a Minimal Cell Model by Generalization of a Model of *Esherichia coli*: Use of Dimensionless Rate Parameters, *Biotechnology and Bioengineering*, vol. 76, No. 3, Nov. 2001, pp. 187-192.

Fox et al., From topology to dynamics in biochemical networks. *Chaos*, vol. 2, No. 4, Dec. 2001, pp. 809-815.

Kierzek, A. STOCKS: STOChastic Kinetic Simulations of biochemical systems with Gillespie algorithm. *Bioinformatics*, vol. 18, No. 3, (Mar. 2002) pp. 470-481.

Shmulevich Ilya et al., Gene perturbation and intervention in Probabilistic Boolean Networks, *Bioinformatics*, vol. 18, No. 10 (Oct. 2002), pp. 1319-1331.

Maimon et al., Diagrammatic Notation and Computational Structure of Gene Networks, Gene Network Sciences; *Proceedings of the Second International Conference on Systems Biology*, Pasadena, CA, 311-317 (2001) pp. 1-7.

\* cited by examiner

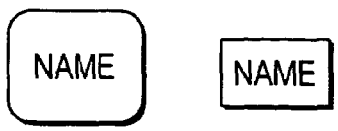

FIG. 3(a)
CHEMICAL OR ATOM -- SINGLE INDIVISIBLE CHEMICAL UNIT

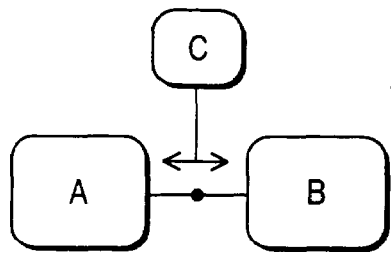

FIG. 3(b)
REVERSIBLE BINDING BETWEEN A AND B. C IS A COMPONENT THAT IS STIMULATING THE UNBINDING BETWEEN A AND B.

FIG. 3(c)
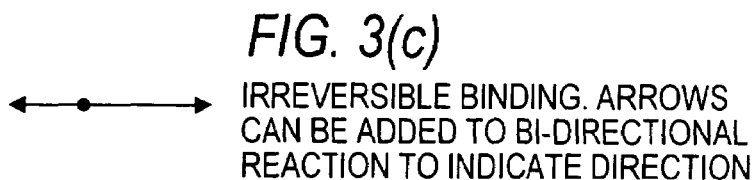

IRREVERSIBLE BINDING. ARROWS CAN BE ADDED TO BI-DIRECTIONAL REACTION TO INDICATE DIRECTION

FIG. 3(d)
LINK BOX. DEPICTS COMPONENTS IN THE CELL WITH COMPLEX STRUCTURE.

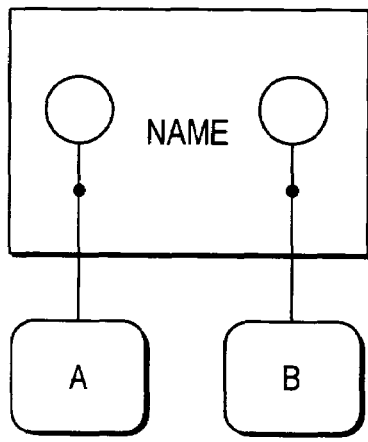

— (0,1) —

RESOLUTION -- PARTICULAR STATES IN A LINK BOX CAN BE RESOLVED VIA THIS NUMBERING SCHEME REPRESENTING THE STATE OF A NOT BOUND AND B BOUND

FIG. 3(e)
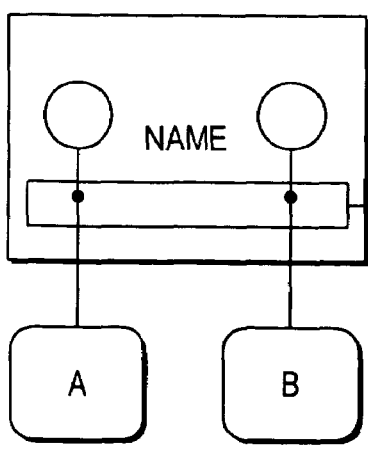

AN INTERNAL LINK BOX. IDENTIFIES A PARTICULAR STATE SIMILAR TO RESOLUTION.

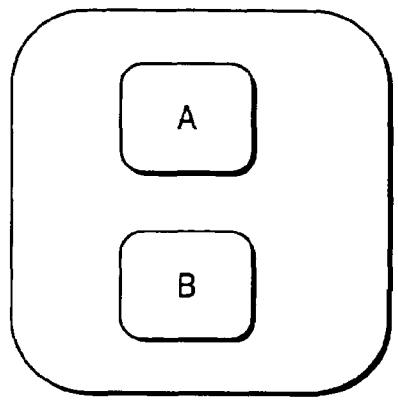
FIG. 3(f)
LIKE BOX.
DEPICTS WHICH GROUPS OF OBJECTS ARE ALIKE IN FUNCTIONALITY.
——— (1) ———
RESOLUTION OF STATE (1) OR COMPONENT B WHICH CAN GO OFF AND REGULATE OTHER THINGS IN THE CELL
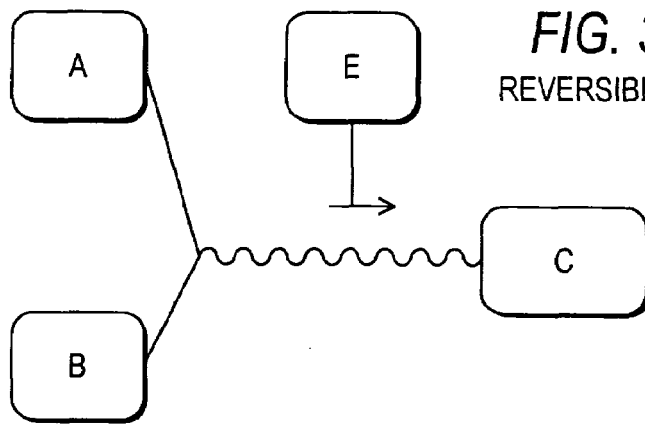
FIG. 3(g)
REVERSIBLE REACTION.
IRREVERSIBLE REACTION (HAS A ONE-WAY ARROW)
FIG. 3(h)
— UNBINDING STIMULATION ⇅
FIG. 3(i)
— BINDING STIMULATION ⊥
FIG. 3(j)
— ENABLES ⟶
FIG. 3(k)
— NO REACTION ⟶×
FIG. 3(l)
— ENHANCES —o
FIG. 3(m)
— DIRECTIONAL STIMULATION ⤴
FIG. 3(n)

NW-R

NE-L

NE-R

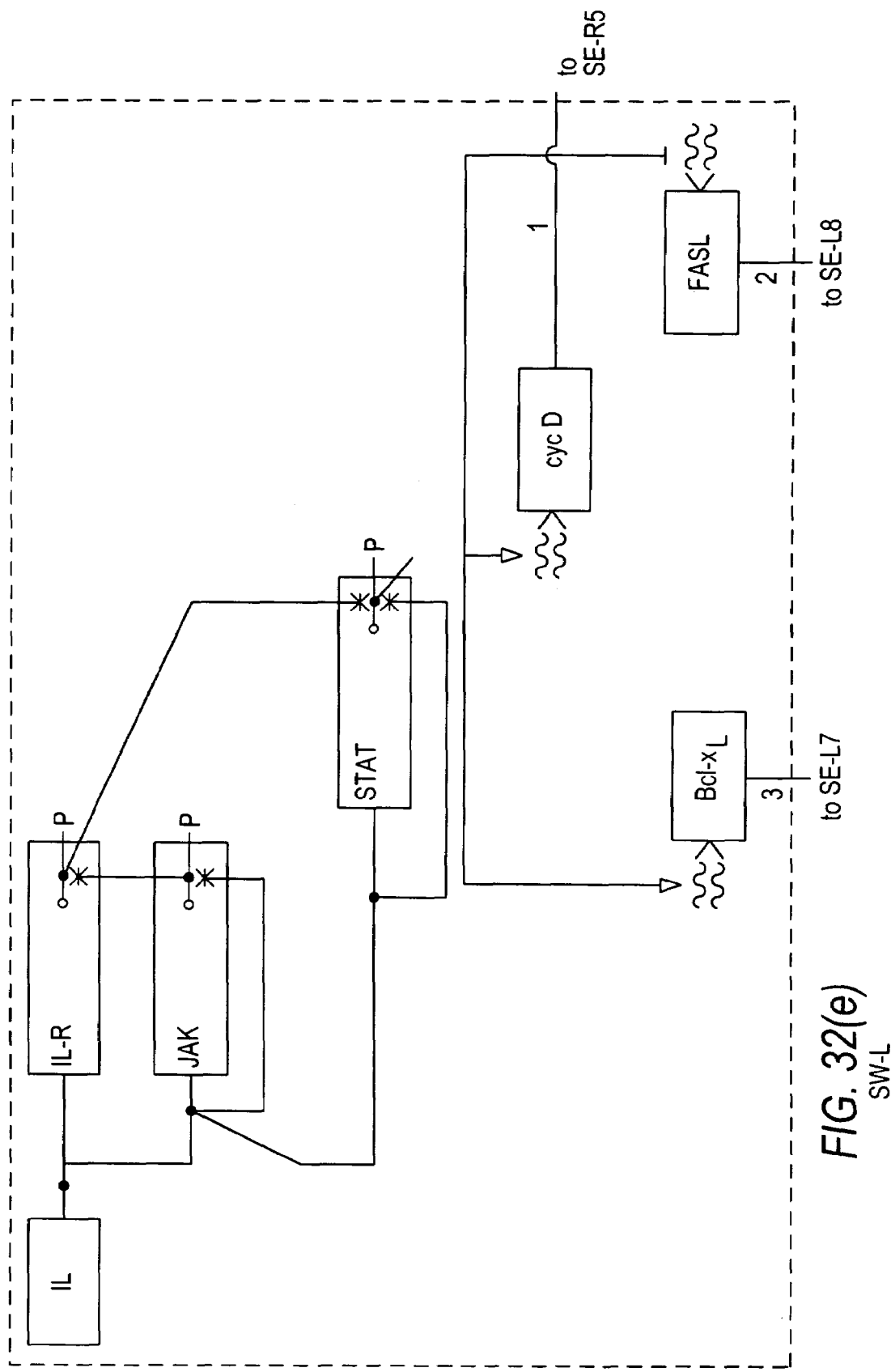
FIG. 32(e) SW-L

SW-R

SE-L

SE-R

| Target | Up/Down | G1-S Arrest | S phase Arrest | G2-M Arrest | Sensitivity to Apoptosis | Apoptosis |
|---|---|---|---|---|---|---|
| Creb | Down | | | | ✓ | |
| CyclinE | Down | ✓ | ✓ | | | |
| c-Myc | Down | ✓ | | | | |
| IGF-1R | Down | ✓ | | | ✓ | |
| CyclinA | | | ✓ | | | |
| AKT | Down | | | | ✓ | |
| c-Myc | Up | | | | ✓ | |
| Rb-Phos | | ✓ | | | | |
| Cdc25B | Up | | | ✓ | | |
| Wee | Up | ✓ | | ✓ | | |
| PI3K | Down | ✓ | | | ✓ | |

FIG. 34

| Target | IAP | Bcl2 | Bcl-xL | Creb | 1433-σ | Erk | Mek | CDK1 | Trail | β-catenin | EGFR | NFKappaB |
|---|---|---|---|---|---|---|---|---|---|---|---|---|
| IAP | | ✓ | ✓ | ✓ | | ✓ | ✓ | | ✓ | | | ✓ |
| Bcl2 | ✓ | | ✓ | | ✓ | | | | ✓ | | | ✓ |
| Bcl-xL | ✓ | ✓ | | | ✓ | ✓ | ✓ | ✓ | ✓ | | | |
| Creb | | | | | | | | | ✓ | | | |
| 1433-σ | | ✓ | ✓ | | | | | | ✓ | | | ✓ |
| Erk | ✓ | ✓ | ✓ | | | | | | ✓ | | | ✓ |
| Mek | ✓ | ✓ | ✓ | | | | | | ✓ | | | ✓ |
| CDK1 | | ✓ | ✓ | | | | | | ✓ | | ✓ | ✓ |
| Trail | | ✓ | | | | | | | ✓ | ✓ | | |
| β-catenin | | | | | | | | | ✓ | | | |
| EGFR | ✓ | | | | | | | ✓ | ✓ | | | ✓ |
| NFkappaB | ✓ | ✓ | | | ✓ | | | | ✓ | | ✓ | ✓ |

FIG. 35

| Target | Up/Down | G1-S Arrest | S phase Arrest | G2-M Arrest | Sensitivity to Apoptosis | Apoptosis |
|---|---|---|---|---|---|---|
| APC | Up | ✓ | | | | |
| β-catenin | Down | ✓ | | | ✓ | |
| p90RSK | Down | | | | ✓ | |
| CDK4 | Down | ✓ | | | | |
| CDK2 | Down | ✓ | ✓ | | ✓ | |
| GADD45 | UP | | | ✓ | ✓ | |
| p21 | Up | ✓ | | ✓ | | |
| p27 | Up | ✓ | | | | |
| CyclinB | Down | | | ✓ | | |
| CyclinD | Down | ✓ | | | ✓ | |
| p16 | Up | ✓ | | | ✓ | |
| p18 | Up | ✓ | | | ✓ | |
| Pten | Up | | | | ✓ | |
| TAK1 | UP | | | ✓ | | |
| FLIP | Down | | | | ✓ | |

| Target | Up/Down/ | G1-S Arrest | S phase Arrest | G2-M Arrest | Sensitivity To Apoptosis | Apoptosis |
|---|---|---|---|---|---|---|
| IAP | Down | | | | ✓ | |
| Trail | Up | | | | | ✓ |
| FASL | Up | | | | | ✓ |
| 1433-σ | Up | | | ✓ | | |
| 1433-σ | Down | | | | ✓ | |
| Cdc25C | Down | | | ✓ | ✓ | |
| CDC25A | Down | | ✓ | | | |
| EGFR | Down | ✓ | | | ✓ | |
| Erb2 | Down | ✓ | | | ✓ | |
| Raf | Down | ✓ | | | ✓ | |
| IKK | Down | | | | ✓ | |
| IkappaB | Down | | | | ✓ | |
| E2F | Up | ✓ | | ✓ | ✓ | |
| TAK1 | UP | | | ✓ | | |
| FLIP | Down | | | | ✓ | |

*FIG. 34 (CONT.)*

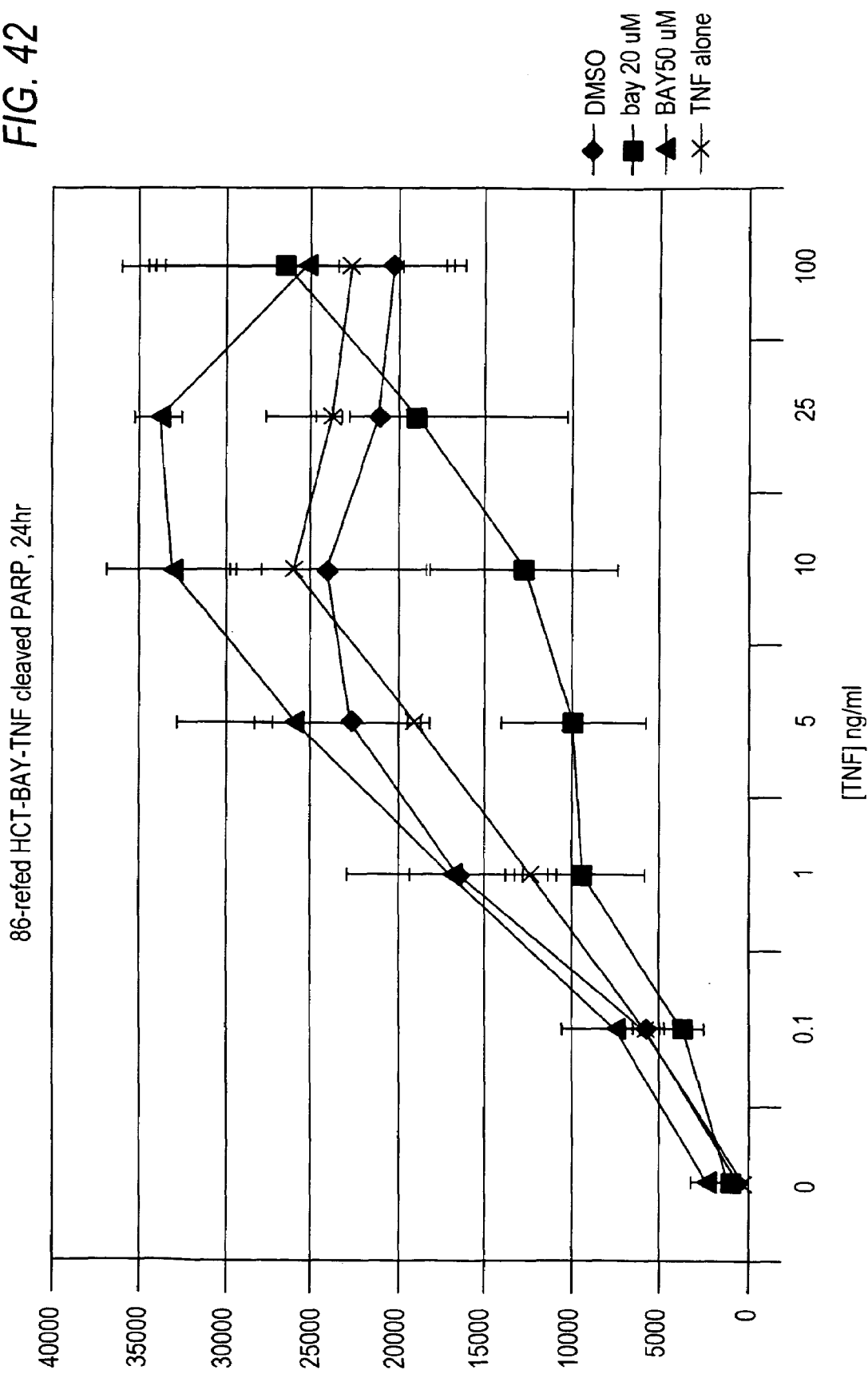

| | |
|---|---|
| ATOM |  |
| REACTION |  |
| DIMERIZATION |  |
| COMPARTMENTS | 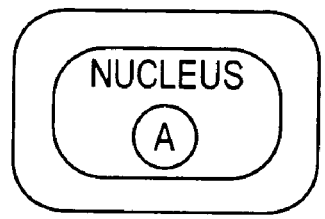 |
| LINKBOX | 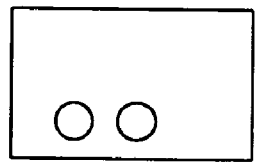 |
| LIKEBOX | 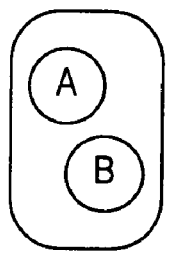 |
| RESOLUTION NOTATION | (1,0,0,0) |
| EQUIVALENCE LINE |  |
FIG. 43(a)

COMPLEX- 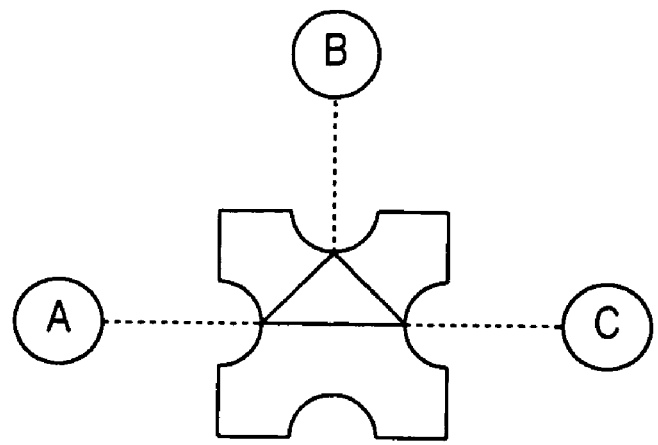
MODIFIER 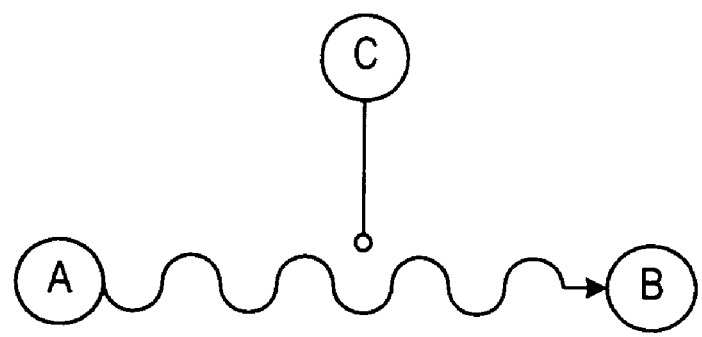
PROCESS- 
FIG. 43(b)

FIG. 49
Observed Chemicals
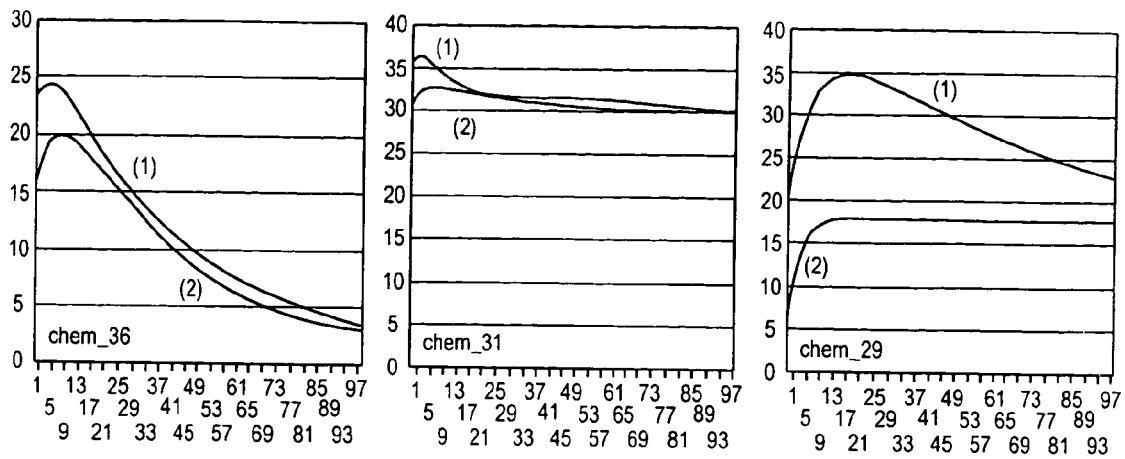
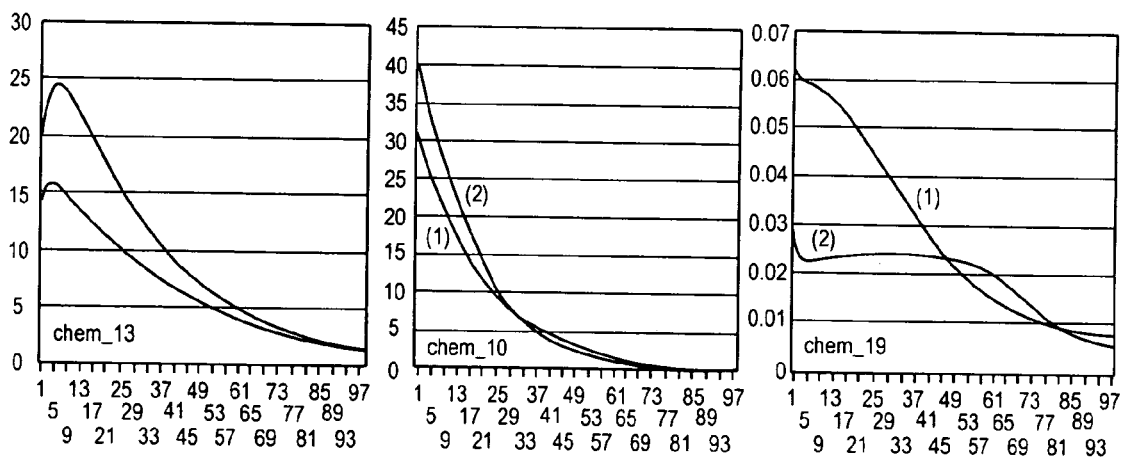
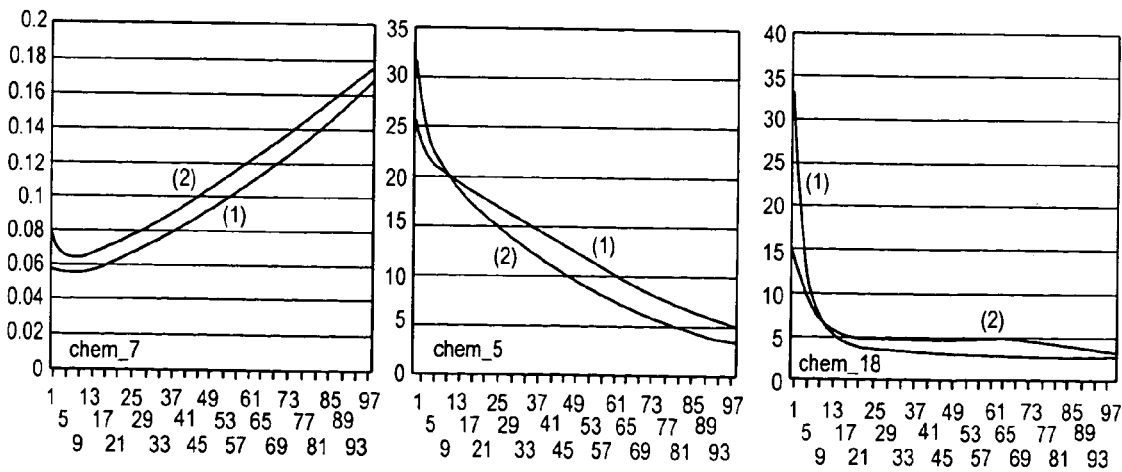

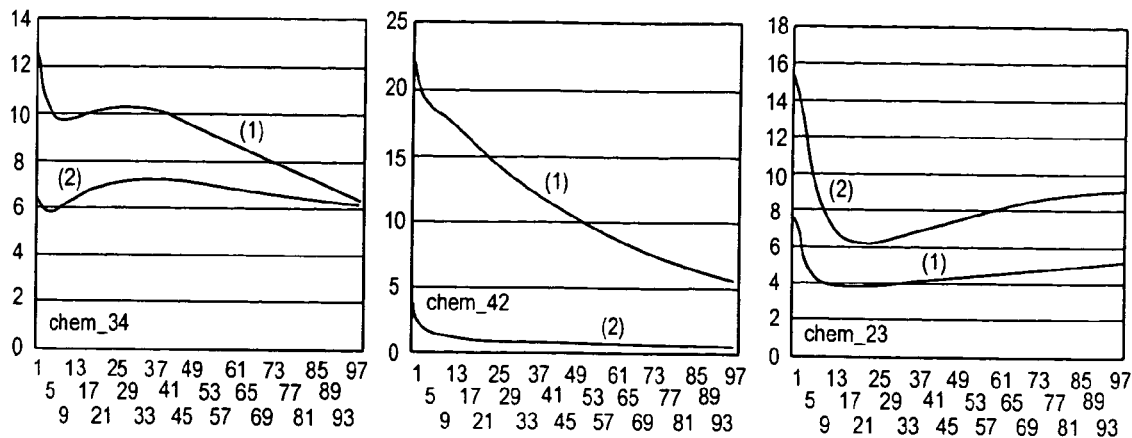
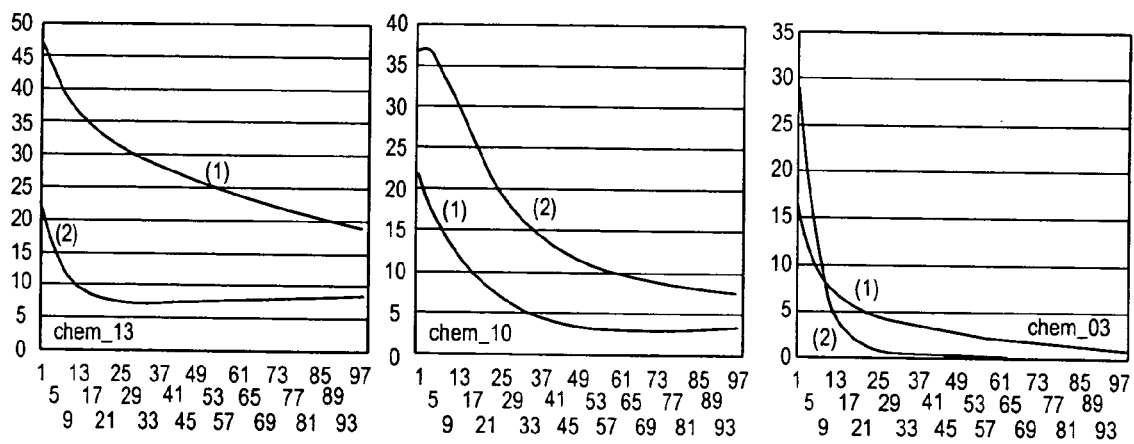
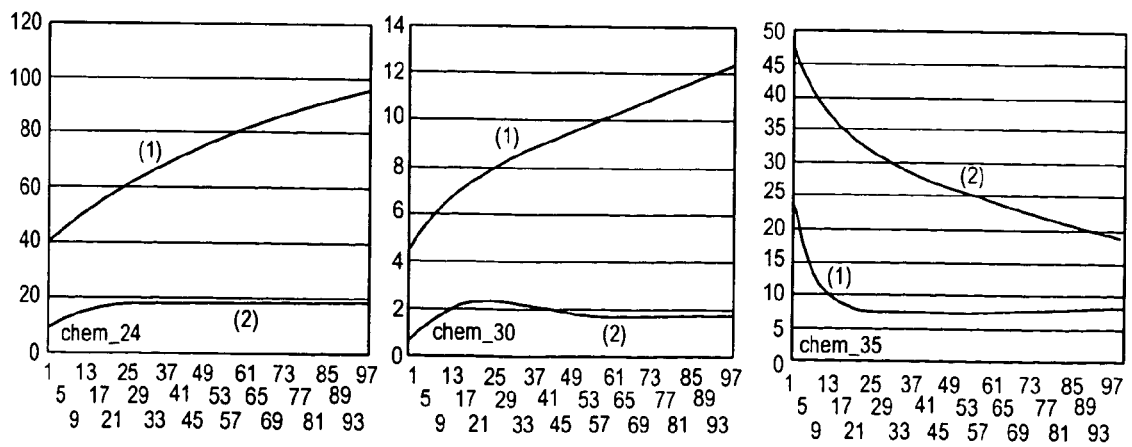
FIG. 50

METHODS AND SYSTEMS FOR THE IDENTIFICATION OF COMPONENTS OF MAMMALIAN BIOCHEMICAL NETWORKS AS TARGETS FOR THERAPEUTIC AGENTS

CROSS REFERENCE TO RELATED APPLICATIONS

This application claims the benefit of the following United States Provisional Patent Applications: "Methods and Systems for the Identification of Components of mamallian Cells as Targets for Therapeutic Agents", U.S. Provisional Patent Application Ser. No. 60/335,999, filed on Nov. 2, 2001; and "Systems and Methods For Inferring Biological Networks", Vipul Periwal, Inventor, U.S. Provisional Patent Application Ser. No. 60/406,764, filed on Aug. 29, 2002.

This application also claims priority to the following United States Patent Application: "Scale-Free Network Inference Methods", Jeff Fox, Cohn Hill and Vipul Periwal, Inventors, U.S. application Ser. No. 10/286,372, filed on Nov. 1, 2002.

GOVERNMENT SUPPORT

This invention was made with Government support under NIH Grant/Contract No. CA094701. The Government has certain rights to this invention.

FIELD OF THE INVENTION

The present invention relates to drug discovery. More particularly, the invention relates to in silico methods for identifying one or more components of a cell as a target for interaction with one or more therapeutic agents. Even more specifically, the invention relates to methods for the simulation or analysis of the dynamic interrelationships of genes and proteins with one another and to the use of those methods to identify one or more cellular components as putative targets for a therapeutic agent.

BACKGROUND OF THE INVENTION

Drug Discovery

Several methods have been employed to find therapeutic compounds useful in the treatment of disease states. Typically, these methods involve empirical studies of organisms or cells and in some cases the components of cells to identify active therapeutic compounds which themselves, or in modified form, may have a beneficial effect on the organism or cell.

Screening methods have been used to find compounds that have a sought after-effect on a cell, i.e. the up regulation or down regulation of a gene. Screening assays are used to identify compounds and those which are identified may be used in further drug development activity. Using such methods, for example, antibodies that bind to receptors on animal tumor cells may be assayed and identified. In further drug development efforts, these antibodies or their epitopes can be analyzed and their therapeutic activity enhanced by methods known in the art.

A difficulty with such methods is that they are basically brute-force empirical methods that reveal little or nothing about the particular phenomena which take place within the cell when it is contacted with the compound identified in the screen. The actual cellular dynamics may not be understood and this may lead to development of candidate drugs deleteriously, which affect other components in the cell and cause undesirable side effects. This brute-force screening method is also limited by the speed at which assays can be conducted.

Another empirical approach used in drug development is that of screening compounds against a particular component of a cell which has been identified as being involved in a disease condition. Assays are conducted to determine the binding effect, chemical interaction or other modification of certain molecules within the cell such as genes or proteins. While the art has developed powerful, high throughput screening techniques by which tens of thousands of compounds are routinely screened for their interactive effect with one or more targets, such methodologies are still inherently empirical and leave the researcher with no fundamental information about the mechanisms of interaction of a compound identified by such methods. Thus the compound so identified may have detrimental interactions with one or more other components of a cell and may cause more harm than good. In order to determine whether the so identified compound may ultimately be useful as a therapeutic, it must be tested using in vitro studies on cells containing the particular gene or protein with which it interacts, or in vitro animal studies to determine both its beneficial and possible detrimental effects. These additional tests are extremely time-consuming and expensive.

Recently, investigators have sought to make the drug discovery process more rational by exploring the effects of a drug under development on various modifications of cells and cellular components. Friend et al., U.S. Pat. No. 6,165,709 describes methods for identifying the cellular targets of a drug by comparing (i) the effects of the drug on a wild-type cell, (ii) the effects on a wild-type cell of modifications to a putative target of the drug, and (iii) the effects of the drug on a wild-type cell which has had the putative target modified. The effect of the drug on the cell can be determined by measuring various aspects of the cell state, including gene expression, concentration of proteins, etc. While the methods described are improved over the brute-force empirical methods described above, multiple "wet" experiments must be conducted in order to determine that a gene or protein component of a cell is in fact a target of a drug and then to determine the effects of the drug on that component, on a modified component and on a wild-type cell.

OBJECTS OF THE INVENTION

It is an object of the invention to expedite the drug discovery process and to avoid costs and delays of present drug-screening methods.

It is a further and related object of the invention to reduce labor and equipment costs of empirical drug discovery processes.

It is still a further object of the invention to reduce or avoid the need for setting up expensive in vitro and in vivo experiments to determine the efficacy, toxicity and side effects of drug candidates.

It is still a further object of the invention to determine the effects of drug candidates on the cell as a whole or the least upon a multiplicity of the components of the cell rather than upon one or two cellular components as is characteristic of prior art methods of drug development.

It is still a further and related object of the invention to increase the fund of knowledge relating to the interaction of a drug candidate with multiple cellular components in order to gain advance knowledge of the overall dynamics of the cell in the presence of a drug candidate.

It is still a further object of the invention to provide a method for determining in advance how a proposed drug will affect the cell as a whole.

It is still a further object to the invention to provide methods for simulating or analyzing the normal and disease states of a cell and for determining how to best interact with one or more cellular components to bring about a change in the phenotype of the cell.

SUMMARY OF THE INVENTION

The invention is broadly in the modeling of the interactions of the several genes, proteins and other components of a cell, the use of mathematical techniques to represent the interrelationships between the cell components and the manipulation of the dynamics of the cell to determine which one or more components of a cell may be targets for interaction with therapeutic agents.

Exemplary methods of the invention for identifying components of a cell as putative targets for interaction with one or more therapeutic agents, based on a cell simulation approach, comprise the steps of:

(a) specifying a cellular biochemical network believed to be intrinsic to a phenotype of said cell;

(b) infering new and missing links and components in the network by using and incorporating experimental data (e.g., DNA sequence, protein sequence, microarray, expression data, time course expression data, protein structure, . . . etc.)

(c) simulating the network by (i) specifying its components, and (ii) specifying interrelationships between those components and representing the interrelationships in one or more mathematical equations;

(d) infering new and missing links and components in the network;

(e) constraining and or determining parameter values in the network by (i) sampling a set of networks and parameter values, (ii) simulating the said networks as described in (c), and (iii) determining the network and parameter values that optimally fits a given set or sets of experimental data (e.g., DNA sequence, protein sequence, microarray, expression data, time course expression data, protein structure, . . . etc.); using optimization, sensitivity analysis, and error analysis to determine validity and robustness of predictions (f) solving those equations representing the network to simulate a first state of the cell;

(g) perturbing the simulated network by deleting one or more components thereof or changing the concentration of one or more components thereof or modifying one or more mathematical equations representing interrelationships between one or more of the components;

(h) solving the equations representing the perturbed network to simulate a second state of the cell; and (i) comparing the first and second simulated states of the network to identify the effect of the perturbation on the state of the network, and thereby identifying one or more components for interaction with one or more agents.

(j) experimentally verifying predictions from the model in order to validate a single prediction or disceren between various predictions or hypotheses and/or using the experimentally derived results to iteratively refine the model.

Exemplary methods of the invention for identifying components of a cell as putative targets for interaction with one or more therapeutic agents based upon an analytical approach, comprise the steps of:

(a) specifying a stable phenotype of a cell;

(b) correlating that phenotype to the state of the cell and the role of that cellular state to its operation;

(c) specifying a cellular biochemical network believed to be intrinsic to that phenotype;

(d) characterizing the biochemical network by
(i) identifying the components thereof, and
(ii) identifying interrelationships between the components and representing those interrelationships in one or more mathematical equations;
(iii) identifying new and missing links and components in the network; and
(iv) constraining and or determining parameter values in the network (e) perturbing the characterized network by deleting one or more components thereof or changing the concentration of one or more components thereof or modifying one or more mathematical equations representing interrelationships between one or more of the components; and (f) solving the equations representing the perturbed network to determine whether the perturbation is likely to cause the transition of the cell from one phenotype to another, and thereby identifying one or more components for interaction with one or more agents.

BRIEF DESCRIPTION OF THE DRAWINGS

FIGS. 3(a) through 3(n) collectively depict the key to reading diagrams in the format of FIG. 3.

FIGS. 32(a)-(h) depicts each module in detail so as to make the reactions visible.

FIGS. 34 and 34(a) depict the results of perturbing 50 individual targets in the exemplary colon cancer cell model.

FIG. 35 lists combinations of certain targets identified by the exemplary colon cancer cell simulation whose absence caused apoptosis.

FIG. 42 depicts the cleavage of PARP as a result of inhibiting IKappab-alpha in combination with the addition of TNF at various levels.

FIGS. 43(a)-(b) show the constructs in Diagrammatic Cell Language.

FIGS. 49-50 shows the results from the exemplary network inference methodology on a 25 node network.

DETAILED DESCRIPTION OF THE INVENTION

Definitions

Figure 1:
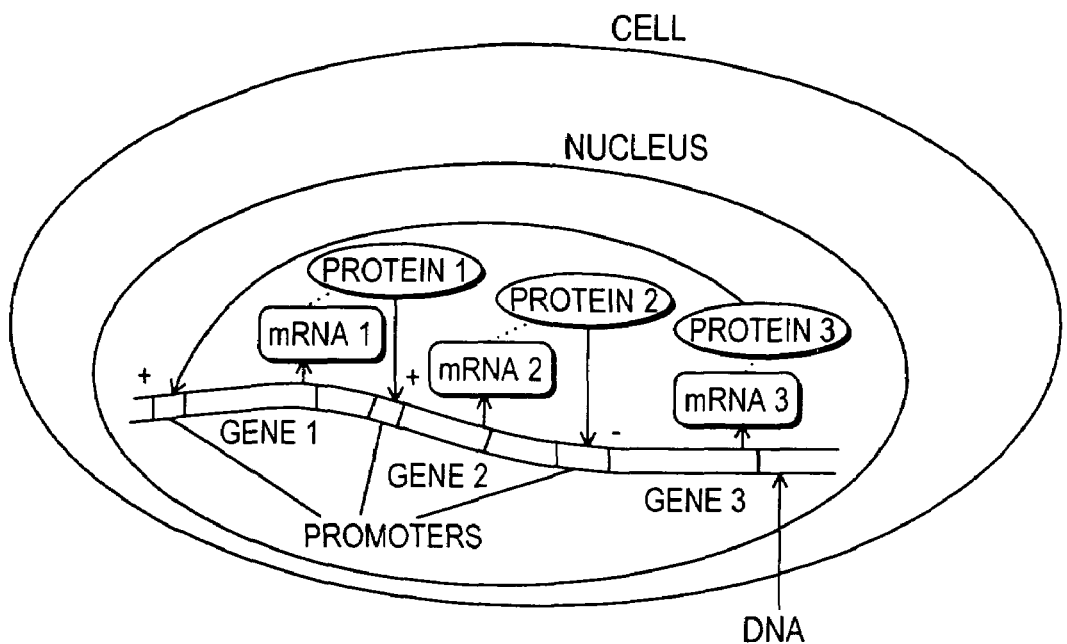
FIG. 1 is a schematic representation of a typical gene expression network.

The "DCL Provisional Patent" refers to that certain US Provisional Patent Application "Cancer" and "Disease" have their usual meanings and may be used interchangably.

"Equation" refers to a general formula of any type or description and also includes computer code and computer readable and/or executable insturctions;

"Formulae" and "Equations" have their normal meanings and are used interchangably and without limitation.

"Phenotype" of a cell means the detectable traits of a cell, i.e. its physical and chemical characteristics, as influenced by its environment;

"State of a cell" means, in the aggregate, the components of the cell, the concentrations thereof and their interactions and interrelationships;

"Cellular biochemical network" means a subset of the components of the cell and their known or posited interactions and interrelationships;

"receptor" a site on a cell (often on a membrane) that can combine with a specific type of molecule to alter the cell's function "EGF" refers to Epidermal Growth Factor "EGFR" refers to Epidermal Growth Factor Receptor "Erk" refers to a kinase in the Ras Map Kinase cascade "Functional output" refers to an output of a simulation which is a function of time, such as, e.g., a time series for a given biochemical;

"Intrinsic to said phenotype" means causing or contributing to the phenotype;

"Mek" refers to a well known kinase in the Ras Map Kinase cascade

"NGF" refers to Nerve Growth Factor

"NGFR" refers to Nerve Growth Factor Receptor

"Parameters" refer to any biochemical network component (such as e.g., chemicals, protiens, genes, rate constants, initial concentrations, etc.) that can vary that can change the final output of a biochemical network;

"Putative target for interaction" means, broadly, any cellular component whose existence or concentration is determined, by practice of the methods of the invention, to have a significant effect on the phenotype of the cell such that when removed from the cell or reduced or increased in concentration, the phenotype may be altered. More specifically, a "putative target for interaction" means a cellular component which appears to be an actual physical or chemical target for a binding agent or reactant which will have the effect of removing the target or changing its concentration;

"Raf" is a kinase in the Ras Map kinase pathway

"Ras" is a small G-protein implicated in over 40% of all cancers;

"Attractors of a cell" are asymptotical dynamic states of a system. These are the fixed points, limit cycles, and other stable states that the cell tends to as a result of its normal behavior, an experimental perturbation, or the onset of a disease.

"degradation" is the destruction of a molecule into its components. The breaking down of large molecules into smaller ones.

"Ubiquitination" refers to the process involving A 76-amino acid polypeptide that latches onto a cellular protein right before that protein is broken down "endocytosis" is the process by which extracellular materials are taken up by a cell "signal transduction" refers to the biochemical events that conduct the signal of a hormone or growth factor from the cell exterior, through the cell membrane, and into the cytoplasm. This involves a number of molecules, including receptors, proteins, and messengers "transcription" the synthesis of an RNA copy from a sequence of DNA (a gene); the first step in gene expression "translation" The process in which the genetic code carried by messenger RNA directs the synthesis of proteins from amino acids "G1" refers to the period during interphase in the cell cycle between mitosis and the S phase (when DNA is replicated). Also known as the "decision" period of the cell, because the cell "decides" to divide when it enters the S phase. The "G" stands for gap.

"S phase" refers to the period during interphase in the cell cycle when DNA is replicated in the cell nucleus. The "S" stands for synthesis.

"G2" refers to the period during interphase in the cell cycle between the S phase (when DNA is replicated) and mitosis (when the nucleus, then cell, divides). At this time, the cell checks the accuracy of DNA replication and prepares for mitosis. The "G" stands for gap.

"mitosis or M phase" refers to the process of nuclear division in eukaryotic cells that produces two daughter cells from one mother cell, all of which are genetically identical to each other.

"apoptosis" refers to programed cell death as signalled by the nuclei in normally functioning human and animal cells when age or state of cell health and condition dictates. Cancerous cells, however, are unable to experience the normal cell transduction or apoptosis-driven natural cell death process "cleavage" refers to the breaking of bonds between the component units of a macromolecule, for example amino acids in a polypeptide or nucleotide bases in a strand of DNA or RNA, usually by the action of enzymes oligomerization refers to the chemical process of creating oligomers from larger or smaller molecules.

"mitochondrion" is an organelle found in eukaryotes responsible for the oxidation of energy-rich substances. They are oval and have a diameter of approximately 1.5 micrometers and width of 2 to 8 micrometers. Mitochondria have their own DNA and are thought to have evolved when an early eukaryote engulfed some primitive bacteria, but instead of digesting them, harnessed them to produce energy.

cytochrome c is a type of cytochrome, a protein which carries electrons, that is central to the process of respiration in mitochondria (an organelle found in eukaryotes which produces energy).

Analysis of Genomic and Cellular Information

In recent years, efforts have been made to harness the information becoming available from the Human Genome Project and other information relating to cellular dynamics. Information at the genetic level determines the form and function of a cell or organism. The information contained in the DNA sequences of the genes of an organism, the genotype, is expressed to determine the phenotype, the state of the cell or organism. With the completion of the Human Genome Project, the goal of predicting how the phenotype of a biological system arises from the information encoded in the genotype has been made more achievable. The challenge for molecular medicine is to understand how particular changes or mutations in the genes lead to the onset of disease and to determine the best strategy for reversing the disease phenotype.

To predict and understand mechanistically how the phenotypes of a cell arise from the gene sequences requires an understanding of biochemical networks. These complex networks consist of genes and proteins that control how specific genes are expressed in response to a cell's current state and its environment.

Gene Expression Networks

FIG. 1 is a schematic representation of a gene expression network. It is well understood that when particular regulatory proteins and transcription factors are bound to the promoter sequence on a gene, the expression of mRNA molecules of the gene is turned 'on' or 'off'. During gene expression, RNA polymerase "reads" the DNA sequence of the gene to transcribe it, i.e., to produce a specific mRNA molecule. This specific mRNA molecule is in turn decoded by a ribosome that translates the mRNA, i.e., creates a specific protein.

Proteins control metabolism, response to environmental cues and regulation of other genes. Regulatory proteins bind to the promoter sequences, which act as a switch to regulate the expression of a nearby gene. FIG. 1 shows gene 1 producing protien 1, which binds to the promoter region of gene 2, activating the expression of gene 2. Gene 2 then produces protien 2, which then binds to the promoter region of gene 3, turning off the expression of gene 3. If gene 3 is active, it will produce a protein that binds to the promoter region of gene 1, which then activates the expression of gene 1. This series of gene-to-protein and protein-to-gene interactions represents a gene expression network. Such networks ultimately control the overall levels of gene expression for the entire genome and consequently determine the phenotypes of the cell.

Signal Transduction Pathways

Figure 2:
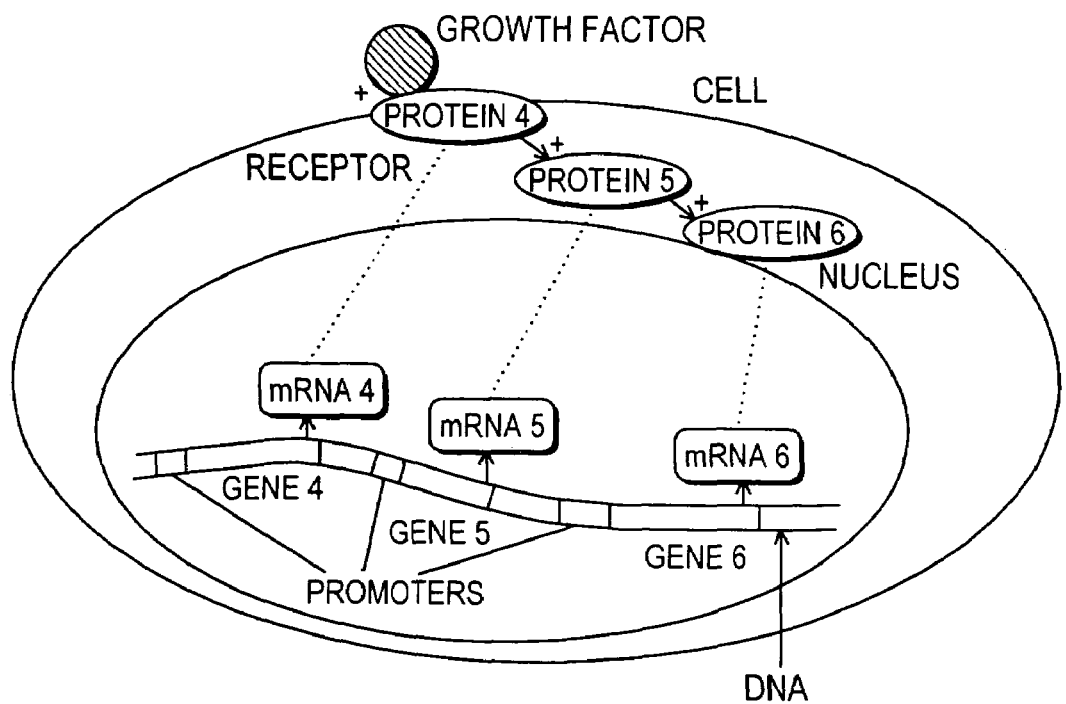
FIG. 2 is a schematic representation of a typical signal transduction/signal translation pathway.

Signal transduction pathways are another important class of biochemical networks. These pathways communicate information about the environment outside of a cell to the genes inside the nucleus of the cell. FIG. 2 is a schematic representation of a typical signal transduction/translation pathway. Genes 4, 5, 6 and 7 produce proteins that reside in the cytoplasm of the cell. Gene 4 codes for a receptor, a signal transduction protein that lies embedded in the membrane of the cell, with one part on the outside facing the environment and the other part on the inside facing the cytoplasm. Growth factors, hormones, and other extracellular signals bind to receptors and activate a cascade of biochemical reactions. The proteins involved in signal transduction pathways, including receptors, are allosteric; i.e., they exist in an inactive and an active state. Biochemical reactions such as phosphorylation of a particular part of a protein or the exchange of a bound GDP molecule for a GTP molecule can change the state of an allosteric protein from inactive to active. Once activated, these proteins bind to or react with other proteins to activate them. Signal transduction pathways are thus activated in a domino-like fashion. A signal at the cell surface from a receptor binding event starts a cascade of biochemical reactions and information flow which leads to the transport of a particular protein into the nucleus where it then activates transcription factors that in turn activate the expression of one or more genes. Signal transduction pathways, which transmit information from outside the cell to the genes, are thereby coupled to the gene expression networks that control the expression patterns of the genes and the state of a cell, i.e. its phenotype.

Disease State Prediction by Modeling Biochemical Networks

Biochemical networks and their interactions with the environment ultimately determine the state of a cell and the development of a disease state. Deciphering the complex intertwined gene expression and signal transduction pathways involving hundreds or thousands of molecules has proven difficult. To predict and understand how mutations, particularly in genes, lead to a disease state, e.g. the development of cancer, requires predicting the behavior of these networks. This necessitates the formulation of mathematical equations that quantitatively describe how the concentrations of gene products, mRNA, inactive and active proteins, change in time in response to extracellular signals such as growth factors and hormones and to the concentrations of such products of other genes.

The equation for the time rate of change of a particular protein or mRNA is comprised of terms derived from enzyme kinetics. These terms describe reactions that create, destroy, or modify the protein, i.e. phosphorylation, dephosphorylation, translation and degradation reactions. The differential equations are nonlinear, but they can be solved analytically or by computer simulation to produce a plot of the concentrations of mRNA and protein as a function of time. The time series of concentrations for any particular mRNA or protein can be high, intermediate, or low or can oscillate in time or even change chaotically in time, Hill et al, Proc. of Statistical Mechanics of Biocomplexity, Springer-Verlag (1999). A particular time series profile corresponds to a particular state of gene expression and thus to a particular biological state. The difference between a normal and a cancerous state manifests itself at this level of description. A particular time series of concentrations corresponds to a healthy cell whereas another time series of concentrations corresponds to a disease state, e.g. cancer.

Previous mathematical modeling has only been applied to relatively simple networks, such as lysis-lysogeny in *E. coli*, McAdams and Shapiro, Science, 650, 1995, the lac operon in *E. coli*, Wong et al, Biotechnol. Prog., 132, (1997), and circadian rhythms in *Drosophila*, Tyson et al., Biophysical Journal, 77:2411, 1999. Some of these models are based on chemical rate equations. A few emphasize the key role played by stochastic fluctuations due to the small numbers of molecules in a given cell, McAdams and Arkin, Proc. Natl. Acad. Sci. USA, 814, 1998. Boolean switching networks, nonlinear and piecewise linear differential equations, stochastic differential equations and stochastic Markov jump processes all provide mathematical frameworks that can represent the time evolution of mRNA and protein concentrations. The kinetic equations for the mRNA and proteins involved in biochemical networks are solved in simple cases (fewer than three genes) with analytical methods from nonlinear dynamics (bifurcation analysis, linear stability analysis, etc.) and statistical physics and probability theory (master equation, stochastic calculus, methods of stochastic averaging). In the more general, high dimensional cases, it is sometimes possible to extend these analytical methods and to use object-oriented computer simulations for deterministic dynamics (Runge-Kutta integration) and stochastic dynamics (Monte Carlo simulation), Gillespie, J. of Comp. Phys. These techniques can make the problem of understanding complex gene expression networks and signal transduction pathways tractable.

A number of difficulties confront researchers who propose to use mathematical and computational frameworks to predict disease states. Among these are the ill-defined nature of networks of interaction, incomplete forms of kinetic equations, incomplete mathematical frameworks, the absence of quantitative measurements of gene product concentrations and the absence of quantitative measurements of reaction rate constants and other kinetic parameters.

Descriptions in the literature of biochemical networks which determine cell phenotypes is incomplete and developing slowly. Protein-protein and protein-gene interactions are detected mainly through immunoprecipitation techniques and footprinting methods. Since only a relatively small number of biological phenomena have well-defined biochemical and genetic circuits, detailed pictures of the molecular interactions in systems such as the mammalian cell cycle, have only begun to emerge over the last decades.

Yeast two-hybrid experiments for "fishing out" the binding partner of a protein have been employed in parallel on the genome scale to find such protein-protein interactions, G. Church, Harvard; Curagen. Methods of computationally mining the genome have also been employed to predict unknown protein-protein interactions, Eisenberg, UCLA; Protein Pathways, Inc. Methods have also been developed to find transcription factors (regulatory proteins) and their corresponding cis-acting binding sites, G. Church, Harvard. In time, these academic and industrial genome-wide efforts will uncover many new biochemical networks and fill in the missing links in more well-defined systems.

Many equations describing the rates of enzyme-catalyzed reactions have been derived empirically, often without rigorous theoretical justification. Despite an increase in the understanding of the mechanisms of many cellular processes (e.g., the discovery of scaffolds, reactions on membranes and active transport), a reformulation and extension of the fundamental kinetic forms used to describe the chemical reactions controlling cellular behavior is not yet available. Some information may become available in the future as biophysicists and biochemists elucidate the molecular mechanisms for many processes, e.g. molecular motors, chromatin structure dynamics, vesicle transport and organelle formation.

Different kinetic forms of biochemical equations can be expressed within several mathematical frameworks that have been developed to model gene networks. All such mathematical frameworks are approximations to reality. Modeling efforts began with nonlinear differential equations, then Boolean approximations, and, more recently, with stochastic formulations. Most such efforts assume that the spatial extent of the cell is not important, thus ignoring diffusion processes. There is still no consensus on what frameworks should be used, and few rigorous results have been reported. More recently, researchers have begun studying stochastic formulations of gene expression. Theoretical progress has been made in understanding the effects that 'noise' can have on biological systems and in determining which mathematical frameworks should be used in which contexts. The recent creation of artificial gene networks also provides a testing ground for some of these theoretical results, Gardener et al, Nature (2000); Elowitz and Leibler, Nature (2000). New techniques such as fluorescence and imaging for dynamically monitoring the expression and activity of biomolecules provide accurate data with which to compare mathematical predictions.

Measurements of the concentrations of proteins and mRNA have rarely been reported in the literature, as biologists have primarily focused their efforts on qualitative observations rather than on quantitative measurements. However, mathematical models of gene networks which can predict a time series of proteins and mRNA concentrations require accurate quantitative concentration measurements of protein and mRNA over time. Without such information it is difficult to validate any predictions from the model. With the recent development of DNA microarrays, it is now possible to monitor the genome-wide concentrations of all mRNA species in a single experiment and to view the state of the cell as determined by mRNA concentrations. Imaging techniques and proteomics also provide in vivo snapshots of protein concentrations and localization.

As well, quantitative measurements of rate constants are also rarely reported. As a result, the measurement of rate constants and other kinetic parameters lags behind the knowledge of the organization of many protein and gene networks. These rate parameters in a mathematical model ultimately determine the model's predictions and are thus of paramount in importance. Changes in the rate parameters define the onset of disease.

The Biochemical Foundations of Cancer

Cells become cancerous when several genes are mutated and their protein products cannot function normally. This dysfunction causes the highly regulated cell cycle machinery to break down, leading to uncontrolled cell growth. The transformation of a normal cell to a cancerouscell is a multi-step process involving a complex biochemical network or networks involving hundreds of genes and proteins. In such transformations several genes are mutated, one after another, often in a particular order. Each of these mutations causes morphological and physiological changes (see Vogelstein 1995). It has also become increasingly apparent that cancer is often caused by a combination of cooperating oncogenes, none of which is dominant. This complex combinatorial genetic origin makes genotype-to-phenotype mapping a difficult problem, and one that must be understood better before rational approaches to cancer chemotherapy can be achieved. Because these genes interact within the gene network to collectively cause transformation to a cancerous state, a mathematical description is required to identify the combination of interacting genes that can reverse or stop uncontrolled cell growth.

While many of the mutated genes that lead to cancer have been identified, because of the complexities in understanding how and in what combinations these genes actually precipitate a cancer, a systematic and quantitative description of the networks involved is required to better understand the cellular dynamics of the disease.

The Mammalian Cell Cycle

The methods of the invention can be broadly applied to find targets for therapeutic agents among the many components of the mammalian cell cycle. The invention is exemplarly described below with respect to one portion of that cycle.

Figure 3:
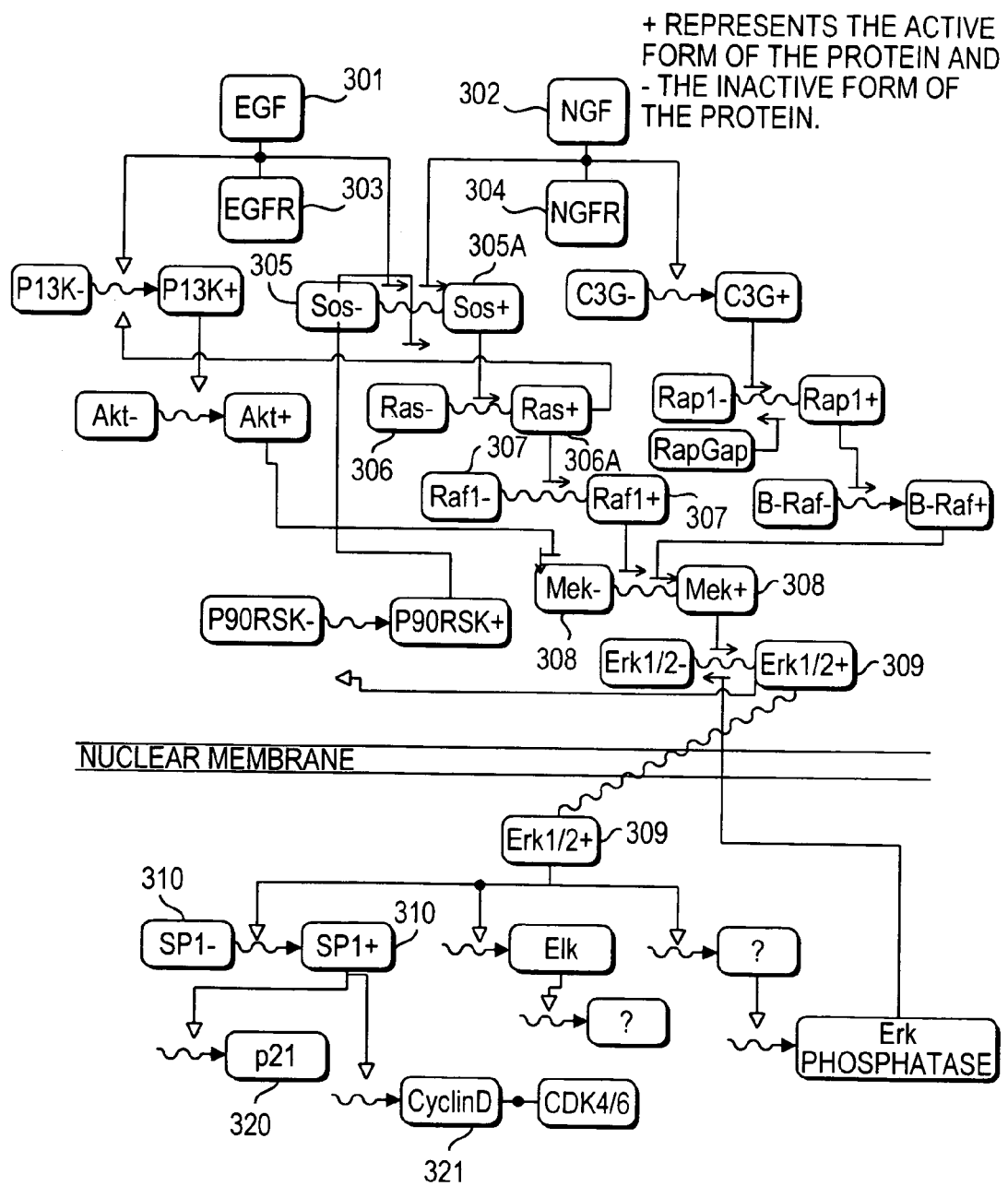
FIG. 3 is an exemplary schematic representation, using the Diagrammatic Cell Language, of a portion of the signal transduction pathway and gene expression network that initiates the mammalian cell cycle.

FIG. 3 depicts a portion of the signal transduction pathway and gene expression network that initiates the mammalian cell cycle. The several gene and protein components of the network are identified and described below.

FIG. 3 was created using the using Diagrammatic Cell Language ("DCL"), a computer based graphic language which has been devised to describe all of the interactions in a cell, or within a particular biochemical network, in a single diagram, with only a few representations of each molecule. The notation is explained in detail in the article entitled "Dramatic Notation and Computational Structure of Gene Networks" by Ron Maimon and Sam Browning, which can be found at www.gnsbiotech.com (the website maintained by the assignee hereof). DCL is a novel means for facilitating interaction between biology and quantitative methods or applied mathematics to biology/biochemistry. The objects available in DCL for modeling chemicals, protiens, genes, and other components of cells, subcellular biochemical netoworks, biochemical pathways, or even virtual biochemical networks involving interactions between numerous cells in variant cell populations, each have built in associated quantitative mathematical expressions. Thus, when a biologist or other biochemical network modeler constructs a model of some cellular or subcellular network in the DCL environment using the objects available in DCL, she need not know the precise mathematical expression of these objects. Nonetheless, the DCL parser can take the constructed model and generate a precise mathematical description of the modeled biochemical network, such that it can be solved, optimized and perturbed according to the methods of the present invention.

By analogy to microelectronics, DCL brings to the biological sciences the equivalent functionalities of SPICE, the well known microelectronic circuit modeling tool. A key to interpreting the DCL language or notation symbology is summarized in FIGS. 3($a$) through 3($n$).

The box shown in FIG. 3($a$) is used to represent a chemical which is a single indivisible chemical unit. Examples are seen at numerous locations in FIG. 3.

FIG. 3($b$) shows reversible binding between chemicals A and B. C is a component which is stimulating the unbinding of A and B.

The symbol in FIG. 3($c$) indicates irreversible binding. FIG. 3($d$) shows a link box which is used to indicate components in the cell with complex structures, such as a protein or DNA. A link box can contain other objects, such as binding nodes (the solid black circles in FIG. 3($d$)) which represent functional binding sites on a protein. The link box shown in FIG. 3($d$) can, for example, bind the two chemical substances A and B. The unbinding symbol is shown in FIG. (1).

The numbers in parenthesis (RES) in the line leading from the Link Box indicate the resolution of the states of the substances in the link box. For example, the numbers shown (0, 1) indicate that component A is not bound, and component B is bound.

FIG. 3($e$) shows an internal link box L. This is used to identify a particular state similar to the resolution shown in FIG. 3($d$). Here, it is shown that the state of box A and B bound (i.e., the dimer comprised of A and B) is chosen to interact with the other entities in the cell.

The combination of boxes in FIG. 3($f$) is called a Like Box. This is used to depict which groups of objects are alike in functionality. Various components within the box also can be resolved to choose a particular state. The resolution indication RES on the line emerging from the large box indicates a state of 1, or component B regulating other cellular or network entities.

In FIG. 3(g) the wavy line R indicates a reversible reaction. In the example shown, A and B are involved in a reversible reaction R to produce C. E is an enzyme driving the reaction towards the product D.

FIG. 3(h) indicates an irreversible reaction, with a characteristic one-way arrow.

FIGS. 3(i) through 3(n) are self-explanatory, illustrating, respectively, an unbinding stimulation; a binding stimulation; an enablement; no reaction, an enhancement, and a directional stimulation.

With refernce to FIG. 3, the components of the network interact as follows. The binding of epidermal growth factor (EGF) 301 or nerve growth factor (NGF) 302 to its respective receptor (EGFR 303, NGFR 304) results in the activation of SOS 305, 305A, a guanine nucleotide exchange factor. SOS then dislodges the GDP molecule from Ras 306, 306A a small G-protein implicated in over 40% of all cancers. When the GDP molecule is dislodged from Ras, Ras then binds a GTP molecule, which shifts Ras into its active form (Ras+ 306A). Ras+ 306A then activates the Map kinase cascade consisting of Raf 307, Mek 308, and Erk 309. When Erk 309 is activated, it is transported to the nucleus where it activates the transcription factor Sp1 310. Sp1 310 then activates the transcription of some of the important cell cycle genes such as p21 320 and cyclin D 321 that drive the cell to replicate its DNA and to ultimately divide into two daughter cells.

While an overview of cell cycle control and cellular response to environmental cues is available, Kohn, Molec. Biol. Cell. 10:2703 1999., available on the World Wide Web at URL (http://[followed by]) discover.nci.nih.gov/kohnk/-interaction_maps.html, there are several examples where networks of genes and gene products respond to cues in ways that are not obvious based on a knowledge of the network constituents. Signal transduction pathways once thought to act independently in determining cell fate (proliferation, apoptosis and differentiation) have been found to interact at a number of molecular "nodes", See Bhalla and Tyengar 1999. This gives rise to "crosstalk" and feedback loops between signal transduction pathways and the genes and gene products that they control (e.g., Ras, p21, etc.), as described by Kohn, Molec. Biol. Cell. This crosstalk leads to unexpected biological outcomes and requires a more sophisticated and systematic description, such as is provided by the present invention. Similarly, differences in both the levels and durations of activation of certain gene products (e.g. Ras or Erk), see Joneson and Bar-Sagi, Traverse et al. 1992, have been shown to result in very different cellular responses. Thus a quantitative predictive model for the relevant interactions is required to make any meaningful predictions. Moreover, due to the complexity of nearly all biochemical networks, to be useful, a quantitative method needs to be capable of managing large scale, multinodal, interconnected systems. Such a quantitative model is provided by the present invention.

The methods and implementations of the present invention are used to discover targets for therapeutic agents by predictions from simulation studies and analytical studies. The methods are supported by mathematical techniques which infer relationships among the various components of a biochemical network.

With complete and accurate information about the biochemical networks being studied, the simulation and analytical studies provide accurate predictions about the behavior of the system and the identity of the targets. Optimization techniques can be used to constrain uncertainty inherent in the use of large genomics data sets. While the simulation and analytical studies are powerful given 'perfect data' as inputs to the models, 'perfect data' does not exist. Therefore, data mining techniques and bioinformatics from the analysis of large data sets of DNA sequence and expression profiles are used to provide meaningful correlations and patterns among the network components. The underlying structures that data mining attempts to locate, such as markers and partitions between normal and cancerous cells, are ultimately a manifestation of the underlying dynamics of the biochemical network. Recent studies on differential gene expression reveal genes that are misregulated in disease states. These genes are potential targets and are used in computer models according to the present invention. As well, pattern recognition algorithms and artificial intelligence methods are used to elucidate subtle relationships among genes and proteins as well as to uncover the underlying data structure, e.g. partitions between cell types, cancer types and stages of malignancy. The combination of the predictive and the inferential approaches leads to the discovery of multiple targets.

Simulation Embodiments of the Invention

For ease of illustration purposes, the present invention will often be described herein in terms of a cell or a biochemical network within a cell. This is for exemplary purposes only, and is not intended to limit the application soft represent invention. The term cell is thus intended to include biochemical networks of any type, now known or which are as yet unkonwn, some cellular, some subcellular, and some supercellular.

One or more components of a cell or other biochemical network may be identified as putative targets for interaction with one or more therapeutic agents by performing a method comprising the steps of:

(a) specifying a cellular biochemical network believed to be intrinsic to a phenotype of said cell;

(b) simulating the network by
(i) specifying its components, and
(ii) specifying interrelationships between those components and representing the interrelationships in one or more mathematical equations;

(c) solving those equations to simulate a first state of the cell;

(d) perturbing the simulated network by deleting one or more components thereof or changing the concentration of one-or more components thereof or modifying one or more mathematical equations representing interrelationships between one or more of the components;

(e) solving the equations representing the perturbed network to simulate a second state of the cell; and (f) comparing the first and second simulated states of the network to identify the effect of the perturbation on the state of the network, and thereby identifying one or more components for interaction with one or more agents.

As well, after each of steps (c) and (e) above, an additional optimization step could be performed, where the solution of the mathematical equations simulating a state of the cell is optimized to have minimum error vis-à-vis the prediction of certain available experimental data. Such optimization would also comprise error analysis and extrapolation emthods. Specific methods of optimization and handling of error are described more fully below.

The mathematical equations representing the interrelationships between the components of the cellular biochemical network are solved using a variety of methods, including stochastic or differential equations, and/or a hybrid solution using both stochastic methods and differential equations. In carrying out the methods of the invention, the concentrations of one or more of the several proteins or genes (generally "components") in the biochemical network are selectively perturbed to identify which ones of those proteins, genes or other components cause a change in the time course of the concentration of a protein or gene implicated in a disease state of the cell.

Thus, a series of perturbations are made, each of which changes the concentration of a protein, gene or other component in the network to a perturbed value. The mathematical equations are then solved with stochastic or differential equations (or some hybrid thereof) to determine whether that protein or gene is implicated in causing a change in the time course and/or spatial localization of the concentration of a protein or gene implicated in a disease state of the cell. In particular embodiments of the invention, the concentration of each of the proteins and genes in the network is reduced to zero in each respective perturbation.

Again referring to FIG. 3, it is known, for example, that the presence of NGF 302 in the network causes the cell to differentiate whereas the presence of EGF 301 in the network causes the cell to proliferate, a condition which may lead to the development of cancer. It is known that the concentrations of NGF 302 and EGF 301 affect the time course of the concentration of Erk 309, NGF 302 causing Erk 309 to increase with time and ultimately reach a steady-state value and EGF 301 causing the concentration of Erk 309 to initially increase and then decrease to a lower level than is present with NGF 302 in the network.

In the example network depicted in FIG. 3, to which an exemplary embodiment of the invention is applied, it is desirable to convert EGF 301, which causes the cell to proliferate, into NGF 302, which causes the cell to differentiate. The system is manipulated by perturbing it to block out, inhibit, activate or overactivate one or more of the components of the network to see if that component is implicated in causing the time course of NGF 302 to increase and the time course of EGF 301 to decrease. The time courses of these components are believed to be a surrogate for predicting whether the cell will proliferate or differentiate and consequently whether the cell will become cancerous or not.

In this particular example, using the methods and implementation of the invention, the concentration of the several components of the network set forth in FIG. 3 were each respectively reduced to zero in a separate perturbation and the time course of the concentrations of NGF and EGF were determined from calculations of the concentrations of cellular components according to the simulation. It was found that when component PI3K was "knocked out", i.e., when its concentration was reduced to zero, this caused the time course of the concentration of NGF to increase and the time course of the concentration of EGF to decrease, indicating a beneficial result in that the cell was, according to this surrogate analysis, caused to differentiate rather than to proliferate. Thus, PI3K was identified as a target which when removed from the cellular network will cause the beneficial result described above.

Analytical Embodiments of the Invention

In another embodiments of the invention, one or more components of a cell (in the general sense, as described above) may be identified as putative targets for interaction with one or more therapeutic agents by performing a method comprising the steps of:

(a) specifying a stable phenotype of a cell;

(b) correlating that phenotype to the state of the cell and the role of that cellular state to its operation;

(c) specifying a cellular biochemical network believed to be intrinsic to that phenotype;

(d) characterizing the biochemical network by (i) specifying the components thereof, and (ii) specifying interrelationships between the components and representing those interrelationships in one or more mathematical equations;

(e) perturbing the characterized network by deleting one or more components thereof or changing the concentration of one or more components thereof or modifying one or more mathematical equations representing interrelationships between one or more of the components; and (f) solving the equations representing the perturbed network to determine whether the perturbation is likely to cause the transition of the cell from one phenotype to another, and thereby identifying one or more components for interaction with one or more agents.

Figure 9:
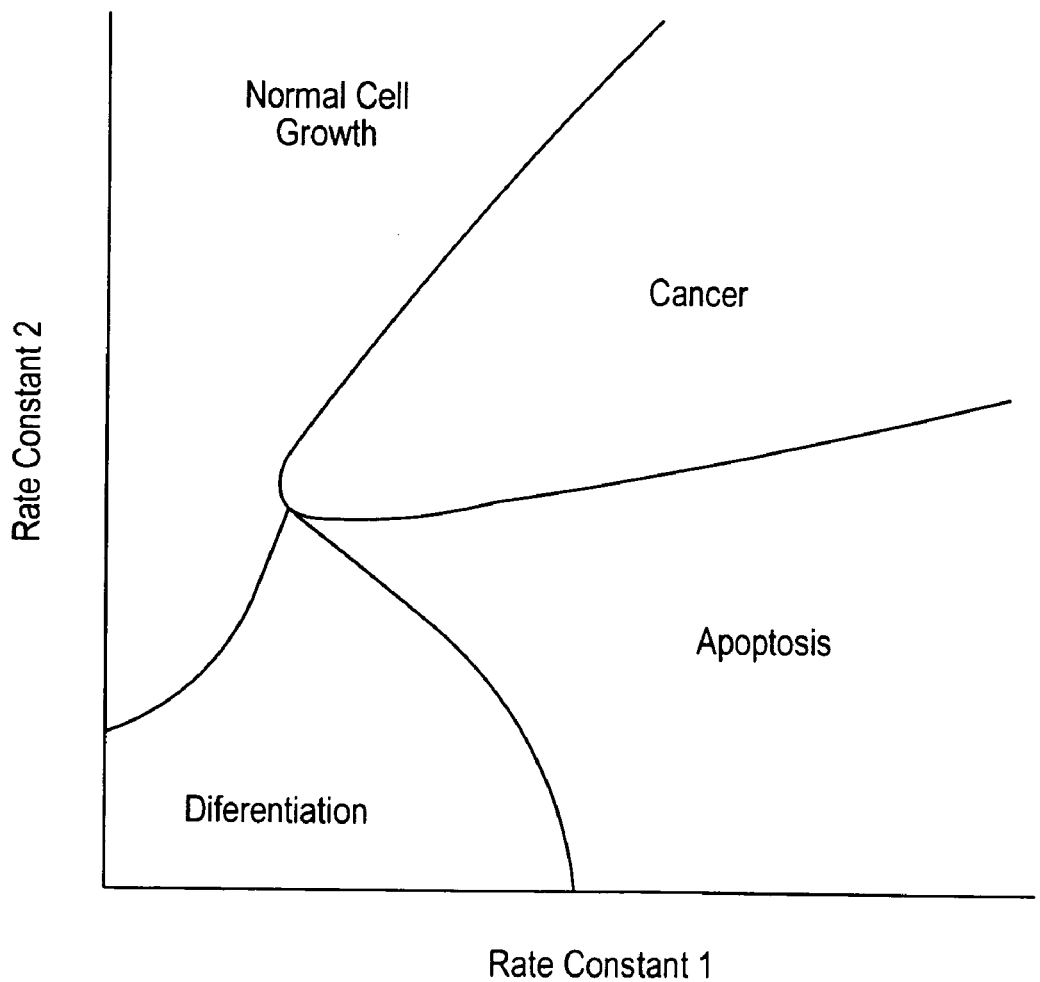
FIG. 9 is a bifurcation diagram showing several states of a cell.

In analytical method embodiments of the invention, the object is not to find numerical values of the several components of the biochemical network, as described above in performing the methods of the invention in a simulated network. In the analytical embodiments, instabilities and transitions of a cell state are identified and a bifurcation analysis is conducted in order to analyze the stability of the cell and determine the probability of its transformation into a different state, e.g. a disease state. Such an exemplary bifurcation analysis is depicted in FIG. 9, which is a bifurcation diagram plotting various cell phenotypes as a function of two rate constants (Rate Constant 1 ("RC1") and Rate Constant 2 ("RC2") in FIG. 9). In FIG. 9, a phenotype of normal cell growth is seen when RC1 is low and RC2 is high. Cancer is seen when RC1 and RC2 are both high, apoptosis when RC1 is high and RC2 is low, and differentiation when both RC1 and RC2 are low.

In an analytical method embodiment of the invention, attractors of the system are identified. These attractors are the equilibrium states of the cell. Attractors may be steady state equilibria, periodically changing equilibria or chaotic equilibria with certain peculiar signatures, of the network. The equilibria may represent normal, disease, growth, apoptosis or other states of the cell, as depicted n the example of FIG. 9.

Once these attractors have been identified, it is possible to perturb the network to determine conditions under which the cell may be transformed from one state to another. Employing stochastic calculus, one may calculate the size of fluctuations around these fixed-point attractors. This permits a determination of the probability of a transformation from one state to another and the length of time of such a transformation and identifies which proteins and/or genes contribute to the stochastic fluctuations. It is also possible to study the degree of stimulation and the duration of stimulation required to move a cell from one biological state to another. It is known that strong stimulation for an extended period of time, e.g. from a growth factor, can "push" a cell from a normal state to a cancerous state. Prolonged stimulus can also deactivate the cell into a stable state. All of these dynamics lead to the identification of drug targets as well as information of value with respect to the duration of a drug treatment that may be needed.

The analytical embodiments of the invention use root findings and continuation algorithms to find bifurcations rather than conducting repeated simulations as in the simulation embodiments. Understanding which parameters and which proteins and genes are important in causing or reversing a cancerous state may lead to the identification of multiple-site drug targets.

It is also possible using the methods of the invention to evolve the biochemical network. By elucidating the connections between the components of the network and their functional dynamics, the methods of the invention lead to a prediction of the changes which may give rise to disease or which may cause a disease state to transition into a normal state. It is also possible to find and "evolve" states that are more stable than the starting state of the network. These evolved states can be experimentally checked to see if the biology is accurately described by the predicted state of the network. Considering evolved networks also helps to rule out poor drug targets. Cancer cells are frequently subject to high mutation rates and a treatment that is predicted by the method of the invention and that is robust in the face of evolved changes in the network will be more desirable than treatments leading to a changed state that is easily sidestepped by minor evolutionary changes in the cell.

In performing the methods of analytical embodiments of the invention, the concentrations of one or more of the several proteins and genes in the biochemical network are selectively perturbed to identify which ones of those proteins or genes are implicated in causing an attractor of the biochemical network to become unstable. Thus a series of perturbations are made which change the concentration of a protein or gene in the network to a perturbed value. Solving the mathematical equations representing the interrelationships between the components of the network then leads to a determination of whether the perturbed protein or gene is implicated in causing a change in the time course of the concentration of a protein or gene implicated in a disease state of the cell. In preferred analytical embodiments of the invention, the concentrations of each of the proteins and genes is reduced to zero in each respective perturbation and the mathematical equations are then solved.

In particular preferred analytical embodiments of the invention, a bifurcation analysis is performed using eigenvalues of a Jacobian matrix based upon the equations describing the interrelationship of network components to characterize the stability of one or more attractors.

Identification and Selection of Biochemical Networks of Disease

The literature provides sources for identification of biochemical networks intrinsic to disease studies. These networks include signal transduction pathways governing the cell cycle; transcription, translation, and transport processes governing the cell cycle; protein-gene and protein-protein interactions, such as, e.g., Kohn maps; protein-protein interactions found through genome data mining techniques; protein-protein interactions from genome-wide yeast-two hybrid methods; trans-acting regulatory proteins or transcription factors and cis-acting binding motifs found through experimental and computational genome-wide search methods; protein-gene and protein-protein interactions inferred through the use of microarray and proteomics data; protein-protein interactions and protein function found from 3-dimensional protein structure information on a genome-wide scale; binding partners and functions for novel uncharacterized human genes found through sequence homology search methods; and protein-protein interactions found from binding motifs in the gene sequence.

The Biochemical Network Involved in Colon Cancer

Figure 4:
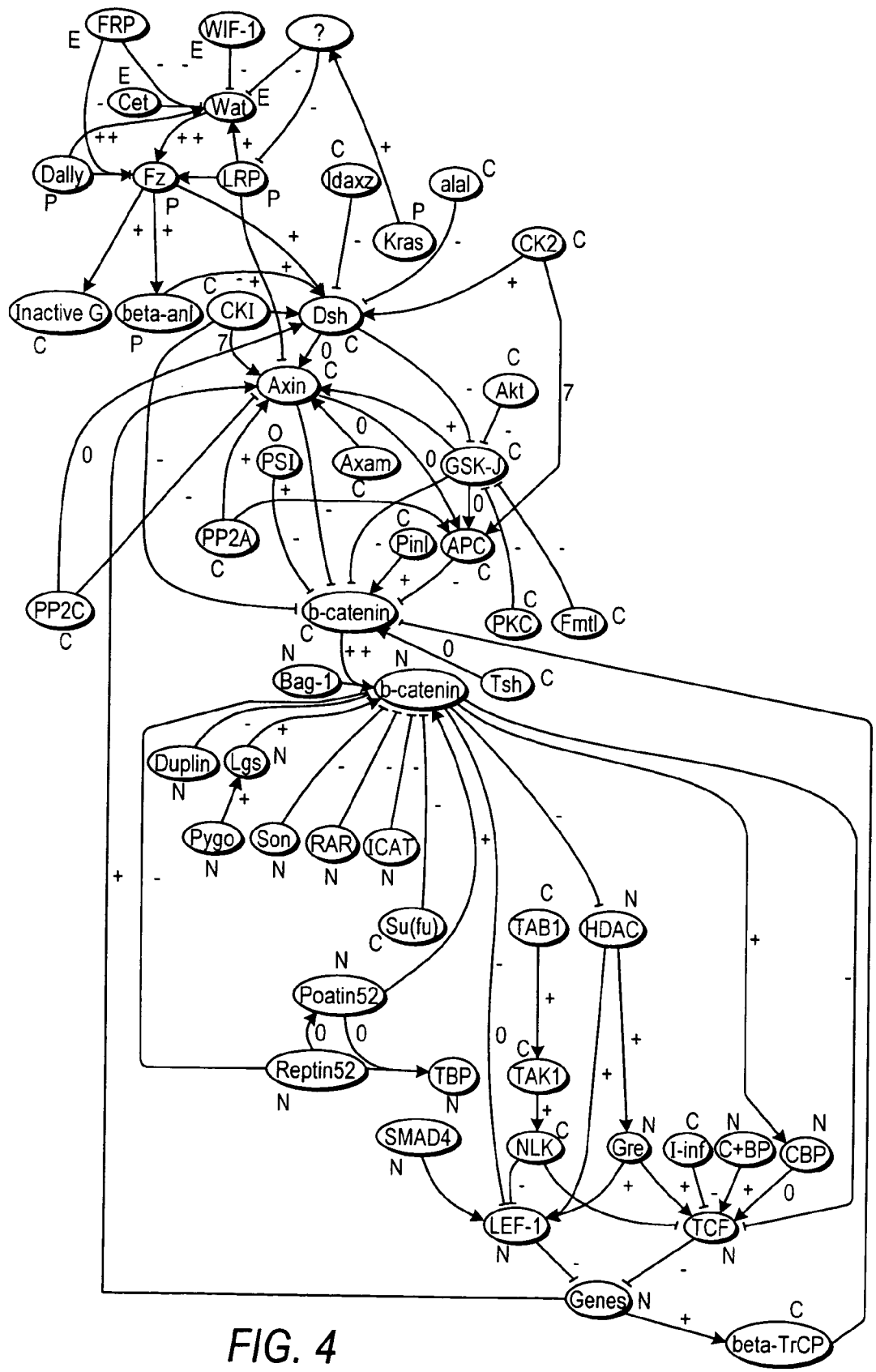
FIG. 4 is a conventional schematic representation of the Wnt/Beta-Catenin signaling pathway that plays a critical role in the progression of colon cancer cells through the cell cycle.

FIG. 4 describes the Wnt/Beta-Catenin signaling pathway that plays a critical role in the progression of colon cancer cells through the cell cycle. FIG. 4 uses a conventional depiction, and comes from Science Magazine, Signal Transduction Knowledge Environment web page at (http://[followed by]) stke.sciencemag.org/cgi/cm/CMP_5533. The various letters labelling the genes and proteins in FIG. 4 indicate the location of the molecules specified in the legend with reference to the cell, where "E" means extracellular, "P" means Plasma membrane, "C" means Cytosol, "N" means Nucleus, and "O" means Other Organelle. The symbols +, -, and 0 indicate the type of interaction between the molecules. A detailed explanation of this pathway is found at the website listed above.

Other subnetworks which can be examined using the methods of the invention, include, for example, (1) Ras-Map Kinase pathway, (2) Wnt/f-Catenin, (3) G1-S transition, (4) Rho-family G proteins (cdc42, etc.), (5) JNK pathway, (6) Apoptosis (Caspases, p53), (7) G2-M transition, (8) Integrin pathway, (9) P13 Kinase pathway, (10) c-Myc pathway, (11) Telomeres, (12) Nuclear Receptors, and (13) Calcium Oscillations.

Kinetic and Expression Data

The creation of quantitative and accurate mathematical models of biochemical networks requires knowledge of all kinetic parameters involved in the network. Concentrations of mRNA and protein as a function of time provide necessary data for optimization routines to locate meaningful values of kinetic parameters. Kinetic parameters such as reaction rate constants, equilibrium constants and expression data and mRNA and protein concentrations for the gene products involved, are found in the literature. Kinetic and expression data are available from literature searches, public databases such as the National Cancer Institute Cancer Anatomy Project, private sources and experimental data. In addition to kinetic parameters and expression data, data on the localization of mRNA and proteins, and the structure and function of molecules may be used.

Mathematical Models of Biochemical Networks

The following equations represent the interrelationships among the components of the biochemical network of FIG. 3. The equations are in terms of more general descriptors of the components of FIG. 3, and thus the general term "FreeReceptor" in the equations relates to EGFR, and the term "Protein" relates to EGFLigand. As well RasGTP appears as Ras+ in the figure, and an asterisk in the equations denotes a "+" in FIG. 3 (refrring to the phosphorylated, or activated form of the component).

$$\frac{d[FreeReceptor]}{dt} = -k_b[FreeReceptor][\text{Protein}] + k_u[FreeReceptor{:}\text{Protein}]$$

$$\frac{d[RasGTP]}{dt} = k_{phos}[SOS^*]\frac{[RasGDP]}{K_m + [RasGDP]} - k_{dephos}[RasGAP]\frac{[RasGTP]}{K_{md} + [RasGTP]}$$

$$\frac{d[Mek^*]}{dt} = k_{phos}[Raf1^*]\frac{Mek}{K_m + Mek} - k_{dephos}\frac{[Mek^*]}{K_{md} + [Mek^*]}$$

$$\frac{d[FreePromoter]}{dt} = -k_b[FreePromoter][\text{Protein}] + k_u[FreePromoter{:}\text{Protein}]$$

The equations quantitatively describe the time rate of change of gene products (mRNA, inactive protein, and active protein) that comprise the biochemical network. Each term in such differential equations represents a particular reaction in the biochemical network. A particular reaction in the biochemical network is represented in FIG. 3 by an arrow connecting two or more biomolecules.

The form of each of these terms is derived through the fundamental relations of enzyme kinetics. For enzyme-catalyzed reactions that satisfy certain criteria, these terms are nonlinear functions of the concentration of inactive substrate: the Michaelis-Menten forms. The differential equation for RasGTP contains a term describing the SOS catalyzed conversion of RasGDP to RasGTP. This first term indicates that the rate of creation of RasGTP is equal to the product of a rate constant, Kphos, the concentration of active SOS and the nonlinear function of the inactive substrate concentration RasGDP. The nonlinear activation of RasGTP causes the rate of activation to saturate at high levels of inactive substrate. This term indicates that RasGTP is rapidly produced when there is a high concentration of active SOS, is slowly produced when there is little active SOS, and is not produced at all when either active SOS or RasGDP concentrations are zero. A similar term describes the enzyme-catalyzed deactivation of RasGTP by RasGTP.

The kinetic form for each reaction often varies with reaction type. For example, in the differential equation describing the rate of change of free promoter concentration, the term describing the binding of free promoter to protein is the product of the binding rate, the free promoter concentration, and the protein concentration.

Mathematical frameworks other than nonlinear differential equations can be used to describe the dynamics of biochemical networks. When certain assumptions are made about the enzyme catalyzed Michaelis-Menten reaction form, the nonlinear term becomes piece-wise linear or 'switch-like' and is more amenable to mathematical analysis. Kauffman 1969, Kauffman and Glass, 1972, Glass 1975.

The nonlinear differential equations are approximations of the more realistic stochastic reaction framework. The stochastic time evolution of this system is a Markov jump process where the occurrence of each chemical reaction changes the concentration of chemicals in discrete jumps as time moves forward. When certain criteria are satisfied, an intermediate description between nonlinear differential equations and the stochastic Markov process emerges, i.e. nonlinear stochastic differential equations.

Implementation of the Mathematical Models in Software

The mathematical models can be implemented with existing software packages. Basic information about the network, about the reactions which occur in the network and the mathematical frameworks which describe these reactions are input to the programs.

The network information includes a list of chemicals and their initial concentrations, a list of rate constants and their values and a list of the reactions which take place in the network, i.e. the reaction, the components and other chemicals involved in the reaction, and the kinetic parameters involved in the reaction. The list of reactions links up the components and other chemicals present in the network to form the topology of the network.

Other reaction information which is input includes that pertaining to reactions such as phosphorylation, dephosphorylation, guanine nucleotide exchange, transport across the nuclear membrane, transcription, translation and receptor binding. Each specific reaction includes the chemicals that are involved in the reaction, the stoichiometry of the reaction, i.e. the number of molecules created or destroyed in the reaction, and the rate of the reaction. The rate depends on the rate constants and the concentration of the chemicals involved.

The mathematical frameworks, or reaction movers, are those that can be used to evolve the state of the system forward in time. They consist of differential equation dynamics and stochastic dynamics movers. In the stochastic dynamics derived class, the occurrence of a particular reaction is calculated in accordance with the reaction rates entered. The concentrations of the components are then changed to reflect the occurrence of the reaction. The rates of each of the reactions is then recomputed. Such a probabilistic time evolution of the biochemical network is known as a continuous time Monte Carlo simulation. In the chemical context it is known as the Gillespie algorithm (Gillespie 1976). In the differential equation derived class, the differential equation that describes the time rate of change for each component is constructed from the kinetic forms and stoichiometry entered. Various numerical integration routines, e.g. Runge-Kutta, are used to solve for the new chemical concentrations as time moves forward. Both the stochastic and nonlinear differential equation frameworks output the concentration of all of the components in the network as a function of time.

When time series data of protein or mRNA concentrations are available for the particular system being studied, optimization routines can be used to fit the rate constants. The values of the rate constants are often not known and these optimization methods can thus be used to make the model and the simulation of the model more accurate. The system is first simulated at a particular set of values for the rate constants. The resulting simulated time series for a particular component is compared to an experimentally measured concentration time series and a 'penalty' or 'cost' is calculated as the sum of the squares of the differences between the data and the simulated time series. The rate constants are then perturbed away from the starting values and the simulation is repeated and the cost recalculated. If the cost is lower after the perturbation, the optimizer adopts the new set of rate constants that resulted in the lower cost and a better fit to the data. The perturbing or changing of the rate constants is sometimes performed randomly and sometimes performed rationally, depending on the optimization routine. The optimizer iterates the changing of the rate constants, simulating the network, and evaluating the change in the 'cost' until the simulation nearly matches the data.

A measure of the predictive power of the mathematical model is the robustness of the predictions obtained from the simulation with optimized parameter values. Methods to accomplish this, known as stochastic sensitivity analyses, are used. When a set of rate constants are found that match the simulation to the data, the parameter values are stochastically perturbed in the vicinity of the minimum cost, and the system is simulated with this ensemble of rate constant sets. If the output from the simulation does not vary significantly within the ensemble of rate constant sets, the prediction is robust and the predictive power of the model is high. On the other hand, if the simulation varies significantly within the ensemble of rate constant sets, the prediction is not robust and the predictive power of the model is low.

EXAMPLE I

Description of a Network Comprising Two Genes

Figure 5:
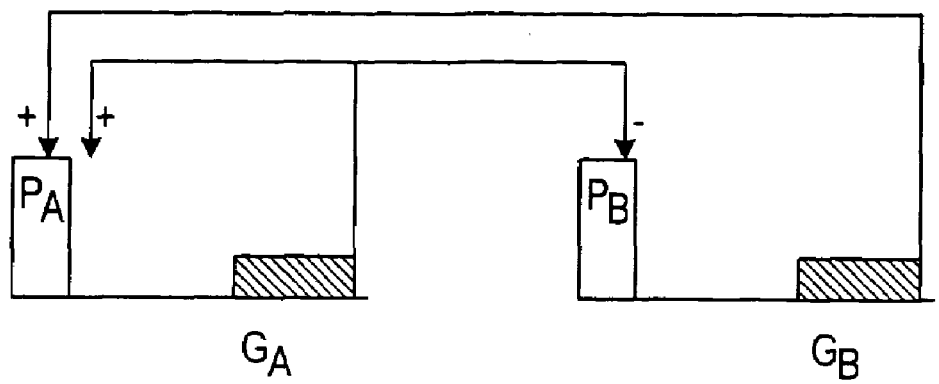
FIG. 5 is a schematic representation of a biological network comprising two genes.

FIG. 5 is a DCL schematic representation of a network comprising two genes, $G_A$ and $G_B$. $G_A$ and $G_B$ are transcribed independently from two separate promoters, $P_A$ and $P_B$, to produce mRNA A and mRNA B, respectively, which are then translated to produce proteins A and B, respectively. Transcription and translation are approximated as a single process.

Protein A inhibits the production of B. Proteins A and B together activate the production of A. This is only physically plausible if the operator DNA sequences in promoters $P_A$ and $P_B$ are similar. $P_A^{total}$ and $P_B^{total}$ represent the total number of promoter copies for genes A and B and is equal to one for a single copy of the gene circuit. Promoter $A_7P_{A7}$ controls the production of protein A from gene $A_7G_A$. Promoter $B_7P$ controls production of protein B from gene B. Protein A represses production of protein B (indicated by −) while protein A and protein B together activate the production of protein A (indicated by +).

It has now been found that it is possible to describe the state of the network, i.e., the concentrations of the gene products, mRNA and proteins, as it evolves as a function of time, by employing certain mathematical models.

The Mathematical Model

A deterministic model is established by deriving a set of coupled nonlinear differential equations $$\frac{dx_i}{dt} = f(\ )$$

where index i labels a chemical species in the network, a chemical species being a particular gene product, mRNA A, mRNA B, protein A or protein B, or part of the gene itself, promoter A, $P_A$ and the complexes that can be formed as a result of allowed biochemical reactions $[P_A:A]$. The following differential equations for this system were integrated with a fourth-order Runge-Kutta routine obtained from Numerical Recipes (Press et. al, *Numerical Recipes in C,* 1992).

$$\frac{d[P_A]}{dt} = k_{uA}([P_A:A]+[P_A:B]) - k_{bA}([P_A][A]+[P_A][B]) \quad (1)$$

$$\frac{d[P_{A:A}]}{dt} = k_{bA}([P_A][A]-[P_A:A][B]) + k_{uA}([P_A:A:B]-[P_A:A]) \quad (2)$$

$$\frac{d[P_{A:B}]}{dt} = k_{bA}([P_A][B]-[P_A:B][A]) + k_{uA}([P_A:A:B]-[P_A:B]) \quad (3)$$

$$\frac{d[P_{A:A:B}]}{dt} = k_{bA}([P_{A:A}][B]+[P_A:B]) - 2k_{uA}[P_A:A:B] \quad (4)$$

$$\frac{d[mRNA_A]}{dt} = k_{tm}[P_A:A:B] - k_{d_7mRNA}[mRNA_A] \quad (5)$$

$$\frac{d[A]}{dt} = k_{tA}[mRNA_A] - k_d[A] - k_{bA}([P_A][A]+[P_A:B][A]) +$$
$$k_{uA}([P_A:A]+[P_A:A:B]) - k_{bB}[P_B][A] + k_{uB}[P_B:A] \quad (6)$$

$$\frac{d[P_B]}{dt} = k_{uB}[P_B:A] - k_{bB}[P_B][A] \quad (7)$$

$$\frac{d[P_B:A]}{dt} = k_{bB}[P_B][A] - k_{uB}[P_B:A] \quad (8)$$

$$\frac{d[mRNA_B]}{dt} = k_{tm}[P_B] - k_{d_7mRNA}[mRNA_B] \quad (9)$$

$$\frac{d[B]}{dt} = k_{tB}[mRNA_B] - k_d[B] - k_b([P_A][B]+[P_A:A][B]) +$$
$$k_{uA}([P_A:B]+[P_A:A:B]) \quad (10)$$

The invention may be used to predict the behavior of the network as represented by these ten differential equations. In one method of the invention, the equations are solved analytically (i.e. mathematically), if necessary, by making some approximations and using tools from nonlinear dynamics or statistical physics. In another method of invention, the equations are solved on a computer by numerically integrating them and thereby simulating the network's behavior as a function of time.

The Analytical Method Using Approximations

In general, the transcription rates $k_{tA}$ and $k_{tB}$ for the two genes are different. The protein degradation rates are assumed to be equal ($k_{dA}=k_{dB}=k_d$) for simplicity. This model assumes no multimerization. Such processes would not qualitatively change the analysis or results that follow. The mass balance for the promoters is expressed as follows:

$$P_A^{total} = [P_A] + [P_A:A:B] \quad (11)$$

$$P_B^{total} = [P_B] + [P_B:A] \quad (12)$$

These equations quantitatively state that the promoters can be either free or bound to specific proteins. In equation (3) it is assumed, for simplicity that $[P_A: A]$ and $[P_A:B]$ are much smaller than $[P_A:A:B]$ and thus these terms do not appear. The dynamics of free promoter concentrations are given by:

$$\frac{d[P_A]}{dt} = k_{uA}([P_A:A:B]) - k_{bA}([P_A][A][B]) \quad (13)$$

$$\frac{d[P_B]}{dt} = k_{uB}([P_B:A]) - k_{bB}[P_B][A] \quad (14)$$

where $k_{uA}(k_{uB})$ and $k_{bA}$ ($k_{bB}$) are the unbinding and binding constants, respectively. The terms in these equations correspond to the creation and destruction of free promoter molecules, respectively. Assuming local equilibrium for the promoter interactions, i.e. binding/unbinding happens at a much faster rate than other processes in the cell, the equations are $$\frac{d[P_A]}{dt} = 0 = k_{uA}[P_A:A:B] - k_{bA}[P_A][A][B] \quad (15)$$

for the steady state concentrations, leading to $$K_{PA} \equiv \frac{k_{bA}}{k_{uA}} = \frac{[P_A:A:B]}{[P_A][A][B]} \quad (16)$$

Combining this result with the mass balance equations for PA results in $$[P_A:A:B] = \frac{P_A^{total} K_{PA}[A][B]}{(1 + K_{PA}[A][B])} \quad (17)$$

A similar calculation can be made by rewriting $[P_B]$ in terms of $K_{PB}$ and $[A]$. Assuming that transcription is very fast, the dynamic equations for mRNA can be set equal to zero. With these approximations, the following system of equations for the dynamics of protein concentrations $[A]$ and $[B]$ emerge:

$$\frac{d[A]}{dt} = k_{tA}[P_A:A:B] - k_d[A] \quad (18)$$

$$\frac{d[B]}{dt} = k_{tB}[P_B] - k_d[B] \quad (19)$$

Inserting the expression derived for [PA:A:B] and [P$_B$] results in $$\frac{d[A]}{dt} = k_{tA} P_A^{total} \frac{K_{PA}[A][B]}{1 + K_{PA}[A][B]} - k_d[A] \quad (20)$$

$$\frac{d[B]}{dt} = k_{tB} P_B^{total} \frac{1}{K_{PB}[A] + 1} - k_d[B] \quad (21)$$

Thus, when a number of approximations are made (such as lumping transcription and translation together as a single process, assuming local equilibrium for promoter binding/unbinding, etc.), the full system consisting of ten differential equations can be reduced to a system of two differential equations. In this framework of reduced dimensionality, the tools of nonlinear dynamics can be employed to construct a phase portrait, analyze the stability of fixed points, and hence predict the dynamics of the system mathematically. The analysis of the two-dimensional system that appears below gives rise to the phase portrait in FIG. 6. The qualitative picture of the network dynamics provided by the phase portrait is representative of the dynamics in the full ten-dimensional system.

To simplify the analysis, the system is non-dimensionalized by first dividing by $k_d$ so that time is now rescaled by $k_d$, i.e. t→$k_d$t. Defining $$\alpha_A \equiv P_A^{total} \frac{k_{tA}}{k_d}, \quad \alpha_B \equiv P_A^{total} \frac{k_{tB}}{k_d}, \quad \mu_A \equiv 1/K_{PA} \equiv \frac{k_{uA}}{k_{bA}}, \quad \mu_B \equiv 1/K_{PB} \equiv \frac{k_{uB}}{k_{bB}},$$

equations (2) and (3) can be rewritten as $$\frac{d[A]}{dt} = \frac{\alpha_A[A][B]}{\mu_A + [A][B]} - [A] \quad (22)$$

$$\frac{d[B]}{dt} = \alpha_B \frac{\mu_B}{\mu_B + [A]} - [B] \quad (23)$$

Figure 6:
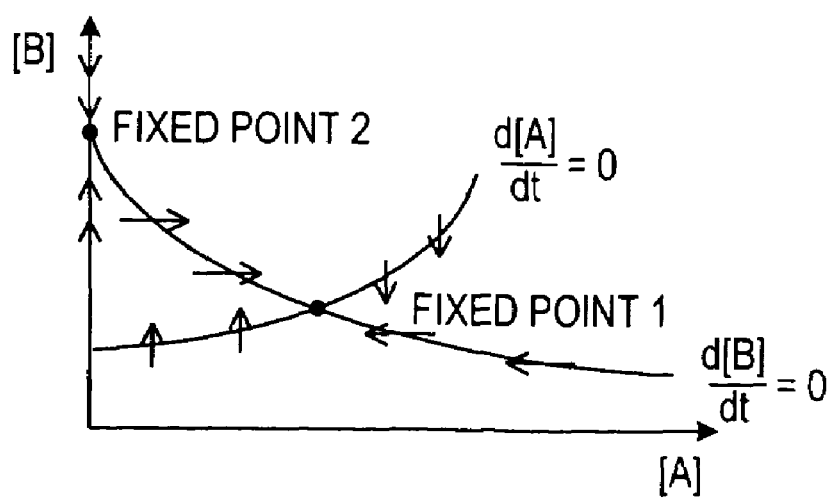
FIG. 6 is a phase portrait for the solution of the differential equation model for the two gene network of FIG. 5.

Setting these two equations equal to zero yields the two nullclines displayed in the phase portrait in FIG. 6. There is a fixed point at the intersection of these two nullclines, $$\frac{(\mu_B(\alpha_A \alpha_B - \mu_A)}{\mu_A + \alpha_B \mu_B}, \frac{\mu_A + \alpha_B \mu_B)}{\mu_B + \alpha_A}$$

fixed point 1, and another fixed point at $(0, \alpha_B)$, fixed point 2.

The Jacobian J of a set of N differential equations is defined as:

$$J = \begin{pmatrix} \frac{df_2}{dx_2} & \frac{df_2}{dx_2} & --- & \frac{df_2}{dIN} \\ \frac{df_2}{dx_2} & \frac{df_2}{dx_2} & --- & \frac{df_2}{dIN} \\ \\ \frac{df_N}{df_N} & \frac{df_N}{df_2} & --- & \frac{df_N}{df_N} \\ \frac{df_N}{df_1} & \frac{df_N}{df_2} & & \frac{df_N}{df_N} \end{pmatrix} \quad (24)$$

For the present system, $$J = \begin{pmatrix} \frac{\alpha_A \mu_{AB}}{(\mu_A + AB)^2} - 1 & \frac{\alpha_A \mu_A A}{(\mu_A + AB)^2} \\ \frac{\alpha_B \mu_B}{(\mu_B + A)^2} & -1 \end{pmatrix} \quad (25)$$

Analysis of the Jacobian matrix reveals that fixed point 1 is a node and fixed point 2 is a saddle point when $\alpha_A \alpha_B \geq \mu_A$. Fixed point 1 is stable when:

$$\frac{\mu_A(\mu_B + \alpha_A)}{\alpha_A(\mu A + \mu_B \alpha_B)}$$

$\geq 2$. This condition changes when the eigenvalues of this Jacobian matrix become positive, indicating that fixed point 1 is now unstable and fixed point 2 is not stable. If fixed point 1 is the normal, healthy state of a cell and fixed point 2 is a cancerous state of a cell, this stability condition identifies which combination of parameters, and thus which combination of genes, are most important in causing the transition or bifurcation from the normal state to the cancer state. This in turn identifies the genes which are putative targets for therapeutic agents for treatment of the disease controlled by this particular network.

The ratio of transcription rates to degradation rates ($\alpha$'s) is normally greater than unity and the ratio of unbinding constants to binding constants ($\mu$'s) is typically much less than unity so that fixed point 1 is a stable node for typical parameter values. The analyses that follow take place in this parameter range. The phase portrait in FIG. 6 indicates that the system will flow to fixed point 1 given any non-zero initial values of protein A. The system flows to fixed point 2 only in the absence of protein A. The kinetic parameters used are set forth in Table 1.

TABLE 1

| Description of Parameters | Symbol | Value | Units |
|---|---|---|---|
| Cell Volume | V | $1.66 \times 10^{-15}$ | Liters |
| Transcription Rate (mRNA$_A$ and mRNA$_B$) | kt$_m$ | 0.1 | mRNA mlces./(DNA mlces. × sec.) |
| mRNA Degradation Rate | kd, mRNA | 1/30 | 1/sec. |
| Translation Rate of A | kt$_A$ | 1/3 | protein mlces./(mRNA mlces. × sec.) |
| Translation Rate of B | kt$_B$ | 1/3 | protein mlces./(mRNA mlces. × sec.) |
| Protein Degradation Rate | kd | 1/300 | 1/sec. |
| Binding Rate of P$_A$ | kb$_A$ | $1.25 \times 10^{-4}$ | 1/sec. |
| Binding Rate of P$_B$ | kb$_B$ | 0.01 | 1/sec. |
| Unbinding Rate of P$_A$ | ka$_A$ | 1/600 | 1/sec. |
| Unbinding Rate of P$_B$ | k$_{Ub}$ | 1/600 | 1/sec. |

Figure 7:
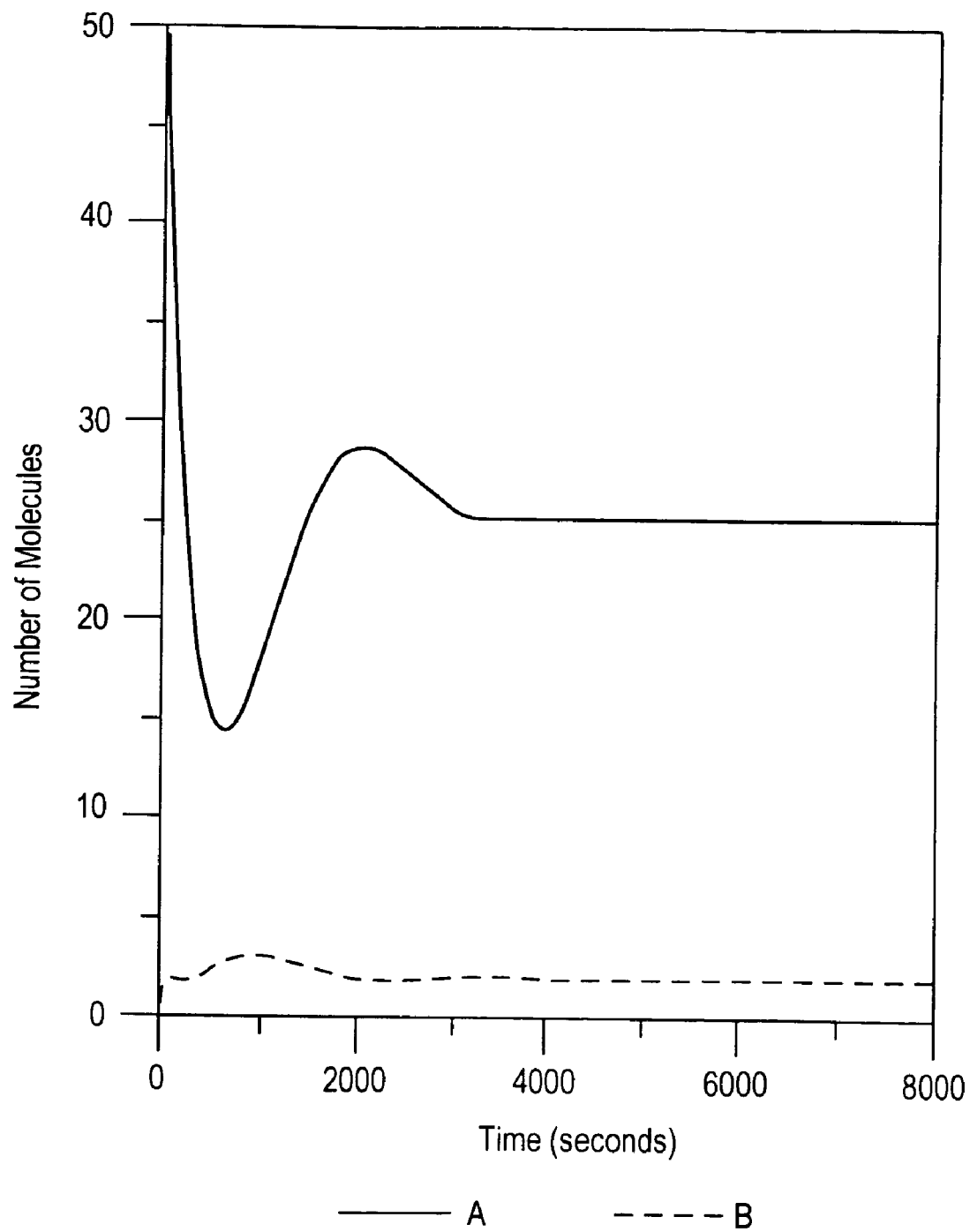
FIG. 7 is a graph showing the time evolution of the differential equation model for a single copy of the gene circuit of FIG. 5
Figure 8:
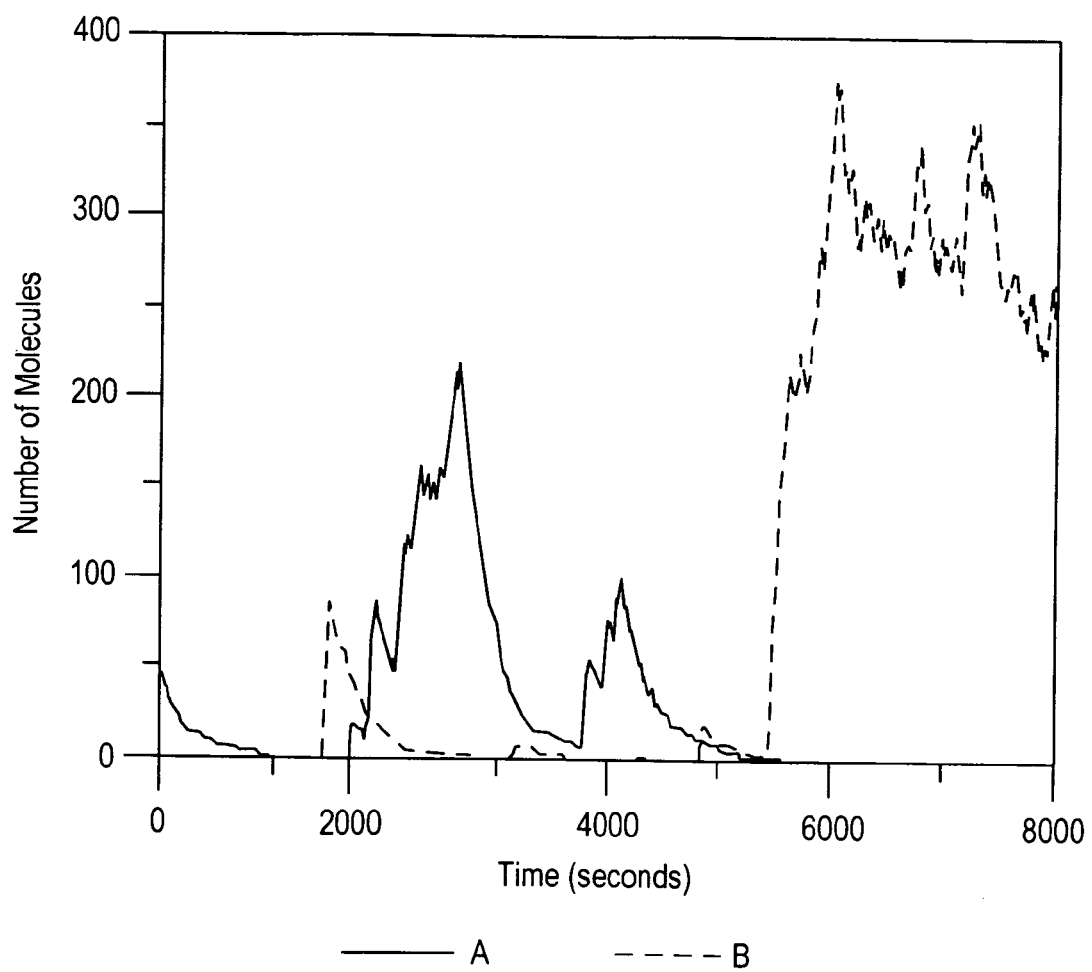
FIG. 8 a graph showing the time evolution of the stochastic equation model for a single copy of the gene circuit of FIG. 5

Table 1 sets forth the parameters used in the differential equation model of FIGS. 6 and 7. In FIGS. 7 and 8, both the stochastic and differential equation systems are initialized with 50 protein A molecules and zero protein B molecules.

The mathematical equations describing the two gene network are as follows:

$$\frac{d[PA]}{dt} = k_{uA}^k([P_A:A] + [P_A:B]) - k_{bA}^k([P_A][A] + [P_A][B]) \quad (26)$$

$$\frac{d[P_A:A]}{dt} = k_{bA}^k([P_A][A] - [P_A:A][B]) + k_{uA}^k([P_A:A:B] - [P_A:A]) \quad (27)$$

$$\frac{d[P_A:B]}{dt} = k_{bA}^k([P_A][B] - [P_A:B][A]) + k_{uA}^k([P_A:A:B] - [P_A:B]) \quad (28)$$

$$\frac{d[P_A:A:B]}{dt} = k_{bA}^k([P_A:A][B] + [P_A:B]) - \frac{2k}{uA}[P_A:A:B] \quad (29)$$

$$\frac{d[mRNA_A]}{dt} = k_{tm}^k[P_A:A:B] - k_{d,mRNA}^k[mRNA_A] \quad (30)$$

$$\frac{d[A]}{dt} = k_{tA}^k[mRNA_A] - k_d^k[A] - k_{bA}^k(P_A][A] + [P_A:B][A]) + \quad (31)$$
$$k_{uA}^k(P_A:A] + [P_A:A:B]) - k_{bB}^k[P_6][A] + k_{uB}^k[P_6:A]$$

$$\frac{d[P_6]}{dt} = k_{uB}^k[P_6:A] - k_{hB}^k[P_6][A] \quad (32)$$

$$\frac{d[P_6:A]}{dt} = k_{bB}^k[P_6][A] - k_{uB}^k[P_6:A] \quad (33)$$

$$\frac{d[mRNA_6]}{dt} = k_{tm}^k[P_6] - k_{d,mRNA}^k[mRNA_6] \quad (34)$$

$$\frac{d[B]}{dt} = k_{tB}^k[mRNA_6] - k_d^k[B] - \quad (35)$$
$$k_b^k([P_A][B] + [P_A:A][B]) + k_{uA}^k(P_A:B] + ([P_A:A:B])$$

The set of equations (non-approximated) that quantitatively describe the time evolution of the concentration of gene products in this system are numerically integrated. The results of this numerical integration simulate the behavior of the two gene network and results in the plots shown in FIGS. 6 through 8. The time course of these plots corresponds to a particular biological state. For example, one particular time course can correspond to the normal progression of a cell through the cell cycle while another time series can correspond to the unregulated cell growth characteristic of cancer. By perturbing particular genes or proteins in the circuit, the time series of a cancerous cell can be changed into the time series of a healthy cell, thereby identifying sets of genes and proteins as putative targets for therapeutic agents.

FIGS. 7 and 8 compare the output of the stochastic model and the differential equation model for the two gene network. FIG. 7 displays the time evolution of the differential equation model for a single copy of the gene circuit. The system quickly flows to the stable fixed point 1 as expected. In the differential equation model, the system would never reach the "extinction" fixed point unless the system started with zero A molecules.

EXAMPLE II

Description of the Wnt β Catenin Pathway

Figure 10:
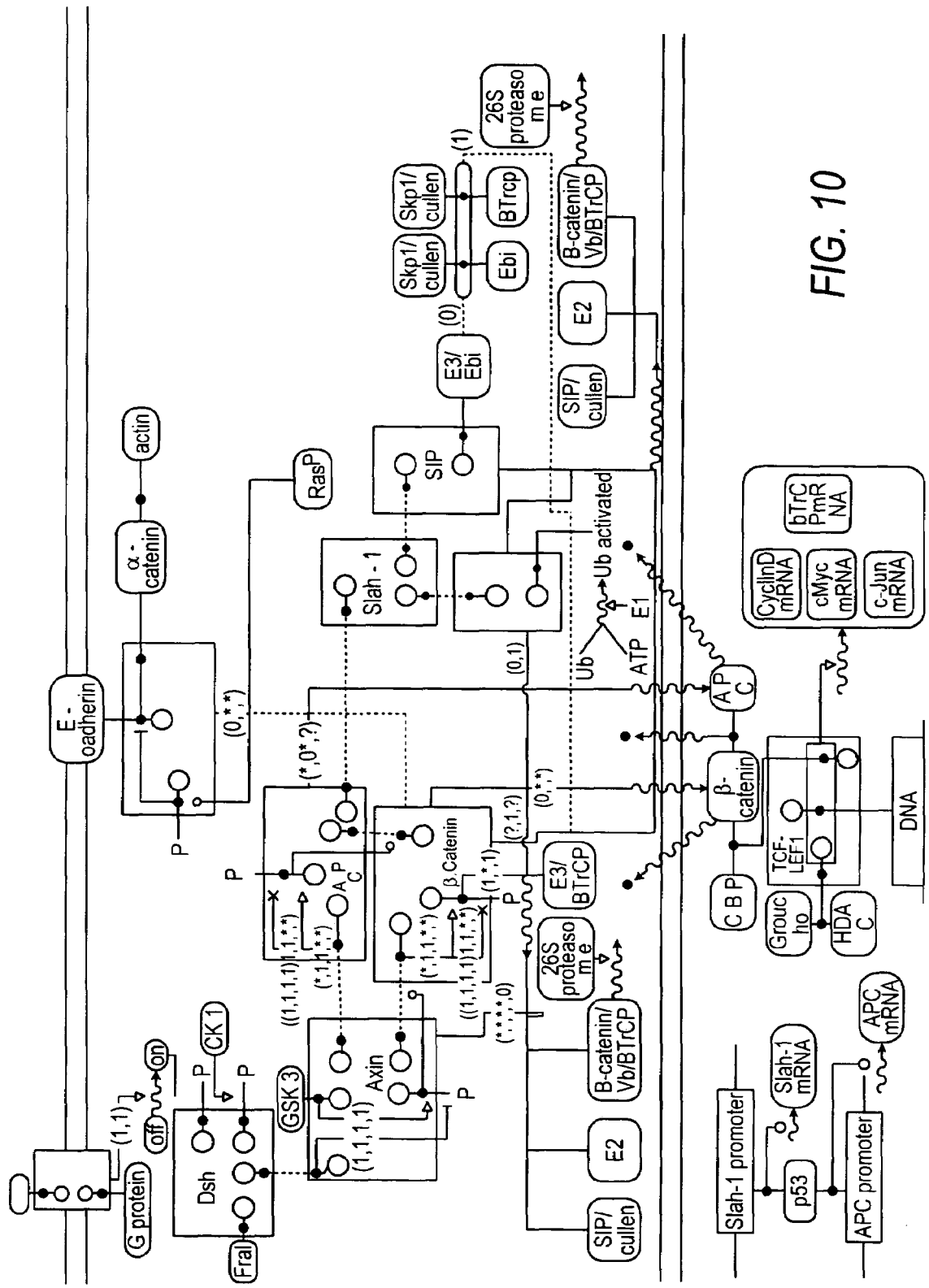
FIG. 10 is a graphical representation of the Wnt beta-catenin pathway in DCL.

FIG. 10 contains a graphical representation of the Wnt β-catenin pathway indicating the role of Axin, APC, and GSK3 in phosphorylating β-catenin and leading to its degradation. FIG. 10 was created as well using Diagrammatic Cell Language, which was discussed above in connection with FIG. 3.

In FIG. 10, there are two broad horizontal lines, CM and NM. The upper broad line CM represents schematically the cell membrane; that is, the outer membrane of the cell, and the lower broad line NM represents the nuclear membrane of the cell. Elements below the line NM are in the nucleus, and elements above the line CM are outside of the cell.

Referring again to FIG. 10, Wnt signaling is induced by secreted Wnt proteins that bind to a class of seven-pass transmembrane receptors encoded by the frizzled genes. Activation of the frizzled receptor leads to the phosphorylation of disheveled (Dsh) through an unknown mechanism. Activated disheveled inhibits the phosphorylation of β-catenin by glycogen synthase kinase 3β (GSK 3 β). Unphosphorylated β-catenin escapes detection by β-TrCP which triggers the ubiquitination of β-catenin and its degradation in the proteasomes. Stabilized β-catenin, as a result of Wnt signaling, enters the nucleus where it interacts with TCF/LEF1 transcription factors leading to the transcription of Wnt target genes such as CyclinD1 and c-Myc.

In the absence of Wnt, β-catenin phosphorylation by GSK3β occurs in a multiprotein complex containing the scaffolding protein Axin, as well as GSK3β and the APC tumor suppressor. In the multiprotein complex, β-catenin is efficiently phosphorylated and then is earmarked for degradation by β-TrCP. Stabilized β-catenin is common to most colon cancers, where mutations in APC, Axin, and β-catenin itself are known to interfere with its effective ubiquitination and consequently its degradation. Accumulation of β-catenin leads to the activation of the Wnt target genes such as CyclinD1 and c-Myc, both of which are intimately involved in cell cycle control and the progression of cancer. Nuclear β-catenin also targets β-TrCP increasing its levels and creating a negative feedback loop in the system.

Common mutations found in colon and other cancers usually effect the $NH_2$-terminal phosphorylation of β-catenin, the binding of APC to Axin, and or mutations in Axin that prevent β-catenin from binding to Axin. These mutations can be represented in the simulation by deleting reactions and setting the rate constants that correspond to these reactions equal to zero.

FIG. 10 depicts a subnetwork that represents the components involved in Wnt signaling in addition to side pathways responsible for β-catenin degradation. These include the Axin degradation machinery and β-catenin transcription of target genes c-Myc and β-TrCP. The representation includes notations depicting all of the components, chemical forms of the components, and reactions involved in the network in a complete yet compact manner. It is directly translatable to various mathematical descriptions.

Simulation of the Network

All of the chemical species in the system are listed. Each chemical species is or may be involved in a reaction. The time course of its quantity or concentration is simulated. In this example, the components include: Axin, β-catenin, APC, GSK3, β-TrCP, HDAC, Groucho, c-Myc gene, c-Myc mRNA, β-TrCP gene, β-TrCP mRNA, and an unknown intermediary protein that facilitates the enhancement of β-TrCP by nuclear β-catenin. Each of these components can exist in an alternate form depending on the species with which it interacts. For example, β-catenin can be phosphorylated directly by GSK3 forming β-catenin phosphorylated. It can also bind to Axin to form a β-catenin:Axin complex. There are a total of 70 components and chemical species in this exemplary simulation. They are listed in Table 2 below.

TABLE 2

Components and Chemical Species in the Wnt b-catenin Network

<APC>
<APCAxin>
<APCAxinG>
<APCAxinp>
<APCAxinpG>
<APCB>
<APCBAxin>
<APCBAxinG>
<APCBAxinp>
<APCBAxinpG>
<APCBP>
<APCBpAxin>
<APCBpAxinG>
<APCBpAxinp>
<APCBpAxinpG>
<APCp>
<APCpAxin>
<APCpAxinG>
<APCPAXinp>
<APCpAxinpG>
<APCpB>
<APCpBAxin>
<APCpBAxinG>
<APCpBAxinp>
<APCpBAxinpG>
<APCpBp>
<APCpBpAxin>
<APCpBPAxinG>
<APCpBpAxinp>
<APCpBpAxinpG>
<AXin>
<AxinG>
<Axinp>
<AxinpG>
<B>
<BAPC>

TABLE 2-continued

Components and Chemical Species in the Wnt b-catenin Network

<SAPCp>
<BAxin>
<BAxinG>
<BAxinp>
<BAxinpG>
<BBTCFcKycGene>
<BBOACGroucho>
<Bnuclear>
<BP>
<SpAPC>
<BpAPCp>
<BpAxin>
<BpAxinG>
<SpAxinp>
<BpAxinpG>
<BPBPTCFcMycGene>
<BpBTCFcMycGene>
<BpHDACGroucho>
<Bpnuclear>
<BpTCFcMycGene>
<BTCFcKycGene>
<bTrCP>
<bTrCPBpUbUb>
<bTrCPGene>
<bTrCPmRNA>
<cMyCMRNA>
<G>
<NDACGroucho>
<HDACGrouchoTCFcMycGene>
<Intermediary>
<Source>
<SourceB>
<TCFcMycGene>
<zero>

The interactions, i.e. reaction steps or binding interactions, between the components are listed in Table 3, below.

TABLE 3

List of Reactions, kinetic forms and kinetic parameters

| Stochiometry of the Reaction: Chemicals entering the reaction and Chemicals emerging from the reaction | | | Reaction Type | Kinetic Paramter |
|---|---|---|---|---|
| $\begin{pmatrix} -1\ B \\ 0\ G \end{pmatrix}$ | → | (1 Bp) | MichaelisMentenKF | $\begin{pmatrix} \text{kpofGsk3noAxin} \\ \text{KmofGsk3noAxin} \end{pmatrix}$ |
| $\begin{pmatrix} -1\ APC \\ 0\ G \end{pmatrix}$ | → | (1 APCp) | MichaelisMentenKF | $\begin{pmatrix} \text{kpofGsk3noAxin} \\ \text{KmofGsk3noAxin} \end{pmatrix}$ |
| $\begin{pmatrix} -1\ AXin \\ -1\ G \end{pmatrix}$ | → | (1 AxinG) | SimpleKF | (kbAxintoG) |
| (−AxinG) | → | $\begin{pmatrix} 1\ Axin \\ 1\ G \end{pmatrix}$ | SimpleKF | (kuAxintoG) |
| (−AxinG) | → | (1 AxinpG) | SimpleKF | (kbG) |
| $\begin{pmatrix} -1\ Axinp \\ -1\ G \end{pmatrix}$ | → | (1 AxinpG) | SimpleKF | (kbAxintoG) |
| (−1 AxinpG) | → | $\begin{pmatrix} 1\ Axinp \\ 1\ G \end{pmatrix}$ | SimpleKF | (kuAxintoG) |

TABLE 3-continued

List of Reactions, kinetic forms and kinetic parameters

| Stochlometry of the Reaction: Chemicals entering the reaction and Chemicals emerging from the reaction | | | Reaction Type | Kinetic Paramter |
|---|---|---|---|---|
| $\begin{pmatrix} -1 \text{ Axin} \\ -1 \text{ B} \end{pmatrix}$ | → | (1 BAxin) | SimpleKF | (kbBtoAxin) |
| (−1 BAxin) | → | $\begin{pmatrix} 1 \text{ Axin} \\ 1 \text{ B} \end{pmatrix}$ | SimpleKF | (kuBtoAxin) |
| $\begin{pmatrix} -1 \text{ Axin} \\ -1 \text{ Bp} \end{pmatrix}$ | → | (1 BpAxin) | SimpleKF | (kbBtoAxin) |
| (−1 BpAxin) | → | $\begin{pmatrix} 1 \text{ Axin} \\ 1 \text{ Bp} \end{pmatrix}$ | SimpleKF | (kuBtoAxin) |
| $\begin{pmatrix} -1 \text{ Axinp} \\ -1 \text{ B} \end{pmatrix}$ | → | (1 BAxinp) | SimpleKF | (kbBtoAxinp) |
| (−1 BAxinp) | → | $\begin{pmatrix} 1 \text{ Axinp} \\ 1 \text{ B} \end{pmatrix}$ | SimpleKF | (kuBtoAxin) |
| $\begin{pmatrix} -1 \text{ Axinp} \\ -1 \text{ Bp} \end{pmatrix}$ | → | (1 BpAxinp) | SimpleKF | (kbBtoAxinp) |
| (−1 Axinp) | → | $\begin{pmatrix} 1 \text{ Axinp} \\ 1 \text{ Bp} \end{pmatrix}$ | SimpleKF | (kuBtoAxinp) |
| $\begin{pmatrix} -1 \text{ APC} \\ -1 \text{ Axin} \end{pmatrix}$ | → | (1 APCAxin) | SimpleKF | (kbAPCtoAxin) |
| (−1 APCAxin) | → | $\begin{pmatrix} 1 \text{ APC} \\ 1 \text{ Axin} \end{pmatrix}$ | SimpleKF | (kuAPCtoAxin) |
| $\begin{pmatrix} -1 \text{ APCp} \\ -1 \text{ Axin} \end{pmatrix}$ | → | (1 APCpAxin) | SimpleKF | (kbAPCtoAxin) |
| (−1 APCpAxin) | → | $\begin{pmatrix} 1 \text{ APCp} \\ 1 \text{ Axin} \end{pmatrix}$ | SimpleKF | (kuAPCtoAxin) |
| $\begin{pmatrix} -1 \text{ APC} \\ -1 \text{ Axinp} \end{pmatrix}$ | → | (1 APCAxinp) | SimpleKF | (kbAPCtoAxin) |
| (−1 APCAxinp) | → | $\begin{pmatrix} 1 \text{ APC} \\ 1 \text{ Axinp} \end{pmatrix}$ | SimpleKF | (kuAPCAxin) |
| $\begin{pmatrix} -1 \text{ APCp} \\ -1 \text{ Axinp} \end{pmatrix}$ | → | (1 APCpAxin) | SimpleKF | (kbAPCtoAxin) |
| (−1 APCAxinp) | → | $\begin{pmatrix} 1 \text{ APCp} \\ 1 \text{ Axinp} \end{pmatrix}$ | SimpleKF | (kuAPCtoAxin) |
| $\begin{pmatrix} -1 \text{ APC} \\ -1 \text{ B} \end{pmatrix}$ | → | (1 BAPC) | SimpleKF | (kbBtoAPC) |
| (−1 BAPC) | → | $\begin{pmatrix} 1 \text{ APC} \\ 1 \text{ B} \end{pmatrix}$ | SimpleKF | (kuBtoAPC) |
| $\begin{pmatrix} -1 \text{ APC} \\ -1 \text{ Bp} \end{pmatrix}$ | → | (1 BpAPC) | SimpleKF | (kbBtoAPC) |

TABLE 3-continued

List of Reactions, kinetic forms and kinetic parameters

| Stochiometry of the Reaction: Chemicals entering the reaction and Chemicals emerging from the reaction | | Reaction Type | Kinetic Paramter |
|---|---|---|---|
| (−1 BpAPC) | → $\begin{pmatrix} 1\ APC \\ 1\ Bp \end{pmatrix}$ | SimpleKF | (kuBtoAPC) |
| $\begin{pmatrix} -1\ APCp \\ -1\ B \end{pmatrix}$ | → (1 BAPCp) | SimpleKF | (kbBtoAPCp) |
| (−1 BAPCp) | → $\begin{pmatrix} 1\ APCp \\ 1\ Bp \end{pmatrix}$ | SimpleKF | (kuBtoAPCp) |
| $\begin{pmatrix} -1\ APCp \\ -1\ Bp \end{pmatrix}$ | → (1 BpAPCp) | SimpleKF | (kbBtoAPCp) |
| (−1 APCp) | → $\begin{pmatrix} 1\ ApCp \\ 1\ Bp \end{pmatrix}$ | SimpleKF | (kuBtoAPCp) |
| $\begin{pmatrix} -1\ BAxin \\ -1\ G \end{pmatrix}$ | → (1 BAxinG) | SimpleKF | (kbAxintoG) |
| (−1 BAxinG) | → $\begin{pmatrix} 1\ Baxin \\ 1\ G \end{pmatrix}$ | SimpleKF | (kuAxintoG) |
| $\begin{pmatrix} -1\ AxinG \\ -1\ Bp \end{pmatrix}$ | → (1 BpAxinG) | SimpleKF | (kbBtoAxin) |
| (−1 BpAxinG) | → $\begin{pmatrix} 1\ AxinG \\ 1\ Bp \end{pmatrix}$ | SimpleKF | (kuBtoAxin) |
| $\begin{pmatrix} -1\ BpAxin \\ -1\ G \end{pmatrix}$ | → (1 BpAxinG) | SimpleKF | (kbAxintoG) |
| (−1 BpAxinG) | → $\begin{pmatrix} 1\ BpAxin \\ 1\ G \end{pmatrix}$ | SimpleKF | (kuAxintoG) |
| $\begin{pmatrix} -1\ AxinpG \\ -1\ B \end{pmatrix}$ | → (1 BAxinpG) | SimpleKF | (kbBtoAxinp) |
| (−1 AxinpG) | → $\begin{pmatrix} 1\ AxinpG \\ 1\ B \end{pmatrix}$ | SimpleKF | (kuBtoAxinp) |
| $\begin{pmatrix} -1\ BAxinp \\ -1\ B \end{pmatrix}$ | → (1 BAxinpG) | SimpleKF | (kbAxintoG) |
| (−1 BAxinpG) | → $\begin{pmatrix} 1\ BAxinp \\ 1\ G \end{pmatrix}$ | SimpleKF | (kuAxintoG) |
| $\begin{pmatrix} -1\ AxinpG \\ -1\ B \end{pmatrix}$ | → (1 BAxinpG) | SimpleKF | (kbBtoAxinp) |
| (−1 AxinpG) | → $\begin{pmatrix} 1\ AxinpG \\ 1\ B \end{pmatrix}$ | SimpleKF | (kuBtoAxinp) |
| $\begin{pmatrix} -1\ BpAxinp \\ -1\ G \end{pmatrix}$ | → (1 BpAxinpG) | SimpleKF | (kbAxintoG) |

TABLE 3-continued

List of Reactions, kinetic forms and kinetic parameters

| Stochiometry of the Reaction: Chemicals entering the reaction and Chemicals emerging from the reaction | | Reaction Type | Kinetic Paramter |
|---|---|---|---|
| (−1 AxinpG) | → (1 BpAxinp / 1 G) | SimpleKF | (kuAxintoG) |
| (−1 AxinpG / −1 Bp) | → (1 BpAxinG) | SimpleKF | (kdBtoAxinp) |
| (−1 BpAxinpG) | → (1 AxinpG / 1 Bp) | SimpleKF | (kuBtoAxinp) |
| (−1 BAxinG) | → (1 BpAxinG) | SimpleKF | (kbGWAxin) |
| (−1 BAxinG) | → (1 BAxinpG) | SimpleKF | (kbGWAxin) |
| (−1 BpAxinG) | → (1 BpAxinG) | SimpleKF | (kbGWAxin) |
| (−1 BAxinpG) | → (1 BpAxinG) | SimpleKF | (kbGWAxin) |
| (−1 Axin / −1 BAPC) | → (1 APCBAxin) | SimpleKF | (kbAPCtoAkin)) |
| (−1 APCBaxin) | → (1 Axin / 1 BAPC) | SimpleKF | (kuAPCtoAxin) |
| (−1 APC / −1 BAxin) | → (1 APCBaxin) | SimpleKF | (kbAPCtoAxin) |
| (−1 APCBaxin) | → (1 APC / 1 BAxin) | SimpleKF | (kuAPCtoAxin) |
| (−1 Axin / −1 BpAPC) | → (1 APCBpAxin) | SimpleKF | (kbAPCtoAxin) |
| (−1 APCBpAxin) | → (1 Axin / 1 BpAPC) | SimpleKF | (kuAPCtoAxin) |
| (−1 APC / −1 BpAxin) | → (1 APCBpAxin) | SimpleKF | (kbAPCtoAxin) |
| (−1 APCBpAxin) | → (1 APC / 1 BpAxin) | SimpleKF | (kuAPCtoAxin) |
| (−1 Axin / −1 BAPCp) | → (1 APCpBAxin) | SimpleKF | (kbAPCtoAxin) |
| (−1 APCpBAxin) | → (1 Axin / 1 BAPCp) | SimpleKF | (kuAPCtoAxin) |
| (−1 APCp / −1 BAxin) | → (1 APCpBAxin) | SimpleKF | (kuAPCptoB) |
| (−1 APCB) | → (1 APCp / 1 BAxin) | SimpleKF | (kuAPCptoB) |

These interactions are translated into a mathematical kinetic form. For example, the binding of Axin to β-catenin has the following mathematical form:

$$[\text{Axin}][\beta\text{-catenin}]k_b$$

where the quantities in brackets represent the concentrations of the two proteins. Not all binding reactions need be represented in an equivalent kinetic form. For example, two receptors binding on the membrane surface may be better represented by the mathematical kinetic form:

$$[\text{ReceptorI}]^\alpha [\text{ReceptorII}]^\beta k_b$$

where α and β are constants greater than 1. This form may better represent the kinetics of proteins interacting in a restricted geometry. Those skilled in the art can derive and express the appropriate kinetic form depending on the geometry, the reactants and the nature of the reaction.

Table 3 lists all of the reactions incorporated into the simulation together with the kinetic form used to represent the reaction and the corresponding kinetic rate constants and their values.

In the stochastic embodiments of the invention, each reaction represents a probability of a reaction occurring. In the deterministic embodiments each reaction represents a term in the differential equation representing the time rate of change of the chemical species. The list of differential equations is set forth in Table 4 below.

TABLE 4

Table of Differential equations for Wnt β-catenin Network

<APC>'[t] == kuAPCtoAxin <APCAxin> [t] + kuAPCtoAxin <APCAxinp> [t] + 2 kuAPCtoAxin <APCAxinpG> [t] + kuAPCtoAxin <APCBAxin> [t] + kuAPCtoAxin <APCBAxinG> [t] + kuAPCtoAxin <APCBAxinp> [t] + kuAPCtoAxin <APCBAxinpG> [t] + kuAPCtoAxin <APCBpAxin> [t] + kuAPCtaAxin <APCBpAxinG> [t] + kuAPCtoAxin <APCBpAxinp> [t] + kuAPCtoAxin <APCBpAxinpG> [t] − kbAPCtoAxin <APC> [t] <Axin> [t] − kbAPCtaAxin <APC> [t] <Axinp> [t] − 2 kbAPCtaAxin <APC> [t] <AxirnpG> [t] − kbBtoAPC <APC> [t] <B> [t] + kuBtoAPC <BAPC> [t] − kbAPCtoAxin <APC> [t] <BAxin> [t] − khAPCtoAxin <APC> [t] <BAxinG> [t] − kbAPCtoAxin <APC> [t] <BAxinp> [t] − kbAPCtoAxin <APC> [t] <BAxinpG> [t] − kbBtoAPC <APC> [t] <Bp> [t] + kuBtAPC <BpAPC> [t] − kbAPCtoAxin <APC> [t] <BpAxin> [t] − kbAPCtoAxin <APC> [t] <BpAxinG> [t] − kbAPotaAxin <APC> [t] <BpAxinp> [t] −

$$kbAPCtoAxin{<}APC{>}\ [t]\ {<}RpAxinpG{>}\ [t] - \frac{kpofGsk3noAxin{<}APC{>}\ [t)\ {<}G{>}\ [t]}{KmofGsk3noAxin + {<}G{>}\ [t]}$$

<APCAxin>'[t] == −kuAPCtoAxin <APCAxin> [t] + kuAxintoG <APCAxinG> [t] + kbAPCtoAxin <APC> [t] <Axin> [t] +

$$\frac{kUbiquitination{<}APCBpAxin{>}\ [t]\ {<}bTrCP{>}\ [t]}{KmUbiquitination + {<}APCBpAxin{>}\ [t]} - kbAxintoG{<}APCAxin{>}\ [t]\ {<}G{>}\ [t]$$

<APCAxinG>'[t] == −2 kpGwAxin <APCAxinG> [t] − kuAxintoG <APCAxinG> [t] + kuiBtOAPC <APCBAxinG> [t] + kuBtoApc (AscBpAxinjG> [t] − kbBtoAPC <APCAxinG> [t] <B> [t] − kbBtoAPC <APCAxinG> [t] <Bp> [t] +

$$\frac{kUbiquitination{<}APCBpAxin[t]\ {<}BTrCP{>}\ [t]}{KmUbiquitination + {<}APCBpAxinG{>}\ [t]} + kbAxintoG{<}APCAxin{>}\ [t]\ {<}G{>}\ [t]$$

<APCAxinp>'[t] == −kuAPCtoAxin <APCAxinp> [t] + kuAxintoG <APCAxirTG> [t] + kbAPCtaAxin <APC> [t] <Axinp> [t] +

$$\frac{kUbiquitination{<}APCBpAxinp{>}\ [t]\ {<}bTrcp{>}\ [t]}{KmUbiquitination + {<}APCBpAxinp{>}\ [t]} - kbAxintoG{<}APCAxinp{>}\ [t]\ {<}G{>}\ [t]$$

<APCAxinpG>'[t] == −kpGwAxin <APCAxinpG> [t] − 2 kuAPCtoAxin <APCAxinpG> [t] − kuAxintoG <APCAxinpG> [t] + kuBtoAPC <APCBAxinpG> [t] + kuBtoAPC <APCBpAxinpG> [t] + 2 kbAPCtoAxin <APC> [t] <AxinpG> [t] − kbBtoAPC <APCAxinpG> [t] <B> [t] − kbBtoAPC <APCAxinpG> [t] <Bp> [t] +

$$\frac{kUbiquitination{<}APCBpAxinpG{>}\ [t]\ {<}bTrCP{>}\ [t]}{KmUbiquitination + {<}APCBpAxinpG{>}\ [t]} + kbAxintoG{<}APCAxinp{>}\ [t]\ {<}G{>}\ [t]$$

<APCB>'[t] == kuAPCtoAxin <APCBAxinG> [t] + kuAPCtoAxin <APCBAxinp> [t] + kuAPCtoAxin <APCBAxinpG> [t] − kbAPCtoAxin <APCB> [t] <AxinG> [t] − kbAPctoAxin <APCB> [t] KAxinp> [t] − kbAPCtoAxin <APCB> [t] <AxinpG> [t]

<APCBAxin>'[t] == −2 kuApctoAxin <APCBAxin> [t] + kuAxintoG <APCBAxinG> [t] + kbAPCtoAxin <Axin> [t] <BAPC> [t] + kbAPCtoAxin <APC> [t] <BAxin> [t] − kbAxintoG <APCBAxin> [t] <G> [t]

<APCEAxinG>'[t] == − 3 kpGwAxin <APCBAxinG> [t] − 2 kuAPCtoAxin <APCBAxinG> [t] − kuAxintoG <APCBAxinG> [t] − kuBtoAPC <APCBAxinG> [t] + kbAPCtoAxin <APCB> [t] <AxinG> [t] + kbBtoAPC <APCAxinG> [t] <B> [t] + kbAPCtoAxin <APC> [t] <BAxinG> [t] + kbAxintoG <APCBAxin> [t] <G> [t]

<APCBAxinp>'[t] ==
−2 kuAPCtoAxin <APCBAxinp> [t] + kuAxintoG <APCBAxinpG> [t] + kbAPCtoAxin <APCB> [t] <Axinp> [t] + kbAPCtoAxin <APC> [t] <BAxinp> [t] − kbAxintoG <APCBAxinp> [t] <G> [t]

<APCBAxinpG>'[t] == kpGwAxin <APCBAxinG> [t] − 2 kpGwAxin <APCBAxinpG> [t] − 2 kuAPCtoAxin <APCBAxinpG> [t] − kuAxintoG <APCBAxinpG> [t] − kuBtoAPC <APCBAxinpG> [t] + kbAPCtoAxin <APCB> [t] <AxinpG> [t] + kbBtOAPC <APCAxinpG> [t]) <B> [t] + kbAPCtoAxin <APC> [t] <BAxinpG> [t] + kbAxintoG <APCBAxinp> [t] <G> [t]

<APCBp>'[t] == kuAPCtoAxin <APCBpAxinG> [t] + kuAPCtoAxin <APCBpAxinpG> [t] − kbAPCtoAxin <APCBp> [t] <AxinG> [t] − kbAPCtoAxin <APCBp> [t] <AxinpG> [t]

<APCBpAxin>'[t] == −2 kuAPCtoAxin <APCBpAxin> [t] + kuAxintoG <APCBpAxinG> [t] + kbAPCtoAxin <Axin> [t] <BpAPC> [t] + kbAPCtoAxin <APC> [t] <BpAxin> [t] −

TABLE 4-continued

Table of Differential equations for Wnt β-catenin Network $$\frac{kUbiquitination\langle APCBpAxin\rangle[t]\langle bTrCP\rangle[t]}{KmUbiquitination+\langle APCBpAxin\rangle[t]} - kbAxintoG\langle APCBpAxin\rangle[t]\langle G\rangle[t]$$

$\langle APCBpAxinG\rangle'[t] ==$ kpGwAxin $\langle APCBAxinG\rangle[t]$ − 4 kpGwAxin $\langle APCBpAxinG\rangle[t]$ − 2 kuAPCtoAxin $\langle APCBpAxinG\rangle[t]$ −
kuAxintocG $\langle APCBpAxinG\rangle[t]$ − kuBtoAPC $\langle APCBpAxinG\rangle[t]$ + kbAPCtoAxin $\langle APCBp\rangle[t]\langle AxinG\rangle[t]$ +
kbBtoAPC $\langle APCAxinG\rangle[t]\langle Bp\rangle[t]$ + kbAPCtoAxin $\langle APC\rangle[t]\langle BpAxinG\rangle[t]$ −

$$\frac{kUbiquitination\langle APCBpAxinG\rangle[t]\langle BTrCP\rangle[t]}{KmUbiquitination+\langle APCBpAxinG\rangle[t]} + kbAxintoG\langle APCBpAxin\rangle[t]\langle G\rangle[t]$$

$\langle APCBpAxinp\rangle'[t] == -2$ kuAPCtoAxin $\langle APCBpAxinp\rangle[t]$ + kuAxintoG $\langle APCBpAxinpG\rangle[t]$ +
kbAPCtoAxin $\langle Axinp\rangle[t]\ |\ \langle BpAPC\rangle[t]$ + kbAPCtoAxin $\langle APC\rangle[t]\langle BpAxinp\rangle[t]$ −

$$\frac{kUbiquitination\langle APCBpAxinp\rangle[t]\langle BTrCP\rangle[t]}{KmUbiquitination+\langle APCBpAxinp\rangle[t]} - kbAxintoG\langle APCBpAxinp\rangle[t]\langle G\rangle[t]$$

$\langle APCBpAxinpG\rangle'[t] ==$ kpGwAxin $\langle APCBAxinpG\rangle[t]$ + 2 kpGwAxin $\langle APCBpAxinG\rangle[t]$ −
kpGwAxin $\langle APCBpAxinpG\rangle[t]$ − 2 kuAPCtoAxin $\langle APCBpAxinpG\rangle[t]$ − kuAxintoG $\langle APCBpAxinpG\rangle[t]$ −
kuBtoAPC $\langle APCBpAxinpG\rangle[t]$ + kbAPCtoAxin $\langle APCBp\rangle[t]\langle AxinpG\rangle[t]$ +
kbBtoAPC $\langle APCAxinpG\rangle[t]\langle Bp\rangle[t]$ + kbAPCtoAxin $\langle APC\rangle[t]\ [BpAxinpG\rangle[t]$ −

$$\frac{kUbiquitination\langle APCBpAxinpG\rangle[t]\langle bTrCP\rangle[t]}{KmUbiquitination+\langle APCBpAxinpG\rangle[t]} + kbAxintoG\langle APCBpAxinp\rangle[t]\langle G\rangle[t]$$

$\langle APCp\rangle'[t] ==$ kuAPCtoAxin $\langle APCpAxin\rangle[t]$ + kuAPCtoAxin $\langle APCpAxinG\rangle[t]$ +
kuAPCtoAxin $\langle APCpAxinp\rangle[t]$ + kuAPCtoAxin $\langle APCpAxinpG\rangle[t]$ + kuAPCptoB $\langle APCPBAxin\rangle[t]$ +
kuAPCptoAxin $\langle APCpBAxinG\rangle[t]$ + kuAPCtoAxin $\langle APCpBAxinp\rangle[t]$ + kuAPCtoAxin $\langle APCpBAxinpG\rangle[t]$ +
kuAPCptoB $\langle APCpBpAxin\rangle[t]$ + kuAPCtoAxin $\langle APCpBpAxinG\rangle[t]$ + kuAPCptoB $\langle APCpBpAxinp\rangle[t]$ +
kuAPCptoAxin $\langle APCpBpAxinpG\rangle[t]$ − kbAPCtoAxin $\langle APCp\rangle[t]\langle Axin\rangle[t]$ −
kbAPCtoAxin $\langle APCp\rangle[t])\langle AxinG\rangle[t]$ − kbAPCtoAxin $\langle APCp\rangle[t]\langle Axinp\rangle[t]$ −
kbAPCtoAxin $\langle APCp\rangle[t]\langle AxinpG\rangle[t]$ − kbBtoAPCp $\langle APCp\rangle[t]\langle B\rangle[t]$ + kuBtoAPCp $\langle BAPCp\rangle[t]$ −
kbAPCptoB $\langle APCp\rangle[t]\ (BAxin\rangle[t]$ − kbAPCtoAxin $\langle APCp\rangle[t]\langle BAxinG\rangle[t]$ −
kbAPCtoAxin $\langle APCp\rangle[t]\ (BAxinp\rangle[t]$ − kbAPCtoAxin $\langle APCp\rangle[t]\langle BAxinpG\rangle[t]$ −
kbBtoAPCp $\langle APCp\rangle[t]\langle Bp\rangle[t]$ + kuBtoAPCp $\langle BpAPCp\rangle[t]$ − kbAPCptoB $\langle APCp\rangle[t]\langle BpAxin\rangle[t]$ −
kbAPCtoAxin $\langle APCp\rangle[t]\langle BpAxinG\rangle[t]$ − kbAPCptoB $\langle APCP\rangle[t]\langle BpAxinp\rangle[t]$ − kbAPCtoAxin$\langle APCp\rangle[t]\langle BpAxinpG\rangle[t] + \dfrac{kpofGsk3noAxin\langle APC\rangle[t]\langle G\rangle[t]}{KmofGsk3noAxin+\langle G\rangle[t]}$ $\langle ABCpAxin\rangle'[t] == -$kuAPCtoAxin $\langle APCpAxin\rangle[t]$ + kuAxintoG $\langle APCpAxinG\rangle[t]$ + kbAPCtoAxin $\langle APCp\rangle[t]\langle Axin\rangle[t]$ +

$$\frac{kUbiquitination\langle APCBpAxin\rangle[t]\langle bTrCP\rangle[t]}{KmUbiquitination+\langle APCpBpAxin\rangle[t]} - kbAxintoG\langle APCpAxin\rangle[t]\langle G\rangle[t]$$

$\langle APCpAxinG\rangle'[t] ==$ kpGwAxin $\langle APCAxinG\rangle[t]$ − kpGwAxin $\langle APCpAxinG\rangle[t]$ −
kuAPCtoAxin $\langle APCpAxinG\rangle[t]$ − kuAxintoG $\langle APCpAxinG\rangle[t]$ + kuBtoAPCp $\langle APCpBAxinG\rangle[t]$ +
kuBtoAPCp $\langle APCpBpAxinG\rangle[t]$ + kbAPCtoAxin $\langle APCp\rangle[t]\langle AxinG\rangle[t]$ −
kbBtoAPCp $\langle APCpAxinG\rangle[t]\langle B\rangle[t]$ − kbBtoAPCp $\langle APCpAxinG\rangle[t]\langle Bp\rangle[t]$ +

$$\frac{kUbiquitination\langle APCpBpAxinG\rangle[t]\langle bTrCP\rangle[t]}{KmUbiquitination+\langle APCpBpAxinG\rangle[t]} + kbAxintoG\langle APCpAxin\rangle[t]\langle G\rangle[t]$$

$\langle APCpAxinp\rangle'[t] == -$kuAPCtoAxin $\langle APCpAxinp\rangle[t]$ + kuAxintoG $\langle APCpAxinpG\rangle[t]$ + kbAPCtoAxin $\langle APCp\rangle[t]\langle Axinp\rangle[t]$ +

$$\frac{kUbiquitination\langle APCpBpAxinp\rangle[t]\langle bTrCP\rangle[t]}{KmUbiquitination+\langle APCpBpAxinp\rangle[t]} - kbAxintoG\langle APCpAxinp\rangle[t]\langle G\rangle[t]$$

$\langle APCpAxinG\rangle'[t] ==$ kpGwAxin $\langle APCpAxinG\rangle[t]$ + kpGwAxin $\langle APCpAxinpG\rangle[t]$ +
kpGwAxin $\langle APCpAxinG\rangle[t]$ − kuAPCtoAxin $\langle APCpAxinpG\rangle[t]$ − kuAxintoG $\langle APCpAxinpG\rangle[t]$ +
kuBtoAPCP $\langle APCpRAxinpG\rangle[t]$ − kuBtoAPCP $\langle APCpBpAxinpG\rangle[t]$ + kbAPCtoAxin $\langle APCp\rangle[t]\langle AxinpG\rangle[t]$ −
kbBtoAPCp $\langle APCpBAxinpG\rangle[t]\langle B\rangle[t]$ − kbBtoAPCp $\langle APCpAxinpG\rangle[t]\ (Bp\rangle[t]$ +

$$\frac{kUbiquitination\langle APCpBpAxinpG\rangle[t]\langle BTrcp\rangle[t]}{KmUbiquitination+\langle APCpBpAxinpG\rangle[t]} + kbAxintoG\langle APCpAxinp\rangle[t]\langle G\rangle[t]$$

$\langle APCpB\rangle'[t] ==$ kuAPCtoAxin $\langle APCpBAxinG\rangle[t]$ + kuAPCtoAxin $\langle APCBRAxinpG\rangle[t]$ −
kbAPCtoAxin $\langle APCpB\rangle[t]\langle AxinG\rangle[t]$ − kbAPCtoAxin $\langle APCpB\rangle[t]\langle AxinpG\rangle[t]$ TABLE 4-continued Table of Differential equations for Wnt β-catenin Network <APCpBAxin>'[t] == −kuAPCptoB <APCpBAxin> [t] − kuAPCtoAxin <APCpBAxin> [t] +
kuAxintoG <APCpBAxinG> [t] + kbAPCtoAxin <Axin> [t] <BAPCp> [t] +
kbAPCPtoB <APCp> [t] <BAxin> [t] − kbAxintoG <APCpBAxin> [t] <G> [t]

<APCpBAxinG>'[t] == kpGwAxin <APCBAxinG> [t] − kuAPCptoAxin <APCpBAxinG> [t] − 2 kuAPCtoAxin <APCpBAxinG> [t] −
kuAxintoG <APCpBAxinG> [t] − kuBtoAPCp <APCpBAxinG> [t] + khAPCtoAxin <APCpB> [t] <AxinG> [t] +
kbAPCtaAxin <APCpBp> [t] <AxinG> [t] + kbBtoAPCp <APCpAxinG> [t] <B> [t] +
kbAPCtoAxin <APCp> [t] <BAxinG> [t] + kbAxintoG <APCpBAxin> [t] <G> [t]

<APCpBAxinp>'[t] ==
−2 kuAPCtoAxin <APCpBAxinp> [t] + kuAxintoG <APCpBAxinpG> [t] + khAPCtoAxin <Axinp> [t] <BAPCp> [t] +
kbAPCtoAxin <APCp> [t] <BAxinp> [t] − kbAxintoG <APCpBAxinp> [t] <G> [t]

<APCpBAxinpG>'[t] == kpGwAxin <APCBAxinpG> [t] − kpGwAxin <APCpBAxinpG> [t] −
2 kuAPCtoAxin <APCpBAxinpG> [t] − kuAxintoG <APCpBAxinpG> [t] − kuBtoAPCp <APCpBAXinpG> [t] +
kbAPCtoAxin <APCpB> [t] <AxinpG> [t] + kbBtoAPCp <APCpAxinpG> [t] <B> [t]
kbAPCtoAxin <APCp> [t] <BAxinpG> [t] + kbAxintoG <APCpBAxinp> [t] <G> [t]

<APCpBp>'[t] == kuAPCtoAxin <APCpBAxinG> [t] + kuAPCtoAxin <APCpBpAxinpG> [t] −
kbAPCtoAxin <APCpBp> [t] <AxinG> [t] − kbAPCtoAxin <APCpBp> [t] <AxinpG> [t]

<APCpBpAxin>'[t] == −kuAPCptoB <APCpBpAxin> [t] − kuAPCtoAxin <APCpBpAxin> [t] +
kuAxintoG <APCpBpAxinG> [t] + kbAPCtoAxin <Axin> [t] <BpAPCp> [t] + kbAPCptoB <APCp> [t] <BpAxin> [t] −

$$\frac{\text{kUbiquitination} \langle APCpBpAxin \rangle \; [t] \langle bTrCP \rangle \; [t]}{\text{KmUbiquitination} + \langle APCpBpAxin \rangle \; [t]} - \text{kbAxintoG} \langle APCpBpAxin \rangle \; [t] \; \langle G \rangle \; [t]$$

<APCpBpAxinG>'[t] == 2kpGwAxin <APCBpAxinG> [t] − kpGwAxin <APCpBpAxinG> [t] −
kuAPCtoAxin <APCpBpAxinG> [t] − kuAxintoG <APCpBpAxinG> [t] − kuBtoApCp <APCpBpAxinG> [t] +
kbBtoAPCp <APCPAxinG> [t] <Bp> [t] + kbAPCtoAxin <APCp> [t] <BpAxinG> [t] −

$$\frac{\text{kUbiquitination} \langle APCpBpAxinG \rangle \; [t] \langle bTrCp \rangle \; [t]}{\text{KmUbiquitination} + \langle APCpBpAxinG \rangle \; [t]} + \text{kbAxintoG} \langle APCPBpAxin \rangle \; [t] \; \langle G \rangle \; [t]$$

<APCPBpAxinp>'[t] ==
kuAPCptoB <APCpBpAxinp> [t] − kuAPCtoAxin <APCpBpAxinp> [t] + kuAxintoG <APCpBpAxinpG> [t] +
kbAPCtoAxin <Axinp> [t] <BpAPCp> [t] + kbAPCptoB <APCp> [t] <BpAxinp> [t] −

$$\frac{\text{kUbiquitination} \langle APCpBpAxinp \rangle \; [t] \langle bTrCp \rangle \; [t]}{\text{KmUbiquitination} + \langle APCpBpAxinp \rangle \; [t]} - \text{kbAxintoG} \langle APCpAxinp \rangle \; [t] \; \langle G \rangle \; [t]$$

<APCpBpAxinpG>'[t] == kpGwAxin <APCBpAxinpG> [t] + kpGwAxin <APCpBAxinpG> [t] +
kpGwAxin <APCpBpAxinG> [t] − kuAPCptoAxin <APCpBpAxinpG> [t] − kuAPCtoAxin <APCpBpAxinpG> [t] −
kuAxintoG <APCpBpAxinpG> [t] − kuBtoAPCp <APCpBpAxinpG> [t] + kbAPCtoAxin <APCpBp> [t] <AXinpG> [t] +
kbBtoAPCp <APCpAxinpG> [t] <Bp> [t] + kbAPCtoAxin <APCp> [t] <BpAxinpG> [t] −

$$\frac{\text{kUbiquitination} \langle APCpBpAxinpG \rangle \; [t] \langle bTrCP \rangle \; [t]}{\text{KmUbiquitination} + \langle APCpBpAxinpG \rangle \; [t]} + \text{kbAxintoG} \langle APCpAxinp \rangle \; [t] \; \langle G \rangle \; [t]$$

<Axin>'[t] == kuAPCtoAxin <APCAxin> [t] + kuAPCtoAxin <APCBAxin> [t] + kuAPCtoAxin <APCBpAxin> [t] +
kuAPCtoAxin <APCpAxin> [t] + kuAPCtoAxin <APCpBAxin> [t] + kuAPCtoAxin <APCpBpAxin> [t] −

$$\text{kbAPCtaAxin} \langle APC \rangle \; [t] \; \langle Axin \rangle \; [t] \text{kbAPCtoAxin} \langle APCp \rangle \; [t] \; \langle Axin \rangle \; [t] - \frac{\text{kdAxin} \langle Axin \rangle \; [t]}{\text{KdmAxin} + \langle Axin \rangle \; [t]} +$$

kuAxintoG <AxinG> [t] − kbBtoAxin <Axin> [t] <B> [t] − kbAPCtoAxin <Axin> [t] <BAPC> [t] −
kbAPCtoAxin <Axin> [t] <BAPCp> [t] + kuBtoAxin <BAxin> [t] − kbBtoAxin <Axin> [t] <Bp> [t] −
kbAPCtoAxin <Axin> [t] <BpAPC> [t] − kbAPCtoAxin <Axin> [t] <BpAPCp> [t] + kuBtoAxin <BpAxin> [t] +

$$\frac{\text{kUbiquitination} \langle BpAxin \rangle \; [t] \langle bTrCP \rangle \; [t]}{\text{KmUbiquitination} + \langle BpAxin \rangle \; [t]} - \text{kbAxintoG} \langle Axin \rangle \; [t] \; \langle G \rangle \; [t] I + \text{ksAxin} \langle Source \rangle \; [t]$$

(AxinG>'[t] == kuAPCtoAxin <APCBAxinG> [t] + kuAPCtoAxin <APCBpAxinG> [t] +
kuAPCtoAxin <APCpAxinG> [t] + 2 kuAPCtoAxin <APCpBAxinG> [t] − kpG <AxinG> [t] −
kuAxintoG <AxinG> [t] − kbAPCtoAxin <APCB> [t] <AxinG> [t] − kbAPCtoAxin <APCBp> [t] <AxinG> [t]
kbAPCtoAxim <APCp> [t] <AxinG> [t] − kbAPCtaAxin <APCpB> [t] <AxinG> [t] −
kbAPCtoAxin <APCpBp> [t] <AxinG> [t] − kbBtoAxin <AxinG> [t] <Bp> [t] + kuBtoAxin <BpAxinG> [t] +

TABLE 4-continued

Table of Differential equations for Wnt β-catenin Network $$\frac{kUbiquitination \langle BpAxinG \rangle [t] \langle bTrCP \rangle [t]}{KmUbiquitination + \langle BpAxinG \rangle [t]} + kbAxintoG \langle Axin \rangle [t] \langle G \rangle [t]$$

⟨Axinp⟩'[t] == kuAPCtoAxin ⟨APCAxinp⟩ [t] + kuAPCtoAxin ⟨APCBAxinp⟩ [t] +
kuAPCtoAxin (APCBpAxinp⟩ [t]) + kuAPCtoAxin ⟨APCpAxinp⟩ [t] + kuAPCtoAxin ⟨APCpBAxinp⟩ [t] +
kuAPCtoAxin ⟨APCpBpAxinp⟩ [t] − kbAPCtoAxin ⟨APC⟩ [t] ⟨Axinp⟩ [t] −
kbAPCtoAxin ⟨APCB⟩ [t] ⟨Axinp⟩ [t] − kbAPCtoAxin ⟨APCp⟩ [t] ⟨Axinp⟩ [t] −

$$\frac{kdAxinp \langle Axinp \rangle [t]}{KdmAxinp + \langle Axinp \rangle [t]} + kuAxintoG \langle AxinpG \rangle [t] - kbBtoAxinp \langle Axinp \rangle [t] \langle B \rangle [t] -$$

kbAPCtcAxin ⟨Axinp⟩ [t] ⟨BAPCp⟩ [t] + kuBtoAxinp ⟨BAxinp⟩ [t] − kbBtoAxinp ⟨Axinp⟩ [t] ⟨Bp⟩ [t] −
kbAPCtoAxin ⟨Axinp⟩ [t] ⟨BpAPC⟩ [t] − kbAPCtoAxin ⟨Axinp⟩ [t] ⟨BpApCp⟩ [t] +

$$kuBtoAxinp \langle BpAxinp \rangle [t] + \frac{kUbiquitination \langle BpAxinp \rangle [t] \langle bTrCP \rangle [t]}{KmUbiquitination + \langle BpAxinp \rangle [t]} - kbAxintoG \langle Axinp \rangle [t] \langle G \rangle [t]$$

⟨AxinpG⟩'[t] ==
2 kuAPCtoAxin ⟨APCAxinpG⟩ [t] + kuAPCtoAxin ⟨APCBAxinpG⟩ [t] + kuAPCtoAxin ⟨APCBpAxinpG⟩ [t] +
kuAPCtoAxin ⟨APCpAxinpG⟩ [t] + kuAPCtoAxin ⟨APCpBAxinpG⟩ [t] + kuAPCtaAxin ⟨APCpBpAxinpG⟩ [t] +
kpG ⟨AxinG⟩ [t] − kuAxintoG ⟨AxinpG⟩ [t] − 2khAPCtoAxin ⟨APC⟩ [t] ⟨AxinpG⟩ [t] −
kbAPCtoAxin ⟨APCB⟩ [t] ⟨AxinpG⟩ [t] − k-bAPCtoAxin ⟨APCBp⟩ [t] ⟨AxinpG⟩ [t] −
kbAPCtoAxin ⟨APCP⟩ [t] ⟨AxinpG⟩ [t] − kbAPCtoAxin ⟨APCpB⟩ [t] ⟨AxinpG⟩ [t] −
kbAPCtoAxin ⟨APCpBp⟩ [t] ⟨AxinpG⟩ [t] − 2 kbBtoAxinp ⟨AxinpG⟩ [t] ⟨B⟩ [t] +
2 kuBtoAxinp ⟨BAxinpG⟩ [t] − kbBtoAxinlp ⟨AxinpG⟩ [t] − ⟨Bp⟩ [t] + kuBtoAxinp ⟨BpAxinpG⟩ [t] +

$$\frac{kUbiquitination \langle BpAxinpG \rangle [t] \langle bTrcp \rangle [t]}{KmUbiquitination + \langle BpAxinpG \rangle [t]} + kbAxintoG \langle Axinp \rangle [t] \langle G \rangle [t]$$

⟨B⟩'[t] == kuBtoAPC ⟨APCBAxinG⟩ [t] + kuBtoAPC ⟨APCBAxinpG⟩ [t] + kuBtoAPCp ⟨APCpBAxinG⟩ [t] +
kuBtoAPCp ⟨ApCpBAxinpG⟩ [t] − kbBtoAPC ⟨APC⟩ [t] ⟨B⟩ [t] − kbBtoAPC ~APCAxinG⟩ [t] ⟨B⟩ [t] −
kbBtoAPC ⟨APCAxinpG⟩ [t] ⟨B⟩ [t] − kbBtoAPCp ⟨APCp⟩ [t] ⟨B⟩ [t] − kbBtoAPCp ⟨APCpAxinG⟩ [t] ⟨B⟩ [t] −
kbBtoAPCp ⟨APCpAxinpG⟩ [t] ⟨B⟩ [t] − kbBtoAxin ⟨Axin⟩ [t] ⟨B⟩ [t] − kbBtoAxinp ⟨Axinp⟩ [t] ⟨B⟩ [t] −

$$2kbBtoAxinp \langle AxinpG \rangle [t] - \langle B \rangle [t] \frac{kdBalone \langle B \rangle [t]}{KmBalone + \langle B \rangle [t]} - \frac{kBtoNucleus \langle B \rangle [t]}{KmBtoNucleus + \langle B \rangle [t]} + kuBtOAPC \langle BAPC \rangle [t] +$$

kuBtoAPCp ⟨BAPCp⟩ [t] + kuBtoAxin ⟨BAxin⟩ [t] + kuBtoAxinp ⟨BAxinp⟩ [t] + 2 kuBtoAxinp ⟨BAxinpG⟩ [t] +

$$\frac{kBtocytcplasm \langle Bnuclear \rangle [t]}{KmBtocytcplasm + \langle Bnuclear \rangle [t]} \frac{kpofGsk3noAxin \langle B \rangle [t] \langle G \rangle [t]}{KmofGsk3noAxin + \langle G \rangle [t]} + ksB \langle SourceB \rangle [t]$$

⟨BApc⟩'[t] == kuAPCtoAxin ⟨APCBAxin⟩ [t] +
kbBtoAPC ⟨APC⟩ [t] ⟨B⟩ [t] − kuBtoAPC ⟨BAPC⟩ [t] − khAPCtoAxin ⟨Axin⟩ [t] ⟨BAPC⟩ [t]

⟨BAPCp⟩'[t] == kuAPCtoAxin ⟨APCpeAxin⟩ [t] + kuAPCtoAxin ⟨APCpBAxinp⟩ [t] + kbBtoAPCp ⟨APCp⟩ [t] ⟨B⟩ [t] −
kuBtoAPCp ⟨BAPCp⟩ [t] − kbAPCtaAxin ⟨Axin⟩ [t] ⟨BAPCp⟩ [t] − kbAPCtoAxin ⟨Axinp⟩ [t] ⟨BAPCp⟩ [t]

⟨BAxin⟩'[t] == kuAPCtoAxin ⟨APCBAxin⟩ [t] + kuAPCptoB ⟨APCpBAxin⟩ [t] +
kbBtoAxin ⟨Axin⟩ [t] ⟨B⟩ [t] − kuBtoAxin ⟨BAxin⟩ [t] − khAPCtoAxin ⟨APC⟩ [t] ⟨BAxin⟩ [t] −
kbAPCptoB ⟨APCp⟩ [t] ⟨BAxin⟩ [t] + kuAxintoG ⟨BAxinG⟩ [t] − khAxintoG ⟨BAxin⟩ [t] ⟨G⟩ [t]

⟨BAxinG⟩'[t] == kuAPCtoAxin ⟨APCBAxinG⟩ [t] + kuAPCptoAxin ⟨APCpBAxinG⟩ [t] −
2 kpGwAxin (BAxinG⟩ [t] − kuAxintoG ⟨BAxinG⟩ [t] − kbAPCtoAxin ⟨APC⟩ [t] ⟨BAxinG⟩ [t] −
kbAPCtoAxin ⟨APCp⟩ [t] ⟨BAxinG⟩ [t] + kbAxintoG ⟨BAxin⟩ [t] ⟨G⟩ [t]

⟨BAxinp⟩'[t] == kuAPCtoAxin ⟨ApcBAxinp⟩ [t] + kuAPCtoAxin ⟨APCpBAxinp⟩ [t] +
kbBtoAxinp ⟨Axinp⟩ [t] ⟨B⟩ [t] − kuBtoAxinp ⟨BAxinp⟩ [t] − kbAPCtoAxin ⟨APC⟩ [t] ⟨BAxinp⟩ [t] −
kbAPCtoAxin ⟨APCp⟩ [t] ⟨BAxinp⟩ [t] + kuAxintoG ⟨bAxinpG⟩ [t] − kbAxintoG ⟨BAxinp⟩ [t] ⟨G⟩ [t]

⟨BAxinpG⟩'[t] == kuAPCtoAxin ⟨APCBAxinpG⟩ [t] + kuAPCtoAxin ⟨APCpBAxinpG⟩ [t] +
2 kbBtoAxinp ⟨AxinpG⟩ [t] ⟨B⟩ [t] + kpGwAxin ⟨BAxinG⟩ [t]) − kpGwAxin ⟨BAxinpG⟩ [t] −
kuAxintoG ⟨BAxinpG⟩ [t] − 2 kuBtoAxinp ⟨BAxinpG⟩ [t] − kbAPCtoAxin ⟨APC⟩ [t] ⟨BAxinpG⟩ [t] −
kbAPCtoAxin ⟨APCp⟩ [t] ⟨BAxinpG⟩ [t] + kbAxintoG ⟨BAxinp⟩ [t] ⟨G⟩ [t]

⟨BBTCFcMycGene⟩'[t] == −kuBtoTCFcMycGene2 ⟨BBTCFcMycGene⟩ [t] +
ktranscriptioncMyc ⟨BpBpTCFcMycGene⟩ [t] + kbBtOTCFCMycGene2 ⟨Bnuclear⟩ [t] ⟨BTCFcMycGene) [t]

(BHDACGroucho⟩'[t] == −kuHDACGrouchotoB ⟨BHDACGroucho) [t] + kbHDACGrouchotoB ⟨Bnuclear⟩ [t] ⟨HDACGroucho⟩ [t]

TABLE 4-continued

Table of Differential equations for Wnt β-catenin Network $$\langle Bnuclear\rangle[t] == \frac{kBtoNucleus \langle B\rangle\ [t]}{KmBtoNucleus+\langle B\rangle\ [t]} + kuBtoTCFcMyGene2 \langle BB = cMycGene\rangle[t] +$$

$$kuHDACGrouchotoB \langle BHMCGroucho\rangle[t] - \frac{kBtocytoplasm \langle Bnuclear\rangle\ [t]}{KmBtocytoplasm+\langle Bnuclear\rangle\ [t]}$$

kuBtoTCFcMycGene2 <bpBTCFcMycGene> [t] − kbBtoTCFcMycGene2 <Bnuclear> [t] <BpTCFcMycGene> [t] +
kuBtoTCFcMycGene <BTCFcMycGene> [t] − kbBtoTCFcMycGene2 <Bnuclear> [t] <BTCFCMycGene> [t] −
kbHDACGrouchotoB <Bnuclear> [t] (HDACGroucho> [t] − kbBtoTCFcMycGene <Bnuclear> [t] <TCFcMycGene> [t]

<Bp>'[t] == kuBtoAPC <APCBpAxinG> [t] + kuBtoAPC <APCBpAxinpG> [t] + kuBtoAPCp <APCpBpAxinG> [t] +
kuBtoAPCp <APCpBpAxinpG> [t] − kbBtoAPC <APC> [t] <Bp> [t] − kbBtoAPC <APCAxinG> [t] <Bp> [t] −
kbBtoAPC <APCAxinpG> [t] <Bp> [t] − kbBtoAPCp <APCp> [t] <Bp> [t] − kbBtoAPCp <APCpAxinG> [t] <Bp> [t] −

$$kbBtoAxinp \langle Axinp\rangle\ [t]\ \langle Bp\rangle\ [t] - kbBtoAxinp \langle AxinpG\rangle\ [t]\ \langle Bp\rangle\ [t] - \frac{kdBalone \langle Bp\rangle\ [t]}{KmBalone+\langle Bp\rangle\ [t]}$$

$$\frac{kBtoNucleus \langle Bp\rangle\ [t]}{KmBtoNucleus+\langle Bp\rangle\ [t]} + kuBtoAPC \langle BpAPC\rangle\ [t] + kuBtoAPCp \langle BpAPCp\rangle\ [t] +$$

kuBtoAxin <BpAxin> [t] + kuBtoAxin <BpAxinG> [t] + kuBtoAxinp <BpAxinp> [t] +

$$kuBtoAxin \langle BpAxinpG\rangle\ [t] + \frac{kBtocytcplasm \langle Bpnuclear\rangle\ [t]}{KmBtocytoplasm+\langle Bpnuclear\rangle\ [t]}\ \frac{kpofGsk3noAxin \langle B\rangle\ [t]\sim\langle G\rangle\ [t]}{KmofGsk3noAxin+\langle G\rangle\ [t]}$$

<BpAPC>'[t] == kuAPCtoAxin <APCBpAxin> [t] + kuAPCtoAxin <APCBpAxinp> [t] + kbBtoAPc <APC> [t] <Bp> [t] −
kuBtoAPC <BpAPC> [t] − kbAPCtoAxin <Axin> [t] <BpAPC> [t] − kbAPCtoAxin <Axinp> [t] <BpAPC> [t]

<BpAPCp>'[t] ==
kuAPCtoAxin <APCpBpAxin> [t] + kuAPCtoAxin <APCpBpAxinp> [t] + kbitoAPCp <APCp> [t] <Bp> [t] −
kuBtoAPCp <BpAPCp> [t] − kbAPCtoAxin <Axin> [t] <BpAPCp> [t] − kbAPCtoAxin <Axinp> [t] <BpAPCp> [t]

<BpAxin>'[t] ==
kuAPCtoAxin <APCBpAxin> [t] + kuAPCptoB <APCpBpAxin> [t] + kbBtaAxin <Axin> [t] <Bp> [t] −
kuBtoAxin <BpAxin> [t] − kbAPCtoAxin <APC> [t] <BpAxin> [t] − kbApCptoB <APCp> [t] <BpAxin> [t] +

$$kuAxintoG \langle BpAxinG\rangle\ [t] \frac{kUbiquitination \langle BpAxin\rangle\ [t]\ \langle bTrCP\rangle\ [t]}{KmUbiquitination+\langle BpAxin\rangle\ [t]} - kbAxintoG \langle BpAxin\rangle\ [t]\ \langle G\rangle\ [t]$$

<BpAxinG>'[t] == kuAPCtoAxin <APCBpAxinG> [t] + kuAPCtoAxin <APCpBpAxinG> [t] + kpGwAxin <BAxinG> [t]
kbBtoAxin <AxinG> [t] <Bp> [t] − kpGwAxin <BpAxinG> [t] − kuAxintoG <BpAxinG> [t]
kuBtoAxin <BpAxinG> [t] − kbAPCtoAxin <APC> [t] <BpAxinG> [t] − kbAPCtoAxin (APCp> [t] <BpAxinG> [t]

$$\frac{kUbiquitination \langle BpAxinG\rangle\ [t]\ \langle bTrCP\rangle\ [t]}{KmUbiquitination+\langle BpAxinG\rangle\ [t]} kbAxintoG \langle BpAxin\rangle\ [t]\ \langle G\rangle\ [t]$$

<BpAxinp>'[t] == kuAPCtoAxin <APCBpAxinp> [t] + kuAPCptoB <APCpBpAxinp> [t] +
kbBtoAxinp <Axinp> [t] <Bp> [t] − kuBtoAxinp <BpAxinp> [t] − kbAPCtoAxin <APC> [t] <BpAxinp> [t]
kbAPCptoB <APCp> [t] <BpAxinp> [t] + kuAxintoG <BpAxinpG> [t] −

$$\frac{kubiquitination \langle BpAxinp\rangle\ [t]\ \langle bTrCP\rangle\ [t]}{KmUbiquitination+\langle BpAxinp\rangle\ [t]} - kbAxintoG \langle BpAxinp\rangle\ [t]\ \langle G\rangle\ [t]$$

<BpAxinpG>'[t] == kuAPCtoAxin <APCBpAxinpG> [t] +
kuAPCptoAxin <APCpBpAxinpG> [t] + kpGwAxin <BAxinpG> [t] + kbBtoAxinp <AxinpG> [t] <Bp> [t] +
kpGwAxin <BpAxinG> [t] − kuAxintoG <BpAxinpG> [t] − kuBtoAxinp <BpAxinpG> [t]
kbAPCtoAxin <APC> [t] <BpAxinpG [t] − kbAPCtoAxin <APCp> [t] <BpAxinpG> [t]

$$\frac{kUbiquitination \langle BpAxinpG\rangle\ [t]\ \langle bTrCP\rangle\ [t]}{KmUbiquitination+\langle BpAxinpG\rangle\ [t]} + kbAxintog \langle BpAxinp\rangle\ [t]\ \langle G\rangle\ [t]$$

<BpBpTCFcMycGene)'[t] == −ktranscriptioncMyc <BpBPTCFcMycGene> [t]
kuBtoTCFcMycGene2 <BpBpTCFcMYcGene> [t] + kbBtoTCFcMycGene2 <Bpnuclear> [t] <BpTCFcMcGene> [t]

<BpBTCFcMycGene>'[t] ==
−2 kuBtoTCFcMycGene2 <BpBpTCFcMycGene> [t] + kbBtoTCFcMycGene2 <Bpnuclear> [t] <BpTCFcMycGene) [t]
kbBtoTCFcMycGene2 <Bpnuclear> [t] <BTCFcMycGene> [t]

TABLE 4-continued

Table of Differential equations for Wnt β-catenin Network

<BpHDACGroucho)'[t] ==
−kuHDAcGrouchotoB <BpHDACGroucho> [t] + kbHDACGroucbotoB <Bpnuclear> [t] (HDACGroucho) [t]

$$<Bpnuclear>'[t] == \frac{kBtcNucleus <Bp> [t]}{KmBtoNucleus+ <Bp> [t]}$$

kuBtoTCFcMycGene2 <BpBpTCFcMycGene) t] + kuBtoTCFcMycGene2 <BpBTCFcMycGene> [t] +

$$kuHDACGrouchotoB <BpBDACGroucho> [t] - \frac{kBtocytoplasm <Bpnuclear> [t]}{KmBtocytoplasm+ <Bpnuclear)[t]}$$

kuBtoTCFcMyoGene <BpTCFcMycGene) [t] − kbBtoTCFcMycGene2 <Bpnuclear> [t] <BpTCFcMycGene) [t] −
kbBtoTCFcMyoGene2 <Bpnuclear> [t] <BTCFcMycGene> [t] − kbHDACGrouchotoB <Bpnuclear> [t] (HDACGroucho) [t] −
kbBtoTCFcMycGene <Bpnuclear> [t] <TCFcMycGene> [t]

<BpTCFMycGene>'[t] ==
kuBtoTCFcMycGene2 <BpBpTCFcMycGene> [t] + kuBtoTCFcMycGene2 <BpBTCFcMycGene> [t] −
kuBtoTCFcMycGene <BpTCFcMycGene> [t] − kbBtoTCFcMycGene2 <Bnuclear> [t] <BpTCFcMycGene) [t] −
kbBtoTCFcMycGene2 <Bpnuclear> [t] <BpTCFcMycGene> [t] + kbBtoTCFcMycGene <Bpnuclear> [t] (TCFcMycGene) [t]

BpAxinpG>'[t] == kuAPCtoAxin <APCBpAxinpG> [t] +
kuAPCptoAxin <APCpBpAxinpG> [t] + kpGwAxin <BAxinpG> [t] + kbBtoAxinp <AxinpG> [t] <Bp> [t] +
kpGwAxin <BpAxinG> [t] − kuAxintoG <BpAxinpG> [t] − kuBtoAxinp <BpAxinpG> [t] −
kbAPCtoAxin <APC> [t] <BpAxinpG> [t] − kbAPCtoAxin <APCp> [t] <BpAxinpG> [t] −

$$\frac{kUbiquitination <BpAxinpG> [t] <bTrCP> [t]}{KmUbiquitination+ <BpAxinpG> [t]} + kbAxintoG <BpAxinp> [t] <G> [t]$$

<BpBpTCFcMycGene>'[t] == −ktranscriptioncMyc <BpBpTCFcMycGene> [t] −
kuBtoTCFcMycGene2 <BpBpTCFcMycGene> [t] + kbBtoTCFcMycGene2 <Bpnuclear> [t] <BpTCFcMycGene) [t]

<BpBTCFcMycGene)'[t] ==
−2 kuBtoTCFCFcMycGene2 (<BpBTCFcMycGene> [t] + kbBtoTCFcMycGene2 <Bnuclear) [t] <BpTCFcMycGene> [t] +
kbBtoTCFcMycGene2 <Bpnuclear> [t] <BTCFcMycGene> [t]

<BpHDACGroucho>'[t] ==
−kuHDACGrouchotoB <BpHDACGroucho> [t] + kbHDACGrouchotoB <Bpnuclear> [t] <HDACGroucho> [t]

$$<Bpnuclear>'[t] == \frac{kBtoNucleus <Bp> [t]}{KmBtoNucleus+ <Bp> [t]} +$$

kuBtoTCFcMycGene2 <BpBpTCFcMycGene> [t] + kuBtoTCFcMycGene2 <BpBTCFcMycGene> [t] +

$$kuHDACGrouchotoB <BpHDACGroucho> [t] - \frac{kBtocytoplasm <Bpnuclear> [t]}{KmBtocytoplasm+ <Bpnuclear> [t]} +$$

kuBtoTCFcMycGene <BpTCFcMycGene> [t] − kbBtoTCFcMycGene2 <Bpnuclear> [t] <BpT'CFcMycGene) [t] −
kbBtoTCFcMycGene2 <Bpnuclear> [t] <BTCFcMycGene) [t] − kbHDACGrouchotoB <Bpnuclear) [t] <HDACGroucho> [t] −
kbBtoTCFcMycGene <Bpnuclear> [t] (TCFcMycGene) [t]

<'BpTCFcMycGene>'[t] ==
kuBtoTCFcMycGene2 <BpBpTCFcMycGene> [t] + kuBtoTCFcMycGene2 <BpBTCFcMycGene) [t] −
kuBtoTCFcMycGene <BpTCFcMycGene> [t] − kbBtoTCFcMycGene2 <Bnuclear> [t] <BpTCFcMycGene> [t] −
kbBtoTCFcMycGene2 <Bpnuclear> [t] <BpTCFcMycGene> [t] + kbBtoTCFcMycGene <Bpnuclear> [t] − <TCFcMycGene> [t]

BTCFcMycGene>'[t] ==
kuBtoTCFcMycGene2 <BBTCFcMycGene> [t] + kuBtoTCFcMycGene2 <BpBTCFcMycGene> [t] −
kuBtoTCFcMycGene <BTCFcMycGene> [t] − kbBtoTCFcMycGene2 <Bnuclear> [t] <BTCFcMycGene> [t] −
kbBtoTCFcMycGene2 <Bpnuclear> [t] <BTCFcMycGene> [t] + kbBtoTCFcMycGene <Bnuclear> [t] TCFcMycGene) [t]

$$<bTrCP>'[t] == -kdbTrCP <bTrCP> [t] \frac{kUbiquitination <APCBpAxin> [t] <bTrCP> [t]}{KmUbiquitination+ <APCBpAxin> [t]} -$$

$$\frac{kUbiquitination <APCBpAxinG> [t] <bTrCP> [t]}{KmUbiquitination+ <APCBpAxinG> [t]} - \frac{kUbiquitination <APCBpAxinp> [t] <bTrCP> [t]}{KmUbiquitination+ <APCBpAxinp> [t]} -$$

$$\frac{kUbiquitination <APCBpAxinG> [t] <bTrCP> [t]}{KmUbiquitination+ <APCBpAxinG> [t]} - \frac{kUbiquitination <APCBpAxinpG> [t] <bTrCP> [t]}{KmUbiquitination+ <APCpBpAxinp> [t]}$$

TABLE 4-continued

Table of Differential equations for Wnt β-catenin Network $$\frac{kUbiquitination <APCpBpAxinG> [t] <bTrCP> [t]}{KmUbiquitination+ <APCpBpAxinG> [t]} - \frac{kUbiquitination < APCpBpAxinp> [t] < bTrCP> [t]}{KmUbiquitination+ < APCpBpAxinp> [t]} -$$

$$\frac{kUbiquitination <APCpBpAxinpG> [t] <bTrCP> [t]}{KmUbiquitination+ <APCpBpAxinpG> [t]} - \frac{kUbiquitination <BpAxinp> [t] <bTrCP> [t]}{KmUbiquitination+ <BpAxinp> [t]} -$$

$$\frac{kUbiquitination <BpAxinpG> [t] <bTrCP> [t]}{KmUbiquitination+ <BpAxinpG> [t]} - \frac{kUbiquitination <BpAxinpG> [t] < bTrCP> [t]}{KmUbiquitination+ < BpAxinp> [t]} -$$

$$\frac{kUbiquitination <BpAxinpG> [t] <btTrCP> [t]}{KmUbiquitination+ <BpAxinpG> [t]} + ktbTrCP <bTrCPmRNA> [t]$$

<bTrCPBpUbUb>'[t] ==

$$\frac{kUbiquitination<APCBpAxinG> [t]bTrCP[t]}{KmUbiquitination+ <APCBpAxin> [t]} + \frac{kUbiquitination<APCBpAxinG> [t] <bTrCP> [t]}{KmUbiquitination+ <APCBpAxinG> [t]} +$$

$$\frac{kUbiquitination<APCBpAxinp> [t] <bTrCP> [t]}{KmUbiquitination+ <APCBpAxinp> [t]} + \frac{kUbiquitination<APCBpAxinpG>[t] <bTrCP> [t]}{KmUbiquitination+ <APCpBpAxinpG> [t]} +$$

$$\frac{kUbiquitination<APCpBpAxinp> [t] <bTrCP> [t]}{KmUbiquitination+ <APCpBpAxinp> [t]} + \frac{kUbiquitination<APCpBpAxinpG> [t] <bTrCP> [t]}{KmUbiquitination+ <APCpBpAxinpG> [t]} +$$

$$\frac{kUbiquitination<APCpBpAxinp> [t] <bTrCP> [t]}{KmUbiquitination+ <APCpBpAxinp> [t]} + \frac{kUbiquitination<APCpBpAxinpG> [t] <bTrCP> [t]}{KmUbiquitination+ <APCpBpAxinpG> [t]} +$$

$$\frac{kUbiquitination<BpAxin> [t] <bTrCP> [t]}{KmUbiquitination+ <BpAxin> [t]} + \frac{kUbiquitination<BpAxinG> [t] <bTrCP> [t]}{KmUbiquitination+ <BpAxinG> [t]} +$$

$$\frac{kUbiquitination<BpAxinp> [t] <bTrCP> [t]}{KmUbiquitination+ <BpAxinp> [t]} + \frac{kUbiquitination<BpAxinpG> [t] <bTrCP> [t]}{KmUbiquitination+ <BpAxinpG> [t]} +$$

<bTrCPGene>'[t] == 0

<BTrCPmRNA>'[t] == ktbTrCPmRNA <bTrCPGene) [t] – kdbTrCPMRNA <bTrCPmRNA> [t] –

$$ktbTrCP <bTrCPmRNA> [t] + \frac{kenhancebTrCP <Bnuclear> [t](Intermediary)[t]}{KmenhancebTrCP+ <Bnuclear> [t]}$$

(cMycmRNA>'[t] == ktranscriptioncMyc <BBTCFcMycGene> [t] + ktranscriptioncMyc <BpBpTCFcMycGene) [t] + ktranscriptioncMyc <BpBTCFcMycGene) [t] – kdcMycmRMA (cMycmRNA> [t]

<G>'[t] == kuAxintoG <APCAxinG> [t] + kuAxintoG <APCAxinpG> [t] +
kuAxintoG <APCBAxinG> [t] + kuAxintoG <APCBAxinpG> [t] + kuAxintoG <APCBpAxinG> [t] +
kuAxintoG <APCBpAxinpG> [t] + kuAxintoG <APCpAxinG> [t] + kuAxintoG <APCpAxinpG> [t] +
kuAxintoG <APCpBAxinG> [t] + kuAxintoG <APCpBAxinpG> [t] + kuAxintoG <APCpBpAxinG> [t] +
kuAxintoG <APCpBpAxinpG> [t] + kuAxintoG <AxinG> [t] + kuAxintoG <AxinpG> [t] +
kuAxintoG <BAxinG> [t] + kuAxintoG <BAxinpG> [t] + kuAxintoG <BpAxinG> [t] +
kuAxintoG <BpAxinpG> [t] – kbAxintoG <APCAxin> [t] <G> [t] – kbAxintoG <APCAxinp> [t] <G> [t] –
kbAxintoG <APCBAxin> [t] <G> [t] – kbAxintoG <APCBAxinp> [t] –<G> [t] –
kbAxintoG <APCBpAxin> [t] <G> [t] – kbAxintoG <APCBpAxinp> [t] <G> [t] –
kbAxintoG <APCpAxin> [t] <G> [t] – kbAxintoG <APCpAxinp> [t] <G> [t] –
kbAxintoG <APCpBAxin> [t] <G> (t) – kbAxintoG <APCpBAxinp> [t] <G> [t] –
kbAxintoG <APCpBpAxin> [t] <G> [t] – kbAxintoG <APCpBpAxinp> [t] <G> [t] –
kbAxintoG <Axin> [t] <G> [t] – kbAxintoG <Axinp> [t] <G> [t] – kbAxintoG <BAxin> [t] <G> [t] –
kbAxintoG <BAxinp> [t] <G> [t] – kbAxintoG <BpAxin> [t] <G> [t] – kbAxintoG <BpAxinp> [t] <G> [t]

(HDACGroucho>'[t] == kuHDACGrouchotoB <BHDACGroucho> [t] +
kuBDACGrouchotoB <BpHDACGroucho> [t] – kbHDACGrouchotoB <Bnuclear> [t] <HDACGroucho> [t] –
kbBDACGrouchotoB <Bpnuclear> [t] <HDACGroucho> [t] +
kuHDACGrouchotoTCFcMycGene <HDACGrouchoTCFcMycGene> [t] –
kbBDACGrouchotoTCFcMycGene <HDACGroucho> [t] <TCFcMycGene> [t]

<bTrCPGene>'[t] == 0

TABLE 4-continued

Table of Differential equations for Wnt β-catenin Network

<bTrCPmRNA>'[t] == ktbTrCPmRNA <bTrCPGene) [t] – kdbTrCPMRNA <bTrCPmRMA> [t] –

$$ktbTrCP \ <bTrCPmRNA> \ [t] + \frac{kenhancebTrCP \ <bnuclear> \ [t](Intermediary)[t]}{KmenhancebTrCP+ \ <Bnuclear> \ [t]}$$

<cMycmRNA>'[t] ==
ktranscriptioncMyc <BBTCFcMycGene> [t] + ktranscriptioncMyc <BpBpTCFcMycGene> [t] +
ktranscriptioncMyc <BpBTCFcMycGene> [t] – kdcMycmRNA <cMyanRNA> [t]

<G>'[t] == kuAxintoG <APCAxinG> [t] + kuAxintoG <APCAxinpG> [t] +
kuAxintoG <APCBAxinG> [t] + kuAxintoG <APCBAxinpG> [t] + kuAxintoG <APCBpAxinG> [t] +
kuAxintoG <APCBpAxinpG> [t] + kuAxintoG <APCpAxinG> [t] + kuAxintoG <APCpAxinpG> [t] +
kuAxintoG <APCpBAxinG> [t] + kuAxintoG <APCpBAxinpG> [t] + kuAxintoG <APCpBpAxinG> [t] +
kuAxintoG <APCpBpAxinpG> [t] + kuAxintoG <AxinG> [t] + kuAxintoG <AxinpG> [t] +
kuAxintoG <BAxinG> [t] + kuAxintoG <BAxinpG> [t] + kuAxintoG <BpAxinG> [t] +
kuAxintoG <BpAxinpG> [t] – kbAxintoG <APCAxin> [t] <G> [t] – kbAxintoG <APCAxinp> [t] <G> [t] –
kbAxintoG <APCBAxin> [t] <G> [t] – kbAxintoG <APCBAxinp [t] <G> [t] –
kbAxintoG <APCBpAxin> [t] <G> [t] – kbAxintoG <APCBpAxinp> [t] <G> [t] –
kbAxintoG <APCpAxin> [t] <G> [t] – kbAxintoG <APCpAxinp> [t] <G> [t] –
kbAxintoG <APCpBAxin> [t] <G> [t] – kbAxintoG <APCpBAxinp> [t] <G> [t] –
kbAxintoG <APCpBpAxin> [t] <G> [t] – kbAxintoG <APCpBpAxinp> [t] <G> [t] –
kbAxintoG <Axin> [t] <G> [t] – kbAxintoG <Axinp> [t] <G> [t] – kbAxintoG <BAxin> [t] <G> [t] –
kbAxintoG <BAxinp> [t] <G> [t] – kbAxintoG <BpAxin> [t] <G> [t] – kbAxintoG <BpAxinp> [t] <G> [t]

<HDACGroucho>'[t] == kuHDACGrouchotoB <BHDACGroucho> [t] +
kuHDACGrouchotoB <BpHDACGroucho> [t] – kbHDACGrouchotoB <Bnuclear> [t] <HDAGroucho> [t] –
kbHDACGrouchotoB <Bpnuclear> [t] <HDACGroucho> [t] +
kuHDACGrouchotoTCFcMycGene <HDACGrouchoTCFcMycGene> [t] –
kbHDACGrouchotoTCFcMycGene <HDACGroucho> [t] <TCFcMycGene> [t]

<HDACGrouchoTCFcMycGene>'[t] == –kuHDACGrouchotoTCFcMycGene <HDACGrouchoTCFcMycGene> [t] +
kbHDACGrouchotoTCFcMycGene <HDAOGroucho> [t] <TCFcMycGene> [t]

<Intermediary>'[t] == 0

<Source>'[t] == 0

<SourceB>'[t] == 0

<TCFcMycGene>'[t] == kuBtoTCFcMycGene <BpTCFcMycGene> [t] +
kuBtoTCFcWcGene <BTCFcMycGene> [t] – kuHDACGrouchotoTCFcMycGene <HDACGrouchoTCFcMycGene> [t] –
kbBtoTCFcMycGene <Bnuclear> [t] <TCFcMycGene> [t] – kbBtoTCFcMycGene <Bpnuclear> [t] <TCFcMycGene) [t] –
kbHDACGrouchotoTCFcMycGene <HDACGroucho> [t] <TCFcMycGene> [t]

$$<zero>' \ [t] == \frac{kdAxin \ <Axin> \ [t]}{KdAxin+ \ <Axin> \ [t]} + \frac{kdAxinp \ <Axinp> \ [t]}{KdmAxinp+ \ <Axinp> \ [t]} + \frac{kdBalone \ <B> \ [t]}{KmBalone+ \ <B> \ [t]} + \frac{kdBalone \ <Bp> \ [t]}{KmBalone+ \ <Bp> \ [t]}$$

kdbTrCP <bTrCP> [t] + kdbTrCPMRNA <bTrCPmRNA> [t] + kdcMycmRNA <cMycmRNA> [t]

Simulations

The initial values of the kinetic parameters are chosen from the literature by incorporating time scale and expression information. For example, it is known that GSK3 phosphorylates Axin on a time scale of about 30 minutes, and hence a rate constant is chosen to reflect that time scale.

Figure 11:
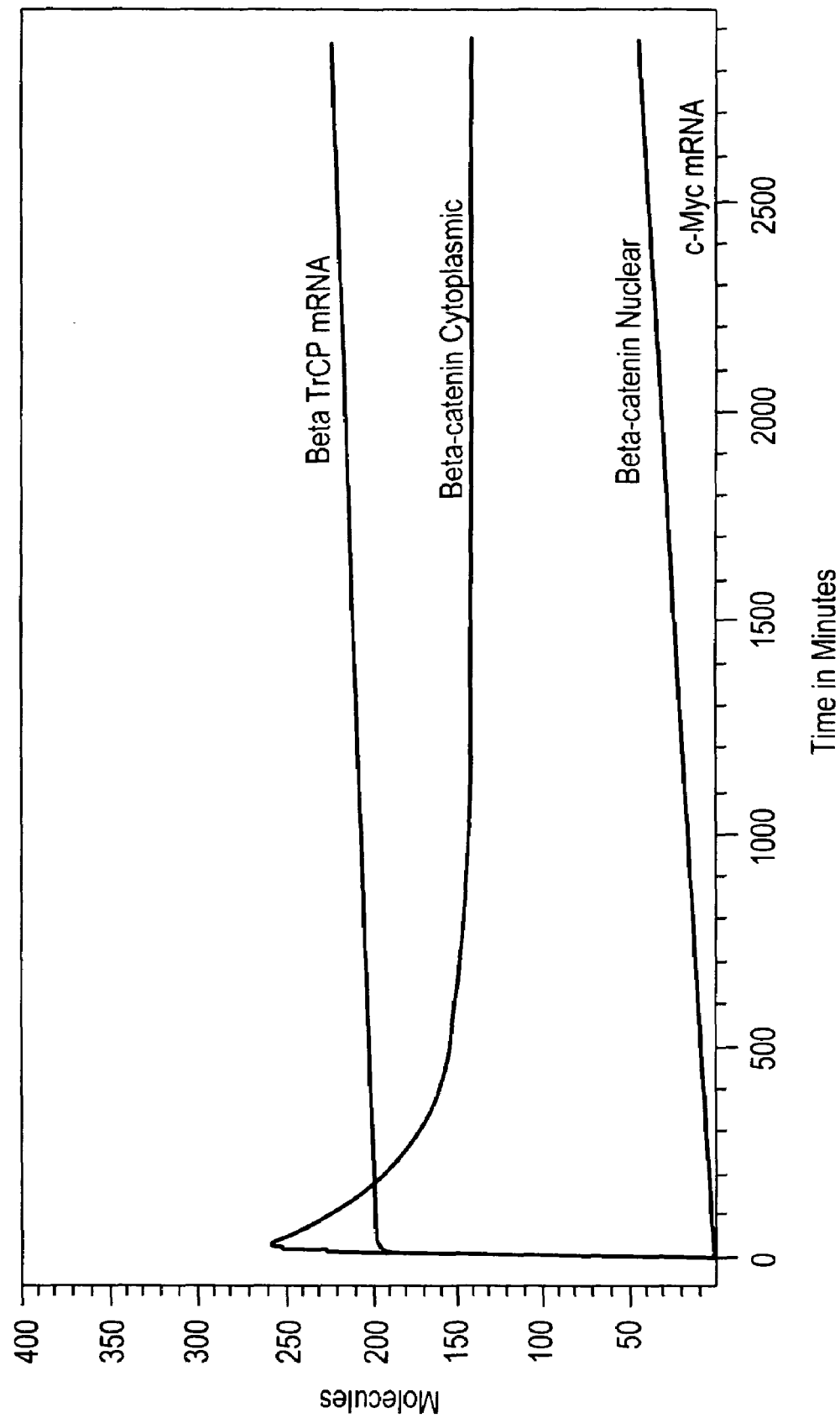
FIG. 11 is a time-series profile of the concentration of several components of a cell and represents the "normal" state of the cell.

Set forth below are deterministic and stochastic solutions of what is considered the "normal state" of the cell. Low levels of β-catenin and of β-catenin target genes such as c-Myc characterize the normal state. In the deterministic solution, the time series profile characterizes the "normal" state where the Axin degradation machinery keeps the levels of β-catenin low and consequently limits the levels of downstream targets such as the proto-oncogene c-Myc. This is shown in FIG. 11.

Figure 12:
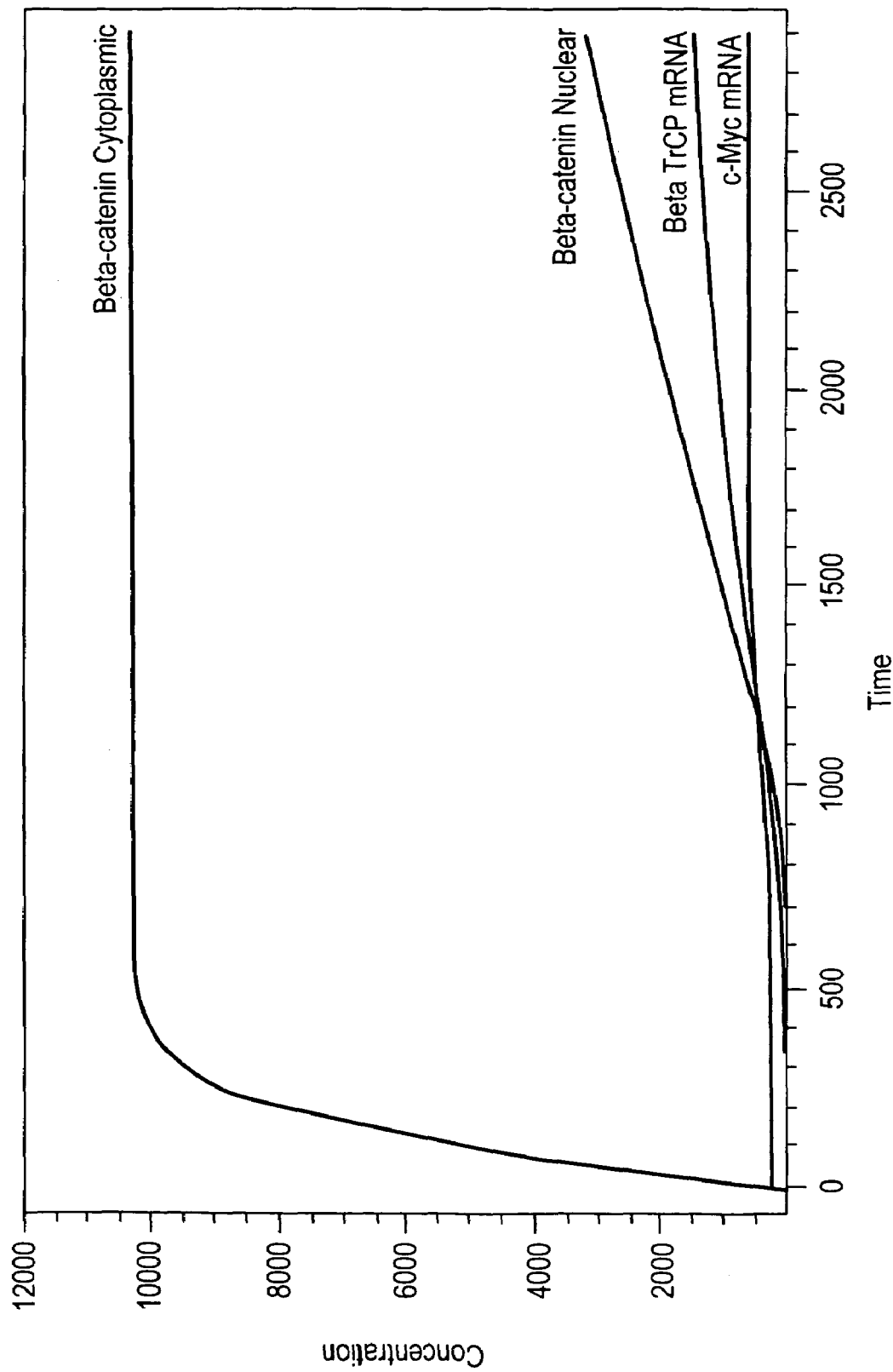
FIG. 12 is a time-series profile which represents the cancerous state of the cell.

Perturbations can be introduced to determine the relevant targets in the network and the effect they have on perturbing the network. For example, the binding rate of Axin to APC can be set to zero, thereby simulating the effects of a mutation in APC that prevents its binding to Axin. FIG. 12 depicts a time series profile which characterizes the "cancerous" state, for example, where a mutation in APC prevents Axin from effectively degrading β-catenin. This results in the up-regulation of c-Myc as well as higher levels of β-TrCP. In this case, the level of β-catenin rises in the cytoplasm and the nucleus and consequently c-Myc transcription rises as well.

EXAMPLE III

One or more components of a cell can be identified as putative targets for interaction with one or more agents within the simulation. This is achieved by perturbing the simulated network by deleting one or more components thereof, changing the concentration of one or more components thereof or modifying one or more of the mathematical equations representing interrelationships between two or more of said components. Alternatively, the concentrations of one or more of the several proteins and genes in the biochemical network are selectively perturbed to identify which ones of said proteins or genes cause a change in the time course of the concentration of a gene or protein implicated in a disease state of the cell.

Deleting One or More Components in the Network

Figure 13:
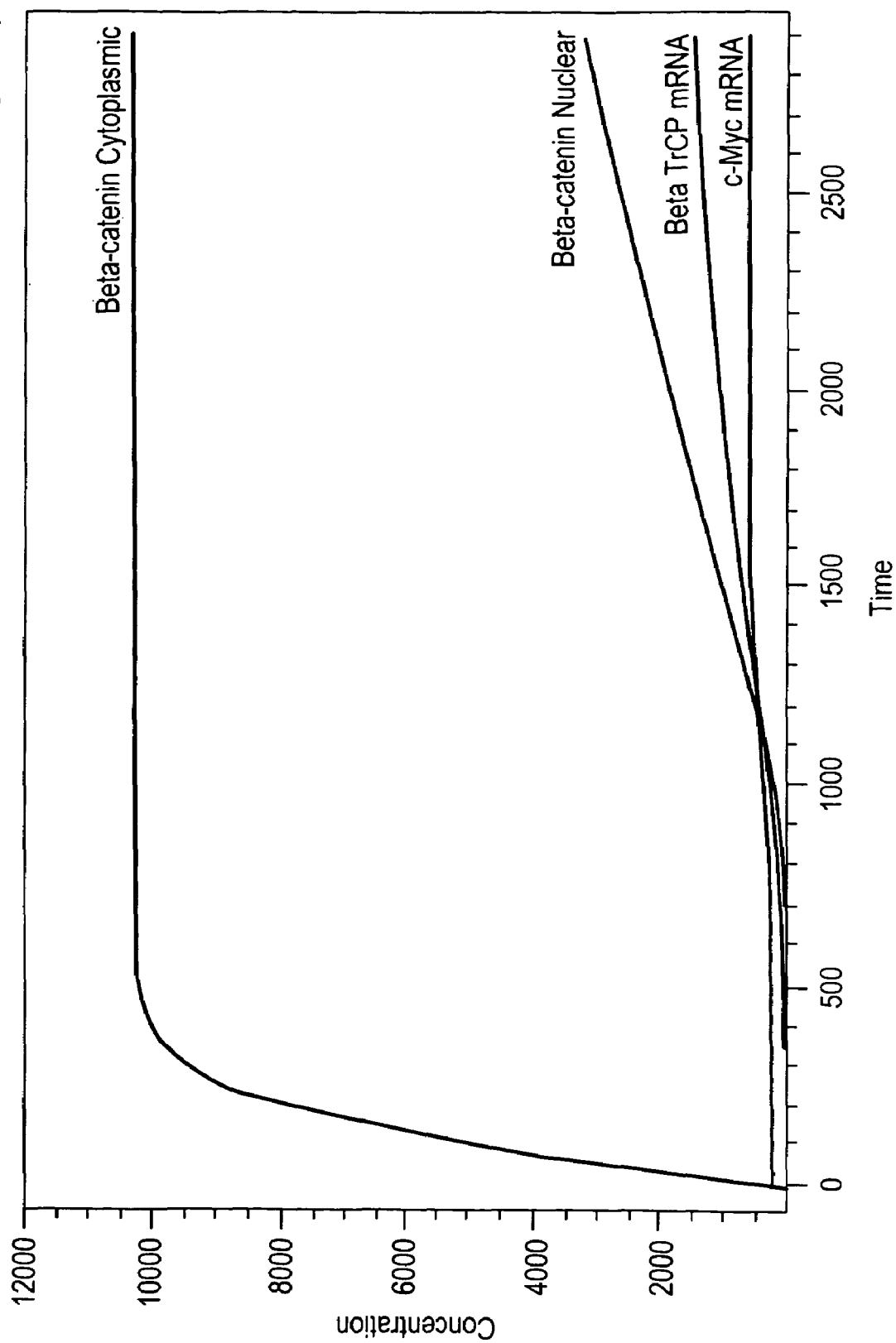
FIG. 13 is a time-series profile which shows the effect of deleting APC from the cell.

The APC protein is deleted by removing the protein from the set of equations in Example II and removing all of the chemical species formed and reactions that take place as a result of interactions with APC. The effect on the state of the cell is to raise the levels of β-catenin so that it continually activates downstream targets such as β-TrCP and c-Myc. This can be seen by comparing FIG. 13 with FIG. 11. APC is thus identified as an important component of the cell which is implanted in a disease state of the cell. When APC is "knocked" out it leads to a high level of β-catenin which can cause the development and progression of colon cancer. In the event that a mutation in APC prevents its interaction with the components in the cell, therapeutics can be sought to rectify this condition.

Figure 14:
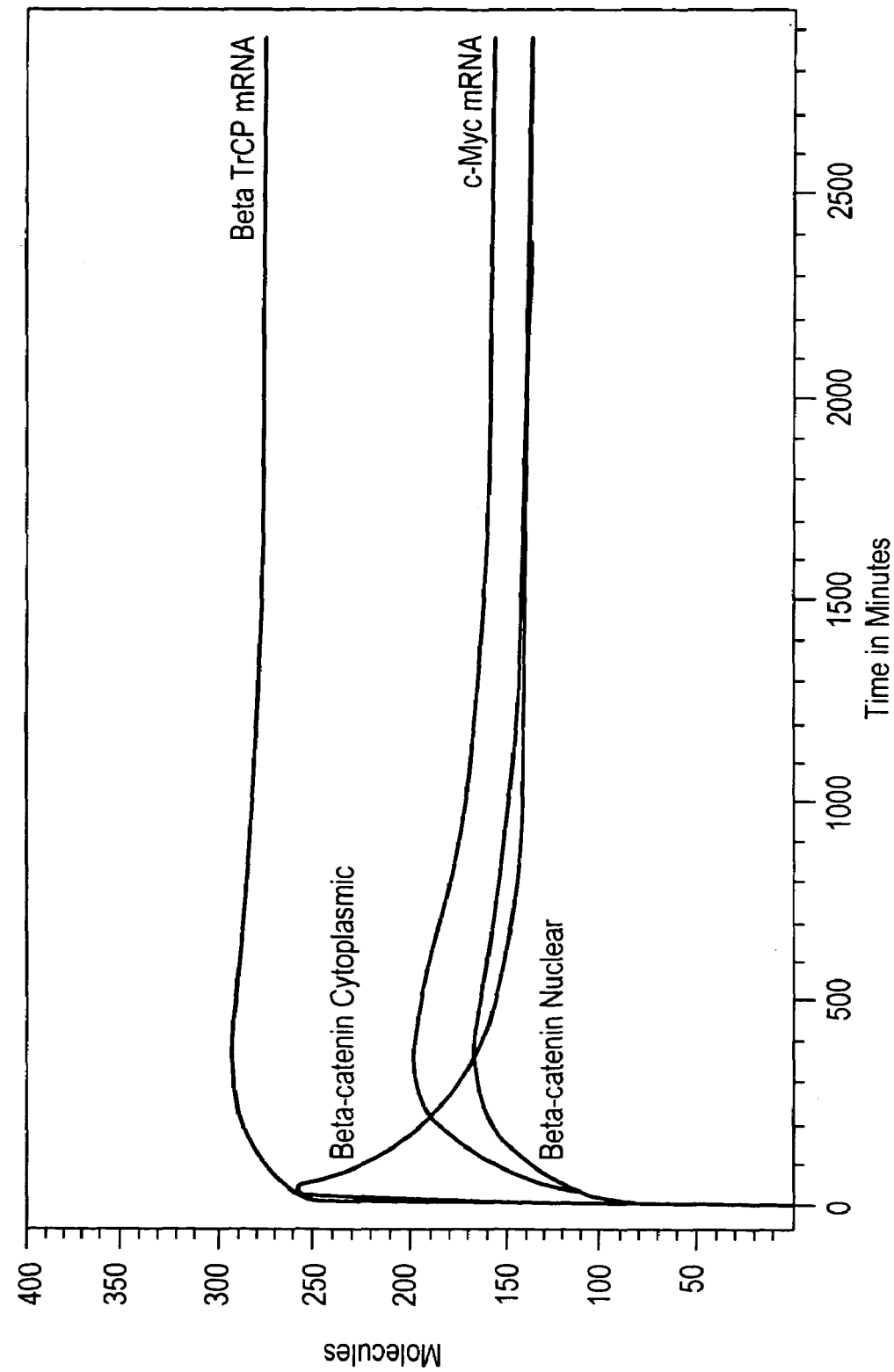
FIG. 14 is a time-series profile which shows the effect of deleting HDC from the cell.

HDAC, a protein that sequesters nuclear β-catenin and represses the c-Myc gene, is deleted by removing HDAC from the set of equations set forth in Example II and thereby removing all of the chemical species that are formed and reactions that take place as a result of interactions with HDAC. The effect on the state of the cell, as simulated, is an increase in the levels of c-Myc. This is shown in FIG. 14. HDAC is thus identified as an important target because when it is "knocked" out, high levels of c-Myc develop and this can lead to the development and progression of colon cancer. In the event that a mutation in HDAC prevents its interaction with the components in the cell, therapeutics can be sought to rectify this condition.

Changing the Concentrations of One or More the Components in the Network

Figure 15:
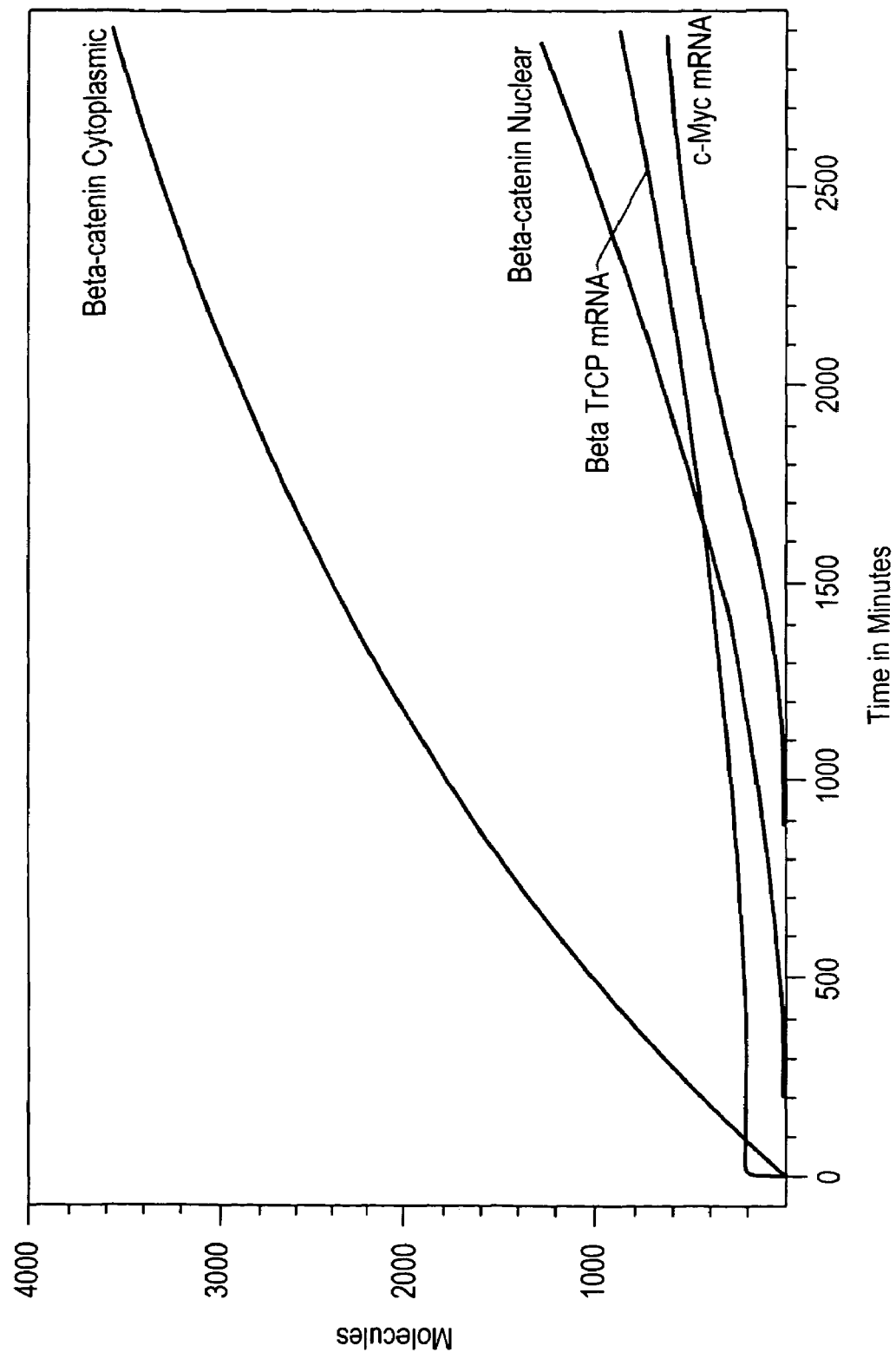
FIG. 15 is a time-series profile which shows the effect of adding Axin to the cancerous cell of FIG. 12.

Starting from the simulated cancerous state depicted in FIG. 12, the concentration of Axin is increased significantly above its normal levels. This results in the reduction of β-catenin levels. This is shown in FIG. 15. This identifies a cellular component, Axin, that can cause a reduction in the time course of the concentration of β-catenin.

Figure 16:
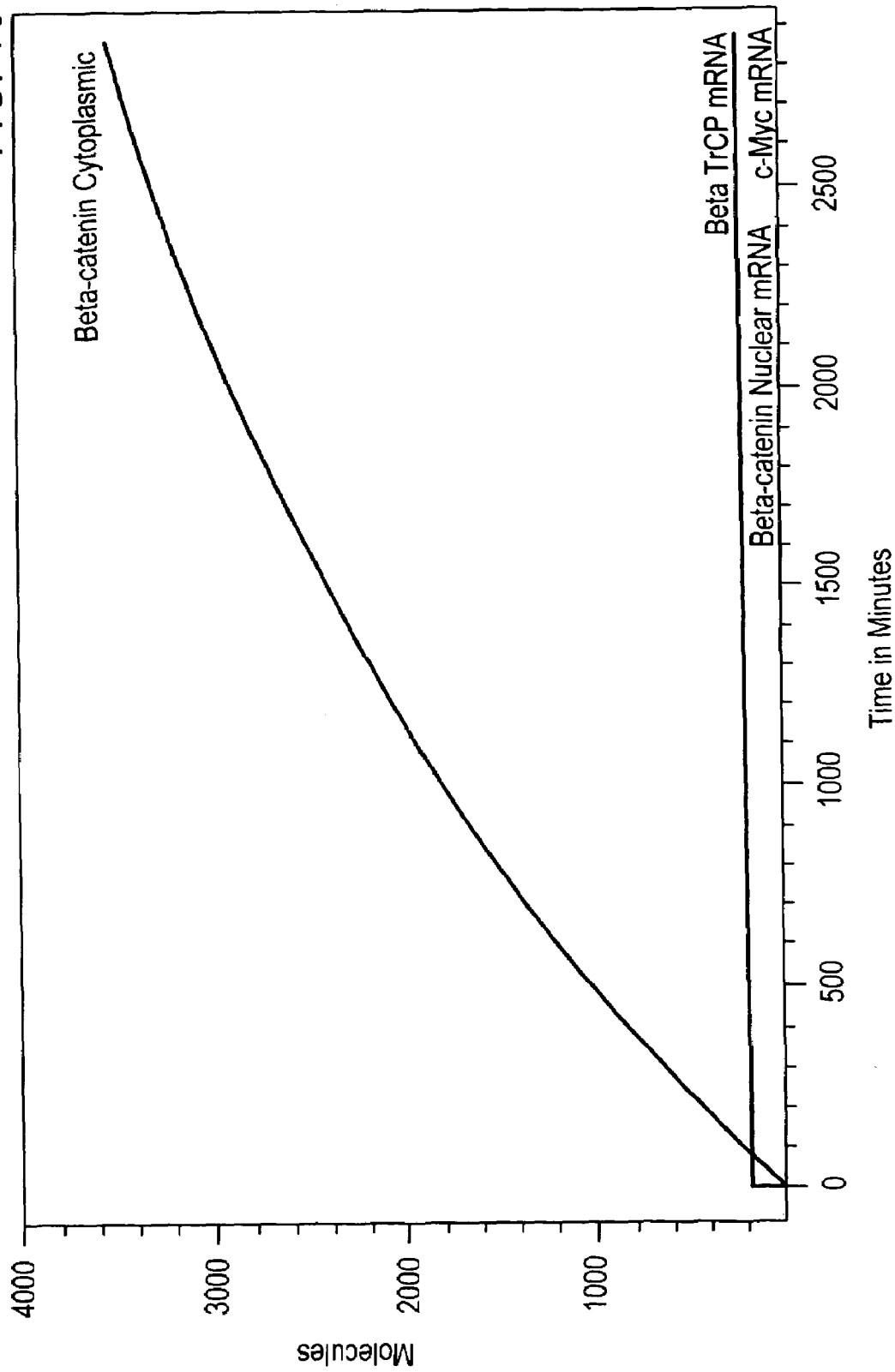
FIG. 16 is a time-series profile which shows the effect of adding HDAC to the cancerous cell of FIG. 12.

The levels of HDAC are then increased in the simulated cell to which Axin has been introduced. This lowers the concentrations of nuclear β-catenin and c-Myc. Both levels are lowered recreating a profile that corresponds to a "normal" cellular state. This is shown in FIG. 16. This identifies HDAC as an important component for control of a disease state.

Figure 17:
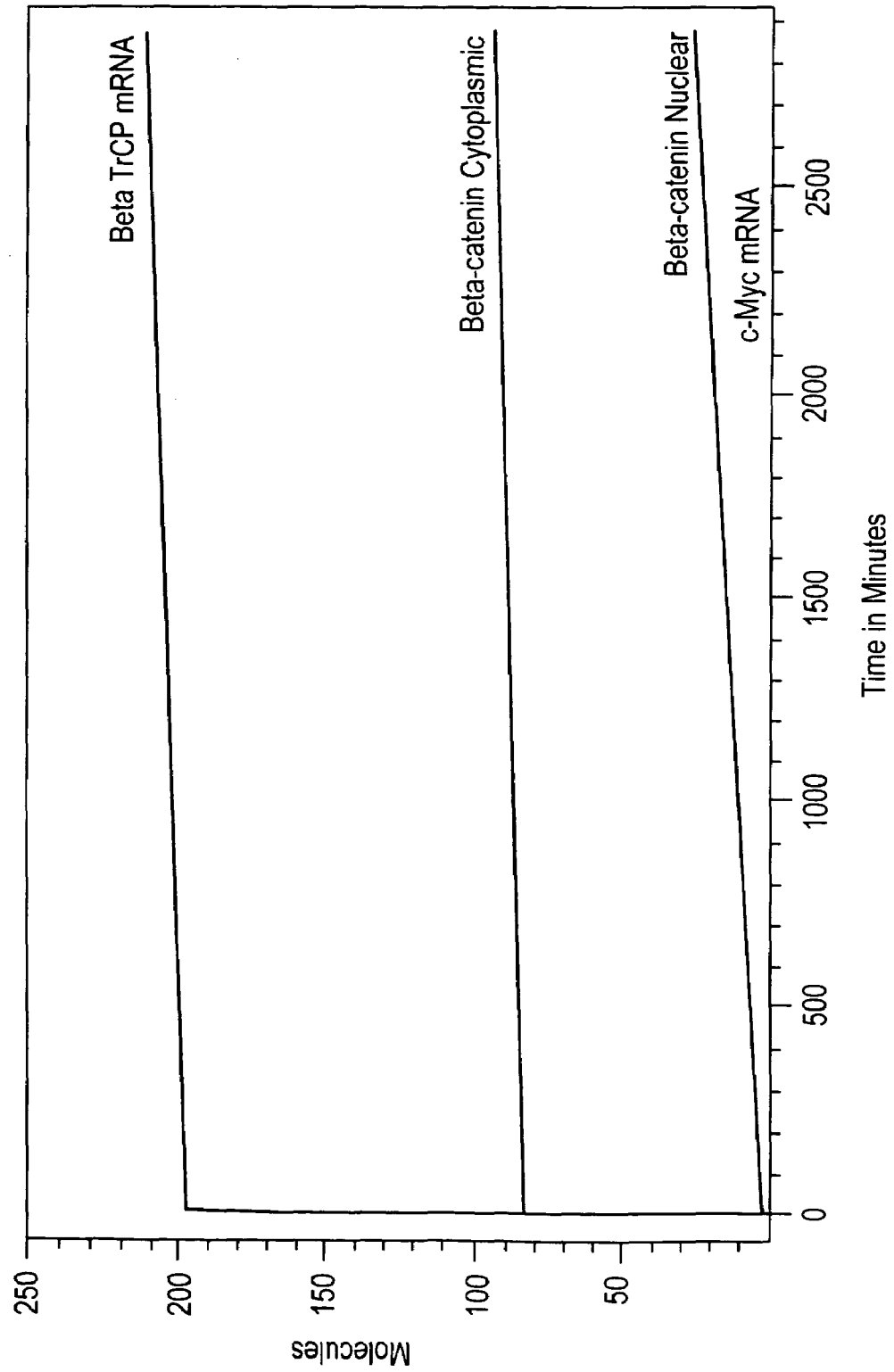
FIG. 17 is a time-series profile which shows the effect of adding Axin and GSK3 to the cancerous cell of FIG. 12.

Starting from the disease state of FIG. 12, the concentrations of Axin and GSK3 are perturbed by increasing their levels significantly above normal. The concentration of Axin is perturbed less than above so that β-catenin levels fall, but not as much. GSK3 concentration is then increased to further reduce β-catenin levels. The levels of β-catenin approach that of the normal state. This is shown in FIG. 17. This identifies Axin and GSK3 as two components which affect the time course of β-catenin.

Figure 18:
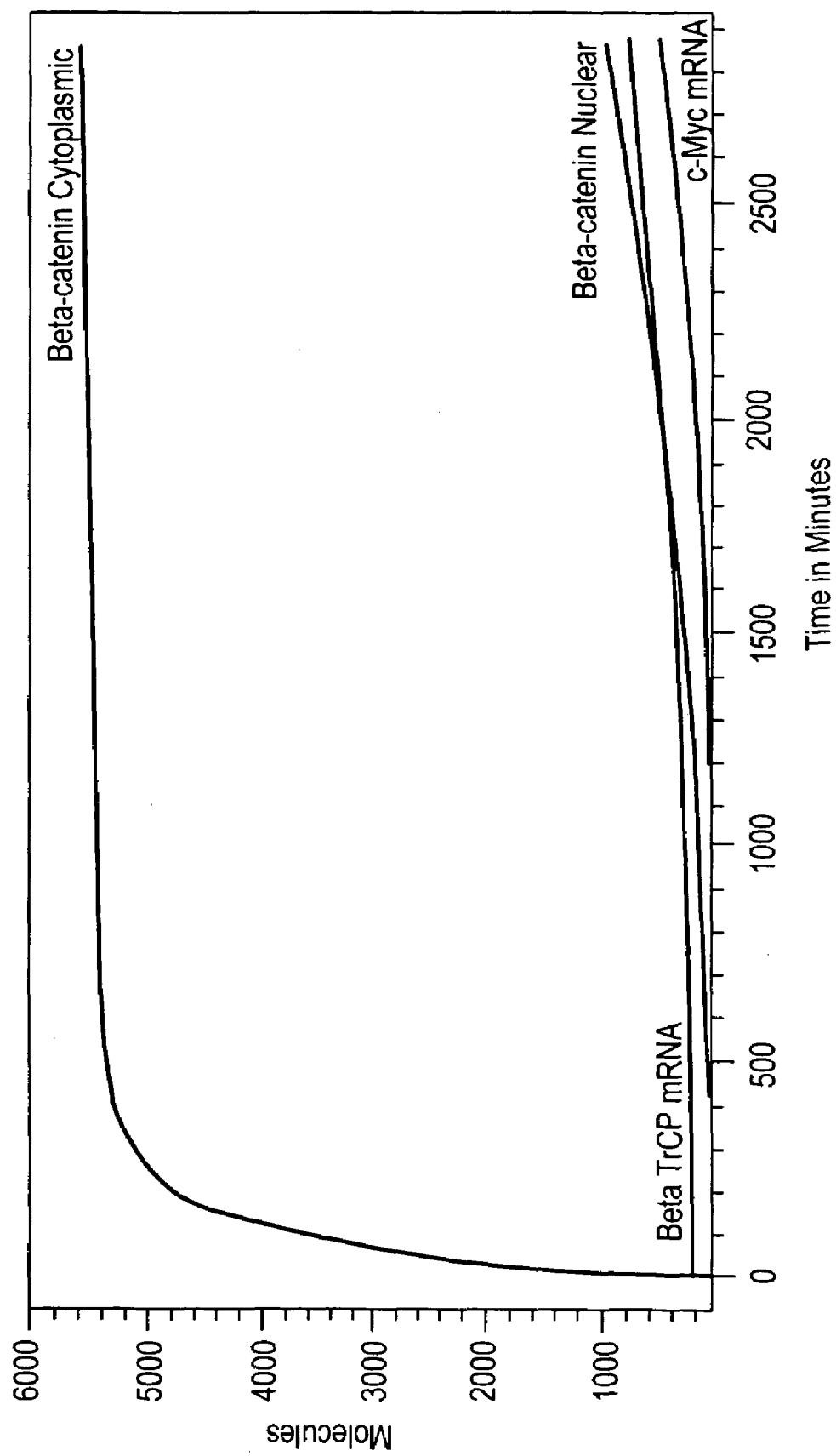
FIG. 18 is a time-series profile which shows the effect of adding Axin to the cancerous cell of FIG. 12.
Figure 19:
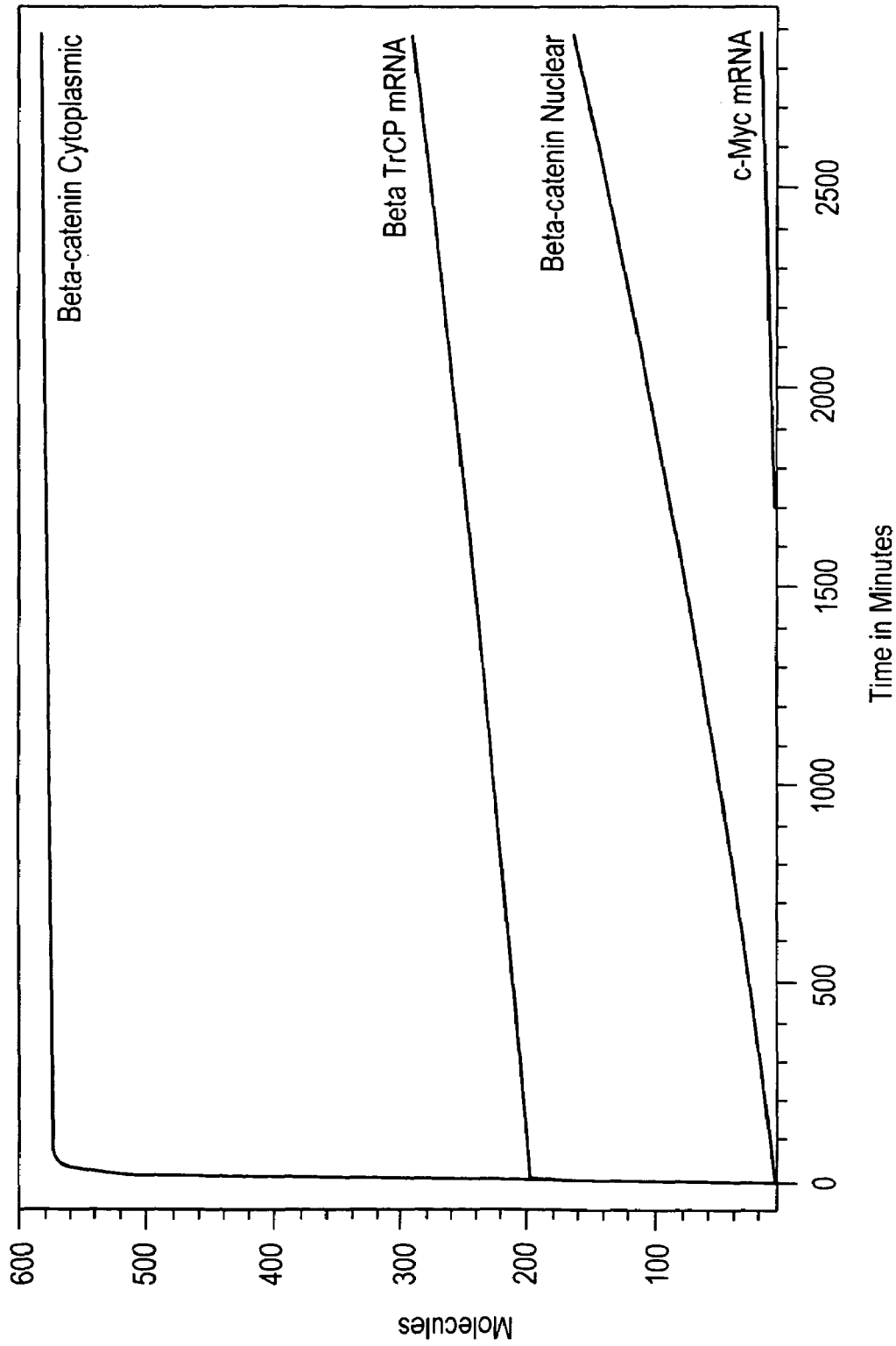
FIG. 19 is a time-series profile which shows the effect of adding GSK 3 to the already perturbed cell of FIG. 18.
Figure 20:
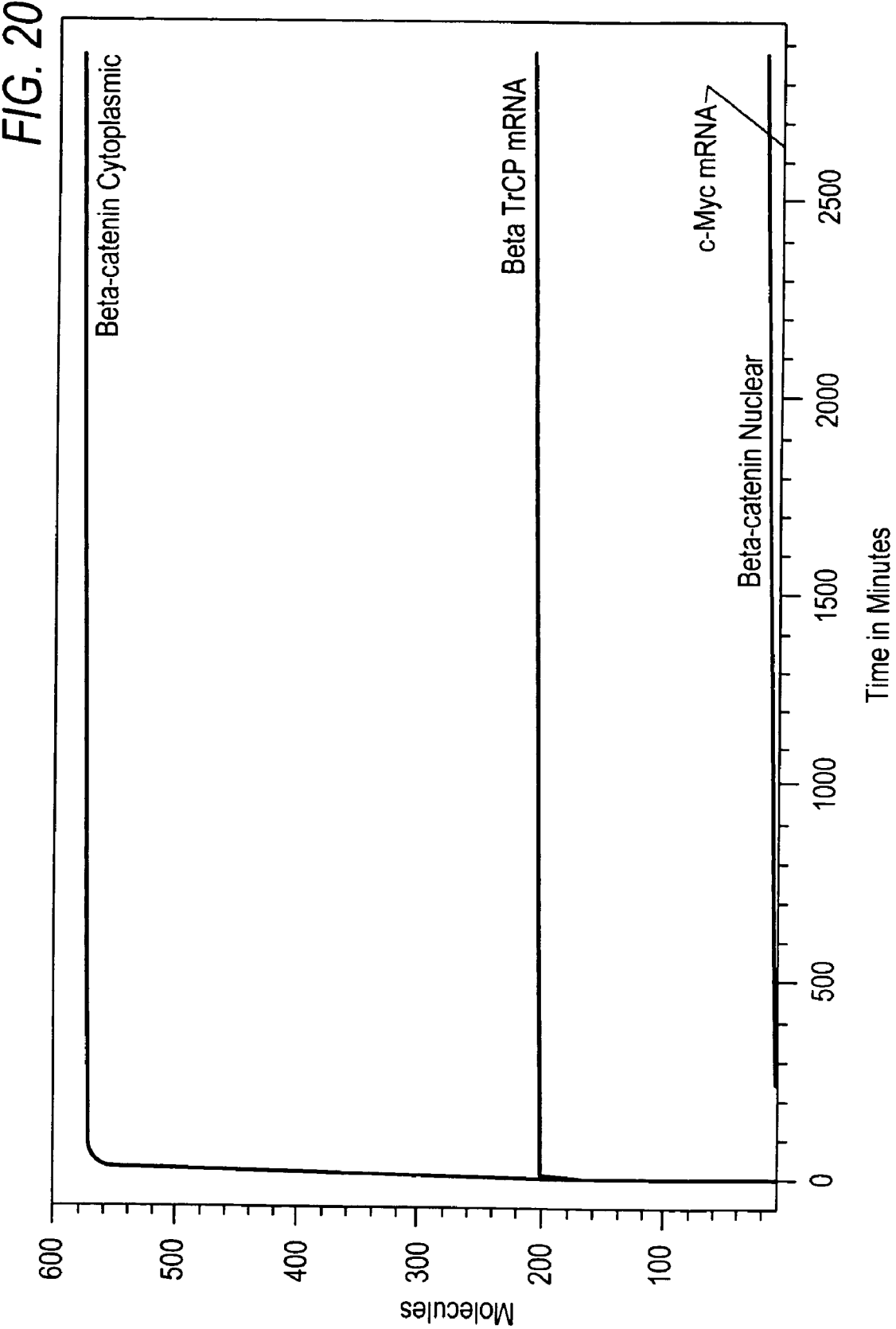
FIG. 20 is a time-series profile which shows the effect of adding HDAC to the twice perturbed cell of FIG. 19.

A further series of perturbations are made, each of the perturbations changing the concentration of a protein or gene in the network to a perturbed value to determine whether that protein or gene is implicated in causing a change in the time course of the concentration of a gene or protein implicated in a disease state of the cell. Starting from the disease state of FIG. 12, the concentrations of Axin and GSK3 are perturbed by increasing their levels significantly above normal. This is shown in FIGS. 18 and 19, respectively. The system is perturbed again by raising the levels of HDAC. This is shown in FIG. 20. Upon each perturbation, the levels of β-catenin are reduced in the cytoplasm and then in the nucleus resulting in reduced levels of c-Myc mRNA. This identifies Axin, GSK3, and HDAC in varying degrees, as causing a change in the time course of the concentration of the gene or protein implicated in the disease state.

Figure 21:
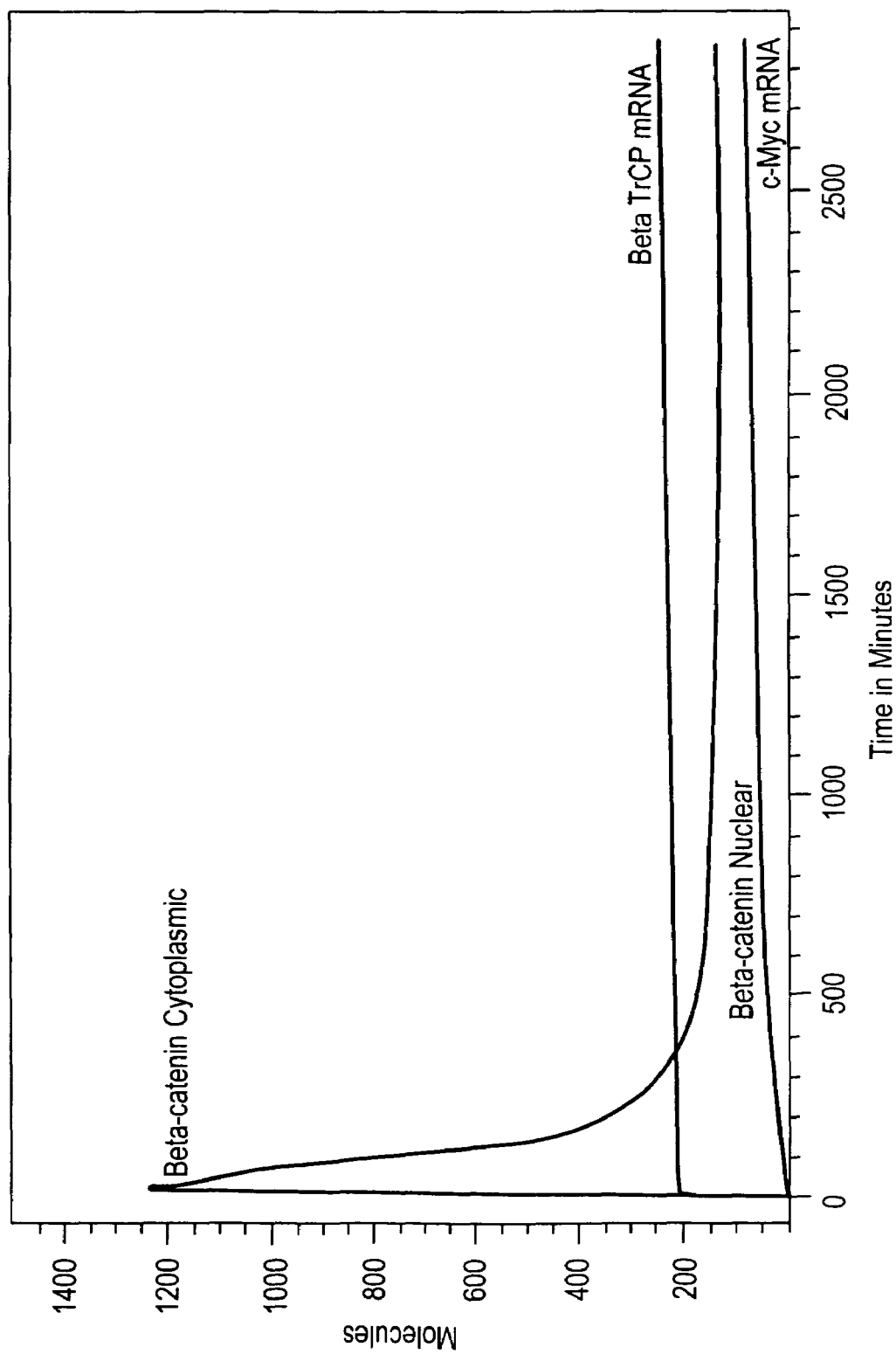
FIG. 21 is a time-series profile which shows the effect of reducing the concentration of Axin to zero in the normal cell of FIG. 11.
Figure 22:
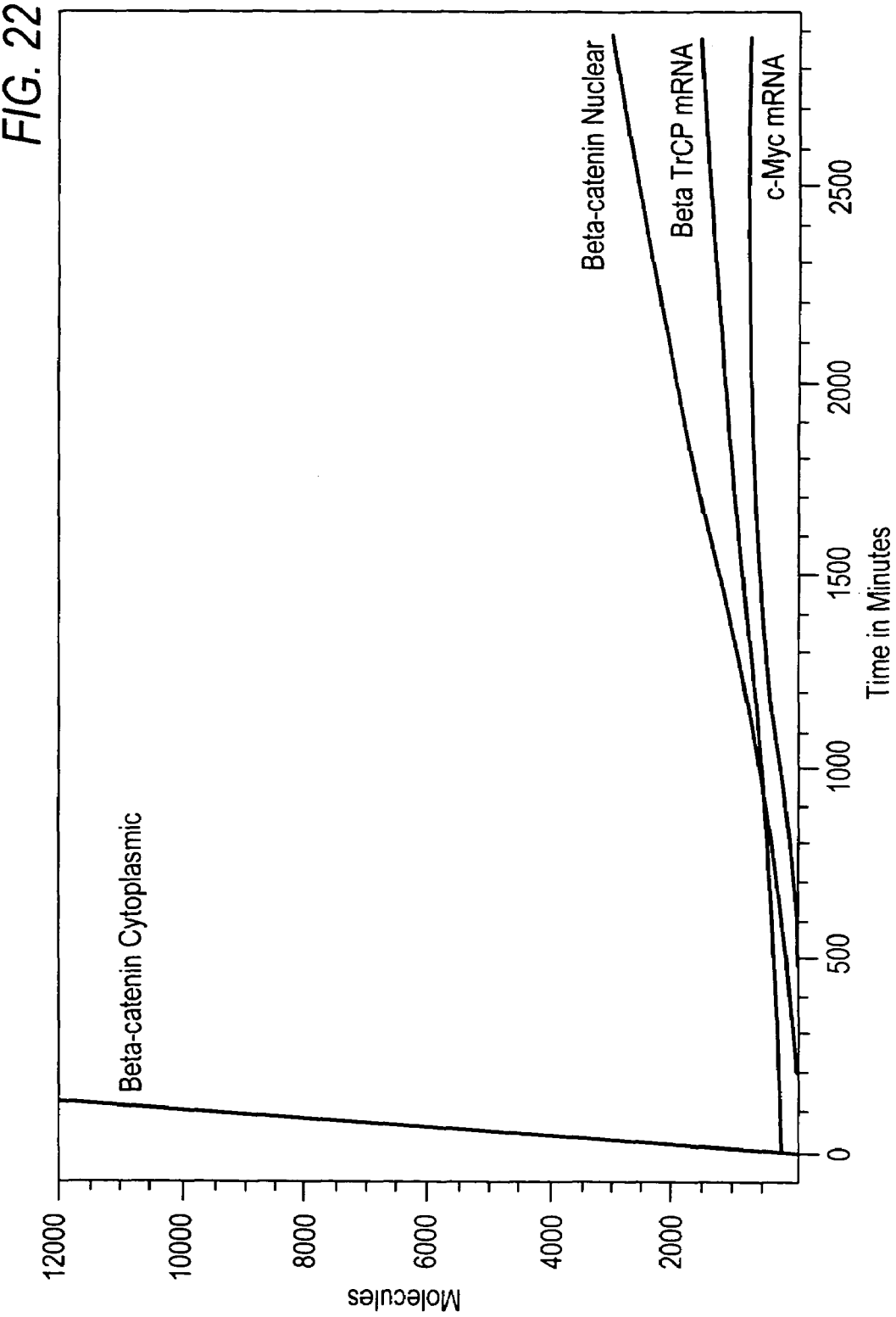
FIG. 22 is a time-series profile which shows the effect of reducing the concentration of GSK3 to zero in the already perturbed cell of FIG. 21.
Figure 23:
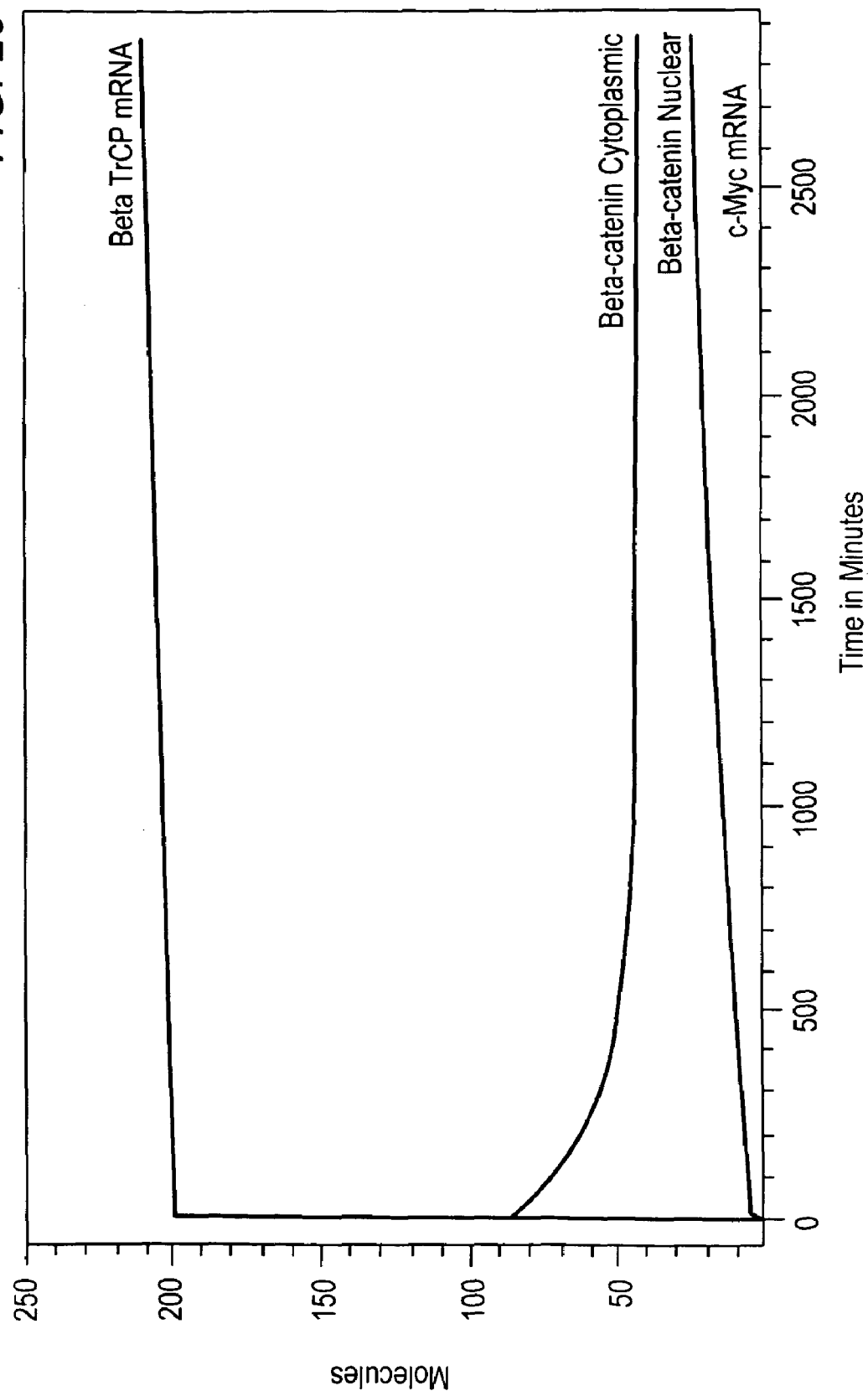
FIG. 23 is a time-series profile which shows the effect of modifying the mathematical equations of the system by adding an additional Facilitator molecule, to enhance the binding of Axin to β-catenin, to the cancerous cell depicted in FIG. 12.

Starting from the normal state of FIG. 11, the sequence of the perturbations described above is repeated, but the concentration of each of the respective components is sequentially set to zero. This raises the cytoplasmic levels of β-catenin for a short duration. Then it raises it significantly over the entire time course. Finally, the levels of nuclear β-catenin are increased further as a result of the final perturbation. This is shown in FIGS. 21, 22 and 23. This identifies Axin, GSK3, and HDAC as components whose interactions have a significant effect on the state of the cell.

Modifying the Mathematical Equations

The mathematical equations in Example II are modified by adding a new component to facilitate the binding of Axin to β-catenin. The reaction term that represents the binding of Axin to β-catenin is changed from $$[\text{Axin}][\beta\text{-catenin}]k_b$$

to $$[\text{Axin}][\beta\text{-catenin}][\text{Facilitator}]k_{bwithFacilitator}$$

where the binding with the Facilitator molecule is greater than without the Facilitator. This perturbation is made to the simulated "cancerous" state of FIG. 12 and is shown in FIG. 23. This identifies the Facilitator as an important putative therapeutic for changing the binding of Axin to β-catenin and thereby changing the condition of the cell from the disease state to the healthy state.

Figure 24:
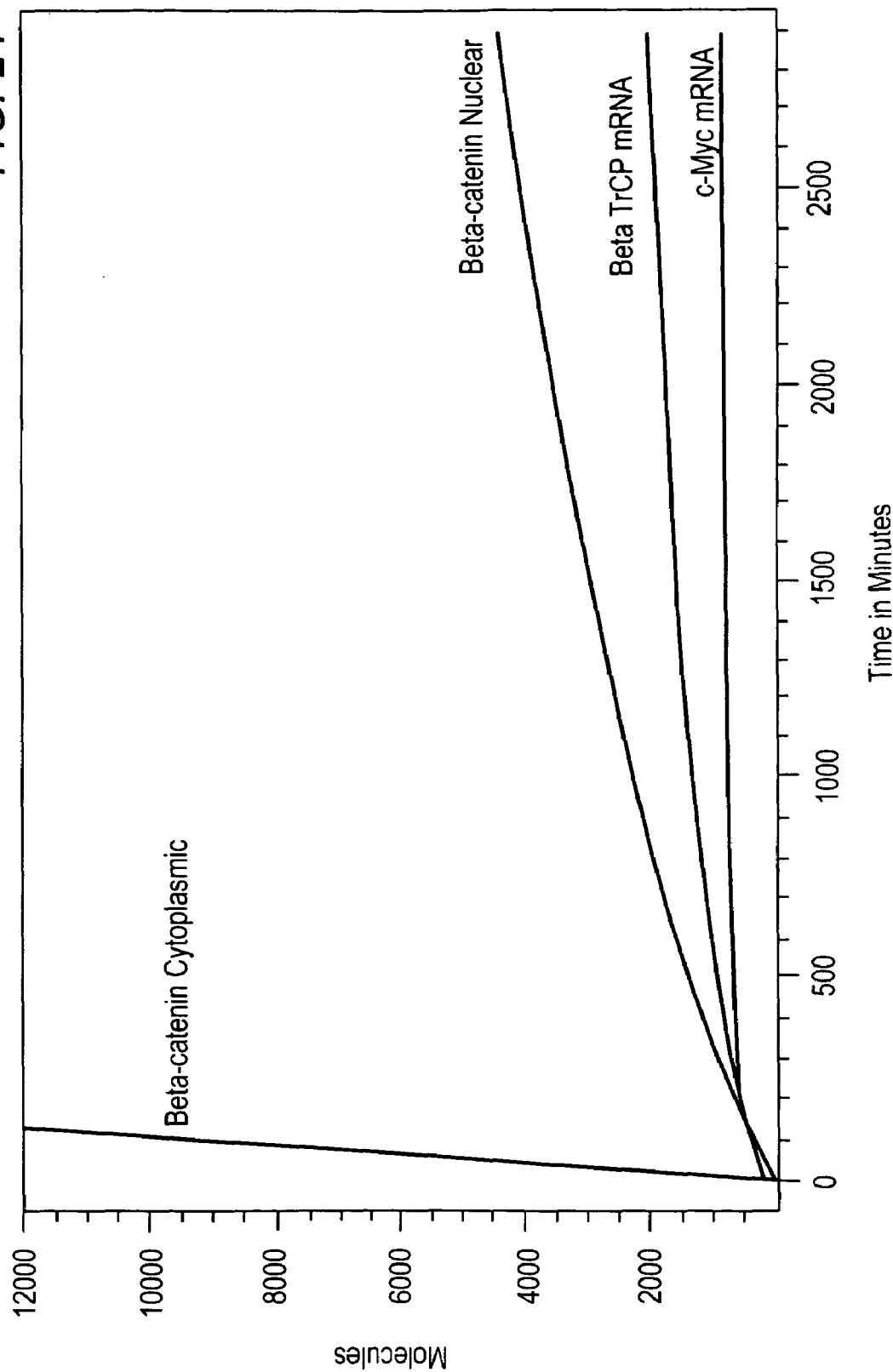
FIG. 24 is a time-series profile which shows the effect of reducing the concentration of HDAC to zero in the twice perturbed cell of FIG. 23.

Starting from the disease state of FIG. 12, the binding rate of Axin to β-catenin is increased. This perturbation allows Axin to bind to β-catenin more quickly and thus enable its phosphorylation and degradation without APC. This is shown in FIG. 24. This identifies Axin as a component of the cell that changes the time course of the disease state.

Figure 25:
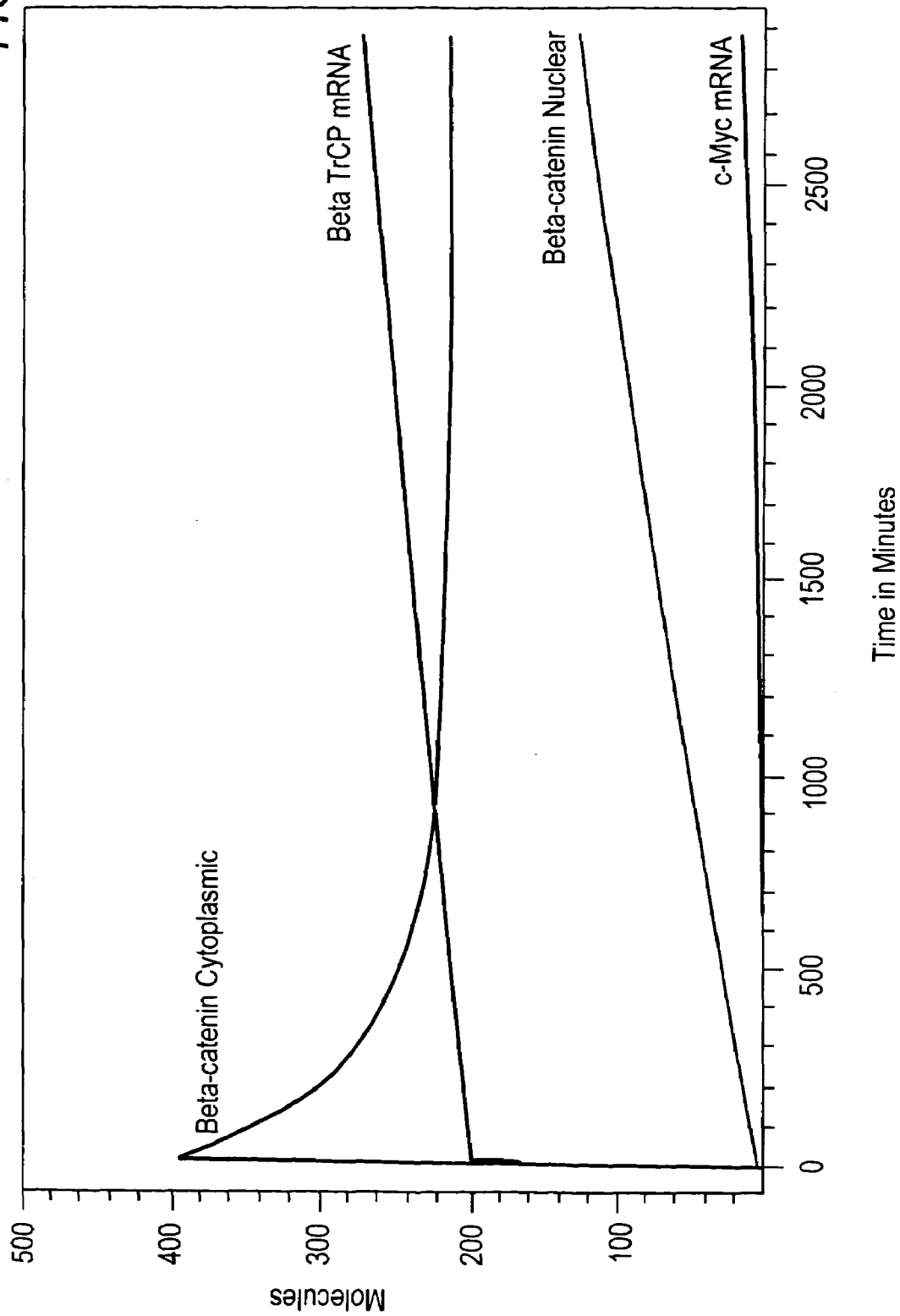
FIG. 25 is a time-series profile which shows the effect of increasing the binding rate of Axin to b-catenin starting from the "cancerous" cell of FIG. 12.
Figure 26:
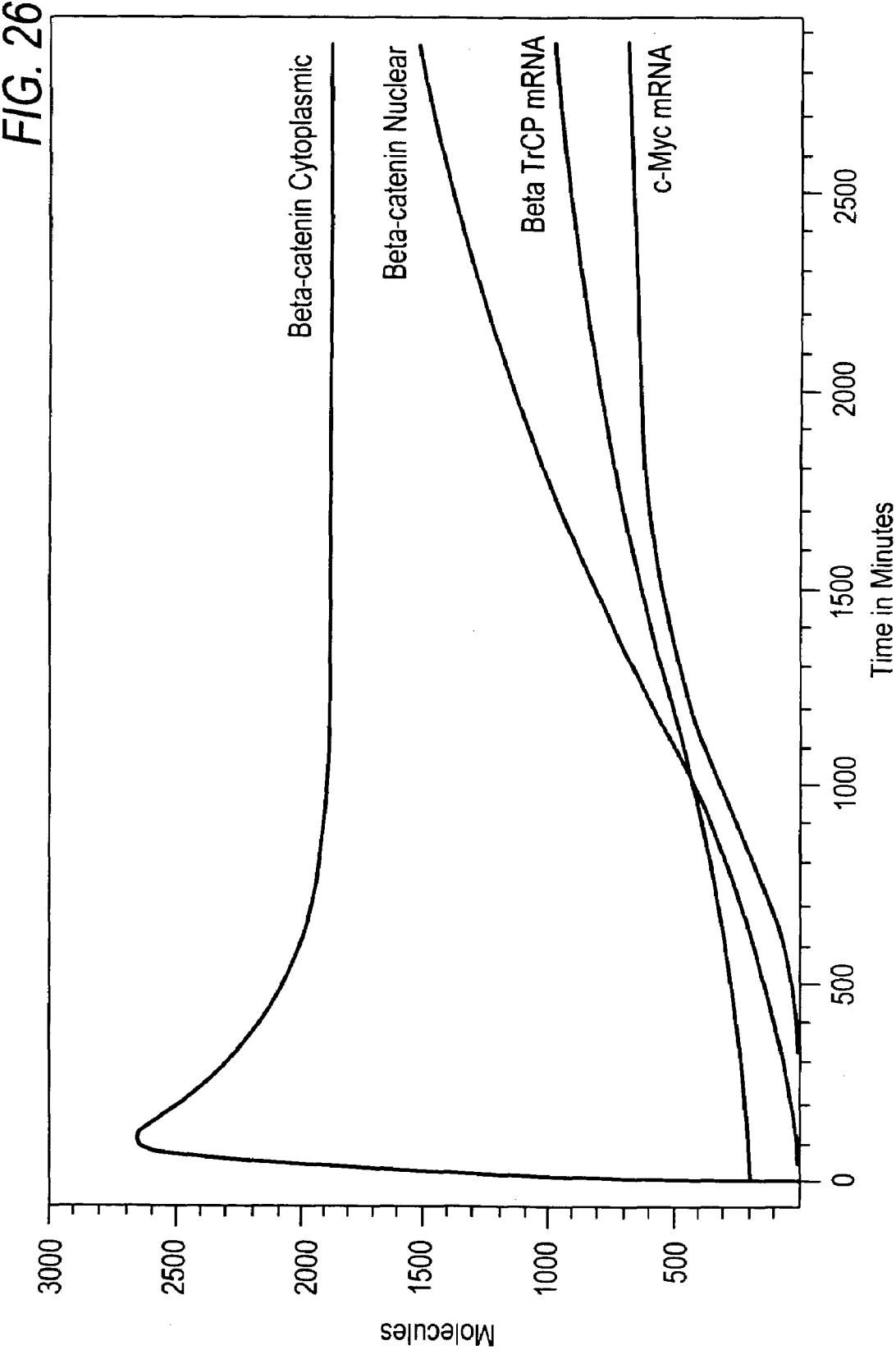
FIG. 26 is a time-series profile which shows the effect of increasing the binding rate of Axin to B-Catenin slightly from the cancerous cell of FIG. 12.
Figure 27:
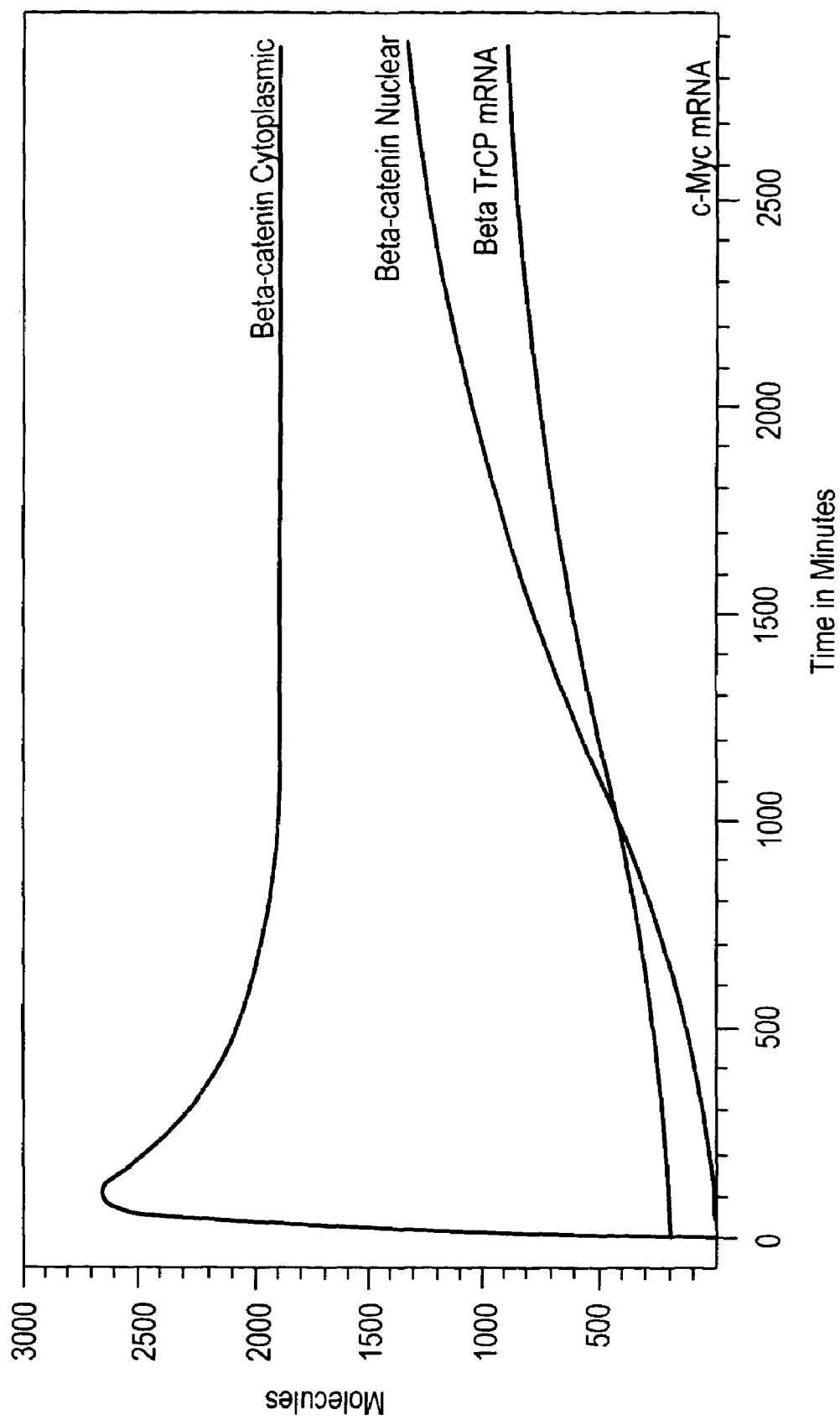
FIG. 27 is a time-series profile which shows the effect of increasing the binding rate of B-catenin to the c-Myc TCF bound gene from the already perturbed cell of FIG. 26.

Starting from the disease state of FIG. 12, the binding rate of Axin to β-catenin is increased slightly. Then the binding rate of β-catenin to the c-Myc TCF bound gene is decreased. Then the binding rate of GSK3 to Axin is increased. This results in a decrease in β-catenin levels and c-Myc transcription levels. The effect on the time series profile of each successive perturbation is shown in FIGS. 25, 26 and 27. This identifies Axin, the TCF bound c-Myc gene, and GSK3 as important targets for intervention.

Figure 28:
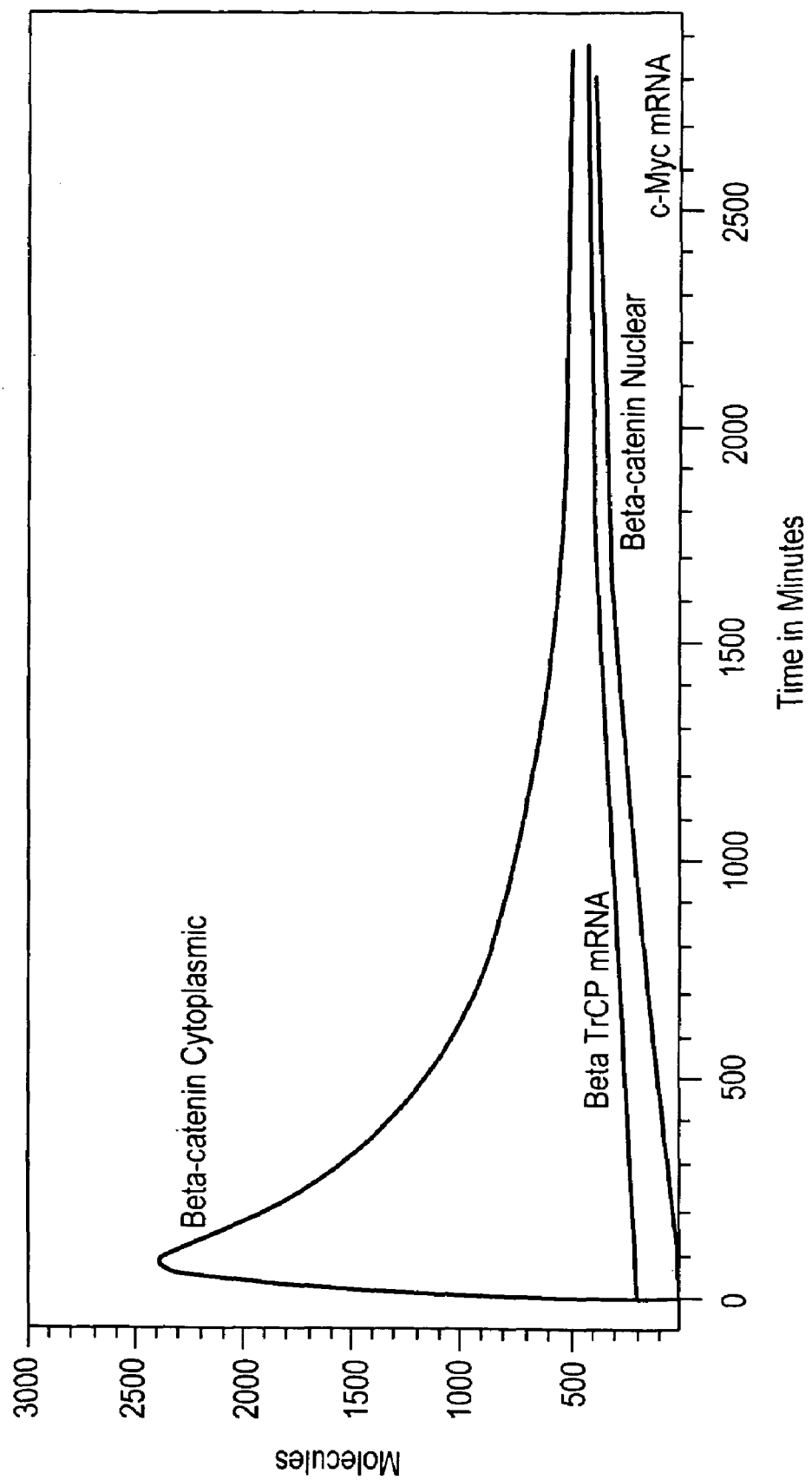
FIG. 28 is a time-series profile which shows the effect of increasing the binding rate of GSK3 to Axin in the twice perturbed cell of FIG. 27.
Figure 29:
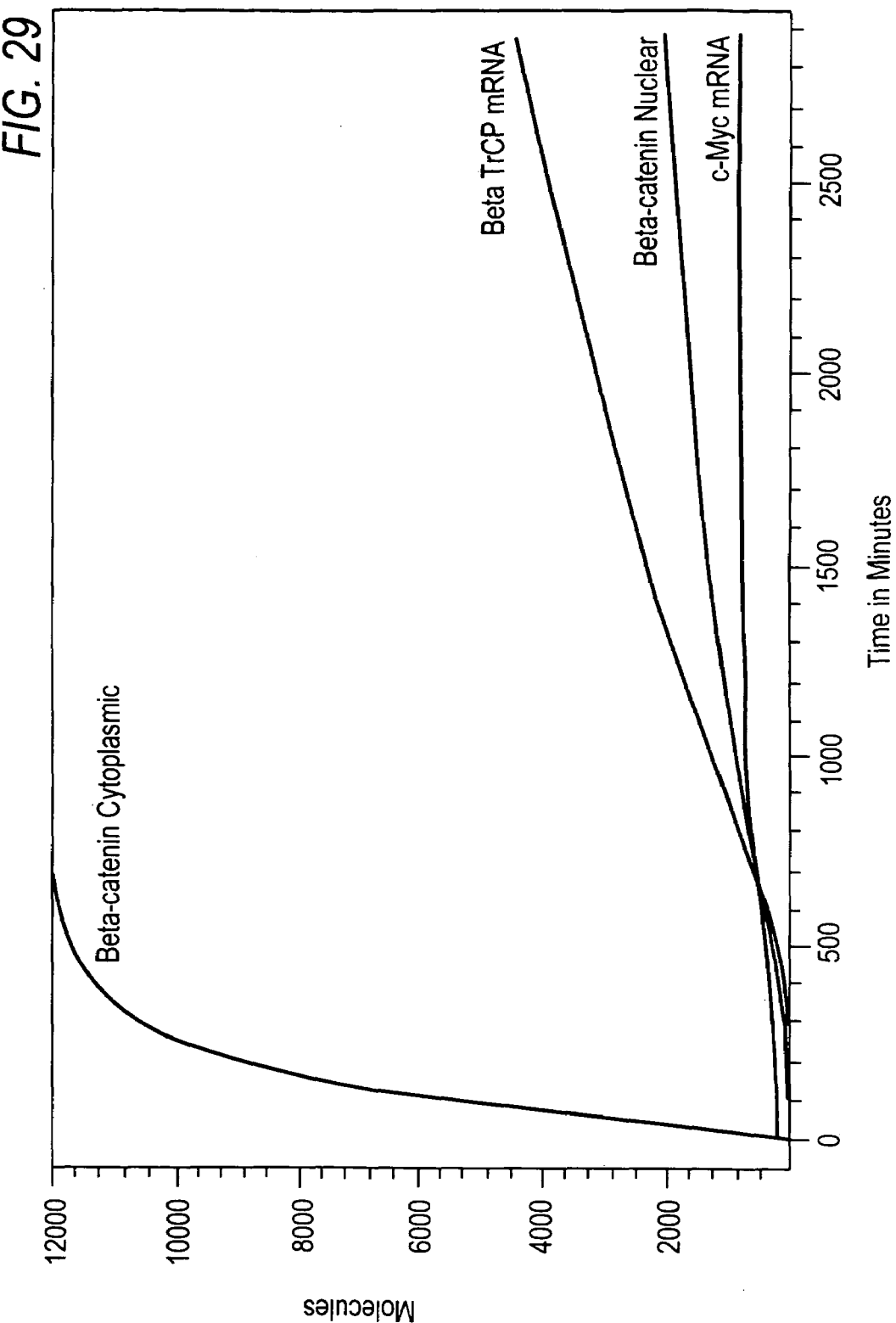
FIG. 29 is a time-series profile which shows the effect of setting the binding rate of Axin to GSK3 to zero in the normal cell of FIG. 11.
Figure 30:
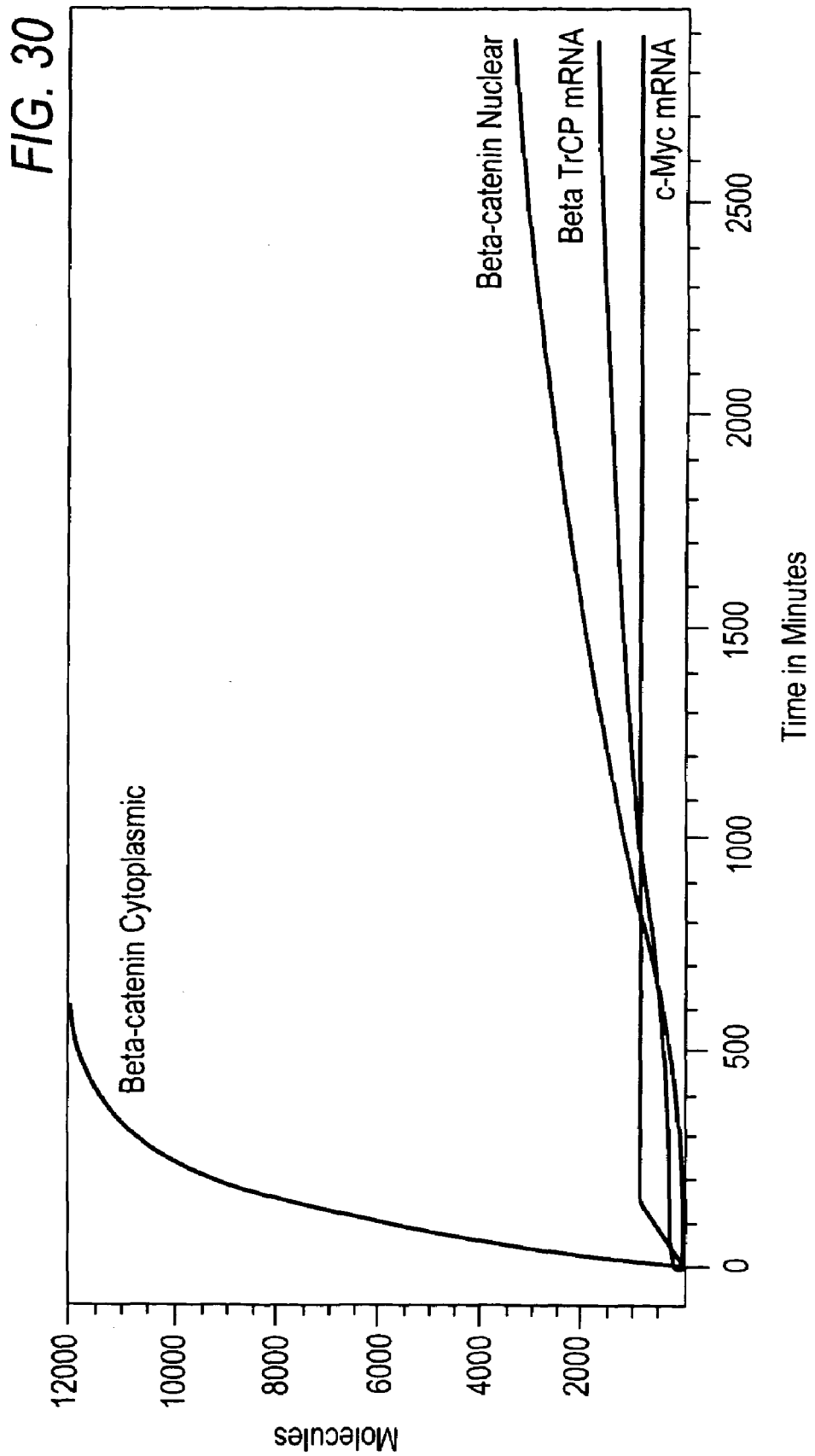
FIG. 30 is a time-series profile which shows the effect of setting the unbinding rate of B-Catenin to the C-Myc gene to zero in the already perturbed cell of FIG. 29.

Starting from the normal state of FIG. 11, the parameter for the binding of Axin to GSK3 is set to zero and then the parameter for the unbinding of β-catenin to the c-Myc gene is set to zero. The first perturbation causes a significant increase in cytoplasmic and nuclear β-catenin. The second perturbation increases c-Myc mRNA levels immediately. This is shown in FIGS. 28 and 29. This identifies GSK3 and nuclear β-catenin with the c-Myc gene as important targets for affecting the time series profile of the disease state.

Figure 31:
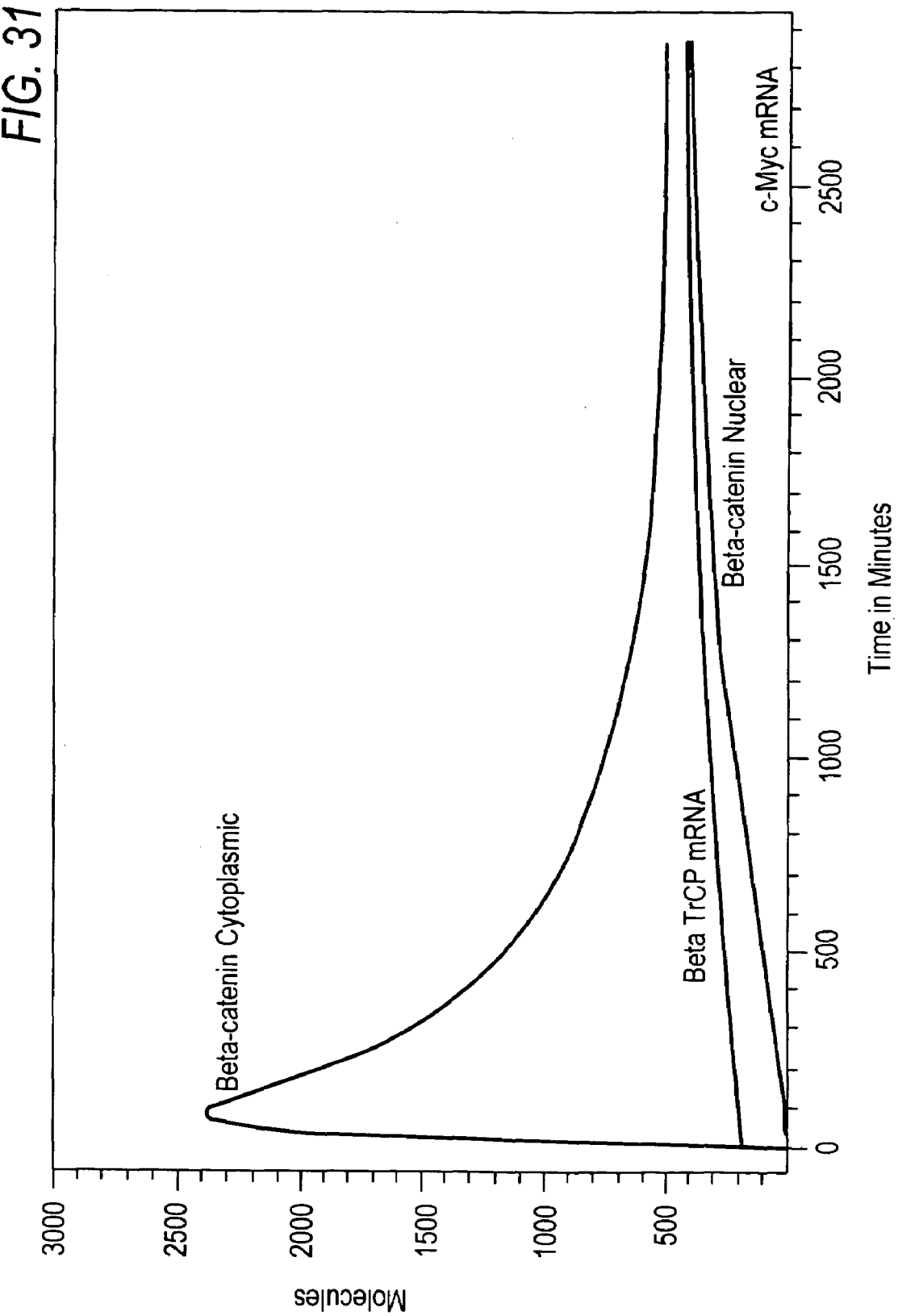
FIG. 31 is a time-series profile which shows the effect of systematically changing parameter values to change the "cancerous" state of FIG. 12 back to a "normal" state similar to FIG. 11.
Figure 31A:
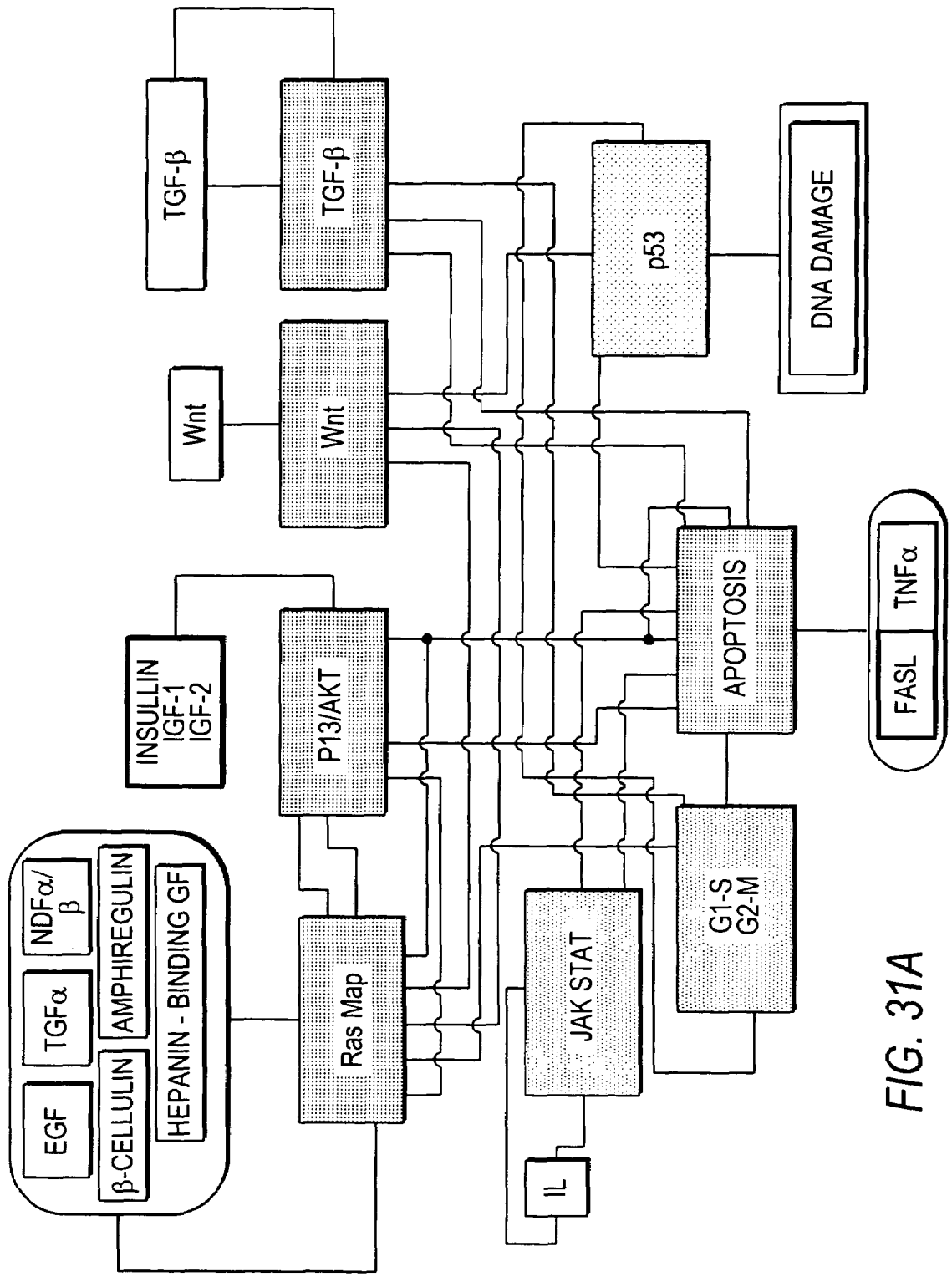
FIG. 31(a) depicts a modular description of an exemplary colon cancer cell simulation.

Starting from the disease state of FIG. 12, the parameters in the system are systematically perturbed until the profile of the time series expression looks "normal." The simulation is run at the starting kinetic and concentration values of the disease state and then a computer code is executed to systematically vary one or more kinetic parameter and concentration value from 0 to some maximum number until the desired time series profile is reached. A criterion is introduced to cease the perturbation when the time series matches the desired output, in this case, that of a "normal" profile similar to FIG. 11. The systematic changes are shown in FIG. 31 and consist of a final change where the binding rate of B-catenin to Axin is increased, the binding rate of B-catenin to c-Myc TCF bound gene is decreased, and the binding rate of GSK3 to Axin is increased.

Colon Cancer Model

Figure 32:
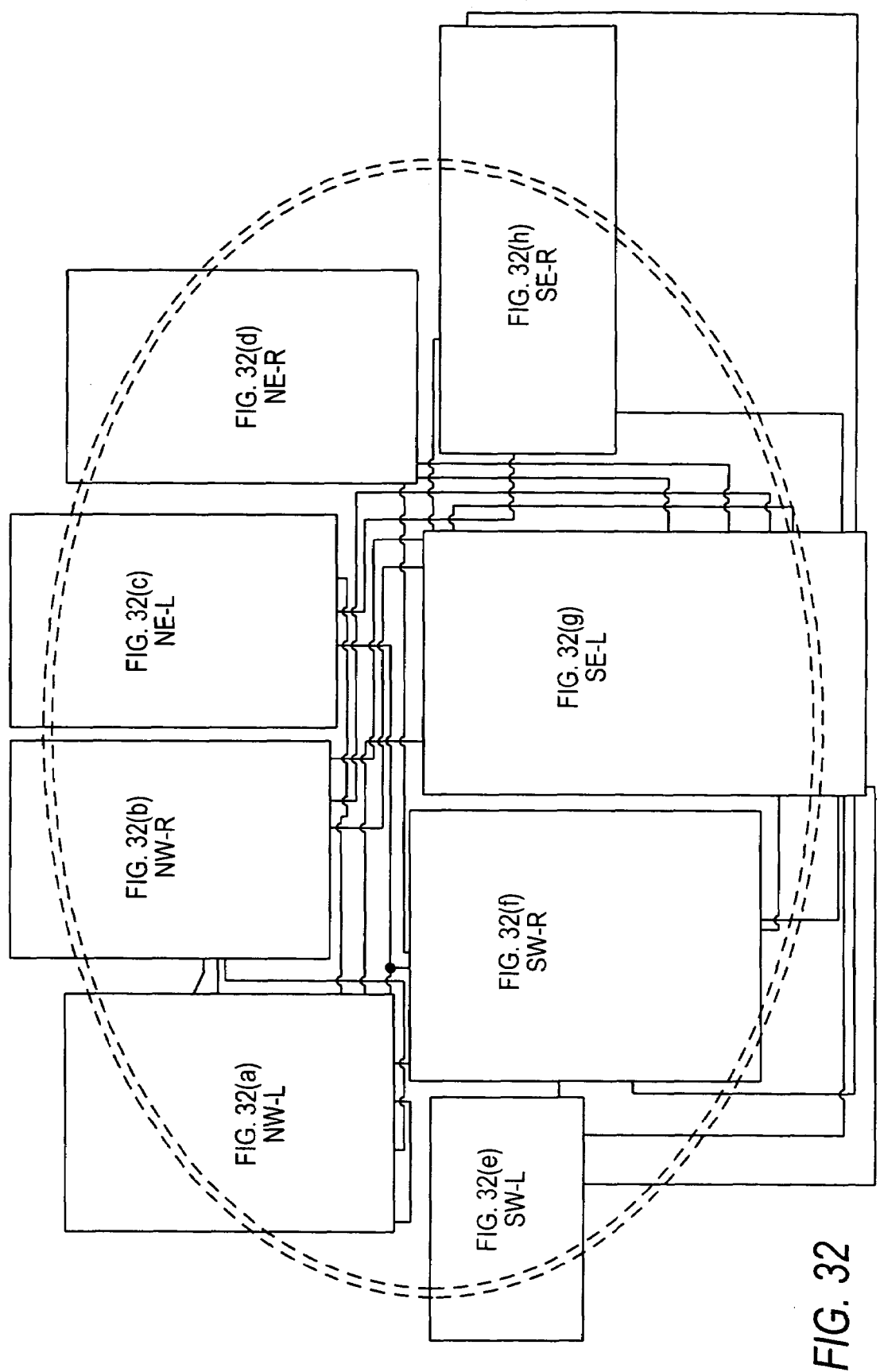
FIG. 32 depicts a modular description of an exemplary colon cancer cell simulation.

A colon cell containing over 200 genes and proteins, over 800 states, and 900 parameters has been simulated. The colon cell simulation incorporates the following networks: Ras MAPK, PI3K/AKT signaling, Wnt signaling through beta-catenin, TGF-beta signaling, TNF signaling, JAK/STAT pathways, NFkB, Fas and TNF signaling through the caspases, and the highly connected p53 node. FIGS. 31 and 32 show the modular description whereby modular we mean a simplification of the model into basic elements to clearly see gross connections between components, major feedback loops, and cross talk between the modules. Each module contains many reaction steps. The lines extending from the modules indicate interactions between the modules. Exhibit A contains the differential equations for each module, the chemical species or states in each module, as well as a list of the initial concentrations and kinetic parameters used in the simulation.

The eight modules comprising FIG. 32 are, for convenience, designated with a quadrant and a right/left deisgnation in order to easily orient a given individual module with the overall modular description of FIG. 32. As well, the interconnections between the various modules are noted on each module, and are summarized in the following table, where for convenience they are designated as "lines", actually referring to biological interconnections.

Table of Interconnections among the Octants of the Modular Cell Diagram

The following table represents the interconnections among the octants of the large modular cell diagram. Each interconnecting line is numbered in a clockwise manner depending on the point where the line exits a particular octant in the large diagram. Each octant corresponds to the following biological system, subsystem or pathway: NW-L=Ras MAPK; NW-R=PI3K/AKT; NE-L=Wat B-catenin; NE-R=TGF-B; SE-R=p53; SE-L=apoptosis; SW-R=G1-S,G2-M; and SW-L=JAK/STAT.

| Line | Original Site | Destination Octant | Destination Site | Corresponding Line |
|---|---|---|---|---|
| NW-L1 | [node] | NW-R | ErbB-R | NW-R6 |
| NW-L2 | [node] | NW-R | RAS:GTP | NW-R5 |
| NW-L3 | ErK$_{Nucl}$ | NE-L | Erk* | NE-L1 |
| NW-L4 | p90RSK | SE-L | P90RSK* | SE-L10 |
| NW-L5 | cycD | NE-L | cyclinD | NE-L3 |
|  |  | SW-R | cycD | SW-R7 |
| NW-L6 | Cip | SW-R | Cip | SW-R6 |
| NW-L7 | (PKB:PIP3)$_2$ | NW-R | (PKB:PIP3)$_2$ | NW-R4 |
| NW-R1 | active TNF-R/TRADD/TRAF/RIP | SE-L | [node] | SE-L2 |
| NW-R2 | (PKB:PIP3)$_2$ | SE-L | (PKB:PIP3)$_2$ | SE-L6 |
| NW-R3 | NFkB$_{NuCl}$ | SE-L | NFkB$_{NuCl}$ | SE-L1 |
| NW-R4 | (PKB:PIP3)$_2$ | NW-L | (PKB:PIP3)$_2$ | NW-L7 |
| NW-R5 | RAS:GTP | NW-L | [node] | NW-L2 |
| NW-R6 | active ErbB-R | NW-L | [node] | NW-L1 |
| NE-L1 | Erk* | NW-L | ErK$_{Nucl}$ | NW-L3 |
| NE-L2 | myc | SE-R | c-myc | SE-R3 |
| NE-L3 | cyclin D | NW-L | cycD | NW-L5 |
| NE-R1 | c-jun | SE-L | jun* | SE-L5 |
| NE-R2 | Jnk* | SE-L | JNK$_{Nuc}$* | SE-L4 |
| NE-R3 | Ink | SW-R | Ink | SW-R1 |
| SE-R1 | p53* | SW-R | p53 | SW-R4 |
| SE-R2 | E2F | SW-R | E2F | SW-R2 |
| SE-R3 | c-myc | NE-L | myc | NE-L2 |
| SE-R4 | p53* | SE-L | p53* | SE-L3 |
| SE-L1 | NFkB$_{Nucl}$ | NW-R | NFkB$_{Nucl}$ | NW-R3 |
| SE-L2 | [node] | NW-R | active TNF-R/TRADD/TRAF/RIP | NW-R1 |
| SE-L3 | p53* | SE-R | p53* | SE-R4 |
| SE-L4 | JNK$_{Nuc}$* | NE-R | Jnk* | NE-R2 |
| SE-L5 | jun* | NE-R | c-jun | NE-R1 |
| SE-L6 | (PKB:PIP3)$_2$ | NW-R | (PKB:PIP3)$_2$ | NW-R2 |
| SE-L7 | Bcl-X$_L$ | SW-L | Bcl-x$_L$ | SW-L3 |
| SE-L8 | FASL | SW-L | FASL | SW-L2 |
| SE-L9 | 14-3-3 sigma | SW-R | cycB | SW-R3 |
| SE-L10 | P90RSK* | NW-L | P90RSK* | NW-L4 |
| SW-R1 | Ink | NE-R | Ink | NE-R3 |
| SW-R2 | E2F | SE-R | E2F | SE-R2 |
| SW-R3 | cycB | SE-L | 14-3-3 sigma | SE-L9 |
| SW-R4 | p53 | SE-R | p53* | SE-R1 |
| SW-R5 | cycD | SW-L | cycD | SW-L1 |
| SW-R6 | Cip | NW-L | Cip | NW-L6 |
| SW-R7 | cycD | NW-L | cycD | NW-L5 |
|  |  | NE-L | cyclinD | NE-L3 |
| SW-L1 | cycD | SW-R | cycD | SW-R5 |
| SW-L2 | FASL | SE-L | FASL | SE-L8 |
| SW-L3 | Bcl-x$_L$ | SE-L | Bcl-X$_L$ | SE-L7 |

Figure 32A:
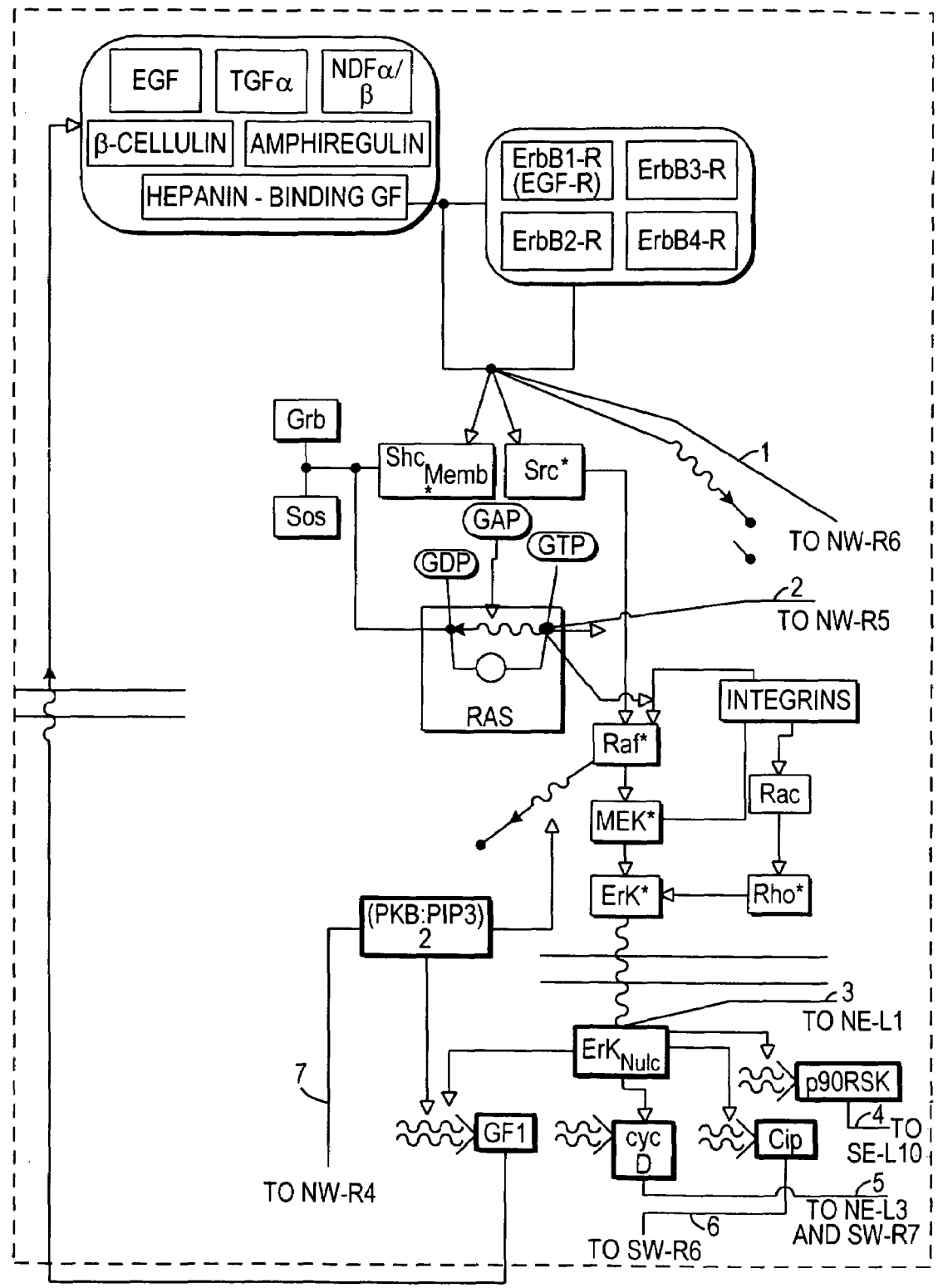

Each module contains components that are important for colon cancer progression and the mammalian cell cycle in general. The Ras MAPK module of FIG. 32(a) contains important growth factors such as EGF, TGF-alpha, and amphiregulin that activate the Erb family of receptors. Once activated these receptors activate a cascade of proteins called Ras, Mek, and Erk. Active Erk plays an important role in turning on genes that are responsible the mammalian cell cycle, genes such as cyclinD which initiate the transition from G1 to S phase. Erk even intiates further cellular division by turning on the same growth factors that lead to its activation in an autocrine manner. Often times, cancer will have a mutations in Ras that inhibits its hydrolysis or conversion from its active GTP bound form to its inactive GDP bound form, thereby promoting activation of Erk and proliferation.

Figure 32B:
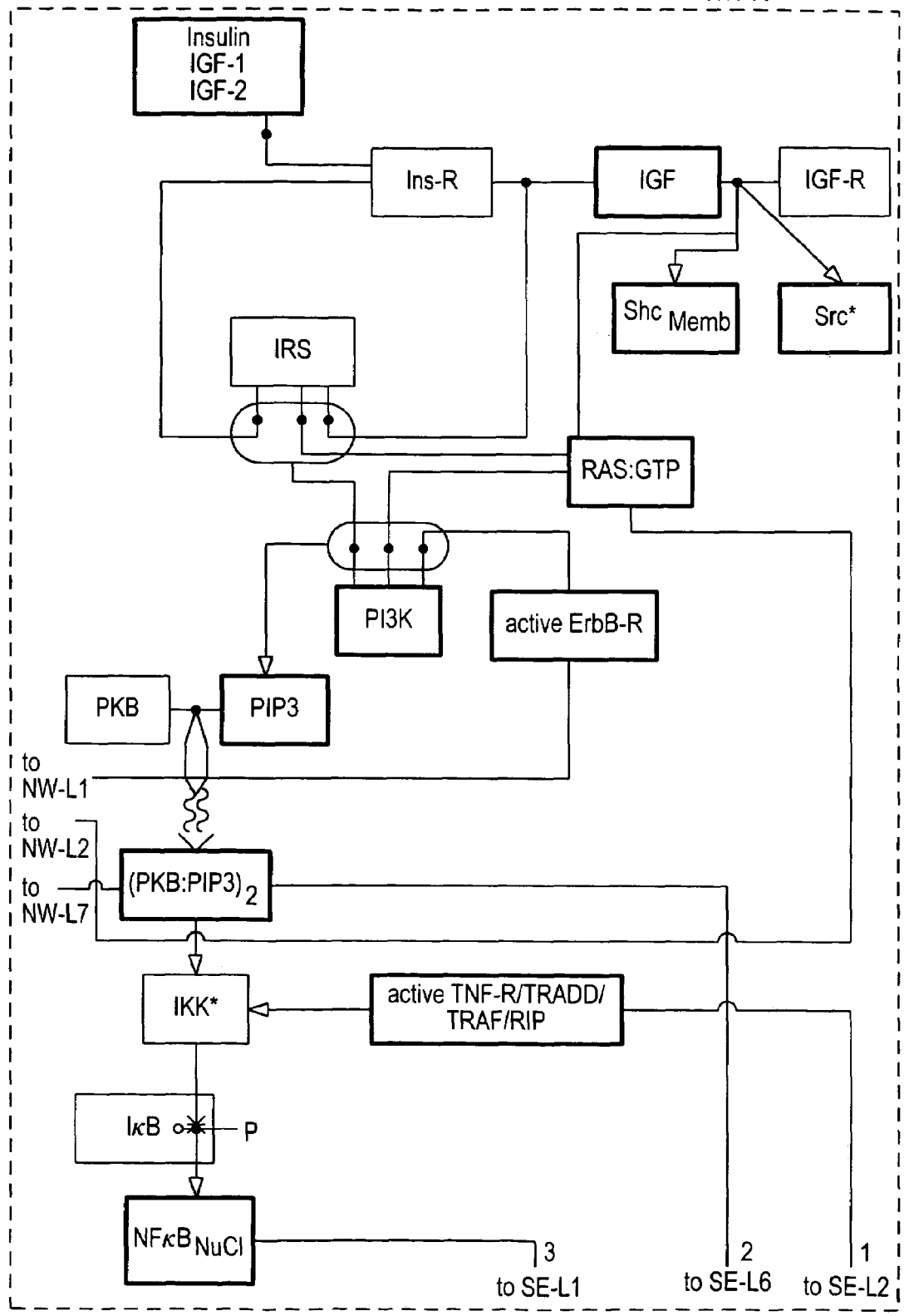

The Ras MAPK module also interacts with the PI3K/AKT module of FIG. 32(b). The same growth factors that lead to Erk activation can also activate the survival factor AKT (sometimes referred to as PKB). AKT can also be activated by a set of growth factors known as Insulin, IGF-1, and IGF-2 as shown in the module description. Once activated by growth factor signals, AKT induces the nuclear translocation of NFkappaB. NFkappaB turns on a set of genes that up-regulate proteins labeled as survival factors such as Bcl2, Bcl-xL, Flips, and LIPs shown in the apoptosis module of FIG. 32(g). These proteins inhibit apoptosis or programmed cell death on many levels. Thus a healthy dividing cell will signal to promote cellular division and to inhibit apoptosis via upregulation of these survival factors.

Figure 32C:
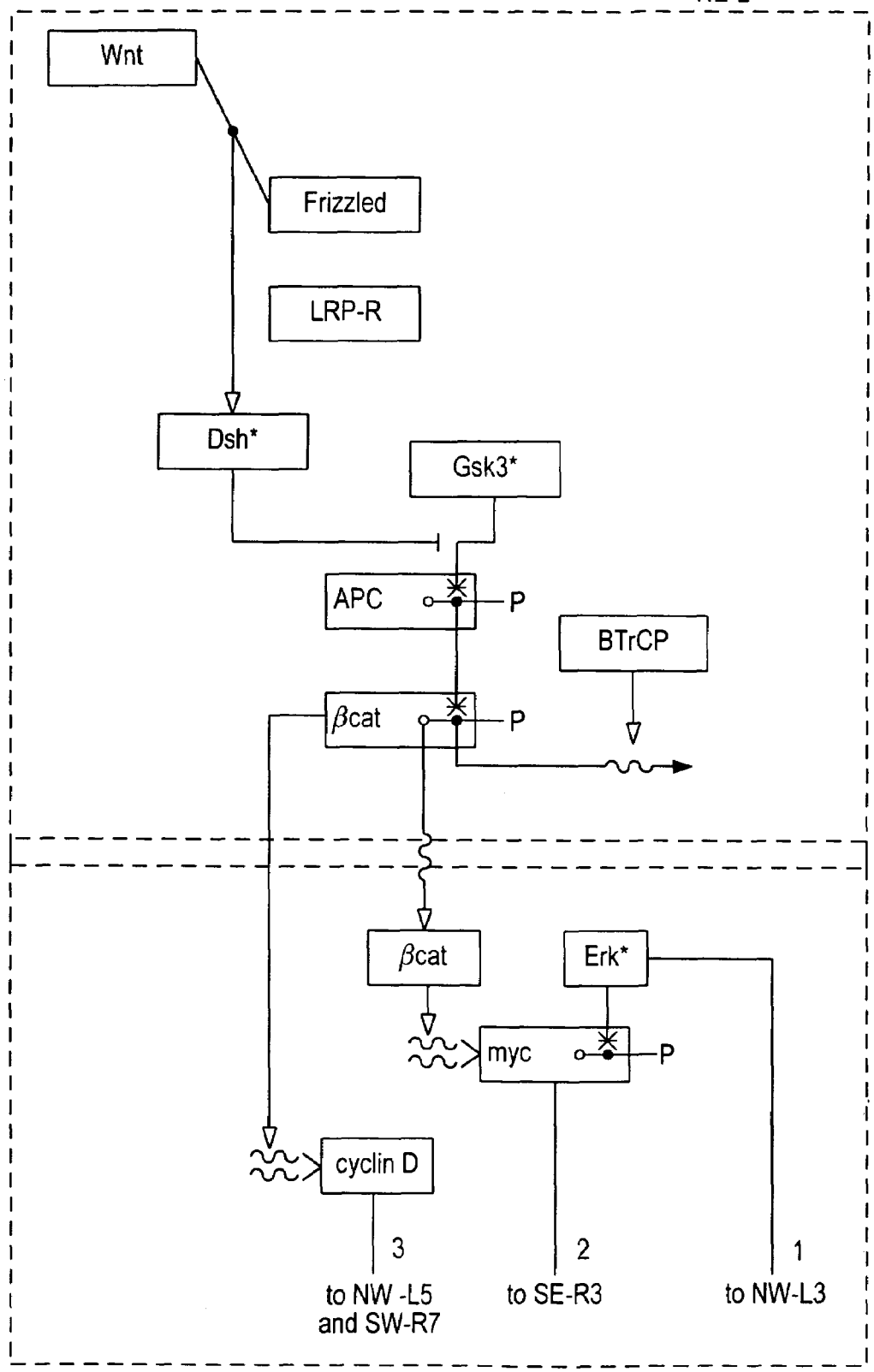
Figure 32D:
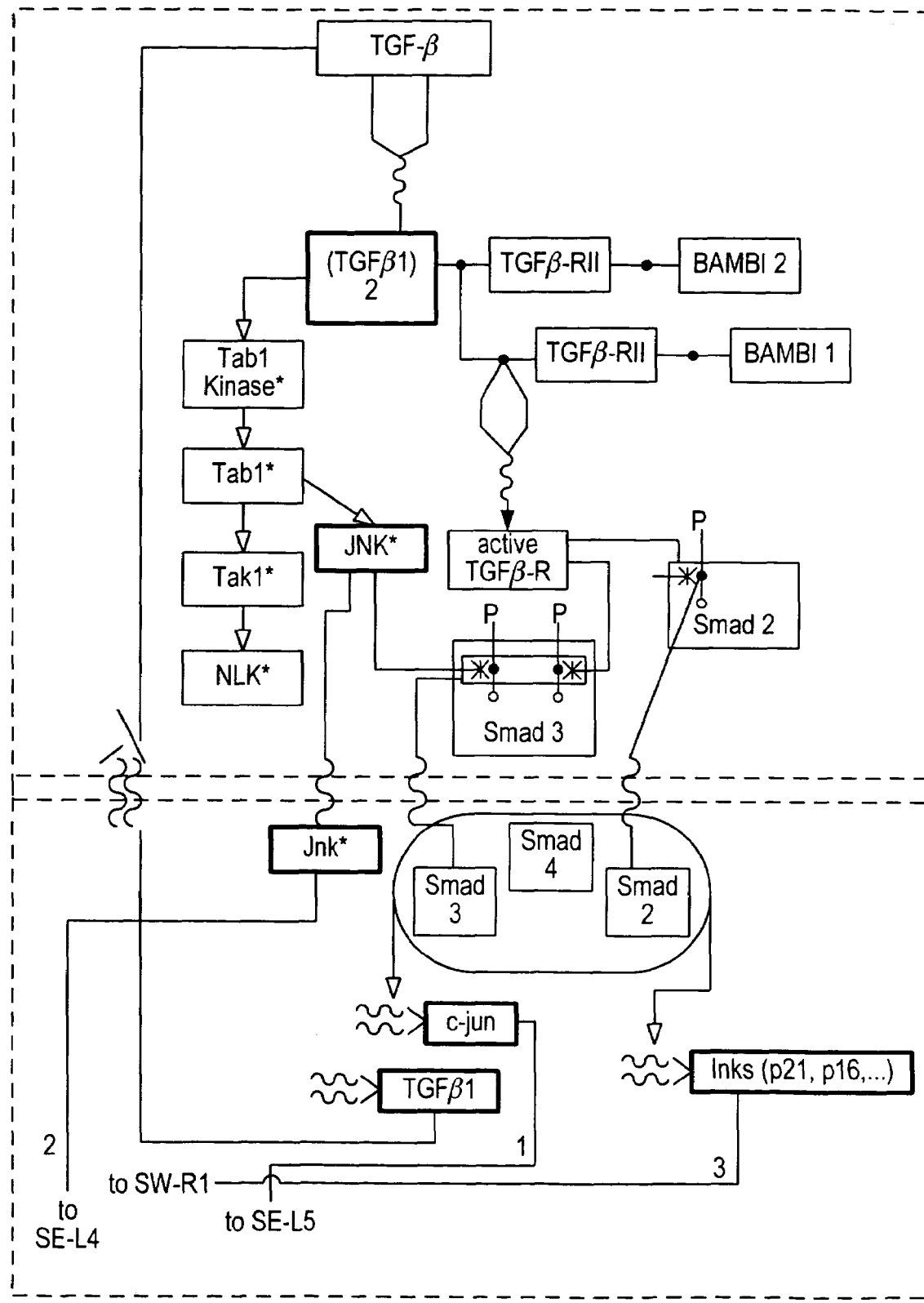

The Wnt beta-catenin module of FIG. 32(c) is another module that signals to promote cellular division. This pathway usually contains a mutation in Beta-catenin that leads to high levels of the protein in the cell. Normally, the pathway is inactive and Beta-catenin levels are low unless the cell is stimulated with the Wnt ligand. Beta-catenin also acts as a transcription factor turning on CylinD and c-Myc both of which lead to the G1-S transition. Excess levels can thus lead to proliferation and uncontrolled cellular division. In addition to promoting cellular division, cancer cells will inhibit the process of differentiation. A colon cancer cell achieves this by mutating the SMADS in the TGF-beta pathway of FIG. 32(d). These are again transcription factors activated by the TGF-beta ligand that promote the transcription of genes like p21 and p16 which halt the cell cycle signaling that it is time for the cell to differentiate.

Figure 32F:
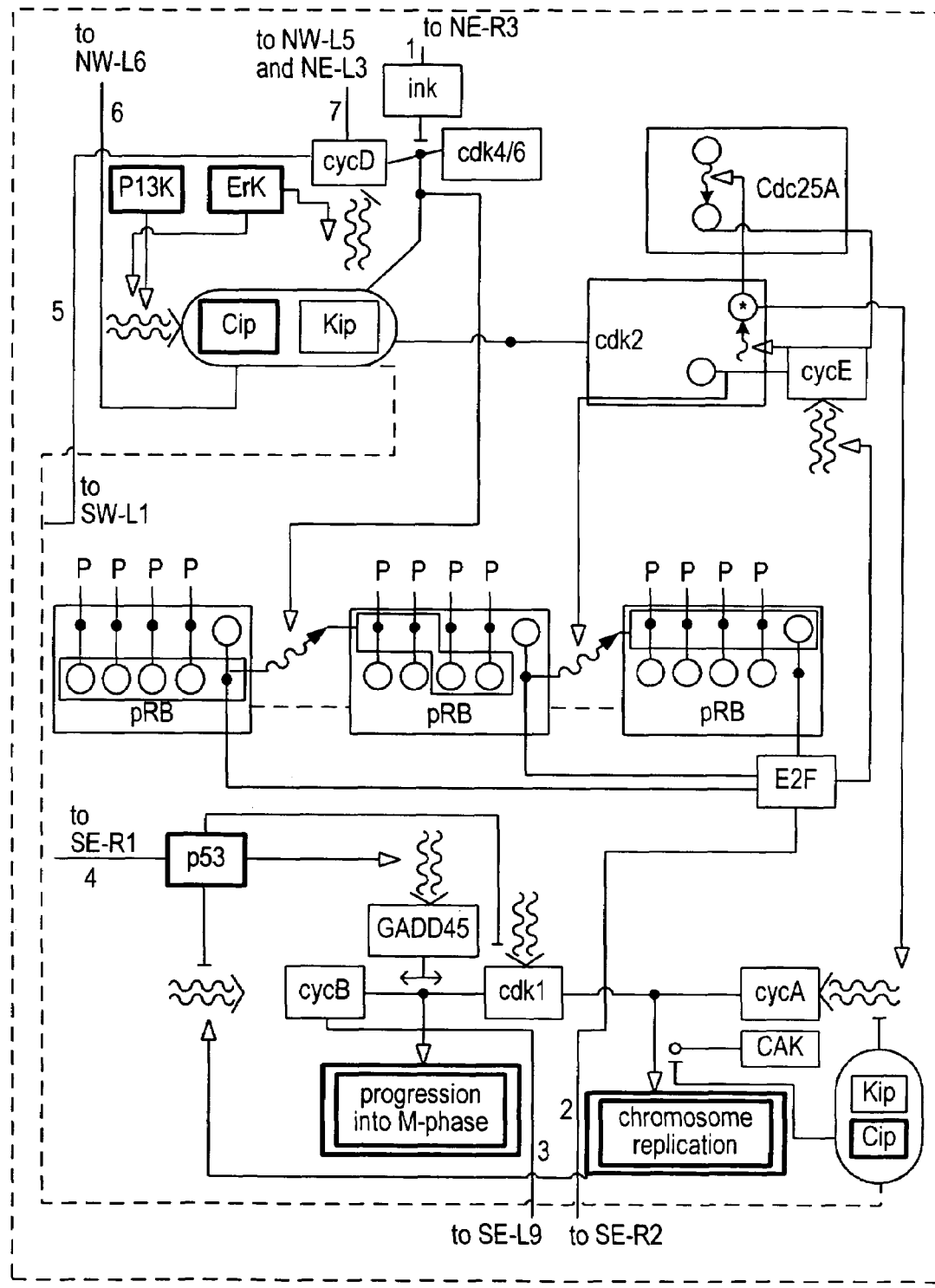

The pathways described above signal to the G1-S and G2-M modules of FIG. 32(f) which control the core cell cycle machinery. Here CyclinD-CDK2/4 complexes are activated by growth factors to in turn activate CylinE-CDK2 complexes which initiates DNA synthesis or S phase. Upon the complition of S phase, CylinA-CDK2 complexes are activates to induce chromosomal replication. The completion of this process is marked by activation of CylinB-CDK1 complexes that induce the onset of M phase or mitosis terminating in the cell successfully replicating its DNA and dividing into two daughter cells.

Often times, though, the cell makes errors in replicating its DNA or in other phases of the cell cycle. In this case, the p53 transcription factor of FIG. 32(h) is activated to up-regulate genes that halt the cell cycle and or genes that promote apoptosis (e.g. Bax and Bad) should the cell not correct its defects in time. p53 is a very commonly mutated gene in colon cancer and thus rather than repairing its DNA or undergoing programmed cell death when the DNA is damaged or mistakenly replicated, the cell can continue to divide. Other signals that effect the state of the cell are received via the JAK/STAT pathway where cytokines activate components like p38 and JNK shown as JAK/STAT in FIG. 32(e). These again, can up-regulate transcription factors that promote cellular death (amongst other signals that even compete with apoptosis) via up-regualtion of death inducing cytokines such as FASL when the cell is stressed.

Figure 32G:
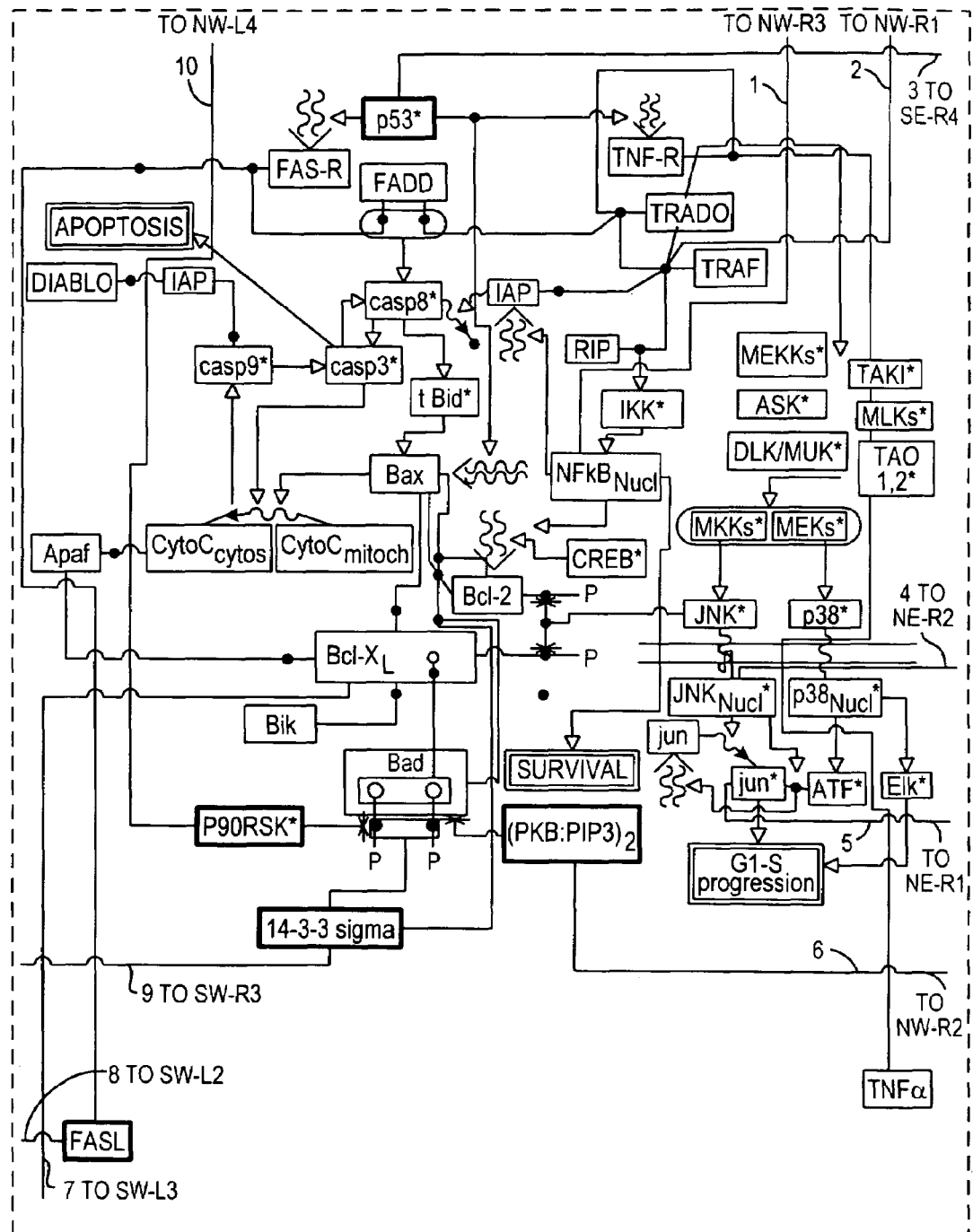
Figure 32H:
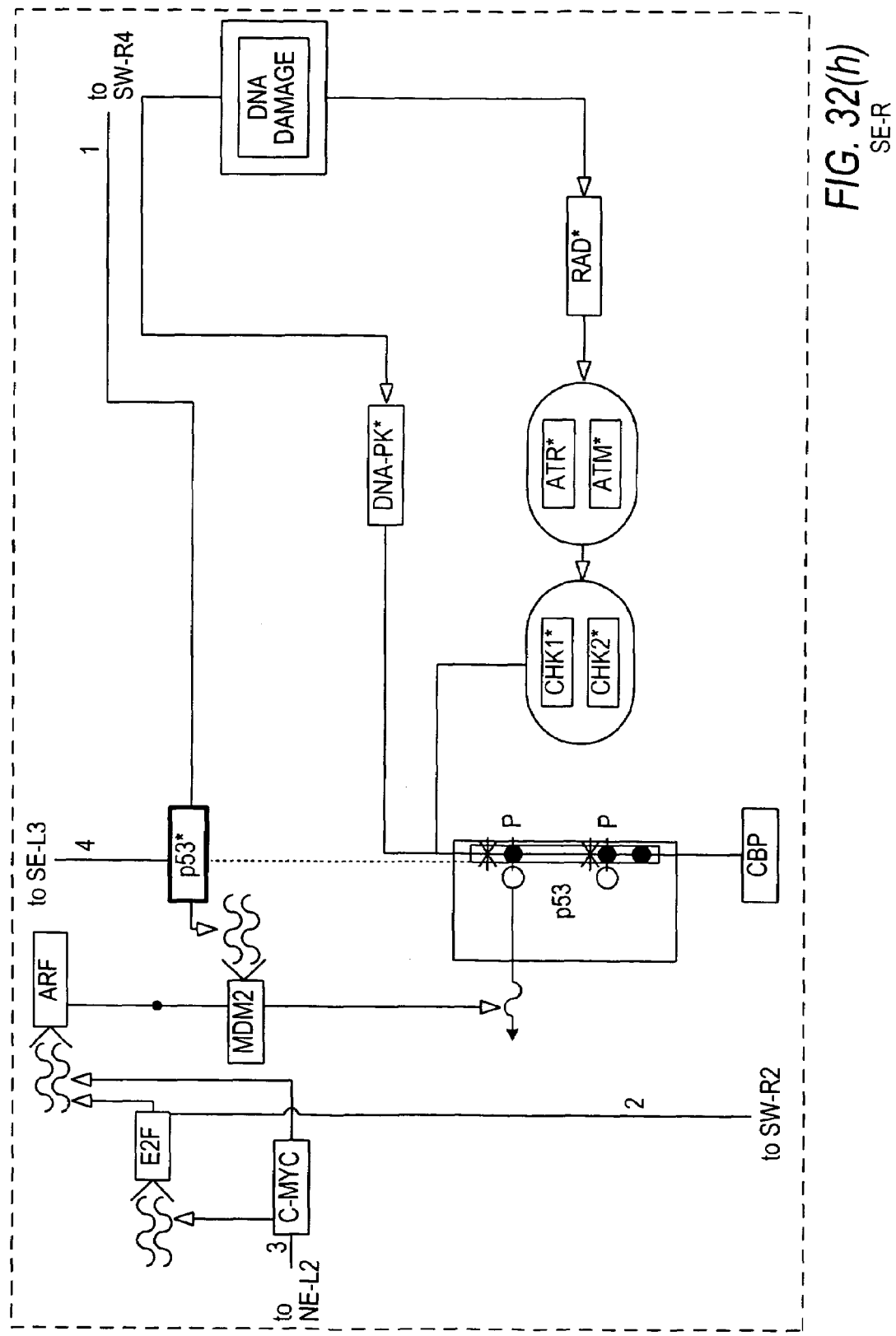
Figure 33A:
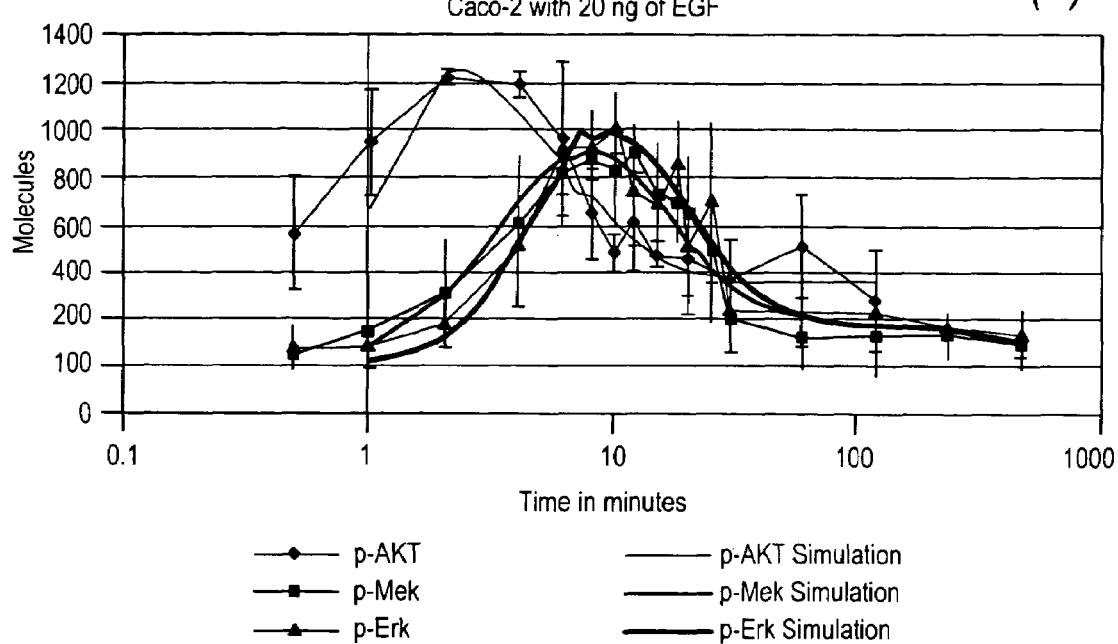
FIGS. 33(a)-(d) contain the data points and simulation for the phosphorylated forms of AKT, MEK and ERK in the exemplary colon cancer cell simulaiton.
Figure 33B:
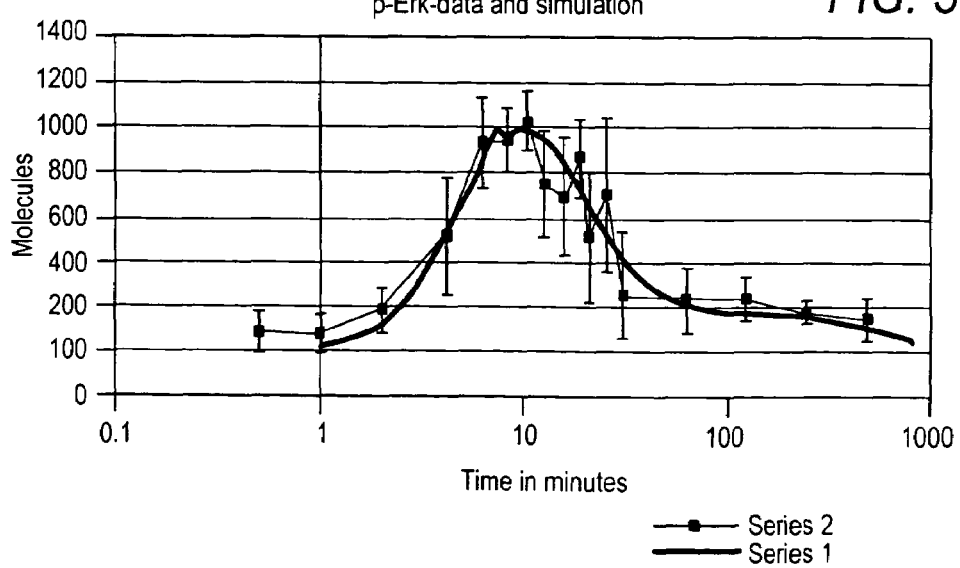
Figure 33C:
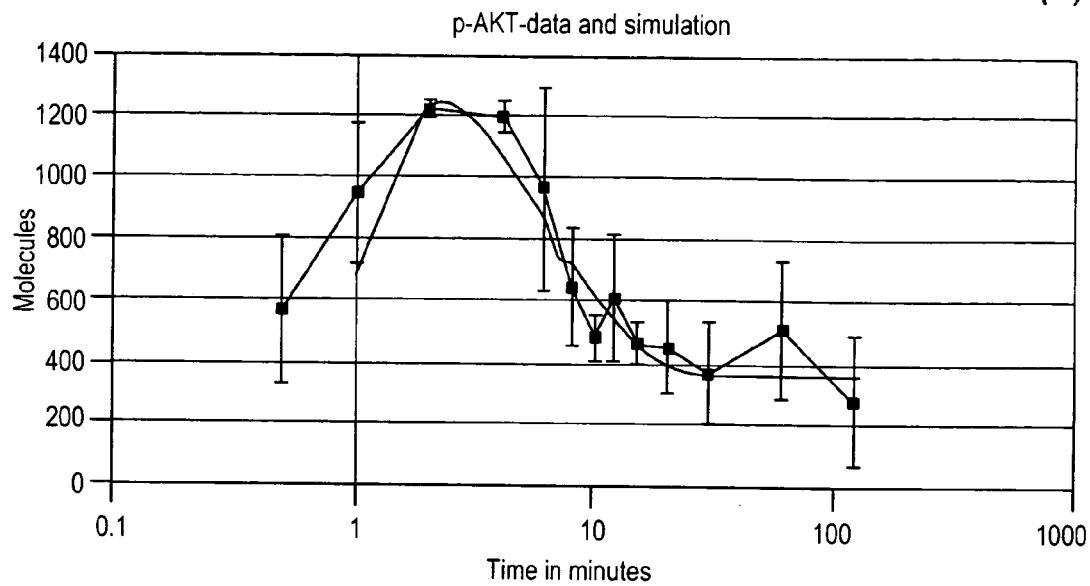
Figure 33D:
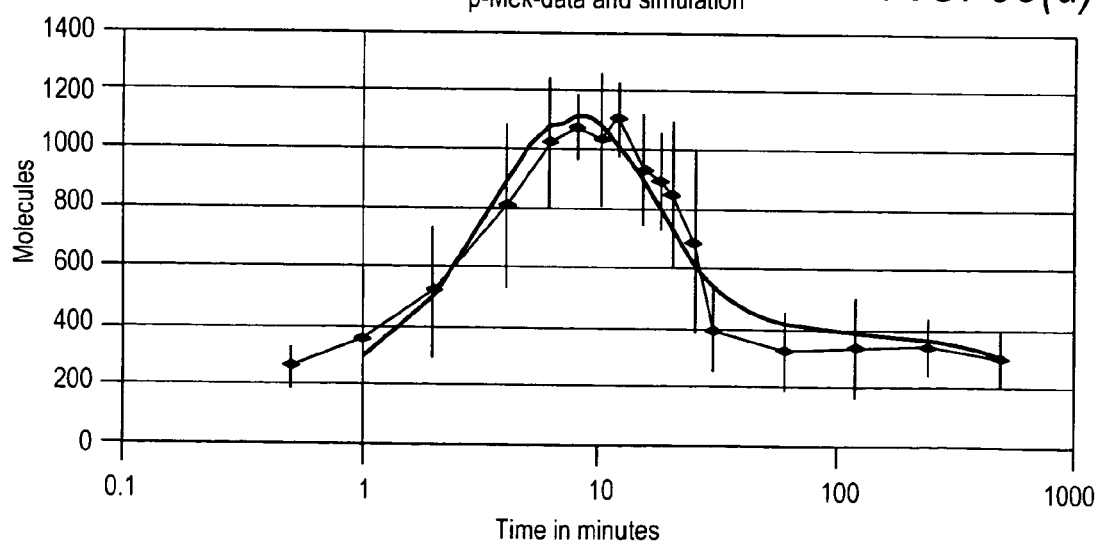

The apoptosis signals converge onto FIG. 32(g). Here apoptosis can be trigerred via activation of death receptors such as FASR and TNFR through the ligands TNF-alpha and FASL. These receptors activate caspase 8 leading to cleavage of Bid which induces the oligomerization of Bad. Bad can disrupt the mitochondrial integrity releasing cytocrome c and activating caspase 9 which in turn activates the executioner caspase 3. The executioner caspases cleave various proteins in the cell and induce programmed cell death. Caspase 8 can also directly activate caspase 3. Many colon cells require both direct caspase 3 activation and disruption of the mitochondrial integrity leading to cytocrome c release to fully activate the executioner caspases and subsequently apoptosis.

By scaling the model to include the networks responsible for the physiological process of the G1-S transition, S phase, G2-M transition, and apoptosis we can use the model to predict the various physiological states of the cell. In addition, by including the major signal transduction pathways that contain key mutations common to colon cancer we can simulate and understand the various stages of colon cancer as given by a series of point mutations. The simulation can be used to model each stage of the disease progressing from a normal state with no muations to carcinoma where multiple mutations have accumulated. Therapeutic strategies can be suggested for each stage of the disease. In addition mutations specific to an individual can be inputted devise individual targeted therapies. Data from that individual on the DNA level, RNA level, and protein level can be incorporated and optimized to this core skeletal model to generate an optimal therapeutic strategy. Technologies are becoming available and widely used to make such patient specific data available.

The network is simulated as a whole. All of the differential equations are solved simultaneously. One can perturb any of the cellular components in the simulation to predict cellular outcome and understand the cross talk and feedback loops between the various modules. In the simulation, cellular mechanisms are represented on multiple levels, including receptor activation, degradation, endocytosis, signal transduction cascades, transport within compartments, transcriptional control of gene expression networks, and protein translation and degradation mechanisms.

Optimization of the Model: Determining and Constraining Parameter Values

Time course measurements of the protein and mRNA levels were incorporated into the model to constrain parameter values using optimization algorithms. These algorithms are incorporated in software, e.g. the Implementation software which simulates HCT116, SW480, and Caco-2 colorectal cell lines. FIGS. 33(a)-(d), show time course profiles of HCT116 cells under 20 ng of EGF stimulation. The figures plot phosophorylated MEK, ErK, AKT, and RAF and simulation data that has been optimized to fit the model. The solid lines show the simulation output and the dots are the measured data from Caco-2 cells stimulated with 20 ng EGF.

Optimization of the model is carried out as follows. When the model is entered into the modeling software some parameter values are known from the literature, e.g. kinetic binding rate constants, phosphorylation rate constants, . . . etc. Some however, are not known, and putative values for those rate constants must be entered. Rate constan values can be gathered from literature sources that have measured their values or by estimating their value from what is known in the literature or otherwise on the activation or deactivation of a particular component or analgious biological component if that information is not available. These starting values may produce simulation outputs that do not necessarily match up with experimental time course measurements of the expression levels of the actual components. The expression levels are the total protein levels, levels of modified forms of the protein (e.g. phosophorylated, cleaved,), and or RNA levels using a multitude of experimental methods.

FIGS. 33(a)-(d) contain the data points for the phosphoryatled forms of AKT, MEK, and ERK. These data points are fed into the simulation and the resulting simulated time series for a particular chemical is compared to an experimentally measured concentration time series. A 'penalty' or 'cost' is calculated as the square of the difference between the data and the simulated time series. The cost function for each experiment, $CF^i(kb_1, ku_2, kp_1, kM_2, \ldots)$ is a function of all of the parameters in the model and is defined as $$CF^i(kb_1, ku_2, kp_1, kM_2, \ldots) = \sum_j \frac{(\text{Exp\_data}_j^i - \text{Sim\_data}_j^i)^2}{\sigma_j^{i2}},$$

where $\text{Exp\_data}_j^i$, $\text{Sim\_data}_j^i$, and $\sigma_j^i$ are the experimental data point, the simulation data point, and the error on each data point for an experiment i, respectively. Other cost functions exist which take into account error in time measurements. The sum over j is taken over all of the data points collected from the experiment. To incorporate the cost from every experiment, e.g. a different experiment would consist of stimulating with another growth factor or a different dose of growth factor or inhibiting a particular component in the network . . . etc., the global cost function, $CF(kb_1,ku_2,kp_1,kM_2,\ldots)$, which is a sum over all experiments i is calculated as $$CF(kb_1, ku_2, kp_1, kM_2, \ldots) = \sum_i CF^i(kb_1, ku_2, kp_1, kM_2, \ldots).$$

Each simulation data point is computed with the conditions specific to that experiment. For example, an EGF experiment with five different levels of EGF would be simulated under each of those conditions and similarly for other treatments and conditions. The goal is to find the parameter values that minimize the overall global cost function $CF(kb_1,ku_2,kp_1,kM_2,\ldots)$. A number of optimization algorithms are used in the software to perform the optimization (e.g. Leven Berg Marquardt, Simulated Annealing, . . . etc.).

To minimize the global cost function, the rate constants are perturbed away from the starting values and the simulation is repeated and the cost recalculated. If the cost is lower, the new set of rate constants that gave the lower 'cost' and a better fit to the data are taken. Perturbing or changing of the rate constants may be carried out almost randomly or more scientifically, depending on the optimization routine. The process of changing the rate constants, simulating the network, and evaluating the change in the 'cost' is repeated until the simulation nearly matches the data. Parameter values are sought that give a simulation output that matches the data. After optimization, the kinetic parameters are constrained such that the simulation output matches the experimental time points as shown in FIGS. 33(a)-(d) where the solid line represents the simulation output.

In this way parameter values were constrained to fit the measured data and the model was then used to predict cellular behavior.

Predictions from the Model of the Physiological State of the Cell and Finding Combination Therapies to Reverse the Cancer State The model predicts physiological outcomes such as proliferation, G1-S, G2-M, S phase arrest, and apoptosis as indicated by molecular markers within the simulation. For example, CyclinE-CDK2 levels are an indicator of the G1-S state, CylinA-CDK2 levels are an indicator for the S phase state, CylinB-CDK1 levels are an indicator for the G2-M state, and caspase 3 and cleaved PARP (a protein that gets cleaved by executioner caspases such as caspase 3) are indicators for apoptosis. The model is used to simulate the "cancer" state indicated by high levels of proliferative signals such as Erk and high levels of pro-apoptotic proteins such as Bcl2. Targets can be perturbed to see if a particular physiological state can be induced. After perturbing the target one can predict whether the cells will go through G1-S arrest, G2-M arrest, S phase arrest and apoptosis.

One can also use the model to predict the cell's sensitivity to being in a particular state, e.g. sensitivity to apoptosis. By way of explanation, normal cells express a certain number of anti-apoptotic proteins. These proteins are analogous to actively applying the brakes in a car at the top of a hill to prevent it from rolling down, or, in the case of the cell, going into apoptosis. If the brakes are released the car will not move forward unless another force is applied, but without the brakes it is much easier to send the car down the hill. Similarly, in a sensitized state, the cell is more likely to go into apoptosis when another perturbation that is pro-apoptotic is applied than when it is not in a sensitized apoptotic state.

FIG. 34 shows the results of perturbing 41 individual targets in the model where the final outcome is the cellular physiological state of the cell. 41 targets were perturbed in the simulation of the cancer cell. A perturbation was applied singly either on the protein or RNA level such that the final outcome was up or down regulation of the target on the protein level. This perturbation can be accomplished systematically or automatically via a computer algorithm that systematically perturbs each component and then checks to see what state the cell is in.

Most of the perturbations shown in FIG. 34 lead to a more sensitized apoptotic state. This is characteristic of a lot of cancer therapeutics which have a single target as a component of the diseased cell. Other putative therapeutics can be found by determining the effect of their action on another node of intervention. Within the simulation one can knock out a combination of targets and thereby identify which combination, when knocked out, is more likely to promote apoptosis.

FIG. 35 lists combinations of targets that were identified by the simulation which when knocked out caused apoptosis in a colon cancer cell. Surprisingly, it was found that many targets when inhibited singly lead to sensitization towards apoptosis or weak induction of apoptosis, but not apoptosis or a strong induction of apoptosis. The combinations of targets synergistically give rise to apoptosis in a cancer cell. For example, when one inhibits Bcl2 or Bcl-xl in combination with CDK1, one can predict apoptosis in the cancer cell. In contrast knocking out these targets singly results in little or no caspase 3 activation. Without being bound by theory, the mechanism for this may be that inhibiting CDK1 in cells that are quickly dividing leads to high levels of free CyclinB. This can sequester 1433-sigma away from the pro-apoptotic proteins Bax and Bad, freeing them up to target the mitochondria. This effect can further be enhanced by inhibiting Bcl2 or Bcl-xL in combination. High levels of Bax and Bad can then promote apoptosis via breakdown of the mitochondrial integrity.

Figure 36:
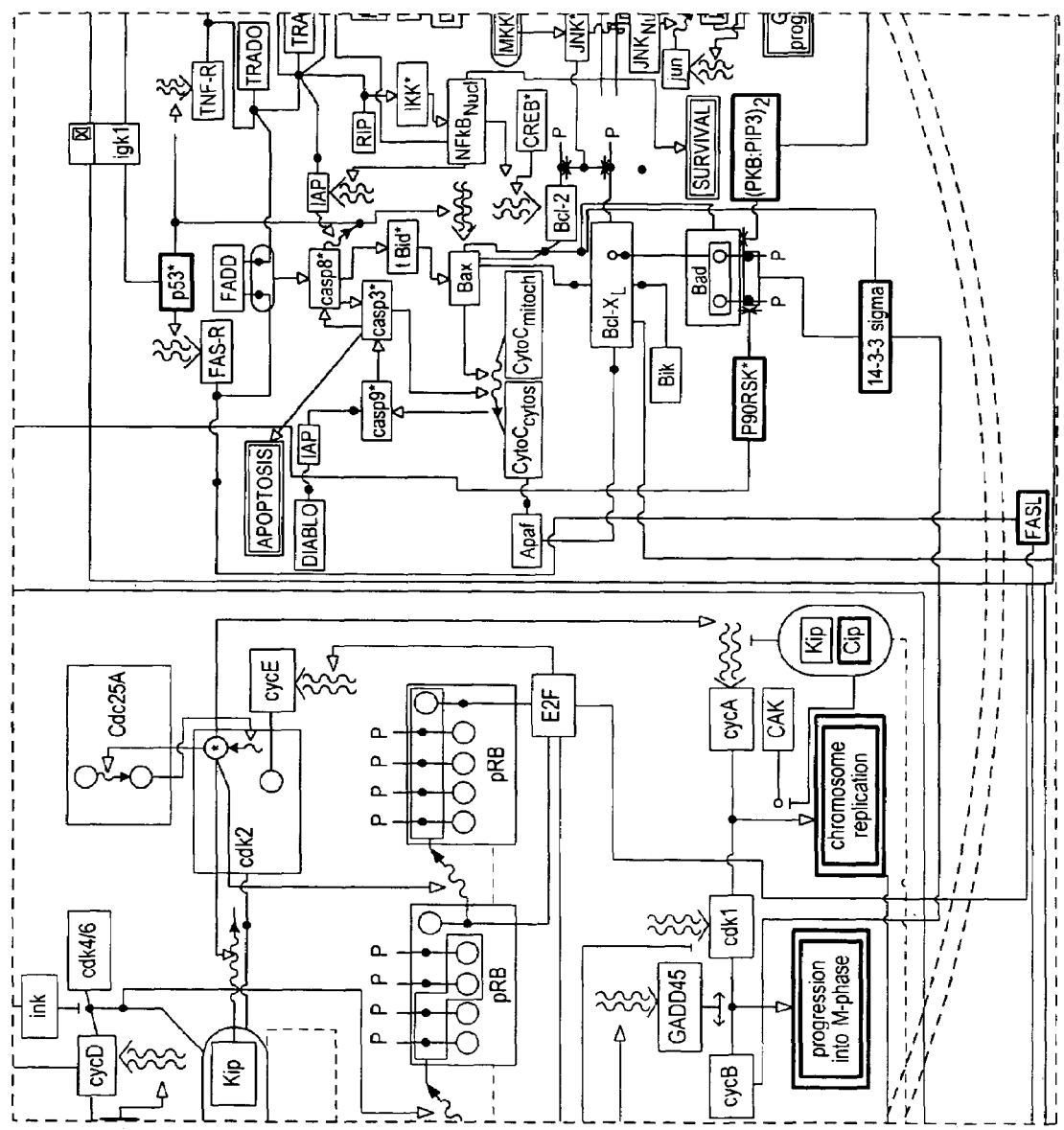
FIG. 36 shows the mechanism of action of the perturbation in the exemplary colon cancer cell simulation.

FIG. 36 shows the mechanism of action of this perturbation as described in the colon cell simulation. It is noted that FIG. 36 depicts a portion of FIGS. 33(f) and 33(g). In cells that are dividing or quickly dividing (e.g. cancer cells), CDK1 can be inhibited leading to induction of free CyclinB. CyclinB can then bind 1433-sigma and sequester it away from Bad, Bax, and other pro-apoptotic Bcl family members.

Identifying Key Nodes of Intervention from the Simulation

The simulation is used to understand the conditions under which oncogenic Ras leads to sustained levels of phosphoyrlated Erk. Based on this analysis one can locate key places in the network that drive sustained Erk levels and this knowledge can then be used to identify new targets for therapeutic intervention.

Mutations in Ras lead to reduced hydrolysis rate such that GAP is unable to efficiently convert GTP bound Ras to GDP bound RAS. This mutation was explicitly put in the simulation by reducing the parameter value controlling Ras hydrolysis rates. A cancerous state is characterized by the cell's ability to create sustained Erk levels with small levels of growth factors. Thus the system was simulated under conditions where low levels of growth factors were added. It was found that the only way one could attain sustained levels of phosphorylated Erk, was where there was autocrine signaling in the system, i.e. a feedback loop wherein Erk can lead to the transcription of growth factors that bind to the EGF receptor and further stimulate the network in an autocrine manner.

Thus another node or region where therapeutic intervention can be helpful was discovered.

Figure 37:
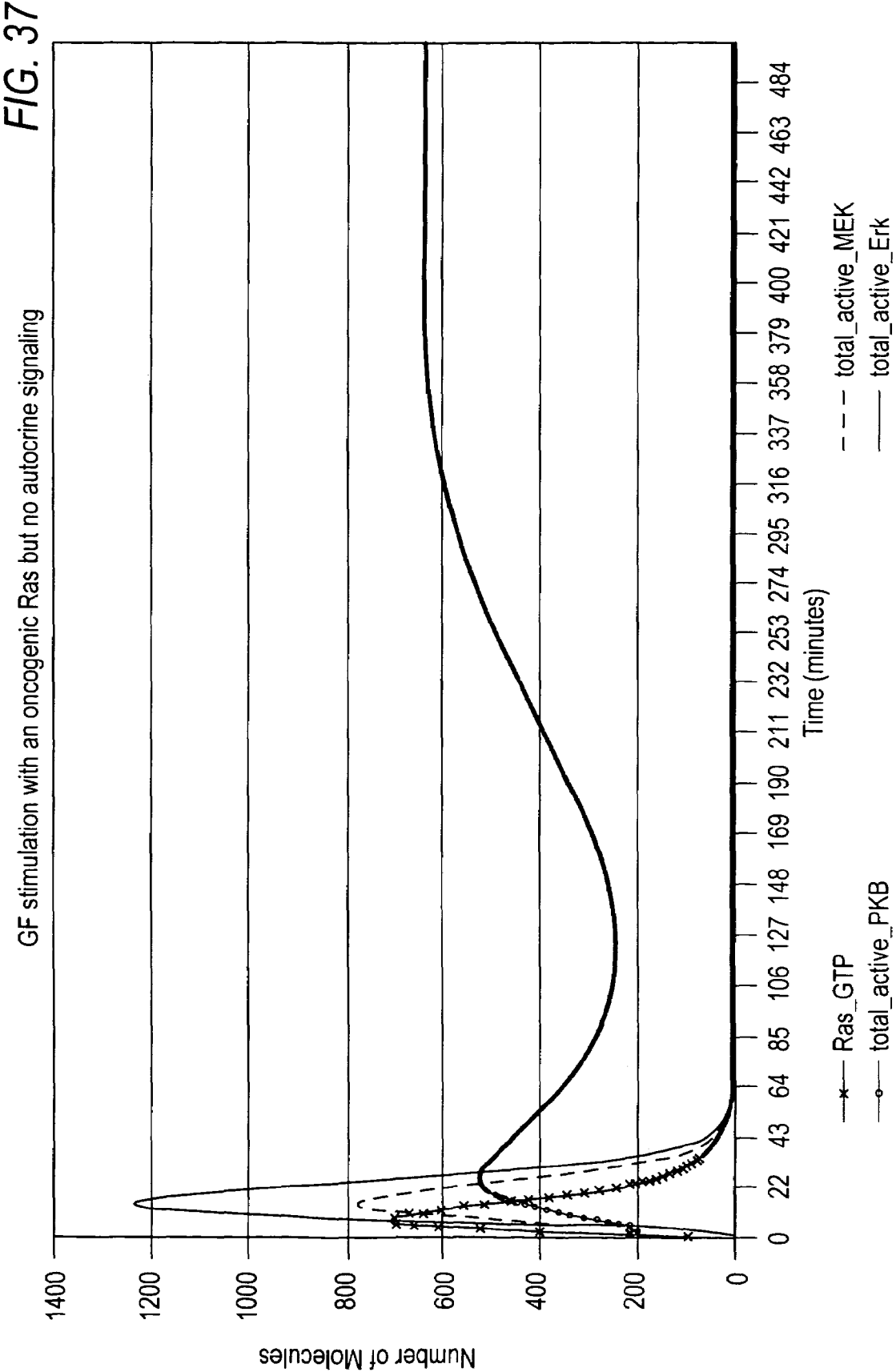
FIG. 37 depicts the simulation output of an oncogenic Ras without autocrine signaling.
Figure 38:
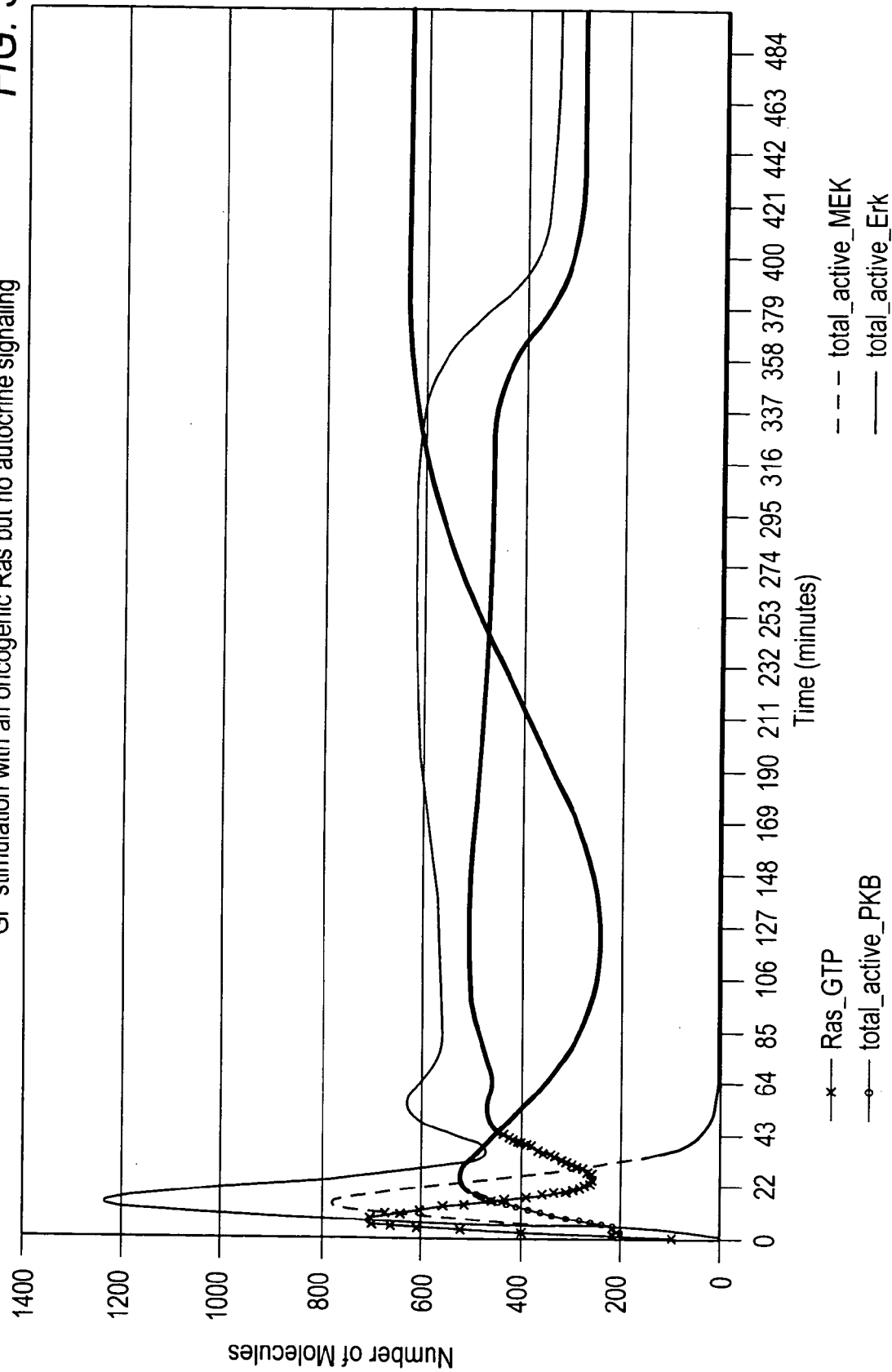
FIG. 38 depicts the simulation output of an oncogenic Ras with autocrine signaling.

One can also perturb Ras or Erk directly and also perturb the nodes that are responsible for the autocrine signaling and thereby reverse the cancer state. FIGS. 37 through 38 show the simulation output of this study. The upper graph depicts Erk stimulation in the normal cell where it is stimulated transiently. The lower graph above shows sustained Erk levels arising as a result of having both an oncogenic Ras and autocrine signaling.

Testing Drugs/Compounds within the Model

A particular cancer state in which several nodes are mutated has been simulated. The mutations in the model were inputted by: (1) deleting beta-catenin Axin interaction so that high levels of beta-catenin accumulate in the nucleus and transcription of cell cycle target genes ensues; (2) mutating the Ras-Map kinase pathway by reducing the kinetic parameter representing the GTP hydrolysis rate of Ras and thus promoting high levels of erk and survival signals; and (3) increasing the expression of bcl2 leading to higher levels of the anti-apoptotic protein in the cell as is found in many colorectal cancers.

An anti-sense bcl2 inhibitor G3139 (e.g. G3139, Benimetskaya et al. 2001) currently in clinical trials was tested within the model to determine whether it had any efficacy against the cancer state. G3139 has been shown to reduce the total levels of Bcl2 over 24 hours. Using the simulation it was found that the cells become sensitized to apoptosis, but most do not undergo apoptosis. The sensitivity to apoptosis depends on the level and activity of pro-apoptotic proteins such as Bax, Bik, and Bok. Cancers that have mutations in these proteins are less sensitive to G3139 therapy.

Figure 39:
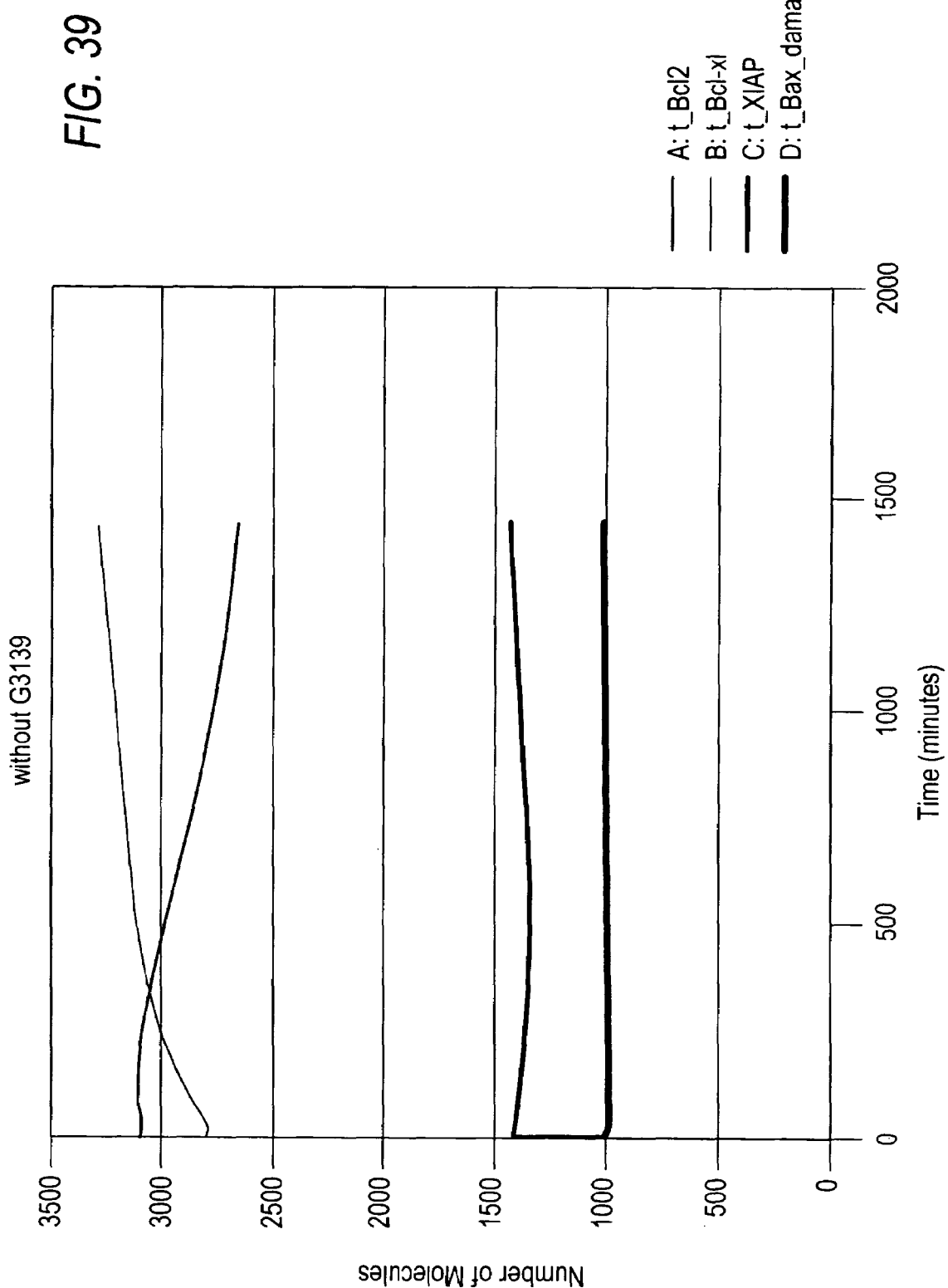
FIG. 39 depicts the simuation output of levels of Bcl2 without the G3139 antisense therapy.
Figure 40:
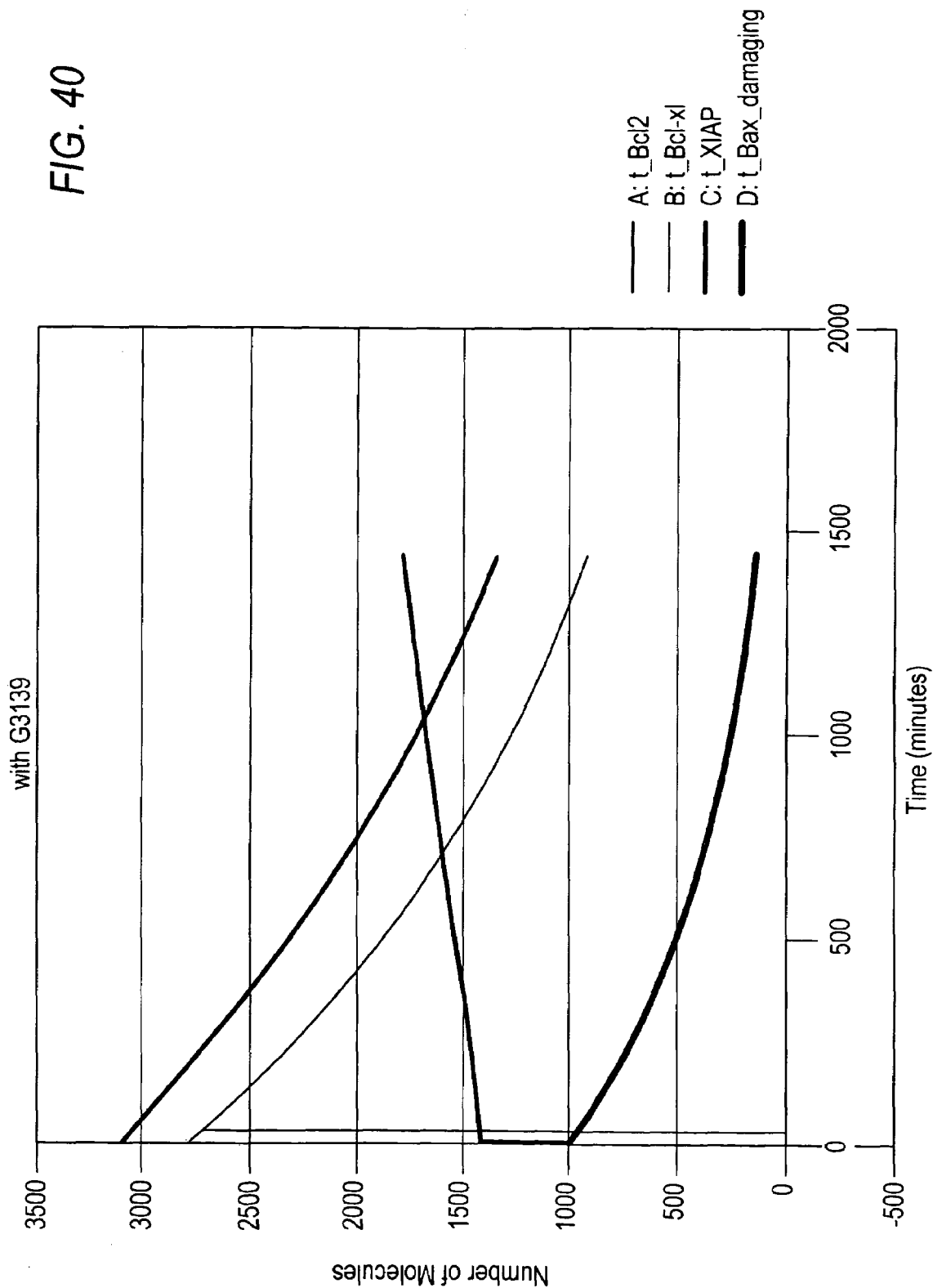
FIG. 40 depicts the simulation output of inhibition of Bcl2 using the G3139 antisense therapy.
Figure 41:
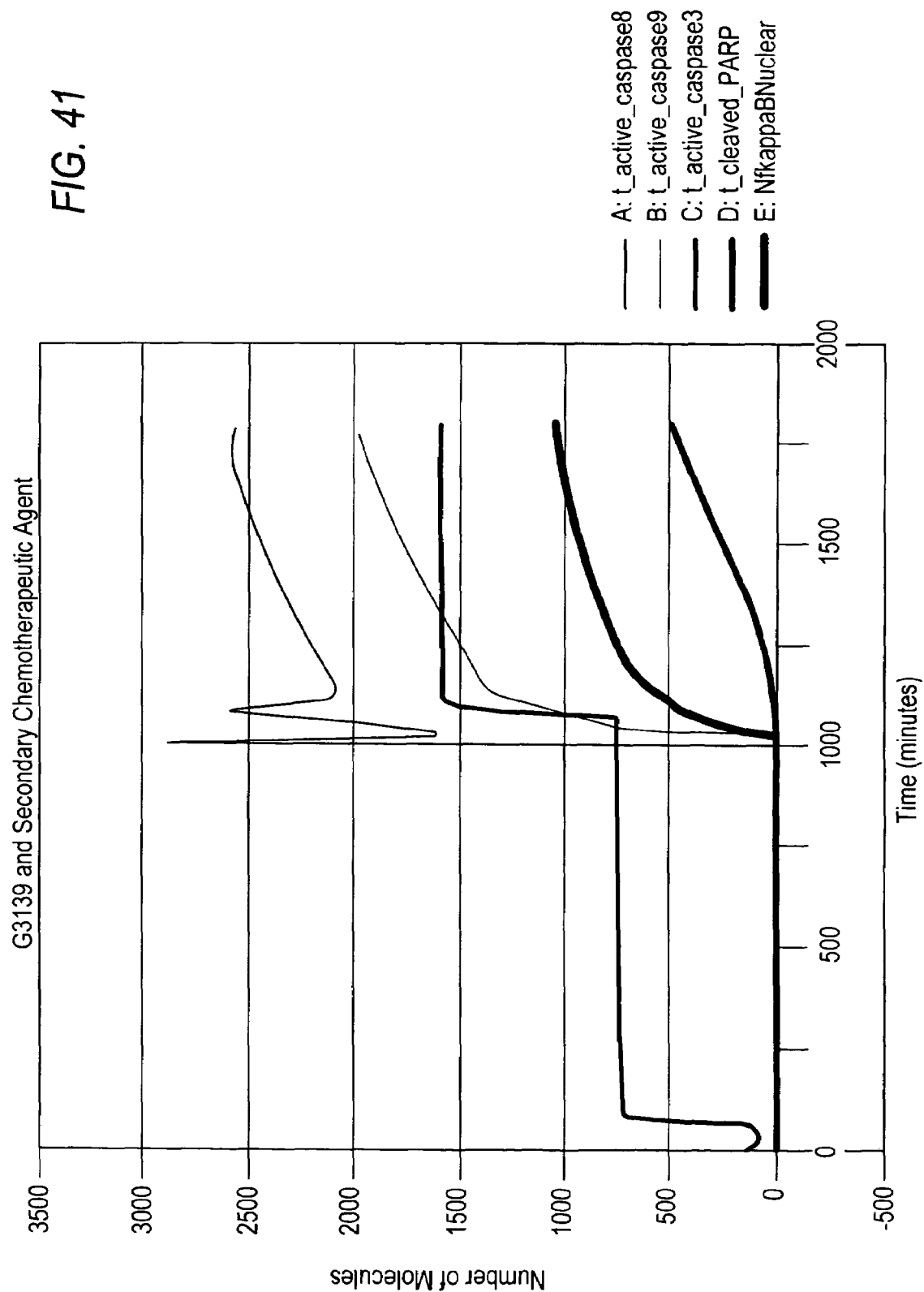
FIG. 41 depicts the simulation output of inhibiting Bcl2 using G3139 antisense therapy in combination with a secondary Chemotherapeutic agent.

It was also found that massive apoptosis can be induced if the microenvironment of the cancer cell contains cytokines such as TNF-alpha and FASL. These cytokines will further induce autocrine and paracrine signaling that will promote apoptosis in the cancer cell and surrounding cells. The cells become even more highly sensitized when non-specific effects of G3139 were simulated, e.g. its ability to inhibit XIAP and Bcl-xL mRNA translation (Benimetskaya et al. 2001). To induce strong apoptosis requires a secondary agent that leads to up-regulation of pro-apoptotic proteins or cytokines. G3139 in and of itself has low toxicity. Without being bound by theory, one can predict that the toxicity induced with the secondary agent depends on the specificity of the secondary agent to cancer cells. The more specific, the less toxic the combination therapy will be. FIGS. 39-41 shows the Inhibition of Bcl2 using G3139 antisense therapy.

This simulation illustrates how one skilled in the art can use the model to simulate the treatment of a patient with a specific stage of cancer by using one or more specific agents that target key proteins controlling cell cycle progression and apoptosis. The methods of invention demonstrate how one can use the model to determine the efficacy of an agent against cancer with a certain mutational profile. The methods of the invention include optimization of the model with patient data and the use of the model to analyze the best treatment strategy. The methods of the invention determine how one can assess toxicity effects from using a single or combination agent therapy on the normal cell.

Iterative Refinement of the Model through Experiments The colon cancer model as optimized above, predicted that inhibiting NFkappaB and stimulating with TNF, in combination, would synergistically promote increased levels of apoptosis. This prediction was based on the fact that TNF concurrently activates the apoptosis pathway via capase 8, 3, and 9 and the survival pathway via IKK and NFkappaB. The latter pathway leads to upregulation of survival signals which thwart or inhibit the apoptotic signaling.

This experiment was performed on HCT116 to see if the prediction was valid. FIG. 42 shows the cleavage of PARP as a result of inhibiting Ikappab-alpha in combination with adding TNF at various levels. FIG. 42 shows the relative levels of cleaved PARP after 24 hours of stimulation with various doses of TNF. The cells were stimulated with TNF alone, with 20 and 50 uM of the Ikappab-alpha inhibitor, and with DMSO, the agent that solublizes the inhibitor as a control. The inhibition of Ikkappab-alpha effectively blocks NFkappaB nuclear translocation preventing NFkappaB from activating the transcription of anti-apoptotic genes. The cleavage of PARP signifies caspase 3 activation and to some extent the degree of apoptosis in the cells. Surprisingly, it was found that the combination did not synergize the promotion of apoptosis. Upon further study it was found that in HCT116 cells, NFkappaB accumulation in the nucleus in response to TNF was transient and down stream anti-apoptotic targets did not get activated. Thus in HCT116 cells the prediction is that the combination therapy will not have a strong effect. This method can be used to predict which cells would be responsive to TNF and NFKappaB inhibition. Only those cells in which NFkappaB signaling is strong as a result of TNF activation will respond strongly to the combination. In this way, the model was refined and in its refined state could be used to determine which cell types or cancers could be treated by inhibiting NFkappaB transcription in combination with adding TNF so as to synergize the promotion of apoptosis.

Exemplary method for determining validity and robustness of the prediction

Since experimental data has associated uncertainties as shown in FIG. 33(a) through 33(d), any parameters inferred by fitting experimental data will also have uncertainties. There are two types of uncertainty that may arise in this manner:

(1) Uncertainty in determining the parameter values around one local minimum of the cost function, and (2) Uncertainty in comparing different local minima of the cost function.

Standard formulae for the propagation of uncertainties from an experimental measurement to a set of fitting parameters apply to case (1). These come from the standard error propagation formula $$(\Delta K)^2 = \text{Sum}\_i (dK/dE\_i)^2 (\Delta E\_i)^2$$

where K is an inferred parameter, E_i(Delta E_i) are the experimental measurements (uncertainties), and Delta K is the uncertainty in K.

For case (2), this formula does not apply. Case (2) arises in the event that there are different sets of dynamical system parameters that fit the data equally well, given the uncertainties in the experimental data. The dynamical system can be used to predict which experimental measurement would be most effective in determining which set of dynamical system parameters is a more accurate description of biology. This proceeds as follows:

(a) Simulate the different dynamical system parameters for some randomly chosen initial conditions;

(b) Calculate for each unobserved molecule M, the root mean square deviation over these randomly chosen initial conditions, for the different dynamical system parameters defined as sigma_M;

(c) Check that the sensitivity of the parameters K in the model which differ between the different dynamical system parameters, with respect to measurements of levels of the molecules E_M;
(d) Experimentally measure the level of the molecule with the highest sum of total sensitivity and root mean square deviation;
(e) Repeat the experimental fitting for all parameters to check that some of the different parameters for local minima are no longer local minima.

This iterative procedure eliminates systematically the different local minima that arise in fitting experimental data to large dynamical systems.

This methodology is useful in discerning between the different predictions that a model might output as a result of being underconstrained. For example, in the apoptosis pathway, the onset of caspase activation shown in FIG. 32(g) can be due to a heavy weighting of parameter values responsible for the positive feedback loop between Caspase 8, Caspase 9, and Caspase 3 shown in FIG. 32(g) or can be due to a heavy weighting of parameter values responsible for autocrine signaling whereby the component JNK further activates cytokines TNF and FASL. In other words, the above methodology would output two fits to the data one with chemical concentrations and parameter sensitvities that favor the feedback mechanism between the caspases and the other that favored high levels of TNF and FASL resulting from autocrine signaling. In the former case, one would predict that perturbing the autocrine loop would not have any consequence on inducing apoptosis in the cell and in the latter case one would predict that it would. In this case, the only way to distinguish between the two hypothesis predicted by the model is to carry out an experiment that perturbed the chemicals and or parameters deemed important by the above analysis. In this way the methodology has been used to generate more than one possible hypothesis. Our goal is to devise a method to distinguish between the hypothesis or to determine where and how the modul is robust. Using this methodology, an experiment can then be designed to perturb the chemicals and or parameters showing the greatest deviation and sensitivity between the hypothesis. The experiment that is devised in this case An Exemplary Modeling Tool: the Diagrammatic Cell Language ("DCL")

The Diagrammatic Cell Language is a language for modeling and simulating biological systems. At its core is the notion that the behavior of biological systems may be best understood as an abstract computation. In this view point, the units of biological heredity are packets of information, and the cell's biochemical circuitry as a layer of computation evolved with the goal of replicating the data stored in the hereditary material.

The Diagrammatic Cell Language is a precise representation designed to be translated into a computer model of the reactions it represents. This translation is referred to as parsing. The parsing can occur via human modlers or a computer algorithm. The is the beauty of the language: biologists can use it to map out describe the biological interactions, modlers can then parse the diagrammatic model built by the biologist and create a dynamical simulation using said simulation environments (mention all other simulation environments). The translation of the Diagrammatic Cell Language into computer code using a computer algorithms has been described in the DCL Provisional Patent.

This language is the best method for concisely representing the massive amounts of cellular interactions that can occur in the cell. This has been used to map the biological interactions of a 200 component network of colon a cell modularly represented in FIGS. 31 and 32. The mathematical equations representing that diagram have been parsed by a human modeler and are represented in Exhibit A. What makes the language so efficient, are higher order structures that can compactly represent all of the interactions a cellular component can under go (e.g. a protein binding to multiple components and getting modified by other entities). The constructs, unique to the language: linkboxes and likeboxes are shown in FIG. 43(a), allow the biologist to compactly create diagrams of the cell without simplifying the functional representation of a compound or reaction. The language is modular: compounds and reactions may be represented at levels of complexity at the discretion of the biologist. It is object-oriented: a bound form of compounds, for example, inherits the states of its constituents.

The in addition to such new constructs as linkboxes and likeboxes, basic "noun" (single chemical entity such as the atom in FIG. 43(a), "verb" (indicate transformations of a set of nouns to a set of nouns), and "reaction/component shortcuts" are utilized. The language constructs are summarized as follows (note: a formal definition of the language is provided in DCL Provisional Patent (see definitions for details) which includes a description of the Diagrammatic or pictorial representation described here, the parsing of the language into computer code, and an abstract representation that uniquely defines the language):

Basic Grammatical Constructs
Atom—An atom is a noun. It is one particular state of a molecule (or a molecule that is modeled as having one state). FIG. 43(a) depicts an example atom, A. (See FIG. 43(a)-43(b) for examples of the graphic symbols in DCL.
Reaction—A reaction is a verb. It is a symbol that represents a transformation of a set of nouns to a set of nouns. Its symbol is a squiggle.
Dimerization—A dimerization is a shorthand symbol that represents two compounds reacting with each other to form a new bound form. Its symbol is a black dot:
Compartments—A compartment is a location with the cell. For instance, as shown in FIG. 43(a), the nucleus (A is in the nucleus):

New Grammatical Constructs
Linkbox—A linkbox is a noun that represents a collection of states. It could be used to automatically represent, for example, the many states of a protein that has several phosphorylation sites, a protein that can undergo modifications, or a promoter. The example linkbox is shown with with two states:
Likebox—A likebox is a noun that represents a group of nouns or reactions that all have a similar function. An example of a likebox which contains molecule A and molecule B (which act alike) appears in FIG. 43(a).
Resolution Notation—Resolution notation is used to identify particular states or subsets of states of a linkbox or likebox. The basic form is a text string like this, which indicates that state (1) is bound, and states (2-4) are unbound:
(1,0,0,0)
Equivalence line—This is a line that connects two nouns that are equivalent. This indicates protein A is equivalent to protein B.
Complex—A complex represents a collection of nouns that bind together in a prescribed way. This is a complex of proteins A, B and C (A binds to B, which binds to C, which in turn binds back to the original A). See top of FIG. 43(b).
Modifier—Modifiers are used to express molecules that are both reactants and products of a reaction, or inhibitions.

They could be used to represent catalysts, for example (C enables the reaction of A to B).

Process—A process is a verb. It is a module which describes either unknown or coarsely modeled behavior. The process is a double-squiggle. Here is a process that could represent, coarsely, the production of B from A.

Unique—The word unique describes a noun. It represents a molecule that only appears once. An example is a Promoter. A unique noun has a double-lined border.

Ubique—The word ubique describes a noun. It represents a molecule that is so common it can be considered to be of constant concentration and continuous availability. An example is Calcium. A ubique noun has either a dashed border or no border.

Common—The word common describes a noun. It represents a molecule that is neither unique or ubique, several copies of it may exist in the cell. A common noun has a single-line border.

Below is a comparison between two approaches to describing a portion of the Ras Activation pathway. The first approach (a) is a more traditional approach to drawing a network diagram. It consists solely of low-level language constructs. Notice how the (a) diagram, alone is imprecise: it requires additional text to explain the function of the molecules and thus can not efficiently be converted into a set of mathematical equations for simulation.

Figure 44A:
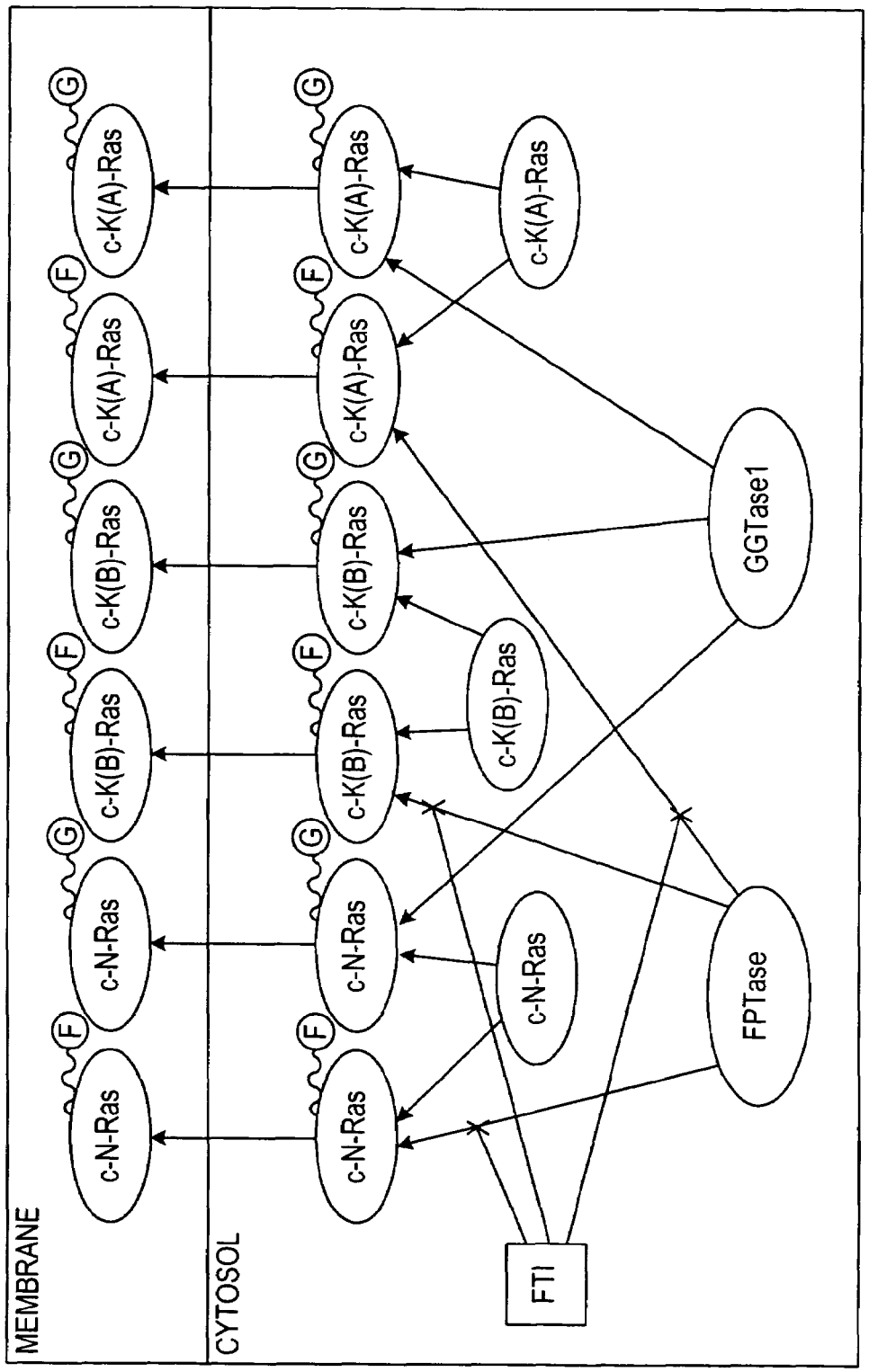
FIGS. 44(a)-(b) compare a simple notation with the Diagrammatic Cell Language.

(a) FIG. 44(a) depicts a portion of the Ras Activation pathway expressed in a traditional way. The traditional depiction, however, is unclear. The following text is required for clarification:

Farnesyl protein transferase (FPTase) catalyzes the addition of a farnesyl group onto C-N-Ras, C-K(A)-Ras, and C-K(B)-Ras. Faresyl transferase inhibitor (FTI) blocks this reaction. Some classes of FTIs work by irreversibly binding to FPTase. Geranylgeranyl transferase 1 (GGTase1) catalyzes the addition of a geranylgeranyl moiety onto the same group of Ras molecules. After lipid modification, each Ras molecules translocates from the cytosol to the membrane.

Figure 44B:
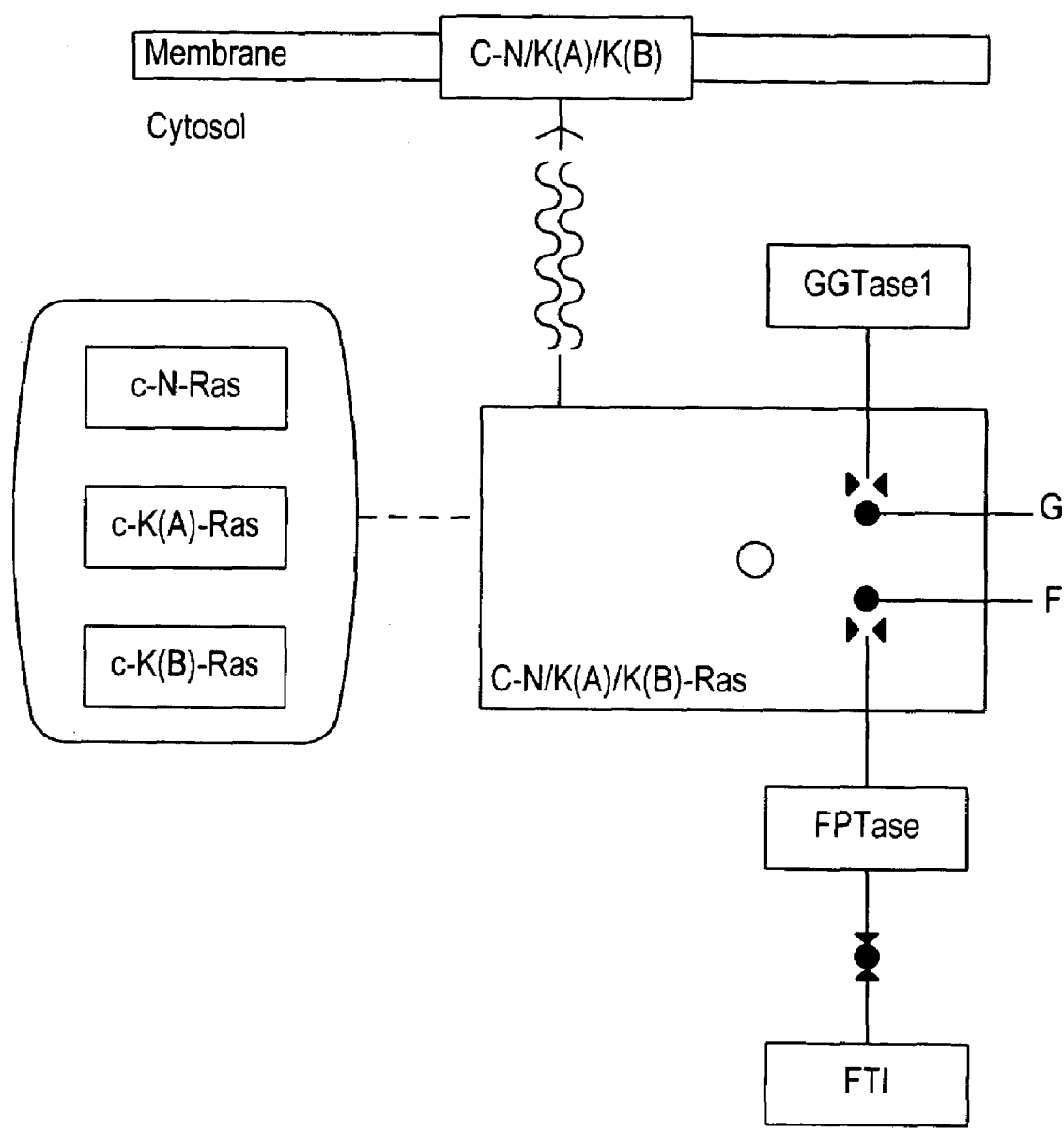

(b) On the other hand, FIG. 44(b) depicts the same pathway expressed with the Diagrammatic Cell Language. Provided that one learns how to read the language, all of the above information in the traditional depiction is contained solely within the DCL visual diagram. Note how no additional text is necessary to explain the function of the molecules, the diagram is much more concise, it is precise, and it is much easier to read. The above diagram can then be parsed into a distinct set of chemical states and a distinct set of reactions. For each reaction the modler or computer algorithm will have to attach a kinetic form and kinetic values to the parameters. The above pictures parses into the following set of states or chemical entities (the underscore here indicates the modified or bound form of the chemical) and reaction steps which the modeler can then attatch a specific kinetic form to:

| Chemical Species | Reaction Steps |
| --- | --- |
| FPTase | GGTase1 Gernyslates C-N-Ras |
| FTI | FPTase Farnyslates C-N-Ras |
| c-N-Ras__G | C-N-Ras__F translocates to the membrane |
| c-N-Ras__F | C-N-Ras__G translocates to the membrane |
| c-N-Ras__G__F | C-N Ras__G__F translocates to the membrane |
| c-K(A)-Ras__G | C-N-Ras translocates to the membrane |
| c-K(A)-Ras__F | . |
| c-K(A)-Ras__G__F | . |
| c-K(B) Ras__G | . |
| c-K(B)-Ras__F | . |
| c-K(B)-Ras__G__F | iterate these steps with c-K(A)-Ras and c-K(B)-Ras in place of C-N-Ras. |
| FPTase__FTI | |
| GGTase1 | |
| c-N-Ras__G__membrane | |
| c-N-Ras__F__membrane | |
| c-N-Ras__membrane | |
| c-K(A)-Ras__G__membrane | |
| c-K(A)-Ras__F__mebrane | |
| c-K(A)-Ras__mebrane | |
| c-K(B) Ras__G__membrane | |
| c-K(B)-Ras__F__membrane | |
| c-K(B)-Ras__membrane | |

Exemplary Software Implementation for the Simulation and Optimization of Biochemical Reaction Networks It is exceedingly difficult to implement the methods of the present invention without utilizing the data processing power of a computer (in the most general sense of the term as a nonhuman automated computational device) to solve the numerous equations and/or formulae used in modeling and optimizing the models for biochemical networks. Thus, in a preferred embodiment of the invention, computer code is utilized to implement the present invention. Such code can take many forms, and be implemented in a variety of languages utilized for such purposes. The following describes various exemplary embodiments of such code which were written to implement the various functionalities of the present invention.

A First Embodiment

Goals:
1) To study the evolution of biochemical pathways in a single cell, as observed in the simulation-generated time evolution of various chemical species (proteins, enzymes, mRNA, etc.), given a certain set of initial conditions, i.e., the initial concentrations of each of the different species.
2) To determine, within some bounds of error, the unknown values of various pathway parameters, namely, the rate constants, which are used to define the rate of reactions in the pathway.

Elements of the Code:

The code was written in C++, with network classes representing the reaction networks, a director class to handle multiple copies of the network, a minimizer class to determine optimizable parameters and integrator classes to simulate the behavior of the network over time. Chemical, reaction and rate constant classes were defined to be used in the network class.

To optimize any given biochemical reaction network the user had to define a network class specifying three lists of objects. The first was a list of chemical objects corresponding to the chemicals participating in the network. The second was a list of rate constant objects that were used to define the rate of the reactions. The third list consisted of reaction objects, each of which used subsets of the chemical and rate constant list defined above. The initial values of the chemicals and rate constants were hard coded into this class.

To simulate multiple experiments on the same network, multiple copies of the network would be defined, with different initial conditions, and a director class would handle the list of these networks. In the case where only one network was optimized, the list in the director contained that single network. The integrator to use was also specified directly in the director class. The time series of chemicals that were to be plotted were also specified in this class.

Method of Use:

To optimize the values of all rate constants specified in a network the user had to go through the following steps, modifying the code and recompiling for each run.

The user first had to create the network classes with the appropriate chemicals, rate constants and reactions. Then he/she would create the director class using these network classes. The integrator to use for each network was specified here, and the various variables controlling the behavior of the integrator were also set in this class. The files containing the experimental time series data against which optimization was done, was set in this class. Then in the main body of the code, the director class, and a minimizer class were instantiated, and the director was passed to the minimizer for optimization of the rate constants.

The basic steps for the parameter optimization algorithm, as found in most cases of optimization, are as follows:

1) Time series for the chemical concentrations of each chemical in each network class are generated. To do this, a set of differential equations is generated by looping over the chemicals, and the reactions that they participate in. Each differential equation corresponds to the rate of change of the concentration of a chemical in the network. The time series are generated by integrating this set of diff. equations, starting with the initial concentrations and the rate constants.

2) Now the available experimental time series data for chemicals in the pathway are compared to the corresponding generated time series. The sum of squares of the differences between the experimental concentration data and simulation-generated concentration data at time points provided by the experiment gives a value for the "objective function" for the network.

3) The "global objective function" value is computed by the director by summing over the objective function value from each network. The optimizable parameters, i.e., the rate constant values, and the calculated global objective function value are then passed to the minimizer. The minimizer then returns a new set of values for the rate constants.

4) Using the new rate constant values the networks are reinitialized, and the code repeats the above steps. While iterating through these steps, the minimizer tries to find parameter values, so as to minimize the objective function. The parameter values thus determined are then considered to best describe the biochemical reaction network, giving sets of time series that are closest to the experimental data for the user provided initial concentrations.

Among the algorithms for integration of a set of ordinary differential equations, this version included the well known Runge-Kutta integrator and variations thereof, that allowed for different levels of accuracy as well as dynamic adjustment of the integration step-size for balancing speed and accuracy. The other type of integration algorithm was an implementation of the stochastic integrator by Gillespie that determined the cumulative probability of occurrence of each reaction in the system and chose one based on a uniform random number that is compared to the cumulative probability. The optimization algorithms used were the deterministic Levenberg-Marquardt method and the stochastic Simulated Annealing method.

Problems Encountered with the First Embodiment of the Computer Implementation:

1) To simulate/optimize different biochemical networks, the user had to setup new classes for each network, and the corresponding director and then recompile the whole code. Even to modify a single value for the initial chemical concentrations, rate constants, integrator variables or minimizer variables, the code had to be recompiled. This implied that a compiler had to be available to the user and that the user had some knowledge of C++, and compilation procedures.

2) The way the code was setup either all or none of the rate constants were optimized. The same was true for the initial chemical concentrations, although the code had not been tested with optimizable initial concentrations. In many cases, we would like to optimize only a small subset of rate constants and initial chemical concentrations.

3) It was not possible to specify concentrations as mathematical functions of other chemicals. This was often needed since many experimental data consisted of time series of sums of chemical concentrations. The rate constants were not variable at all.

4) Bounds could not be specified on the optimizable parameters.

5) When optimizing over multiple networks, the networks class had to be exactly the same except for the initial concentrations of the chemicals.

6) Even though the code had very little graphical output, it was tied to the Windows platform.

7) Besides the above-mentioned problems, there were obvious problems in regards to it's efficiency, and extensibility. It was very hard to introduce prewritten libraries of minimizers and integrators into the code. Also the code was not parallelizable.

The Preferred Embodiment:

Goals:

In addition to the goals stated above, code was created to eliminate the problems first encountered, as described above.

Elements of the Code:

The user defines a biochemical network by creating a text file for the describing the network. Hence, the network class is defined generally, and is filled in during runtime, based on the description file. In addition, the chemicals and rate constants can be made optimizable selectively through this file.

The director for multiple networks is specified in a separate file. The networks, over which parameter identification is to be done, are included in the director by including their file names in the director file. The integrators and identifiers are also defined through this file. Now a sequence of identifiers can be used by specifying multiple identifiers in the input file.

By introducing input via the text files (see example), the requirement for the user to have access to a compiler is eliminated. Thus there is no requirement that a user have any knowledge of C++. This also allows for a easier platform independent architecture in regards to user input.

In the preferred embodiment, chemical concentrations and rate constants are treated equally, as variables defining the state of the network. If the user chooses, they can now be defined as mathematical functions of other variables (both chemical concentrations and rate constants) and numeric constants. They can also be sent into the code with a predefined time series. To take care of all these changes the mechanism for handling time series was completely changed. A hierarchy of various time series classes to handle the various types of definitions for chemicals and rate constants was created. The form of the time series is specified in the input file.

Summarizing the above improvements, where network variables imply both chemicals and rate constants—

Network variables can be explicitly written as functions of time.

Network variables can be expressed as mathematical functions of other Network variables.

Rate constants can be unknowns, i.e., they can be treated as state variables for which there is a differential equation to integrate, just like the chemical state variables.

Network variables in the network can include time delays, so they can depend on states of network variables at different times.

Network variables can be expressed as switches, allowing reactions to be turned on/off at specified times, or depending on the state of some other network variable.

Time series expressing these network variables can be expressed in terms of
- a cubic spline
- a polynomial interpolation
- a mathematical formula—sum, product, difference, quotient, power, elementary function (sin, cos, tan, arcsin, arccos, arctan, log, exp), switch or gaussian.

Chemical concentrations can be either continuous or discrete.

The code enables parallelization of the code using the MPI (Message Passing Interface) library. The simulated annealing parameter identifier was completely rewritten, allowing for the use of a parallel architecture.

The preferred code now supports the integration of "stiff" systems of differential equations, resulting from reactions occurring on very different time scales. A stochastic integrator is included based on the "Next-Reaction" method by Gibson, which is more efficient than the previously used Gillespie algorithm.

The preferred code can compute the sensitivity of the cost function to changes in the parameters. The cost function sensitivities are computed by solving the sensitivity equations, which give the sensitivity of each chemical concentration with respect to the parameters. The chemical sensitivities are used to compute a raw value for the cost function sensitivity. Since these raw values depend on the scale of the associated parameters, they are normalized so that the sum of the squares of the normalized values is equal to one. With the normalized values, one can determine immediately which parameters have the greatest effect on the cost function; i.e., on the goodness of fit of the model.

The parameter identification has as also been improved. The new simulated annealing algorithm has been parallelized. The preferred code introduces a separate temperature schedule to gradually limit the range in parameter space, over which the next step can move. The deterministic Levenberg-Marquardt can use the parameter sensitivities to compute the gradient. This is both more efficient and more accurate than a finite difference approximation. Both parameter identifiers now allow for imposing a lower and upper bound on each optimizable parameter, thus narrowing the parameter search space.

Other features of the preferred code include a new parameter identification engine that has Optimizable parameters can be selected based on sensitivities.

An adaptive minimizer which iteratively chooses a subset of the parameters to make optimizable.

An analysis tool to aid the modeler in determining which parameters have the greatest effect on the concentration of specified chemicals.

When solving a system of stiff ODEs, it is necessary to solve a system of nonlinear equations at each time step. The solution of this nonlinear system uses Newton's method which is an iterative method that requires solving a linear system using the Jacobian matrix at each step. For most problems the Jacobian matrix is sparse, and the code has been written to take advantage of this sparsity. The linear system can be solved using either a preconditioned Krylov method or a banded solver. The new code has the ability to reorder the state variables in such a way that the bandwidth of the Jacobian matrix is reduced, making the solution much more efficient. For some problems, the speed-up in the new code is as much as two orders of magnitude.

Figure 45:
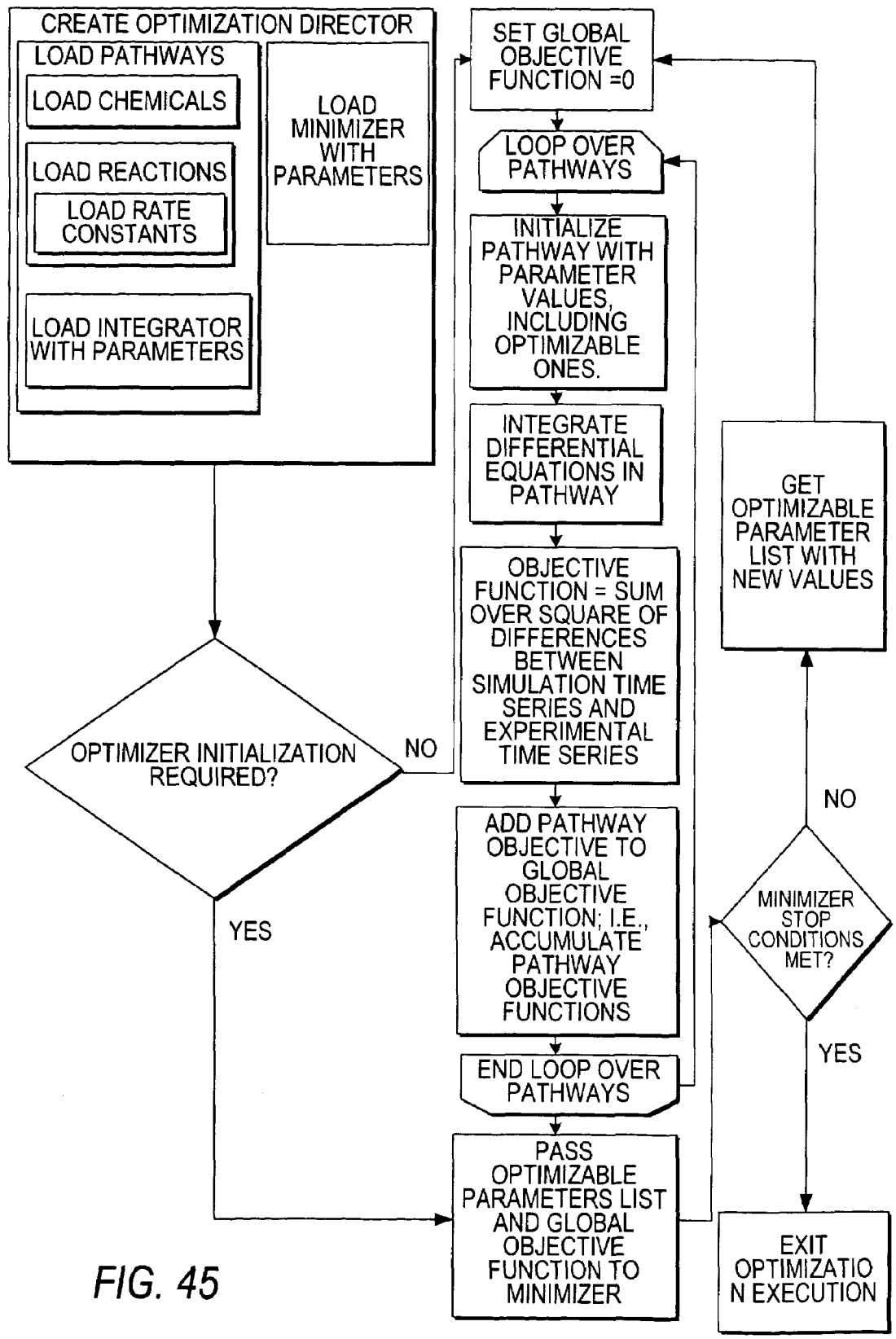
FIG. 45 is a flowchart of the execution of an optimization procedure of an exemplary software system according to the present invention.

The basic set of steps to run an optimization are depicted in the flowchart of FIG. 45.

Alternative Embodiment of the Preferred Code

Additional features of an alternative embodiment of the preferred code include:

Object-Oriented Database: An object-oriented database (OODB) to house data for various biochemical reaction networks. Using a separate code the user will be able to use the database to setup a simulation or parameter identification run. The input portion of the code reads the database directly from the database and then save the outputs back to it. The OO nature of the database simplifies the task of communicating with the database since the same classes for the code can be used, as those that are used to define the database.

Improved parallel algorithms for optimization: In this embodiment, the parallel simulated annealing code is improved by implementing various parallel architectures in the code. The Levenberg-Marquardt identifier is also be improved by a straightforward parallelization of the algorithm.

Multi-threaded integration: The integration algorithms are made multi-threaded. This leads to a better performance than using only parallel code.

Hybrid method: Standard intergrations methods are either purely continuous or purely stochastic. For many of the large systems contemplated to be analyzed by the methods of the present invention, a purely stochastic algorithm is too slow. On the other hand a purely continuous algorithm inaccurately describes reactions involving chemicals with few molecules in the system. Very often a biochemical network contains some molecules which play a central role, yet they have a very occurrences of them in the system. Hence to properly yet efficiently simulate a system a hybrid stochastic-continuous integrator is optimal.

Among other parameter identification algorithms, genetic algorithms and the direct fit method are implemented.

Example Showing the Use of the Preferred Code:

The following example shows how users can input models into the software and specify the integration and optimization algorithms to use. The first file the code reads is the director file. This file specifies the network(s), the integrator and the method(s) to be used for parameter identification.

```
director = p53_director {
    network = p53_network {
        source = "p53_network.txt";
    };
    integrator = cvode {
        relative_tolerance = 1e−5;
```

```
            final_time = 1200;
        };
    };
    parameter_identification = {
        identifier = simulated_annealing {
            max_temp_scale_factor = 100
            max_steps_per_temperature = 100;
            num_initial_trial_steps = 100;
            temp_anneal_factor = 0.9;
            parameter_temp_anneal_factor = 0.95;
        };
        identifier = levenberg_marquardt {
            max_iterations = 5;
            f_precision = 1e-5;
        };
    };
```

The director file contains a director block and a parameter_identification block. The director block contains one or more network blocks and an integrator block. In this example, the director has one network which is read in from the file "p53_network.txt". The integrator block specifies the integrator to use (in this case CVode, which is a third-party package for integrating stiff systems of ODEs) and parameters which control the behavior of the integrator. The parameter_identification block is optional; if it is omitted, the code will run a simulation and exit. If included, it specifies one or more identifiers to run along with options controlling their behavior. If multiple identifiers are specified, the first will run with the initial values of the parameters specified by the user, the second will start with the optimized values found by the first identifier, etc.

In keeping with the modular design, the network is usually read in from a separate file as in this example. In addition, different parts of the network (chemicals, parameters, reactions, etc.) are typically contained in separate files as well. For this example, the file "p53_network.txt" has the following lines:

```
            includefile = "p53_inputchems.txt";
            includefile = "p53_chemsnpars.txt";
            includefile = "p53_reactions.txt";
            includefile = "p53_expdata.txt";
            includefile = "p53_display.txt";
```

These lines tell the code to read in the named files in the order listed. The file "p53_inputchems.txt" has the following lines:

```
            chemicals = {
                damagedDNA = (0);
                E2F = (500);
                ChromosomeSignal = (0);
            };
```

These lines specify the names of three chemicals and their initial concentrations. Enclosing the initial concentrations in parentheses tells the code that these chemicals are state variables; i.e., their concentrations can be changed as the result of some reaction in the network. The equal sign ("=") means that the initial concentrations are fixed; they will not be changed in the course of the optimization.

Next is the file "p53_chemsnpars.txt":
```
chemicals = {
One = 1.0;
DNAPK = (1000);
Rad = (1000);
ATR = (1000);
ATM = (1000);
Chk1 = (1000);
Chk2 = (1000);
p53 = (50);
CKI = (1000);
CBP = (1000);
ARF = (1000);
Mdm2 = (1000);
XXXPromoter = (1.0);
YYYPromoter = (1.0);
};
parameters = {
kd_damagedDNA = 0.02;
kp_DNAPK_a = 0.2;
km_DNAPK_a = 500;
kt_DNAPK_i = 0.005;
kp_Rad_a = 0.2;
km_Rad_a = 500;
kt_Rada_preG2 = 0.1;
kp_Rada_postG2 = 10;
km_Rada_postG2 = 10;
kt_Rad_i = 0.005;
kp_ATR_a = 0.2;
km_ATR_a = 500;
kt_ATR_i = 0.005;
kp_Chk1_Phos = 0.2;
km_Chk1_Phos = 500;
kt_Chk1_Dephos = 0.005;
kp_ATM_a = 0.2;
km_ATM_a = 500;
kt_ATM_i = 0.005;
kp_Chk2_Phos = 0.2;
km_Chk2_Phos = 500;
kt_Chk2_Dephos = 0.005;
ks_p53 ~ 500;
kd_p53 ~ 0.5;
kt_p53_Nucl ~ 0.2;
kt_p53_Cyto ~ 0.2;
kt_Mdm2_Nucl = 0.2;
kt_Mdm2_Cyto = 0.2;
kt_Mdm2_p53_Nucl = 0.2;
kt_Mdm2_p53_Cyto = 0.2;
kp_p53_15Phos = 0.2;
km_p53_15Phos = 500;
kp_p5315Phos_15Phos = 0.2;
km_p5315Phos_15Phos = 500;
kp_p53_20Phos1 = 0.2;
km_p53_20Phos1 = 500;
kp_p53_20Phos2 = 0.2;
km_p53_20Phos2 = 500;
kb_p53_CBP = 0.001;
ku_p53_CBP = 0.5;
kp_p53_37Phos = 0.2;
km_p53_37Phos = 500;
ks_ARF = 500;
kd_ARF = 0.5;
kb_ARF_E2F = 0.001;
ktd_E2F = 0.1;
kb_ARF_Mdm2 = 0.001;
ku_ARF_Mdm2 = 0.5;
kb_Mdm2_p53 = 0.01;
ku_Mdm2_p53 = 0.5;
ktd_p53 = 1;
kb_XXXPromoter_p53 = 0.001;
ku_XXXPromoter_p53 = 0.5;
ks_XXXmRNA = 50;
kt_XXXmRNA_Cyto = 0.1;
ks_XXX = 0.5;
kd_XXXmRNA = 0.01;
kd_XXX = 0.001;
kb_Mdm2Promoter_p53 = 0.001;
ku_Mdm2Promoter_p53 = 0.5;
ks_Mdm2mRNA = 50;
```

-continued

```
kt_Mdm2mRNA_Cyto = 0.1;
ks_Mdm2 = 0.5;
kd_Mdm2mRNA = 0.01;
kd_Mdm2 = 0.001;
kb_YYYPromoter_p53 = 0.001;
ku_YYYPromoter_p53 = 0.5;
ks_YYYmRNA = 50;
kt_YYYmRNA_Cyto = 0.1;
ks_YYY = 0.5;
kd_YYYmRNA = 0.01;
kd_YYY = 0.001;
};
```

This file defines some more chemicals and some parameters. The values of most of the parameters are specified by the equal sign, so they will not be changed by the optimizer. The lines

```
ks_p53 ~ 500;
kd_p53 ~ 0.5;
kt_p53_Nucl ~ 0.2;
kt_p53_Cyto ~ 0.2;
``` indicate that these four parameters are optimizable; when the optimizer runs, it will change the values of these four parameters in an attempt to fit the experimental data.

Next the file "p53_reactions.txt" lists all the reactions that define the network:

```
reactions = {
UDR(damagedDNA|kd_damaged DNA);
MMR(damagedDNA,DNAPK,DNAPKa|kp_DNAPK_a,km_DNAPK_a);
TR(DNAPKa,DNAPK|kt_DNAPK_i);
MMR(damagedDNA,Rad,Rada|kp_Rad_a,km_Rad_a);
TR(Rada,RadpreG2|kt_Rada_preG2);
MMR(ChromosomeSignal,Rada,RadpostG2|kp_Rada_postG2,km_Rada_postG2);
TR(RadpreG2,Rad|kt_Rad_i);
TR(RadpostG2,Rad|kt_Rad_i);
MMR(RadpreG2,ATR,ATRa|kp_ATR_a,km_ATR_a);
TR(ATRa,ATR|kt_ATR_i);
MMR(ATRa,Chk1,Chk1Phos|kp_Chk1_Phos,km_Chk1_Phos);
TR(Chk1Phos,Chk1|kt_Chk1_Dephos);
MMR(RadpostG2,ATM,ATMa|kp_ATM_a,km_ATM_a);
TR(ATMa,ATM|kt_ATM_i);
MMR(ATMa,Chk2,Chk2Phos|kp_Chk2_Phos,km_Chk2_Phos);
TR(Chk2Phos,Chk2|kt_Chk2_Dephos);
%%%%%%%%%%%%%%%%%%%%%%%%%
%% p53 generation and natural degradation %%
%%%%%%%%%%%%%%%%%%%%%%%%%
GR(One,p53|ks_p53);
UDR(p53|kd_p53);
UDR(p5337Phos|kd_p53);
UDR(p5320Phos|kd_p53);
UDR(p5320Phos37Phos|kd_p53);
UDR(p5320Phos_CBP|kd_p53);
UDR(p5320Phos37Phos_CBP|kd_p53);
UDR(p5315Phos|kd_p53);
UDR(p5315Phos37Phos|kd_p53);
UDR(p5315Phos20Phos|kd_p53);
UDR(p5315Phos20Phos37Phos|kd_p53);
UDR(p5315Phos20Phos_CBP|kd_p53);
UDR(p5315Phos20Phos37Phos_CBP|kd_p53);
UDR(p5315PhosPhos|kd_p53);
UDR(p5315PhosPhos37Phos|kd_p53);
UDR(p5315PhosPhos20Phos|kd_p53);
UDR(p5315PhosPhos20Phos37Phos|kd_p53);
UDR(p5315PhosPhos20Phos_CBP|kd_p53);
UDR(p5315PhosPhos20Phos37Phos_CBP|kd_p53);
%%%%%%%%%%%%%%%%%%%%%%%%%
%% nuclear shuttling of p53 and Mdm2 %%
%%%%%%%%%%%%%%%%%%%%%%%%%
TR(p53Cyto,p53|kt_p53_Nucl);
TR(p53,p53Cyto|kt_p53_Cyto);
TR(p5337PhosCyto,p5337Phos|kt_p53_Nucl);
TR(p5337Phos,p5337PhosCyto|kt_p53_Cyto);
TR(p5320PhosCyto,p5320Phos|kt_p53_Nucl);
TR(p5320Phos,p5320PhosCyto|kt_p53_Cyto);
TR(p5320Phos37PhosCyto,p5320Phos37Phos|kt_p53_Nucl);
TR(p5320Phos37Phos,p5320Phos37PhosCyto|kt_p53_Cyto);
TR(p5320Phos_CBPCyto,p5320Phos_CBP|kt_p53_Nucl);
TR(p5320Phos_CBP,p5320Phos_CBPCyto|kt_p53_Cyto);
TR(p5320Phos37Phos_CBPCyto,p5320Phos37Phos_CBP|kt_p53_Nucl);
TR(p5320Phos37Phos_CBP,p5320Phos37Phos_CBPCyto|kt_p53_Cyto);
TR(p5315PhosCyto,p5315Phos|kt_p53_Nucl);
TR(p5315Phos,p5315PhosCyto|kt_p53_Cyto);
```

```
TR(p5315Phos37PhosCyto,p5315Phos37Phos|kt_p53_Nucl);
TR(p5315Phos37Phos,p5315Phos37PhosCyto|kt_p53_Cyto);
TR(p5315Phos20PhosCyto,p5315Phos20Phos|kt_p53_Nucl);
TR(p5315Phos20Phos,p5315Phos20PhosCyto|kt_p53_Cyto);
TR(p5315Phos20Phos37PhosCyto,p5315Phos20Phos37Phos|kt_p53_Nucl);
TR(p5315Phos20Phos37Phos,p5315Phos20Phos37PhosCyto|kt_p53_Cyto);
TR(p5315Phos20Phos_CBPCyto,p5315Phos20Phos_CBP|kt_p53_Nucl);
TR(p5315Phos20Phos_CBP,p5315Phos20Phos_CBPCyto|kt_p53_Cyto);
TR(p5315Phos20Phos37Phos_CBPCyto,p5315Phos20Phos37Phos_CBP|kt_p53_Nucl);
TR(p5315Phos20Phos37Phos_CBP,p5315Phos20Phos37Phos_CBPCyto|kt_p53_Cyto);
TR(p5315PhosPhosCyto,p5315PhosPhos|kt_p53_Nucl);
TR(p5315PhosPhos,p5315PhosPhosCyto|kt_p53_Cyto);
TR(p5315PhosPhos37PhosCyto,p5315PhosPhos37Phos|kt_p53_Nucl);
TR(p5315PhosPhos37Phos,p5315PhosPhos37PhosCyto|kt_p53_Cyto);
TR(p5315PhosPhos20PhosCyto,p5315PhosPhos20Phos|kt_p53_Nucl);
TR(p5315PhosPhos20Phos,p5315PhosPhos20PhosCyto|kt_p53_Cyto);
TR(p5315PhosPhos20Phos37PhosCyto,p5315PhosPhos20Phos37Phos|kt_p53_Nucl);
TR(p5315PhosPhos20Phos37Phos,p5315PhosPhos20Phos37PhosCyto|kt_p53_Cyto);
TR(p5315PhosPhos20Phos_CBPCyto,p5315PhosPhos20Phos_CBP|kt_p53_Nucl);
TR(p5315PhosPhos20Phos_CBP,p5315PhosPhos20Phos_CBPCyto|kt_p53_Cyto);
TR(p5315PhosPhos20Phos37Phos_CBPCyto,p5315PhosPhos20Phos37Phos_CBP|kt_p53_Nucl);
TR(p5315PhosPhos20Phos37Phos_CBP,p5315PhosPhos20Phos37Phos_CBPCyto|kt_p53_Cyto);
TR(Mdm2Cyto,Mdm2|kt_Mdm2_Nucl);
TR(Mdm2,Mdm2Cyto|kt_Mdm2_Cyto);
TR(Mdm2_p53Cyto,Mdm2_p53|kt_Mdm2_p53_Nucl);
TR(Mdm2_p53,Mdm2_p53Cyto|kt_Mdm2_p53_Cyto);
TR(Mdm2_p5337PhosCyto,Mdm2_p5337Phos|kt_Mdm2_p53_Nucl);
TR(Mdm2_p5337Phos,Mdm2_p5337PhosCyto|kt_Mdm2_p53_Cyto);
%%%%%%%%%%%%%%%%%%%
%% p53_15Phos by DNAPKa %%
%%%%%%%%%%%%%%%%%%%
MMR(DNAPKa,p53,p5315Phos|kp_p53_15Phos,km_p53_15Phos);
MMR(DNAPKa,p5337Phos,p5315Phos37Phos|kp_p53_15Phos,km_p53_15Phos);
MMR(DNAPKa,p5320Phos,p5315Phos20Phos|kp_p53_15Phos,km_p53_15Phos);
MMR(DNAPKa,p5320Phos37Phos,p5315Phos20Phos37Phos|kp_p53_15Phos,km_p53_15Phos);
MMR(DNAPKa,p5320Phos_CBP,p5315Phos20Phos_CBP|kp_p53_15Phos,km_p53_15Phos);
MMR(DNAPKa,p5320Phos37Phos_CBP,p5315Phos20Phos37Phos_CBP|kp_p53__15Phos,km_p53_15Phos);
%%%%%%%%%%%%%%%%%%%%
%% p5315Phos_15Phos by CKI %%
%%%%%%%%%%%%%%%%%%%%
MMR(CKI,p5315Phos,p5315PhosPhos|kp_p5315Phos_15Phos,km_p5315Phos_15Phos);
MMR(CKI,p5315Phos37Phos,p5315PhosPhos37Phos|kp_p5315Phos_15Phos,km_p5315Phos_15Phos);
MMR(CKI,p5315Phos20Phos,p5315PhosPhos20Phos|kp_p5315Phos_15Phos,km_p5315Phos_15Phos);
MMR(CKI,p5315Phos20Phos37Phos,p5315PhosPhos20Phos37Phos|kp_p5315Phos_15Phos,km_p5315Phos_15Phos);
MMR(CKI,p5315Phos20Phos_CBP,p5315PhosPhos20Phos_CBP|kp_p5315Phos_15Phos,km_p5315Phos_15Phos);
MMR(CKI,p5315Phos20Phos37Phos_CBP,p5315PhosPhos20Phos37Phos_CBP|kp_p5315Phos_15Phos,km_p5315Phos_15Phos);
%%%%%%%%%%%%%%%%%%%%%%
%% p53_20Phos by Chk1 and Chk2 %%
%%%%%%%%%%%%%%%%%%%%%%
MMR(Chk1Phos,p53,p5320Phos|kp_p53_20Phos1,km_p53_20Phos1);
MMR(Chk1Phos,p5337Phos,p5320Phos37Phos|kp_p53_20Phos1,km_p53_20Phos1);
MMR(Chk1Phos,p5315Phos,p5315Phos20Phos|kp_p53_20Phos1,km_p53_20Phos1);
MMR(Chk1Phos,p5315Phos37Phos,p5315Phos20Phos37Phos|kp_p53_20Phos1,km_p53_20Phos1);
MMR(Chk1Phos,p5315PhosPhos,p5315PhosPhos20Phos|kp_p53_20Phos1,km_p53_20Phos1);
```

-continued

```
MMR(Chk1Phos,p5315PhosPhos37Phos,p5315PhosPhos20Phos37Phos|kp_p5
3_20Phos1,km_p53_20Phos1);
MMR(Chk2Phos,p53,p5320Phos|kp_p53_20Phos2,km_p53_20Phos2);
MMR(Chk2Phos,p5337Phos,p5320Phos37Phos|kp_p53_20Phos2,km_p53_2
0Phos2);
MMR(Chk2Phos,p5315Phos,p5315Phos20Phos|kp_p53_20Phos2,km_p53_2
0Phos2);
MMR(Chk2Phos,p5315Phos37Phos,p5315Phos20Phos37Phos|kp_p53_20Pho
s2,km_p53_20Phos2);
MMR(Chk2Phos,p5315PhosPhos,p5315PhosPhos20Phos|kp_p53_20Phos2,k
m_p53_20Phos2);
MMR(Chk2Phos,p5315PhosPhos37Phos,p5315PhosPhos20Phos37Phos|kp_p5
3_20Phos2,km_p53_20Phos2);
%%%%%%%%%%%%%%%%%
%% b+u_p5320Phos_CBP %%
%%%%%%%%%%%%%%%%%
HDR(p5320Phos37Phos,CBP,p5320Phos37Phos_CBP|kb_p53_CBP);
HDDR(p5320Phos37Phos_CBP,p5320Phos37Phos,CBP|ku_p53_CBP);
HDR(p5320Phos37Phos,CBP,p5320Phos37Phos_CBP|kb_p53_CBP);
HDDR(p5320Phos37Phos_CBP,p5320Phos37Phos,CBP|ku_p53_CBP);
HDR(p5315Phos20Phos37Phos,CBP,p5315Phos20Phos37Phos_CBP|kb_p53_
CBP);
HDDR(p5315Phos20Phos37Phos_CBP,p5315Phos20Phos37Phos,CBP|ku_p53_
CBP);
HDR(p5315Phos20Phos37Phos,CBP,p5315Phos20Phos37Phos_CBP|kb_p53_
CBP);
HDDR(p5315Phos20Phos37Phos_CBP,p5315Phos20Phos37Phos,CBP|ku_p53_
CBP);
HDR(p5315PhosPhos20Phos37Phos,CBP,p5315PhosPhos20Phos37Phos_
CBP|kb_p53_CBP);
HDDR(p5315PhosPhos20Phos37Phos_CBP,p5315PhosPhos20Phos37Phos,CBP
|ku_p53_CBP);
HDR(p5315PhosPhos20Phos37Phos,CBP,p5315PhosPhos20Phos37Phos_CBP|
kb_p53_CBP);
HDDR(p5315PhosPhos20Phos37Phos_CBP,p5315PhosPhos20Phos37Phos,CBP
|ku_p53_CBP);
%%%%%%%%%%%%%%%%%%%
%% p53_37Phos by DNAPKa %%
%%%%%%%%%%%%%%%%%%%
MMR(DNAPKa,p53,p5337Phos|kp_p53_37Phos,km_p53_37Phos);
MMR(DNAPKa,p5320Phos,p5320Phos37Phos|kp_p53_37Phos,km_p53_37Ph
os);
MMR(DNAPKa,p5320Phos_CBP,p5320Phos37Phos_CBP|kp_p53_37Phos,km_p
53_37Phos);
MMR(DNAPKa,p5315Phos,p5315Phos37Phos|kp_p5315Phos_37Phos,km_p53
15Phos_37Phos);
MMR(DNAPKa,p5315Phos20Phos,p5315Phos20Phos37Phos|kp_p5315Phos_3
7Phos,km_p5315Phos_37Phos);
MMR(DNAPKa,p5315Phos20Phos_CBP,p5315Phos20Phos37Phos_CBP|kp_p531
5Phos_37Phos,km_p5315Phos_37Phos);
MMR(DNAPKa,p5315PhosPhos,p5315PhosPhos37Phos|kp_p5315PhosPhos_3
7Phos,km_p5315PhosPhos_37Phos);
MMR(DNAPKa,p5315PhosPhos20Phos,p5315PhosPhos20Phos37Phos|kp_p531
5PhosPhos_37Phos,km_p5315PhosPhos_37Phos);
MMR(DNAPKa,p5315PhosPhos20Phos_CBP,p5315PhosPhos20Phos37Phos_CBP
|kp_p5315PhosPhos_37Phos,km_p5315PhosPhos_37Phos);
%%%%%%%%%%%%%%%%%%%%%%%%%%%%%%%
%% p53 degradation through Mdm2, inhibition of that by Arf %%
%%%%%%%%%%%%%%%%%%%%%%%%%%%%%%%
GR(E2F,ARF|ks_ARF);
UDR(ARF|kd_ARF);
TR(ARF_E2F,E2F|kd_ARF);
TR(ARF_Mdm2,Mdm2|kd_ARF);
HDR(ARF,E2F,ARF_E2F|kb_ARF_E2F);
TR(ARF_E2F,ARF|ktd_E2F);
HDR(ARF,Mdm2,ARF_Mdm2|kb_ARF_Mdm2);
HDDR(ARF_Mdm2,ARF,Mdm2|ku_ARF_Mdm2);
HDR(Mdm2,p53,Mdm2_p53|kb_Mdm2_p53);
HDDR(Mdm2_p53,Mdm2,p53|ku_Mdm2_p53);
HDR(Mdm2Cyto,p53Cyto,Mdm2_p53Cyto|kb_Mdm2_p53);
HDDR(Mdm2_p53Cyto,Mdm2Cyto,p53Cyto|ku_Mdm2_p53);
HDDR(Mdm2_p53Cyto,Mdm2Cyto,dumpedp53|ktd_p53);
HDR(Mdm2,p5337Phos,Mdm2_p5337Phos|kb_Mdm2_p53);
HDDR(Mdm2_p5337Phos,Mdm2,p5337Phos|ku_Mdm2_p53);
HDR(Mdm2Cyto,p5337PhosCyto,Mdm2_p5337PhosCyto|kb_Mdm2_p53);
HDDR(Mdm2_p5337PhosCyto,Mdm2Cyto,p5337PhosCyto|ku_Mdm2_p53);
HDDR(Mdm2_p5337PhosCyto,Mdm2Cyto,dumpedp53|ktd_p53);
UDR(dumpedp53|kd_p53);
%%%%%%%%%%%%%%%%%%%%%%
```

-continued

```
%% various transcriptions caused by p53 %%
%%%%%%%%%%%%%%%%%%%%%%%%%%%%
HDR(XXXPromoter,p5315PhosPhos20Phos37Phos_CBP,XXXPromotera|kb_XX
XPromoter_p53);
HDDR(XXXPromotera,XXXPromoter,p5315PhosPhos20Phos37Phos_CBP|ku_X
XXPromoter_p53);
GR(XXXPromotera,XXXmRNA|ks_XXXmRNA);
TR(XXXmRNA,XXXmRNACyto|kt_XXXmRNA_Cyto);
GR(XXXmRNACyto,XXXCyto|ks_XXX);
UDR(XXXmRNA|kd_XXXmRNA);
UDR(XXXmRNACyto|kd_XXXmRNA);
UDR(XXXCyto|kd_XXX);
HDR(Mdm2Promoter,p5315PhosPhos20Phos37Phos_CBP,Mdm2Promotera|kb_
Mdm2Promoter_p53);
HDDR(Mdm2Promotera,Mdm2Promoter,p5315PhosPhos20Phos37Phos_CBP|ku_
Mdm2Promoter_p53);
GR(Mdm2Promotera,Mdm2mRNA|ks_Mdm2mRNA);
TR(Mdm2mRNA,Mdm2mRNACyto|kt_Mdm2mRNA_Cyto);
GR(Mdm2mRNACyto,Mdm2Cyto|ks_Mdm2);
UDR(Mdm2mRNA|kd_Mdm2mRNA);
UDR(Mdm2mRNACyto|kd_Mdm2mRNA);
UDR(Mdm2|kd_Mdm2);
UDR(Mdm2Cyto|kd_Mdm2);
%%%%%%%%%%%%%%%%%%%%%%%%%%%%%%
%% various transcriptions inhibited by p53 %%
%%%%%%%%%%%%%%%%%%%%%%%%%%%%%
HDR(YYYPromoter,p5315PhosPhos20Phos37Phos_CBP,YYYPromoteri|kb_YY
YPromoter_p53);
HDDR(YYYPromoteri,YYYPromoter,p5315PhosPhos20Phos37Phos_CBP|ku_Y
YYPromoter_p53);
GR(YYYPromoter,YYYmRNA|ks_YYYmRNA);
TR(YYYmRNA,YYYmRNACyto|kt_YYYmRNA_Cyto);
GR(YYYmRNACyto,YYYCyto|ks_YYY);
UDR(YYYmRNA|kd_YYYmRNA);
UDR(YYYmRNACyto|kd_YYYmRNA);
UDR(YYYCyto|kd_YYY);
};
```

Each reaction is specified by an abbreviation (e.g., HDR means HeteroDimerization Reaction, MMR means Michaelis-Menton Reaction, etc.) followed by a list of chemicals and rate constants (parameters) that participate in the reaction. The chemicals are listed first followed by a vertical bar ("|") and the list of rate constants. The chemicals and rate constants must be listed in the correct order. For example the line HDR(A,B,C|kb);

defines a reaction in which a molecule of A and a molecule of B bind to form a molecule of C., Thus A and B can be listed in either order, but C must be specified in the third position. The lines in the above example that begin with a percent sign ("%") are comments and are ignored by the code. Any chemical that is used in a reaction without being defined in a chemicals block is created with a default initial concentration of zero.

The file "p53_expdata.txt" contains the experimental data used by the optimizers:

```
experimental_data = {
    data = p53 {
        data_type = value;
        values =
            ( (0, 50, 1), (20, 100, 1), (40, 70, 1),
              (80, 60, 1) );
    };
};
```

In this case, there is experimental data for only one chemical, p53. The values are specified in triples in which the first number is the time of the observation, the second is the concentration, and the third is the error.

Finally, the file "p53_display.txt" controls the output of the code.

```
chemicals = {
t_p5315Phos = SUM(
p5315Phos,p5315Phos37Phos,
p5315Phos20Phos,p5315Phos20Phos37Phos,
p5315Phos20Phos_CBP,p5315Phos20Phos37Phos_CBP);
t_p5315PhosPhos = SUM(
p5315PhosPhos,p5315PhosPhos37Phos,
p5315PhosPhos20Phos,p5315PhosPhos20Phos37Phos,
p5315PhosPhos20Phos_CBP,p5315PhosPhos20Phos37Phos_CBP);
t_p5320Phos_NoCBP = SUM(
p5320Phos,p5320Phos37Phos,
p5315Phos20Phos,p5315Phos20Phos37Phos,
p5315PhosPhos20Phos,p5315PhosPhos20Phos37Phos);
t_p5320Phos_CBP = SUM(
p5320Phos_CBP,p5320Phos37Phos_CBP,
p5315Phos20Phos_CBP,p5315Phos20Phos37Phos_CBP,
p5315PhosPhos20Phos_CBP,p5315PhosPhos20Phos37Phos_CBP);
t_p5320Phos = SUM(t_p5320Phos_NoCBP,t_p5320Phos_CBP);
t_p5337Phos = SUM(
p5337Phos,p5320Phos37Phos,p5320Phos37Phos_CBP,
p5315Phos37Phos,p5315Phos20Phos37Phos,
p5315Phos20Phos37Phos_CBP,
p5315PhosPhos37Phos,p5315PhosPhos20Phos37Phos,
p5315PhosPhos20Pho
s37Phos_CBP);
a_p53 = SUM(p5315PhosPhos20Phos37Phos_CBP);
t_p53_NoMdm2 = SUM(
p53,p5320Phos,p5320Phos_CBP,
p5315Phos,p5315Phos20Phos,p5315Phos20Phos_CBP,
p5315PhosPhos,p5315PhosPhos20Phos,p5315PhosPhos20Phos_CBP,
```

```
p5337Phos,p5320Phos37Phos,p5320Phos37Phos_CBP,
p5315Phos37Phos,p5315Phos20Phos37Phos,
p5315Phos20Phos37Phos_CBP,
p5315PhosPhos37Phos,p5315PhosPhos20Phos37Phos,
p5315PhosPhos20Pho
s37Phos_CBP);
t_p53_Mdm2 = SUM(Mdm2_p5337Phos,Mdm2_p5337Phos);
};
save_timeseries = {
    variables = (t_p5315Phos, t_p5315PhosPhos,
        t_p5320Phos, t_p5337Phos,
        a_p53, t_p53_NoMdm2);
    save to directory = "data";
};
plot = timeseries {
    plot_title = "Plot1";
    simulation_TS = (t_p5315Phos,
        t_p5315PhosPhos, t_p5320Phos, t_p5337Phos,
        a_p53, t_p53_NoMdm2);
};
plot = timeseries {
    plot_title = "Plot2";
    simulation_TS = (Mdm2, ARF_Mdm2, Mdm2_p53,
        Mdm2_p5337Phos);
};
plot = timeseries {
    plot_title = "Plot3";
    simulation_TS = (p53);
    experimental_TS = (p53);
};
```

This file defines some new chemicals which are used only for output. They are total levels of certain chemicals, so they are defined as a mathematical function (SUM) of these other chemicals. Any chemical can be saved to a file or plotted.

When the code runs, it produces the following output (the amount of output can be controlled by specifying the verbosity):

```
Starting with the following parameter values:
ks_p53 ~ (500, , )
kd_p53 ~ (0.5, , )
kt_p53_Nucl ~ (0.2, , )
kt_p53_Cyto ~ (0.2, , )
There are 4 optimizable parameters
Director has 1 networks
Network 1 has 78 states and 76 parameters
Using parameter identifier: Simulated Annealing
Executing Serial Simulated Annealing
Initializing temperature...
Done – Initial cost = 521945 Initial temperature = 10000
New lowest cost = 217203
ks_p53 ~ (1473.71, , )
kd_p53 ~ (3.01649, , )
kt_p53_Nucl ~ (1.10296, , )
kt_p53_Cyto ~ (0.148332, , )
```

Each time the code finds a new lowest cost, it writes the chemicals and parameters to disk files in a format which can be read back in to restart the run. Depending on the verbosity setting, it also writes the values of the optimizable parameters to the screen. All optimizable parameters have three values: the current value, the lower bound and the upper bound. In this example, the bounds are not specified, so they have their default values which are determined by taking the original value and dividing by 10 for the lower bound and multiplying by 10 for the upper bound. When the code has finished running the optimizer, it writes out a summary:

```
New lowest cost = 134.676
ks_p53 ~ (148.928, , )
kd_p53 ~ (1.07345, , )
kt_p53_Nucl ~ (1.72851, , )
kt_p53_Cyto ~ (1.6086, , )
Simulated Annealing Minimizer
Starting cost = 521945
Minimum cost = 134.676
Initial temperature = 10000
Final temperature = 646.108
Number steps generated = 286
Number steps accepted = 50
Simulated Annealing took 19.489 seconds.
```

The code then takes the values found by the simulated annealing minimizer as starting values for the Levenberg-Marquardt minimizer. After this minimizer has finished, the code again writes a summary:

```
New lowest cost = 0.255947
ks_p53 ~ (148.92, , )
kd_p53 ~ (0.285072, , )
kt_p53_Nucl ~ (0.537043, , )
kt_p53_Cyto ~ (2.45473, , )
Reached maximum number of iterations, solution may not be local
minimum
Levenberg-Marquardt Minimizer
Number iterations = 5
Number objective function evaluations = 28
Number Jacobian evaluations = 5
Starting cost = 134.676
Minimum cost = 0.255947
Gradient norm = 38.853
Levenberg Marquardt took 3.815 seconds.
```

The results of the optimization are written back to a set of output files that mimic the input files, except for the fact that the original values of the optimizable parameters are replaced with the new optimized values. The files can then used as input to a new optimization or simulation run.

Exemplary Method for the Network Inference Methodology

Described herein is a system for inferring one or a population of biochemical interaction networks, including topology and chemical reaction rates and parameters, from dynamical or statical experimental data, with or without spatial localization information, and a database of possible interactions. Accordingly, the invention, as described herein, provides systems and methods that will infer the biochemical interaction networks that exist in a cell. To this end, the systems and methods described herein generate a plurality of possible candidate networks and then apply to these networks a forward simulation process to infer a network. Inferred networks may be analyzed via data fitting and other fitting criteria, to determine the likelihood that the network is correct. In this way, new and more complete models of cellular dynamics may be created.

Figure 46:
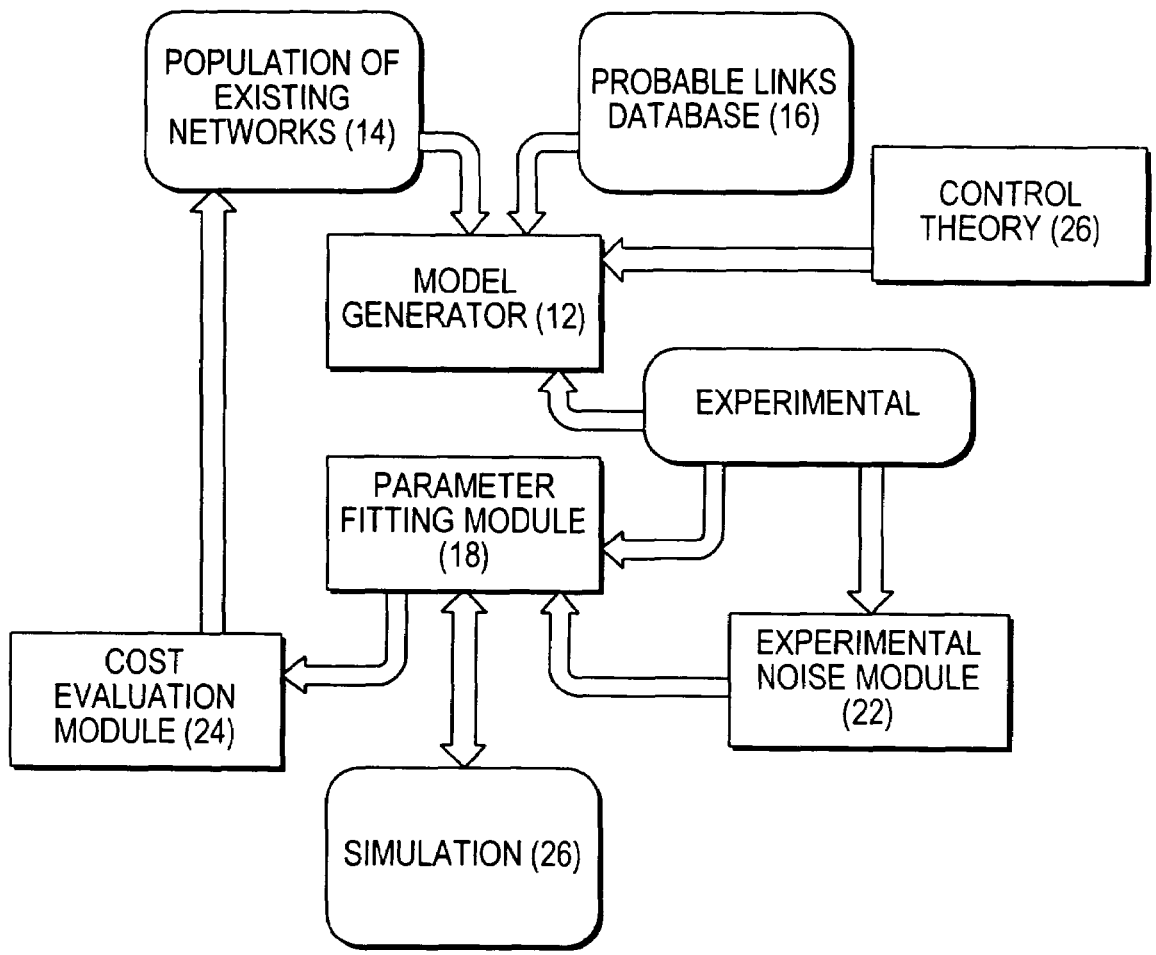
FIG. 46 depicts schematically one process according to the invention for inferring a biological network.

FIG. 46 depicts a model generator 12 that creates new model networks, drawing from a combination of sources including a population of existing networks 14 and a probable links database 16. Once generated, a parameter-fitting module 18 evaluates the model network, determining parameter values for the model network based on experimental data 20. A simulation process 26 may aid the optimization of the parameters in the parameter-fitting module 18. An experimental noise module 22 may also be used in conjunction the parameter-fitting module 18 to evaluate the model's sensitivity to fluctuations in the experimental data 20. Finally, a cost evaluation module 24 may test the reliability of the model and parameters by examining global and local fitness criteria.

A population of existing networks 14 stores previously inferred network models in a computer database and may provide network models to a model generator 12 for the generation of new network models. Completed network models are added to the population of existing models 14 for storage, transferred from a cost-evaluation module 24.

A probable links database 16 stores data representative of biochemical interactions obtained from bioinformatics predictions, and may also include hypothetical interactions for which there is some support in the published literature. The probable links database 16 couples with the model generator 12 to provide links for the formation of new network models where necessary.

The model generator 12 uses any of a number of model-fitting techniques that are known to those of skill in the art to generate new biochemical network models. In one embodiment, the model generator 12 employs genetic algorithms to generate new networks, using two networks present in the population. Such genetic algorithms may use other information to guide the recombination of networks used in constructing new networks, such as sensitivity analysis of the parameters of one or both of the parent networks. They may also use the results of clustering analyses to group together networks in the population that behave in similar ways dynamically, and selectively recombine networks belonging to the same dynamical cluster or, for heterotic vigor, recombine networks belonging to different dynamical clusters but which fit the data approximately equally well. In creating the new network model, the model generator 12 may draw one or more networks from the population of existing networks 14 and incorporate any number of possible interactions from the probable links database 16. Alternatively, the model generator 12 may rely solely on the probable links database 16, generating a new network model without relying on the population of existing networks 14.

In one practice, the model generator 12 uses multiple evaluation criteria, e.g. finite state machines, to test generated networks for compatibility with experimental data, as in Conradi et al. (C. Conradi, J. Stelling, J. Raisch, IEEE International Symposium on Intelligent Control (2001) 'Structure discrimination of continuous models for (bio)chemical reaction networks via finite state machines', p. 138). The model generator may also use Markov Chain Monte Carlo methods (W. Gilks, S. Richardson and D. Spiegelhalter, 'Markov Chain Monte Carlo in Practice', Chapman and Hall, 1996), or variational methods(M. Jordan, Z. Ghahramani, T. Jaakkola, L. Saul, 'An introduction to variational methods for graphical models', in 'Learning in Graphical Models' (M. Jordan, ed.), MIT Press, 1998), or loopy belief propagation (J. Pearl, 'Causality: Models, Reasoning and Inference', Cambridge Univ. Press, 2000), for inferring the likelihood of a given network topology, given the experimental data. Network topologies that are unlikely, given the experimental data, would be accepted at a lower rate than those that are likely, as in the Metropolis algorithm for Monte Carlo simulations. The model generator may also use the results of clustering large-scale or high-throughput experimental measurements, such as mRNA expression level measurements, perhaps combined with bioinformatics predictions such as for genes with common binding sites for transcription factors, or secondary structure predictions for proteins that may be possible transcription factors, to generate models consistent with these clustering and bioinformatics results, in combination or singly. The model generator may also include reactions suggested by a control theory based module, which can evaluate portions of a given network in the population and modify them according to calculations based on robust control theory (F. L. Lewis, Applied Optimal Control and Estimation, (Prentice-Hall, 1992)).

As will be understood by one of ordinary skill in the art, the systems and methods described herein allow for generating a population of networks and evaluating predictions, from this population in a manner that is similar or equivalent to a Monte Carlo evaluation, of the likelihood that the model is correct, in the Bayesian sense over the ensemble of all networks, weighted by the a priori measure of the space of networks. With model generation complete, the newly generated network model passes from the model generator 12 to a parameter fitting module 18 for optimization of the network parameters.

A parameter fitting module 18 optimizes the model parameters received from the model generator 12 using experimental data 20 as a calibration point, either in a single step or by coupling with a simulation module 26 for iterative parameter fitting. Optimization methods may be according to any global or local routine or combination of routines known to one of skill in the art. Examples include, but are not limited to local optimization routines such as Levenberg-Marquardt, modified Levenberg-Marquardt, BFGS-updated secant methods, sequential quadratic programming, and the Nelder-Mead method, or global optimization routines such as simulated annealing or adaptive simulated annealing, basic Metropolis, genetic algorithms, and direct fitting. Following parameter optimization, the parameter fitting module 18 passes the network model to a cost evaluation module 24.

The experimental data 20 consists of qualitative or quantitative experimental data, such as mRNA or protein levels, stored in a computer database. The experimental data 20 may be obtained through any of a variety of high-throughput data collection techniques known to one of skill in the art, including but not limited to immunoprecipitation assays, Western blots or other assays known to those of skill in the art, and gene expression from RT-PCR or oligonucleotide and cDNA microarrays. The experimental data 20 couples directly with the parameter fitting module 18 for parameter optimization, and possibly with an experimental noise module 22. In other practices the systems and methods described herein employ other types of data, including, for example, spatial localization data. Preferably the model has (x,y,z,t) spatial and temporal coordinates for components as well. Confocal microscopy is one of the technologies for getting both dynamical and spatial localization. One example of why this is important, is that the total levels of protein A may not change at all as a result of the perturbation. But its levels in the cytosol versus nucleus may be changing as a result of the perturbation whereby A is getting translocated from cytosol to nucleus to participate in other processes. Our inference may use both dynamical and static data, as well as information on spatial localization. An experimental noise module 22 may be used to provide an indication of the model's sensitivity to small variations in experimental measurements. The noise module 22 acts as an interim step between the experimental data 20 and the parameter fitting module 18, introducing variations into the experimental data 20 for evaluation following parameter optimization in a cost-evaluation module 24. The noise generation could be implemented by modeling the uncertainty in any given experimental observation by an appropriate distribution (e.g. log-normal for expression data) and picking noise values as dictated by the distribution for that experimental observation.

With a completed biochemical network model, an optional cost evaluation module 24 may evaluate the network model received from the parameter fitting module 18 according to cost or fitness criteria. The cost evaluation module 24 ranks a model's reliability according to the chosen fitness or cost criteria. The criteria employed by the cost evaluation module 24 may include, but are not limited to: (1) insensitivity of the model to changes in the initial conditions or chemical reaction parameters, (2) robustness of the model to the random removal or addition of biochemical interactions in the network, (3) insensitivity to variations in the experimental data (with variations introduced into the experimental data in the experimental noise data 22), and (4) overall bioinformatics costs associated with the model. Examples of bioinformatics costs are the number of gene prediction algorithms that simultaneously agree on a particular gene, the number of secondary structure prediction algorithms that agree on the structure of a protein, and so on. Coupled to this, some bioinformatics algorithms allow comparison to synthetically generated sequence (or other) data, thereby allowing the calculation of likelihoods or confidence measures in the validity of a given prediction. The cost evaluation module 24 then adds the new network model and the results of its cost criteria to the population of existing networks 14.

Models in the population of existing networks continue to be evaluated and tested by adding and removing links in iterative operations of the system herein described. There is no specific starting point in the system. Users of the system may generate networks entirely from the probable links database 16, or from a combination of the probable links database 16 with the population of existing networks 14. Iterative refinement may continue until a single network attains a goodness of fit to experimental data, perhaps combined with low costs for dynamical robustness or other criteria, below a user defined threshold, or a stable dynamically similar cluster of networks emerges from the population of networks. This stable cluster may then be used to compute robust predictions by averaging over the predictions of elements of the cluster of networks, in a cost-weighted average, where the costs include, but are not limited to, goodness of fit to the experimental data, dynamical robustness, probabilistic or exact evaluation of insensitivity to experimental noise and/or parameter values. Thus networks with lower costs contribute more to predictions than networks with higher costs. The refinement of the pool of networks may be continued until the (average or best) goodness of fit of the networks in the stable cluster is below some user defined threshold, or until the number of networks in the cluster is above some user defined threshold. In the case of the single network that may be the result of the inference process, the single network may be solely used for generating predictions.

The depicted process shown in FIG. 1 can be executed on a conventional data processing platform such as an IBM PC-compatible computer running the Windows operating systems, or a SUN workstation running a Unix operating system. Alternatively, the data processing system can comprise a dedicated processing system that includes an embedded programmable data processing system. For example, the data processing system can comprise a single board computer system that has been integrated into a system for performing micro-array analysis. The process depicted in FIG. 46 can be realized as a software component operating on a conventional data processing system such as a Unix workstation. In that embodiment, the process can be implemented as a C language computer program, or a computer program written in any high level language including C++, Fortran, Java or basic. The process may also be executed on commonly available clusters of processors, such as Western Scientific Linux clusters, which are able to allow parallel execution of all or some of the steps in the depicted process.

Accordingly, the systems and methods described herein include systems that create a pool of candidate or possible networks that have been generated to match data, including data that is biologically realistic as it arises from relevant literature or experiments. The systems described herein may, in certain embodiments, apply a discriminator process to the generated pool of possible networks. In an iterative process, the system may employ pools identified by the discriminator process as data that may be applied to a network generation module. The network generation module can process these possible networks with data from the probable links database to generate output data that can be processed by the fitting module as described above. In this way the systems and methods described herein may derive predictions from a pool of networks, instead of processing biological data to generate a single unique network.

Those skilled in the art will know or be able to ascertain using no more than routine experimentation, many equivalents to the embodiments and practices described herein. Accordingly, it will be understood that the invention is not to be limited to the embodiments disclosed herein, but is to be interpreted as broadly as allowed under the law.

Figure 47:
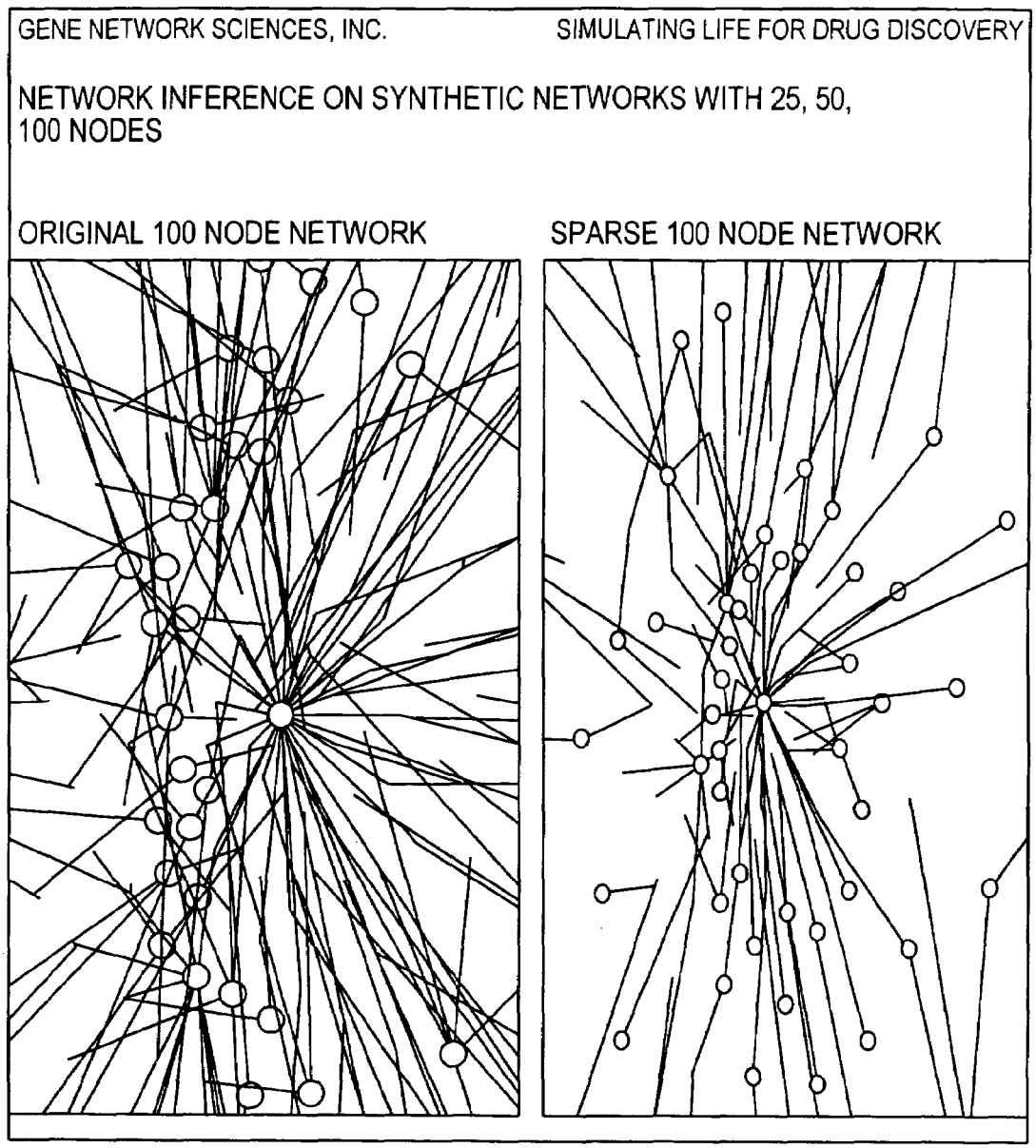
FIG. 47 shows the network topology of the synthetic network before and after links are removed.
Figure 48:
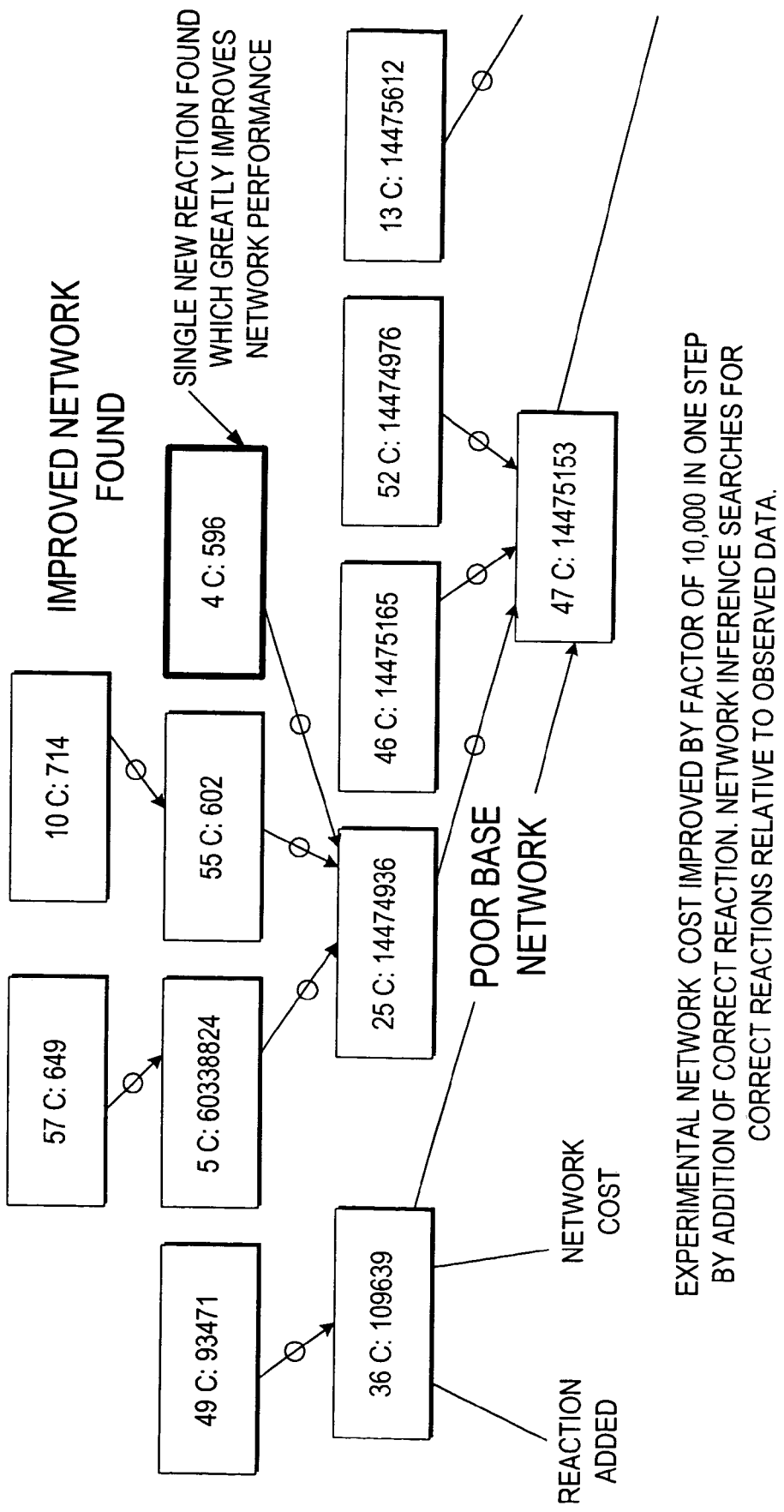
FIG. 48 displays the cost to fitting the data with one link perturbed.

This methodology has been practiced on synthetic networks of 25, 50, and 100 compoents. By a synthetic network we mean one that is composed of many interacting components, but those components may not necessarily have a basis in the literature. These were derived as a test case for the methodology. FIG. 47 dispalys an example of a 100 node network where 50% of the interactions are removed to reflect what one normally deals with in regards to real biological networks—most of the interactions are not known. We then used the methodology to reconstruct the original links or infer back the original networks. The network inference algorithm gives back populations of networks that satisfy the cost criteria described above and reproduces the dynamical behavior of the original network. Predictions are then dispalyed as a cost weighted average from this population. FIG. 48 displays the cost function to fitting the data as one changes or perturbs the links for a 25 component network. We note that the starting network has a very high cost on the order of millions. One link away and the cost is drastically reduced indicating the need to infer missing components and not just constrain parameter values via parameter optimization. FIGS. 49-50 contain the predicted time course data from chemicals for which we had observed data for and unobserved data for (the curves labeled (1) are for the experimental time course and those labeled (2) are for the reconstructed time course from the network inference methodology described above). Not only are we able to resonstruct the dynamical behavior for the observed chemicals, but we are also able to predict the trends in the unobserved chemicals as well.

Particular Uses of the Methods of the Invention

The methods in the invention, as described, can be used to perform dread discovery. In addition to finding specific targets, series of targets, therapeutic agents and combinations of therapeutic agents, the methods of the invention can be used to determine which populations of patients have specific targets and are therefore amenable to treatment with specific therapeutics, based upon the biological data representing those populations. In another embodiment of the invention, the biological data of specific persons can be used in the simulations of the invention to find the best therapeutic strategy for treating that person, i.e. the dose, time, order, etc. of different therapeutics affecting specific targets in that person.

In still other important embodiments, the methods of the invention can contribute to finding useful therapies for "failed compounds", i.e. compounds which have not performed well in clinical trials, by altering offering the combinations of targets for such compounds, combining other therapeutic compounds with the failed compounds, determining specific populations to treat, etc. In yet another use of the invention, simulations can be used to identify a molecular marker as a predictor of a disease condition such that diagnosing physicians may perform analytical tests for such markers as a precondition to diagnosing that condition. In yet another embodiment of the invention, compounds which are found to have therapeutic value can be altered in structure or function to make them more effective, e.g. by reducing the number of targets which are addressed, creating higher binding affinities in the therapeutic, etc. The biological data can be used to infer what target the drug is impacting based on network inferences.

What is claimed:

1. A method of predicting an altered physiological state of a cell comprising:
   (a) specifying a biochemical network of a cell;
   (b) simulating said network by
      (i) specifying the components of said network,
      (ii) representing interrelationships between said components in one or more mathematical equations and setting the quantitative parameters of said components, said mathematical equations including nonlinear differential equations where each such nonlinear differential equation includes the time rate of change of one or more gene products that comprise the biochemical network, and including various rate constants associated with said mathematical equations, and
      (iii) solving said mathematical equations to produce an initial simulated state of the cell;
   (c) optimizing said simulated biochemical network by determining and constraining the values of the parameters of said components by comparing experimental data regarding the value of at least one component with the value of said at least one component in said simulated biochemical network, said optimizing including comparing said simulation to at least one experimentally measured concentration time series and calculating an accuracy cost representing 2 a measure of the overall differences between the experimental data and the simulated time series;
   (d) perturbing the optimized simulated network by adding or deleting one or more components thereof, changing the concentration of one or more components thereof or modifying one or more mathematical equations representing interrelationships between one or more of said component, including modifying said rate constants away from their starting values;
   (e) solving the equations representing the perturbed network to simulate a modified state of the network, including calculating a new set of rate constants;
   (f) comparing said initial and modified simulated states of the network to identify the effect of said perturbation on the state of the network;
   (g) repeating said optimizing and said perturbing until the accuracy cost ceases to decrease by a defined increment; and
   (h) outputting the results of said comparison, the results of the perturbation(s) and the predicted state of the cell as perturbed to a user.

2. The method of claim 1, wherein said perturbing includes storing in computer memory a plurality of values for use in said perturbing and using an algorithm to apply said values separately or in combination with one another to automatically change the perturbations in accordance with a predetermined sequence.

3. A method as recited in claim 1 wherein the simulated network is systematically perturbed.

4. A method as recited in claim 1 wherein the simulated network is systematically perturbed by deleting two or more components.

5. A method as recited in claim 1 wherein the physiological state is proliferation.

6. A method as recited in claim 1 wherein said physiological state is G1-S and wherein Cyclin E-CDK2 is used as the marker for said determination.

7. A method as recited in claim 1 wherein said physiological state is G2-M and wherein Cyclin B-CDK1 is used as the marker for said determination.

8. A method as recited in claim 1 wherein said physiological state is S phase arrest and wherein Cyclin A-CDK2 is used as the marker for said determination.

9. A method as recited in claim 1 wherein said physiological state is apoptosis and wherein caspase 3 and cleaved PARP are the markers of said state.

10. A method as recited in claim 1 including storing said mathematical formulae in computer memory and storing algorithms in computer memory for solving said mathematical formulae, wherein said solving comprises retrieving said algorithms and applying them to solve said formulae.

11. A method as recited in claim 10 wherein said perturbing includes storing in computer memory a plurality of values for use in said perturbing and using an algorithm to apply said values separately or in combination with one another to automatically change the perturbations in accordance with a predetermined sequence.

12. A method of predicting the physiological state of a cell, comprising:
   (a) specifying a biochemical network of a cell;
   (b) simulating said network by
      (i) specifying the components of said network, and
      (ii) representing interrelationships between said components in one or more mathematical equations, said mathematical equations including nonlinear differential equations where each such nonlinear differential equation includes the time rate of change of one or more gene products that comprise the biochemical network, and setting the quantitative parameters of said components, and including various rate constants associated with said mathematical equations;
   (c) iteratively optimizing said simulated biochemical network by determining and constraining the values of the parameters of said components by comparing experimental data regarding the value of at least one component with the value of said at least one component generated by said simulated biochemical network, said optimizing including comparing said simulation to at least one experimentally measured concentration time series and calculating an accuracy cost representing a measure of the overall differences between the experimental data and the simulated time series, said iterative optimizing continuing until said accuracy cost ceases to decrease by a defined increment;

(d) determining the state of said optimized network by solving the mathematical equations and thereby simulating the physiological state of said network; and (e) outputting the simulated state of said network and the associated predicted state of the cell to a user.

13. The method of claim 12 wherein said cell is a cancer cell.

14. The method of claim 12 including storing optimization algorithms in computer memory, storing in computer memory values corresponding to said quantitative parameters, and applying said algorithms to said parameters to optimize said simulated biochemical network.

15. The method of claim 1, wherein said optimizing said biochemical network includes comparing experimental time series data for one or more components of the network with the corresponding time series data generated by the simulated network.

16. The method of claim 12, wherein said optimizing said biochemical network includes comparing experimental time series data for one or more components of the network with the corresponding time series data generated by the simulated network.

17. A method of predicting an altered physiological state of a cell comprising:

(a) specifying a biochemical network of a cell;

(b) simulating said network by
   (i) specifying the components of said network,
   (ii) representing interrelationships between said components in one or more mathematical equations, said mathematical equations including nonlinear differential equations where each such nonlinear differential equation includes the time rate of change of one or more gene products that comprise the biochemical network, and setting the quantitative parameters of said components, and including various rate constants associated with said mathematical equations, and
   (iii) solving said mathematical equations to produce an initial simulated state of the network;

(c) optimizing said simulated biochemical network by determining and constraining the values of the parameters of said components by comparing experimental data regarding at the value of at least one component with the value of said at least one component in said simulated biochemical network, said optimizing including calculating an accuracy cost representing a measure of the overall differences between the exDerimental data and the simulated biochemical network;

(d) perturbing the optimized simulated network by adding or deleting one or more components thereof, changing the concentration of one or more components thereof or modifying one or more mathematical equations representing interrelationships between one or more of said components, including modifying at least one of said rate constants away from their starting values;

(e) solving the equations representing the perturbed network to simulate a modified state of the network, including calculating a new set of rate constants;

(f) optimizing said perturbed simulated biochemical network by determining and constraining the values of the parameters of said components by comparing experimental data regarding at the value of at least one component with the value of said at least one component in said simulated biochemical network and calculating a new accuracy cost;

(g) comparing said initial and modified simulated states of the network to identify the effect of said perturbation on the state of the network, including calculating the change in accuracy cost; and (h) outputting the results of said comparison and the associated predicted altered physiological state of the cell to a user.

* * * * *